(12) United States Patent
Srivastava et al.

(10) Patent No.: US 12,358,954 B2
(45) Date of Patent: *Jul. 15, 2025

(54) CAPSID-MODIFIED rAAV VECTOR COMPOSITIONS AND METHODS THEREFOR

(71) Applicant: University of Florida Research Foundation, Incorporated, Gainesville, FL (US)

(72) Inventors: Arun Srivastava, Gainesville, FL (US); George Vladimirovich Aslanidi, Gainesville, FL (US); Sergei Zolotukhin, Gainesville, FL (US); Mavis Agbandje-McKenna, Gainesville, FL (US); Kim M. Van Vliet, Gainesville, FL (US); Li Zhong, Gainesville, FL (US); Lakshmanan Govindasamy, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 333 days.

This patent is subject to a terminal disclaimer.

(21) Appl. No.: 17/929,256

(22) Filed: Sep. 1, 2022

(65) Prior Publication Data

US 2023/0136849 A1  May 4, 2023

Related U.S. Application Data

(63) Continuation of application No. 16/179,818, filed on Nov. 2, 2018, now abandoned, which is a continuation of application No. 15/987,993, filed on May 24, 2018, now Pat. No. 10,815,279, which is a continuation of application No. 14/214,011, filed on Mar. 14, 2014, now Pat. No. 10,011,640, which is a continuation-in-part of application No. 13/899,481, filed on May 21, 2013, now Pat. No. 9,920,097, and a continuation-in-part of application No. PCT/US2013/041234, filed on May 15, 2013, which is a continuation-in-part of application No.
(Continued)

(51) Int. Cl.
| | |
|---|---|
| A61K 48/00 | (2006.01) |
| A61K 38/42 | (2006.01) |
| A61K 39/00 | (2006.01) |
| C07K 14/005 | (2006.01) |
| C07K 14/805 | (2006.01) |
| C12N 9/64 | (2006.01) |
| C12N 15/86 | (2006.01) |
| C07K 14/015 | (2006.01) |

(52) U.S. Cl.
CPC ............ *C07K 14/005* (2013.01); *A61K 38/42* (2013.01); *C07K 14/805* (2013.01); *C12N 15/86* (2013.01); *C07K 14/015* (2013.01); *C12N 2750/14122* (2013.01); *C12N 2750/14123* (2013.01); *C12N 2750/14143* (2013.01); *C12N 2750/14145* (2013.01); *C12N 2750/14171* (2013.01); *C12N 2810/6027* (2013.01)

(58) Field of Classification Search
CPC .. C07K 14/005; C07K 14/805; C07K 14/015; A61K 38/42; A61K 48/0041; A61K 2039/5158; A61K 48/0091; C12N 15/86; C12N 2750/14122; C12N 2750/14123; C12N 2750/14143; C12N 2750/14145; C12N 2750/14171; C12N 2810/6027; C12N 9/644; C12Y 304/21022
See application file for complete search history.

(56) References Cited

U.S. PATENT DOCUMENTS

| | | |
|---|---|---|
| 6,156,303 A | 12/2000 | Russell et al. |
| 6,491,907 B1 | 12/2002 | Rabinowitz et al. |
| (Continued) | | |

FOREIGN PATENT DOCUMENTS

| | | |
|---|---|---|
| CA | 2720097 A1 | 10/2008 |
| CA | 2826273 A1 | 8/2012 |
| (Continued) | | |

OTHER PUBLICATIONS

Petrs-Silva et al (2009). High-efficiency transduction of the mouse retina by tyrosine-mutant AAV serotype vectors. Mol Ther. 17(3): 463-71. (Year: 2009).*
Zhong et al (2008). Next generation of adeno-associated virus 2 vectors: point mutations in tyrosines lead to high-efficiency transduction at lower doses. Proc Natl Acad Sci U S A. 105 (22):7827-32. (Year: 2008).*
(Continued)

*Primary Examiner* — Janet L Andres
*Assistant Examiner* — Samadhan Jaising Jadhao
(74) *Attorney, Agent, or Firm* — Wolf, Greenfield & Sacks, P.C.

(57) ABSTRACT

Disclosed are capsid-modified rAAV expression vectors, as well as infectious virions, compositions, and pharmaceutical formulations containing them. Also provided are methods of preparing and using the disclosed capsid-protein-mutated rAAV constructs in a variety of diagnostic and therapeutic modalities, including, inter alia, as mammalian cell-targeting delivery agents, and as human gene therapy vectors. Also disclosed are large-scale production methods for capsid-modified rAAV expression vectors, viral particles, and infectious virions having improved transduction efficiencies over those of the corresponding, un-modified, rAAV vectors, as well as use of the disclosed compositions in the manufacture of medicaments for a variety of in vitro and/or in vivo applications.

20 Claims, 75 Drawing Sheets

Specification includes a Sequence Listing.

Related U.S. Application Data

13/840,224, filed on Mar. 15, 2013, now Pat. No. 9,725,485.

(60) Provisional application No. 61/647,318, filed on May 15, 2012.

(56) References Cited

U.S. PATENT DOCUMENTS

| | | | |
|---|---|---|---|
| 7,052,692 | B1 | 5/2006 | Srivastava et al. |
| 8,445,267 | B2 | 5/2013 | Zhong et al. |
| 8,802,440 | B2 | 8/2014 | Zhong et al. |
| 9,157,098 | B2 | 10/2015 | Zhong et al. |
| 9,611,302 | B2 | 4/2017 | Srivastava et al. |
| 9,725,485 | B2 | 8/2017 | Srivastava et al. |
| 9,775,918 | B2 | 10/2017 | Zhong et al. |
| 9,920,097 | B2 | 3/2018 | Zhong et al. |
| 10,011,640 | B2* | 7/2018 | Srivastava .............. A61P 25/16 |
| 10,294,281 | B2 | 5/2019 | Srivastava et al. |
| 10,308,957 | B2 | 6/2019 | Boye et al. |
| 10,426,844 | B2 | 10/2019 | Agbandje-McKenna et al. |
| 10,648,000 | B2 | 5/2020 | Hauswirth et al. |
| 10,723,768 | B2 | 7/2020 | Zhong et al. |
| 10,793,606 | B2 | 10/2020 | Zolotukhin et al. |
| 10,815,279 | B2* | 10/2020 | Srivastava .............. A61P 25/02 |
| 10,900,053 | B2* | 1/2021 | Lu .......................... C12N 15/86 |
| 10,927,150 | B2 | 2/2021 | Aslanidi et al. |
| 10,934,327 | B2 | 3/2021 | Srivastava et al. |
| 11,124,544 | B2 | 9/2021 | Srivastava et al. |
| 11,332,502 | B2 | 5/2022 | Zolotukhin et al. |
| 11,434,260 | B2 | 9/2022 | Srivastava et al. |
| 12,065,467 | B2* | 8/2024 | Srivastava ........... C07K 14/005 |
| 2003/0138772 | A1 | 7/2003 | Gao et al. |
| 2003/0219733 | A1 | 11/2003 | Clark et al. |
| 2006/0088936 | A1 | 4/2006 | Warrington et al. |
| 2006/0292117 | A1 | 12/2006 | Loiler et al. |
| 2009/0197338 | A1 | 8/2009 | Vandenberghe et al. |
| 2010/0104561 | A1 | 4/2010 | Zhong et al. |
| 2013/0203841 | A1 | 8/2013 | Zhong et al. |
| 2013/0216501 | A1 | 8/2013 | Zhong et al. |
| 2013/0224836 | A1 | 8/2013 | Muramatsu |
| 2013/0310443 | A1 | 11/2013 | Srivastava et al. |
| 2014/0050701 | A1* | 2/2014 | Zhong ................ C12N 15/8645 435/456 |
| 2014/0341852 | A1 | 11/2014 | Srivastava et al. |
| 2015/0065562 | A1 | 3/2015 | Yazicioglu et al. |
| 2015/0133530 | A1 | 5/2015 | Srivastava et al. |
| 2016/0106865 | A1 | 4/2016 | Zhong et al. |
| 2016/0333372 | A1 | 11/2016 | Srivastava et al. |
| 2016/0361439 | A1 | 12/2016 | Agbandje-McKenna et al. |
| 2016/0369299 | A1 | 12/2016 | Boye et al. |
| 2017/0275337 | A1 | 9/2017 | Srivastava et al. |
| 2017/0356009 | A1 | 12/2017 | Lu et al. |
| 2018/0030096 | A1 | 2/2018 | Aslanidi et al. |
| 2018/0036428 | A1 | 2/2018 | Zhong et al. |
| 2018/0105559 | A1 | 4/2018 | Zhong et al. |
| 2018/0135074 | A1 | 5/2018 | Srivastava et al. |
| 2018/0193489 | A1 | 7/2018 | Hobbs et al. |
| 2018/0223312 | A1 | 8/2018 | Srivastava et al. |
| 2018/0244727 | A1 | 8/2018 | Zhong et al. |
| 2019/0000943 | A1 | 1/2019 | Aslanidi |
| 2019/0016759 | A1 | 1/2019 | Srivastava et al. |
| 2019/0127424 | A1 | 5/2019 | Srivastava et al. |
| 2019/0284244 | A1 | 9/2019 | Srivastava et al. |
| 2020/0010510 | A1 | 1/2020 | Aslanidi et al. |
| 2020/0093938 | A1 | 3/2020 | Pan et al. |
| 2021/0040156 | A1 | 2/2021 | Zhong et al. |
| 2021/0253644 | A1 | 8/2021 | Srivastava et al. |
| 2021/0269487 | A1 | 9/2021 | Aslanidi et al. |
| 2022/0347317 | A1 | 11/2022 | Srivastava et al. |
| 2023/0129762 | A1 | 4/2023 | Srivastava et al. |
| 2024/0109938 | A1 | 4/2024 | Aslanidi et al. |
| 2024/0181083 | A1 | 6/2024 | Srivastava et al. |

FOREIGN PATENT DOCUMENTS

| | | |
|---|---|---|
| CN | 102159713 A | 8/2011 |
| CN | 102994549 A | 3/2013 |
| CN | 103060331 A | 4/2013 |
| CN | 104470945 A | 3/2015 |
| EP | 1310571 A2 | 5/2003 |
| EP | 1486567 A1 | 12/2004 |
| EP | 2660325 A2 | 11/2013 |
| JP | 2002/538770 A | 11/2002 |
| JP | 7004328 B2 | 2/2022 |
| WO | WO 2000/65038 A2 | 11/2000 |
| WO | WO 2001/83692 A2 | 11/2001 |
| WO | WO 2003/006616 A2 | 1/2003 |
| WO | WO 2003/052052 A2 | 6/2003 |
| WO | WO 2004/027019 A2 | 4/2004 |
| WO | WO 2004/111248 A2 | 12/2004 |
| WO | WO 2004/112727 A2 | 12/2004 |
| WO | WO 2005/033321 A2 | 4/2005 |
| WO | WO 2006/110689 A2 | 10/2006 |
| WO | WO 2006/119150 A2 | 11/2006 |
| WO | WO 2008/124724 A1 | 10/2008 |
| WO | WO 2008/145400 A2 | 12/2008 |
| WO | WO 2009/154452 A1 | 12/2009 |
| WO | WO 2011/133890 A1 | 10/2011 |
| WO | WO 2012/057363 A2 | 5/2012 |
| WO | WO 2013/158879 A1 | 10/2013 |
| WO | WO 2013/173512 A1 | 11/2013 |
| WO | WO 2014/193716 A1 | 12/2014 |
| WO | WO 2016/126857 A1 | 8/2016 |

OTHER PUBLICATIONS

Srivastava et al (2008). Adeno-associated virus as a delivery vector for gene therapy of human diseases. Journal of Cellular Biochemistry 105:17-24. (Year: 2008).*

Qiao et al (2010). Adeno-associated virus serotype 6 capsid tyrosine-to-phenylalanine mutations improve gene transfer to skeletal muscle. Hum Gene Ther. 21(10): 1343-8. (Year: 2010).*

Examination Report dated Oct. 22, 2013, issued in CIPO 2,720,097 (2 pages).

EP Examination Report dated Jan. 27, 2011, issued in EP 08733161. 7-2405 (3 pages).

Response to EP Examination Report dated Jul. 25, 2011, issued in EP 08733161.7-2405 (8 pages).

Extended European Search Report for Application No. EP 18201865.5 mailed Feb. 27, 2019.

International Search Report and Written Opinion for Application No. PCT/US2008/059647 mailed Sep. 10, 2008.

International Preliminary Report on Patentability for Application No. PCT/US2008/059647 mailed Oct. 22, 2009.

Partial European Search Report for Application No. EP 20210108.5 mailed Jun. 2, 2021.

Extended European Search Report for Application No. EP 20210108.5 mailed Sep. 13, 2021.

International Search Report and Written Opinion for Application No. PCT/US2013/041234 mailed Feb. 13, 2014.

International Preliminary Report on Patentability for Application No. PCT/US2013/041234 mailed Nov. 27, 2014.

Partial European Search Report for Application EP 18202680.7 mailed Apr. 29, 2019.

Extended European Search Report for Application No. EP 18202680.7 mailed Jul. 31, 2019.

International Search Report and Written Opinion for Application No. PCT/US2014/039015 mailed Nov. 24, 2014.

International Preliminary Report on Patentability for Application No. PCT/US2014/039015 mailed Dec. 3, 2015.

International Search Report and Written Opinion for Application No. PCT/US2016/016422 mailed May 5, 2016.

International Preliminary Report on Patentability for Application No. PCT/US2016/016422 mailed Aug. 17, 2017.

Invitation to Pay Additional Fees for Application No. PCT/US2022/025916, mailed Oct. 19, 2022.

[No Author Listed] Database UniProt KB, Accession B4Y866 (B4Y886_9VIRU9), Integrated into UniProt KB/TrEMBL Sep. 23, 2008, Last modified Jul. 31, 2019. 4 pages.

(56) References Cited

OTHER PUBLICATIONS

[No Author Listed] Database UniProt KB, Accession Q808W7 (Q808W7-9VIRU), Integrated into UniProt KB/TrEMBL Jun. 1, 2003, Last modified Jul. 31, 2019. 4 pages.
[No Author Listed] Database UnitprotKB, Accession No. Q9YIJ1 (Q9YIJ1_9VIRU), Integrated into UniProt KB/TrEMBL May 1, 2009, Last modified Jun. 2, 2021.
[No Author Listed] NCBI Blast Alignment of instant SEQ ID No. 1 and SEQ ID No. 1 of 10815279 (Year: 2022).
[No Author Listed] NCBI Blast Alignment of instant SEQ ID No. 1 and SEQ ID No. 1 of Zhong et al. (Year: 2022).
[No Author Listed] NCBI Blast Alignment of instant SEQ ID No. 1 and SEQ ID No. 6 of 10011640 (Year: 2022).
[No Author Listed] NCBI Blast Alignment of instant SEQ ID No. 1 and SEQ ID No. 6 of 9920097 (Year: 2022).
[No Author Listed], Genbank Submission; NIH/NCBI Accession No. YP_680426. Major coat protein VP1 [Adeno-associated virus]. Jul. 25, 2006.
Asher et al., Clinical development on the frontier: gene therapy for duchenne muscular dystrophy. Expert Opin Biol Ther. Mar. 2020;20(3):263-274. doi: 10.1080/14712598.2020.1725469. Epub Feb. 12, 2020.
Aslanidi et al, High-efficiency transduction of human monocyte-derived dendritic cells by capsid-modified recombinant AAV2 vectors. Vaccine. Jun. 6, 2012;30(26):3908-17. doi: 10.1016/j.vaccine.2012.03.079. Epub Apr. 10, 2012.
Aslanidi et al, Optimization of the capsid of recombinant adeno-associated virus 2 (AAV2) vectors: the final threshold? PLoS One. 2013;8(3):e59142. doi: 10.1371/journal.pone.0059142. Epub Mar. 19, 2013.
Aslanidi et al., Abstract 116. Site-directed mutagenesis of surface-exposed tyrosine, serine, and threonine residues leads to high-efficiency transduction by recombinant adeno-associated virus 2 vectors. Mol Ther. May 2012;20(S1):S48.
Aslanidi et al., Abstract 333: High-Efficiency Transduction of Primary Human Monocyte-Derived Dendritic Cells by Recombinant AAV6 Vectors Containing Mutations in Surface-Exposed Serine and Threonine Residues. Molecular Therapy. May 2013;21(S1):S129.
Aslanidi et al., Abstract 334: Optimization of the capsid of recombinant adeno-associated virus 2 (AAV2) vectors: the final threshold? Molecular Therapy. May 2013;21(S1):S129.
Aslanidi et al., Abstract 368. High-Efficiency transduction of primary human monocyte-derived dendritic cells by recombinant adeno-associated virus 2 vectors containing mutations in surface-exposed serine and threonine residues. Mol Ther. May 2012;20(S1):S144.
Aslanidi et al., Abstract C240: Modification on the capsid of recombinant adeno-associated virus vectors (rAAV) leads to high-efficiency transduction of human monocyte-derived dendritic cells (moDCs). Mol Cancer Ther. Nov. 2011. 10(11): Abstract C240. 3 Pages.
Asokan et al., The AAV vector toolkit: poised at the clinical crossroads. Mol Ther. Apr. 2012;20(4):699-708. doi: 10.1038/mt.2011.287. Epub Jan. 24, 2012.
Auricchio et al., Exchange of surface proteins impacts on viral vector cellular specificity and transduction characteristics: the retina as a model. Hum Mol Genet. Dec. 15, 2001;10(26):3075-81. doi: 10.1093/hmg/10.26.3075.
Bantel-Schaal et al., Human adeno-associated virus type 5 is only distantly related to other known primate helper-dependent parvoviruses. J Virol. Feb. 1999;73(2):939-47.
Cheng et al, Development of optimized AAV3 serotype vectors: mechanism of high-efficiency transduction of human liver cancer cells. Gene Ther. Apr. 2012;19(4):375-84. doi: 10.1038/gt.2011.105. Epub Jul. 21, 2011. Author Manuscript, 24 pages.
Chiorini et al., Capsid Protein [Adeno-associated virus -5] Genbank Accession No. YP-068409 Dec. 8, 2008. 2 pages.
Dalkara et al., Enhanced gene delivery to the neonatal retina through systemic administration of tyrosine-mutated AAV9. Gene Ther. Feb. 2012;19(2):176-81. doi: 10.1038/gt.2011.163. Epub Oct. 20, 2011.
De Oliveira et al., Herpes simplex virus type 1/adeno-associated virus hybrid vectors. Open Virol J. Jun. 18, 2010;4:109-22. doi: 10.2174/1874357901004030109.
Doroudchi et al., Virally delivered channelrhodopsin-2 safely and effectively restores visual function in multiple mouse models of blindness. Mol Ther. Jul. 2011;19(7):1220-9. doi: 10.1038/mt.2011.69. Epub Apr. 19, 2011.
Duan et al., Enhancement of muscle gene delivery with pseudotyped adeno-associated virus type 5 correlates with myoblast differentiation. J Virol. Aug. 2001;75(16):7662-71. doi: 10.1128/JVI.75.16.7662-7671.2001.
Endell, Generation of enhanced gene delivery vectors by directed evolution of adeno-associated virus. Dissertation, LMU Munchen: Faculty of Chemistry and Pharmacy. 2006, 126 pages.
Gabriel et al., Bioengineering of AAV2 capsid at specific serine, threonine, or lysine residues improves its transduction efficiency in vitro and in vivo. Hum Gene Ther Methods. Apr. 2013;24(2):80-93. doi: 10.1089/hgtb.2012.194. Epub Mar. 15, 2013.
Gabriel et al., Targeted Mutagenesis of Ubiquitin-Binding Lysine Residues on the Adeno-Associated Virus (AAV)2 Capsid Improves Its Transduction Efficiency. Mol Ther. 2012;20(Supp 1):S146.
Gao et al., Clades of Adeno-associated viruses are widely disseminated in human tissues. J Virol. Jun. 2004;78(12):6381-8.
Gao et al., Novel adeno-associated viruses from rhesus monkeys as vectors for human gene therapy. Proc Natl Acad Sci U S A. Sep. 3, 2002;99(18):11854-9. Epub Aug. 21, 2002.
Genbank Accession No. AAC55049.1. capsid protein [Adeno-associated virus—3]. Muramatsu et al., Dated Jul. 14, 1996. 2 pgs.
Genbank Accession No. AAN03857.1. capsid protein [Adeno-associated virus—8]. Gao et al., Dated Sep. 5, 2002. 2 pgs.
Genbank Accession No. AAS99284.1 . capsid protein VP1 [Adeno-associated virus]. Gao et al., Dated Jun. 24, 2004. 2 pgs.
Glushakova et al., 459. High-Efficiency Transduction of Human Hepatoblastoma and Hepatocellular Carcinoma Cells by the Wild-Type and the Tyrosine-Mutant AAV3 Serotype Vectors. Mol Ther. 2009;17(S1):S179.
Grimm et al., Liver transduction with recombinant adeno-associated virus is primarily restricted by capsid serotype not vector genotype. J Virol. Jan. 2006;80(1):426-39. doi: 10.1128/JVI.80.1.426-439.2006.
Grimm et al., Titration of AAV-2 particles via a novel capsid ELISA: packaging of genomes can limit production of recombinant AAV-2. Gene Ther. Jul. 1999;6(7):1322-30. doi: 10.1038/sj.gt.3300946.
Halbert et al., Repeat transduction in the mouse lung by using adeno-associated virus vectors with different serotypes. J Virol. Feb. 2000;74(3):1524-32. doi: 10.1128/jvi.74.3.1524-1532.2000.
Hareendran et al., 115. Bio-Engineering of Adeno-Associated Virus Serotype (AAV)-2 Capsid at Serine/Threonine Residues Improves Its Transduction Efficiency Both In Vitro and In Vivo. Mol Ther. May 2012;20(S1):S47.
Horowitz et al., Tyrosine cross-linking reveals interfacial dynamics in adeno-associated viral capsids during infection. ACS Chemical Biology, pubs.acs.org/acschemicalbiology, ACS Publications, ACS Chem Biol. Jun. 15, 2012;7(6):1059-66. doi: 10.1021/cb3000265. Epub Apr. 6, 2012.
Jayandharan et al., 372. Human Hematopoietic Stem Cell Transduction by AAV Vectors: Identification of AAV6 as the Most Efficient Serotype, and Further Augmentation in Transduction Efficiency with Point-Mutations at Tyrosine Residues 705 and 731in the Viral Capsid. Mol Ther. 2009;17(S1):S145-6.
Jayandharan et al., Activation of the NF-kappaB pathway by adeno-associated virus (AAV) vectors and its implications in immune response and gene therapy. Proc Natl Acad Sci U S A. Mar. 1, 2011;108(9):3743-8. doi: 10.1073/pnas.1012753108. Epub Feb. 14, 2011.
Kauss et al., 457. Tyrosine-Modified rAAV2 Vectors Display Enhanced Transduction of Human Hematopoietic Stem Cells. Mol Ther. 2009;17(S1):S178.
Kauss et al., Enhanced long-term transduction and multilineage engraftment of human hematopoietic stem cells transduced with

(56) References Cited

OTHER PUBLICATIONS tyrosine-modified recombinant adeno-associated virus serotype 2. Hum Gene Ther. Sep. 2010;21(9):1129-36. doi: 10.1089/hum.2010.016.
Kay et al., Targeting photoreceptors via intravitreal delivery using novel, capsid-mutated AAV vectors. PLoS One. Apr. 26, 2013;8(4):e62097. doi: 10.1371/journal.pone.0062097. Print 2013.
Kern et al., Identification of a heparin-binding motif on adeno-associated virus type 2 capsids. J Virol. Oct. 2003;77(20):11072-81.
Ku et al., Gene therapy using self-complementary Y733F capsid mutant AAV2/8 restores vision in a model of early onset Leber congenital amaurosis. Hum Mol Genet. Dec. 1, 2011;20(23):4569-81. doi: 10.1093/hmg/ddr391. Epub Aug. 31, 2011.
Le Meur et al., Restoration of vision in RPE65-deficient Briard dogs using an AAV serotype 4 vector that specifically targets the retinal pigmented epithelium. Gene Therapy 14(4):292-303 (Feb. 2007), 12 pages.
Li et al., High-efficiency transduction of fibroblasts and mesenchymal stem cells by tyrosine-mutant AAV2 vectors for their potential use in cellular therapy. Hum Gene Ther. Nov. 2010;21(11):1527-43. doi: 10.1089/hum.2010.005. Epub Oct. 6, 2010.
Li et al., Site-Directed Mutagenesis of Surface-Exposed Lysine Residues Leads to Improved Transduction by AAV2, But Not AAV8, Vectors in Murine Hepatocytes In Vivo. Hum Gene Ther Methods. Dec. 2015;26(6):211-20. doi: 10.1089/hgtb.2015.115. Epub Oct. 27, 2015.
Li et al., Site-Directed Mutagenesis of Surface-Exposed Lysine Residues Leads to Improved Transduction by Recombinant Aav2 and Aav8 Vectors in Murine Hepatocytes in Vivo. Mol Ther. 2013;21(Supp 1):S208-9.
Li et al., The fecal viral flora of California sea lions. J Virol. Oct. 2011;85(19):9909-17. doi: 10.1128/JVI.05026-11. Epub Jul. 27, 2011.
Ling et al, Selective in vivo targeting of human liver tumors by optimized AAV3 vectors in a murine xenograft model. Hum Gene Ther. Dec. 2014;25(12):1023-34. doi: 10.1089/hum.2014.099.
Ling et al., Development of Optimized AAV Serotype Vectors for High-Efficiency Transduction at Further Reduced Doses. Hum Gene Ther Methods. Aug. 2016;27(4):143-9. doi: 10.1089/hgtb.2016.054.
Ling et al., Enhanced transgene expression from recombinant single-stranded D-sequence-substituted adeno-associated virus vectors in human cell lines in vitro and in murine hepatocytes in vivo. J Virol. Jan. 15, 2015;89(2):952-61. doi: 10.1128/JVI.02581-14. Epub Oct. 29, 2014.
Ling et al., The role of glucocorticoid receptor signaling in adeno-associated virus 2 infection. Molecular Therapy. May 2016;24(S1):S6.
Lochrie et al., Mutations on the External Surfaces of Adeno-Associated Virus Type 2 Capsids That Affect Transduction and Neutralization. Journal of Virology 80(2):821-834 (Jan. 2006), 14 pages.
Locke et al., Transduction of Human Adipose-Derived Mesenchymal Stem Cells by Recombinant Adeno-Associated Virus Vectors. COPYRGT. Mary Ann Liebert, Inc., DOI: 10.1089/ten.tec.2011.0153, Tissue Engineering: Part C; vol. 17, No. 9,2011, pp. 949-959.
Maheshri et al., Directed evolution of adeno-associated virus yields enhanced gene delivery vectors. Nat Biotechnol. Feb. 2006;24(2):198-204. doi: 10.1038/nbt1182. Epub Jan. 22, 2006.
Markusic et al., 765. Novel AAV2 Tyrosine Mutant Capsids Provide Long-Term Therapeutic Factor IX Expression in a Difficult To Tolerize Murine Hemophilia Model. Mol Ther. 2009;17(S1):S292.
Markusic et al., High-Efficiency Transduction and Correction of Murine Hemophelia B Using AAV2 Vectors Devoid of Multiple Surface-Exposed Tyrosines. Molecular Therapy. Dec. 2010;18(12):2048-56. doi: 10.1038/mt.2010.172. Epub Aug. 24, 2010.
Martino et al., Engineered AAV vector minimizes in vivo targeting of transduced hepatocytes by capsid-specific CD8+ T cells. Blood. Mar. 21, 2013;121(12):2224-33. doi: 10.1182/blood-2012-10-460733. Epub Jan. 16, 2013.
McClements et al., Gene therapy for retinal disease. Transl Res. Apr. 2013;161(4):241-54. doi: 10.1016/j.trsl.2012.12.007. Epub Jan. 8, 2013. Author Manuscript, 23 pages.
Mendell et al., Assessment of Systemic Delivery of rAAVrh74.MHCK7.micro-dystrophin in Children With Duchenne Muscular Dystrophy: A Nonrandomized Controlled Trial. JAMA Neurol. Sep. 1, 2020;77(9):1122-1131. doi: 10.1001/jamaneurol.2020.1484.
Mori et al., Two novel adeno-associated viruses from cynomolgus monkey: pseudotyping characterization of capsid protein. Virology. Dec. 20, 2004;330(2):375-83.
Nelson et al., Lehninger Principles of Biochemistry. 2005. 4th edition. Chapter 3. Amino Acids, Peptides, and Proteins. W.H. Freeman and Company, New York: 75-115.
Opie et al., Identification of amino acid residues in the capsid proteins of adeno-associated virus type 2 that contribute to heparan sulfate proteoglycan binding. J Virol. Jun. 2003;77(12):6995-7006.
Pandya et al., Rationally designed capsid and transgene cassette of AAV6 vectors for dendritic cell-based cancer immunotherapy. Immunol Cell Biol. Feb. 2014;92(2):116-23. doi: 10.1038/icb.2013.74. Epub Nov. 12, 2013.
Pang et al., Long-Term Retinal Function and Structure Rescue Using Capsid Mutant AAV8 Vector in the rd10 Mouse, a Model or Recessive Retinitis Pigmentosa.COPYRGT. The American Society of Gene & Cell Therapy, Molecular Therapy, pp. 1-9,2010.
Petrs-Silva et al., High-Efficiency Transduction of the Mouse Retina by Tyrosine-Mutant AAV Serotype Vectors. COPYRGT. The American Society of Gene & Cell Therapy, www.moleculartherapy.org, Molecular Therapy, vol. 17, No. 3, pp. 463-471, Mar. 2009.
Petrs-Silva et al., Novel Properties of Tyrosine-Mutant AAV2 Vectors in the Mouse Retina. COPYRGT. The American Society of Gene & Cell Therapy, www.moleculartherapy.org, Molecular Therapy, vol. 19, No. 2, pp. 293-301, Feb. 2011.
Qi et al., Comparison of Transduction Efficiency of Tyrosine-Mutant AAV Serotype Vectors in Kidney. COPYRGT. 2012 The Authors Clinical and Experimental Pharmacology and Physiology, .COPYRGT. 2012 Wiley Publishing Asia Pty Ltd., doi:10.1111/1440-1681.12037, 8 pages.
Qiao et al., 451. Comparison of Transduction Efficiency of Tyrosine-Mutant AAV Vectors in Muscle. Mol Ther. 2009;17(S1):S175-6.
Qiao et al., Adeno-Associated Virus Serotype 6 Capsid Tyrosine-to-Phenylalanine Mutations Improve Gene Transfer to Skeletal Muscle. Human Gene Therapy 21:1343-1348 (Oct. 2010), .COPYRGT. Mary Ann Liebert, Inc., doi: 10.1089/hum.2010.003, pp. 1343-1348.
Qiao et al., Single Tyrosine Mutation in AAV8 and AAV9 Capsids Is Insufficient to Enhance Gene Delivery to Skeletal Muscle and Heart. Human Gene Therapy Methods: Part B 23:29-37 (Feb. 2012), .COPYRGT. Mary Ann Liebert, Inc., doi: 10.1089/hgtb.2011.229, pp. 29-37.
Qing et al., Development of Capsid-Modified Next Generation AAVrh74 Vectors with Increased Transduction Efficiency in Primary Human Skeletal Muscle Cells: Implications in Gene Therapy of Muscular Dystrophies. Molecular Therapy. Apr. 27, 2021; 29(4 Supp 1):159-160.
Qing et al., Role of tyrosine phosphorylation of a cellular protein in adeno-associated virus 2-mediated transgene expression. Proc Natl Acad Sci U S A. Sep. 30, 1997;94(20):10879-84. doi: 10.1073/pnas.94.20.10879.
Radivojac et al., Identification, analysis, and prediction of protein ubiquitination sites. Proteins. Feb. 1, 2010;78(2):365-80. Author manuscript, 30 pages.
Rakoczy et al., Development of Gene Therapy-Based Strategies for the Treatment of Eye Diseases. Drug Development Research. 1999;46:277-285.
Rosario et al., Microglia-specific targeting by novel capsid-modified AAV6 vectors. Mol Ther Methods Clin Dev. Apr. 13, 2016;3:16026. doi: 10.1038/mtm.2016.26.
Ruan et al., Development of an Anti-Angiogenic Therapeutic Model Combining scAAV2-delivered siRNAs and Noninvasive Photoacoustic Imaging of Tumor Vasculature Development. Cancer Lett. (2012), dx.doi.org/10.1016/j.canlet.2012.11.016,Dec. 4, 2012, 10 pages.

(56) References Cited

OTHER PUBLICATIONS

Rutledge et al., Infectious clones and vectors derived from adeno-associated virus (AAV) serotypes other than AAV type 2. J Virol. Jan. 1998;72(1):309-19.
Ryals et al., Quantifying Transduction Efficiencies of Unmodified and Tyrosine Capsid Mutant AAV Vectors in Vitro Using Two Ocular Cell Lines. Molecular Vision 2011; 17:1090-1102 (www.molvis.org/molvis/v17/a124), Apr. 29, 2011,pp. 1090-1102.
Schaffer et al., GenBank Submission: ADW24578. Apr. 7, 2005. 2 pages.
Sen et al., Improved adeno-associated virus (AAV) serotype 1 and 5 vectors for gene therapy. Sci Rep. 2013;3:1832. doi: 10.1038/srep01832.
Sen et al., Targeted modifications in adeno-associated virus serotype 8 capsid improves its hepatic gene transfer efficiency in vivo. Hum Gene Ther Methods. Apr. 2013;24(2):104-16. doi: 10.1089/hgtb.2012.195.
Shieh et al., Re: "Moving Forward After Two Deaths in a Gene Therapy Trial of Myotubular Myopathy" by Wilson and Flotte. Hum Gene Ther. Aug. 2020;31(15-16):787. doi: 10.1089/hum.2020.217.
Shin et al., A Simplified Immune Suppression Scheme Leads to Persistent Micro-Dystrophin Expression in Duchenne Muscular Dystrophy Dogs. Human Gene Therapy 23:202-209 (Feb. 2012), .COPYRGT. Mary Ann Libert, Inc., doi:10.1089/hum.2011,147, pp. 202-209.
Shoti et al., Development of Genome-Modified Generation X Single-Stranded AAVrh74 Vectors with Improved Transgene Expression in Primary Human Skeletal Muscle Cells. Molecular Therapy. Apr. 27, 2021;29(4 Supp 1):184-185.
Song et al., High-efficiency transduction of primary human hematopoietic stem cells and erythroid lineage-restricted expression by optimized AAV6 serotype vectors in vitro and in a murine xenograft model in vivo. PLoS One. 2013;8(3):e58757. doi: 10.1371/journal.pone.0058757. Epub Mar. 14, 2013.
Song et al., Optimizing the transduction efficiency of capsid-modified AAV6 serotype vectors in primary human hematopoietic stem cells in vitro and in a xenograft mouse model in vivo. Cytotherapy. 2013;15:986-98. Author Manuscript, 22 pages.
Ussher et al., Optimized Transduction of Human Monocyte-Derived Dendritic Cells by Recombinant Adeno-Associated Virus Serotype 6. Human Gene Therapy 21:1675-1686 (Dec. 2010), .COPYRGT. Mary Ann Liebert, Inc., doi: 10.1089/hum.2010.078,pp. 1675-1686.
Vandenberghe et al., [Naturally occurring singleton residues in AAV capsid impact performance and illustrate structural constraints in 70012] B4Y882_9VIRU sequence alignment, Submitted Sep. 23, 2008. 2 Pages. [Also cited as Vandenberghe et al., Naturally occurring singleton residues in AAV capsid impact performance and illustrate structural constraints. Submitted 2007. EMBL/GenBank/DDBJ databases. Accession No. B4Y882_9VIRU.
Wang et al., Limitations of encapsidation of recombinant self-complementary adeno-associated viral genomes in different serotype capsids and their quantitation. Hum Gene Ther Methods. Aug. 2012;23(4):225-33. doi: 10.1089/hgtb.2012.090.
Yan et al. Ubiquitination of both Adeno-Associated Virus Type 2 and 5 Capsid Proteins Affects the Transduction Efficiency of Recombinant Vectors, Journal of Virology 76(5):2043-2053 (Mar. 2002), 11 pages.
Zhang et al., 453. Novel Tyrosine Mutant Vectors Expand the Utilities of AAV-Mediated Muscle Gene Therapy. Mol Ther. 2009;17(S1):S176-7.
Zhong et al., 371. High-Efficiency Transduction of Human Cells In Vitro and Murine Hepatocytes In Vivo at Further Reduced Doses of AAV2 Vectors Containing Multiple-Mutations in Surface-Exposed Tyrosine Residues in the Viral Capsid. Mol Ther. May 2009;17(S1):S145.
Zhong et al., 90. Critical Requirement of a Cellular Chaperone Protein, FKBP52, for Intracellular Trafficking and Nuclear Transport of Tyrosine-Mutant AAV2 Vectors for High-Efficiency Transduction of Murine Embryo Fibroblasts. Mol Ther. May 2009; 17(S1):S36-7.
Zhong et al., A Dual Role of EGFR Protein Tyrosine Kinase Signaling in Ubiquitination of AAV2 Capsids and Viral Second-strand DNA Synthesis. The American Society of Gene Therapy, Molecular Therapy 15(7):1323-1330 (Jul. 2007), 8 pages.
Zhong et al., Evaluation of Primitive Murine Hematopoietic Stem and Progenitor Cell Transduction In Vitro and In Vivo by Recombinant Adeno-Associated Virus Vector Serotypes 1 Through 5. Human Gene Therapy 17(3):321-333 (Mar. 2006), 13 pages.
Zhong et al., Next generation of adeno-associated virus 2 vectors: Point mutations in tyrosines lead to high-efficiency transduction at lower doses. Proc Natl Acad Sci U S A. Jun. 3, 2008;105(22):7827-32. doi: 10.1073/pnas.0802866105. Epub May 29, 2008. Erratum in Proc Natl Acad Sci U S A. Aug. 5, 2008;105(31):11032.
Zolotukhin et al., Production and purification of serotype 1, 2, and 5 recombinant adeno-associated viral vectors. Methods. Oct. 2002;28(2):158-67. doi: 10.1016/s1046-2023(02)00220-7.
International Search Report and Written Opinion for Application No. PCT/US2022/025916 mailed Feb. 1, 2023.
International Preliminary Report on Patentability for Application No. PCT/US2022/025916 mailed Nov. 2, 2023.
[No Author Listed], NCBI Blast alignment of Seq. ID No. 13 from PCT App No. PCT/US2004/019884, filed Jun. 2, 20041 and Seq. IDS No. 2 from U.S. Appl. No. 17/810,729. Report generated 2023 by USPTO examiner in U.S. Appl. No. 17/810,729.
Bartel et al., Enhancing the clinical potential of AAV vectors by capsid engineering to evade pre-existing immunity. Front. Microbiol. Oct. 4, 2011;2:10 pages.
Chan et al., Rational Design of AAV-rh74, AAV3B, and AAV8 with Limited Liver Targeting. Viruses. Oct. 28, 2023;15(11):2168. doi: 10.3390/v15112168.
Diprimio et al., Surface loop dynamics in adeno-associated virus capsid assembly. J Virol. Jun. 2008;82(11):5178-89. doi: 10.1128/JVI.02721-07. Epub Mar. 26, 2008.
Johnson et al., Enhancement of adeno-associated virus infection by mobilizing capsids into and out of the nucleolus. J Virol. Mar. 2009;83(6):2632-44. doi: 10.1128/JVI.02309-08. Epub Dec. 24, 2008.
Li et al., Engineering adeno-associated virus vectors for gene therapy. Nat Rev Genet. Apr. 2020;21(4):255-272. doi: 10.1038/s41576-019-0205-4. Epub Feb. 10, 2020.
Mendell et al., Limb-girdle muscular dystrophy type 2D gene therapy restores alpha-sarcoglycan and associated proteins. Ann Neurol. Sep. 2009;66(3):290-7. doi: 10.1002/ana.21732.
Stagg et al., Cryo-electron Microscopy of Adeno-associated Virus. Chem Rev. Sep. 14, 2022;122(17):14018-14054. doi: 10.1021/acs.chemrev.1c00936. Epub May 16, 2022.
Wu et al., Adeno-associated virus serotypes: vector toolkit for human gene therapy. Mol Ther. Sep. 2006;14(3):316-27. doi: 10.1016/j.ymthe.2006.05.009. Epub Jul. 7, 2006.
Xiao et al., Production of high-titer recombinant adeno-associated virus vectors in the absence of helper adenovirus. J Virol. Mar. 1998;72(3):2224-32. doi: 10.1128/JVI.72.3.2224-2232.1998.
Yazicioglu et al., AAV-Rh74 capsid protein VP1 variant Y253F/Y275F/Y447F/Y703F/Y707F/Y733F, GSP Database Accession No. BAX21206, Dec. 19, 2013. 1 page.
U.S. Appl. No. 18/772,340, filed Jul. 15, 2024, Srivastava et al.
U.S. Appl. No. 18/164,942, filed Feb. 26, 2023, Aslanidi et al.
U.S. Appl. No. 18/287,711, filed Oct. 20, 2023, Srivastava et al.

\* cited by examiner

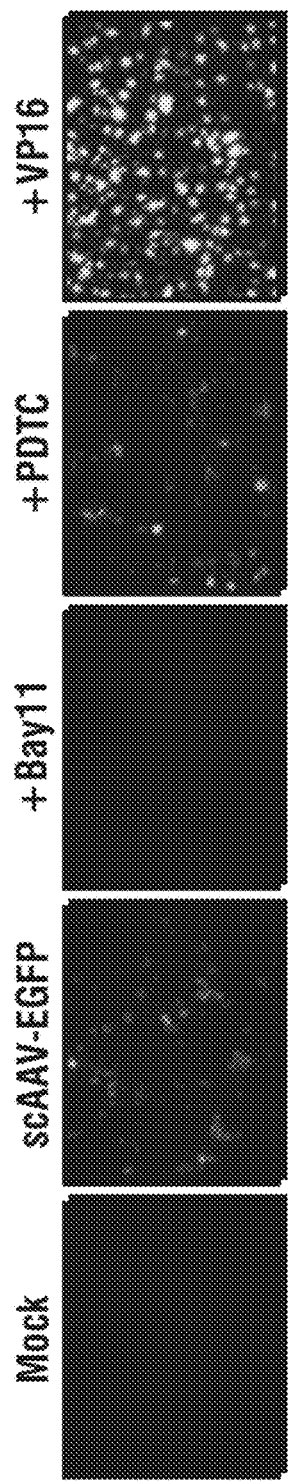
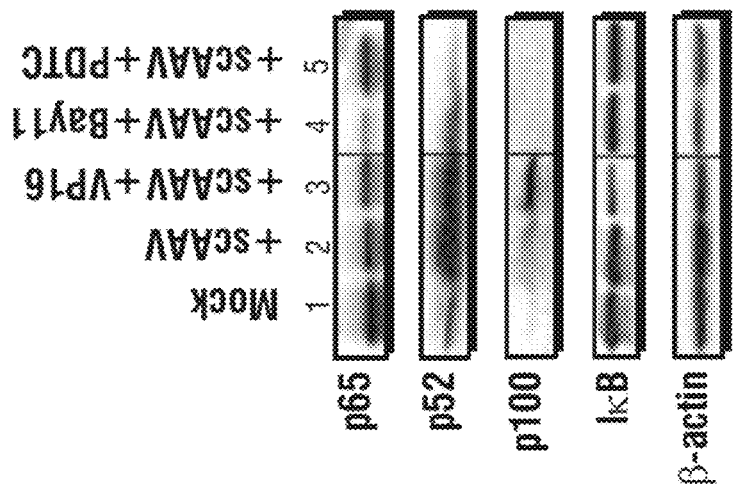
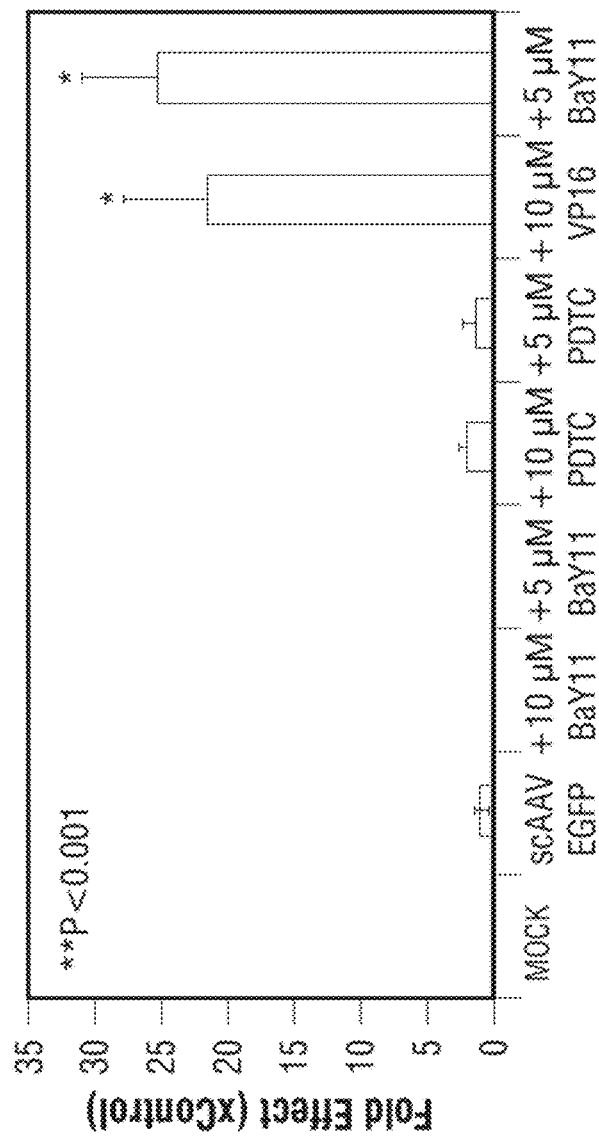
FIG. 1A
FIG. 1B
FIG. 1C

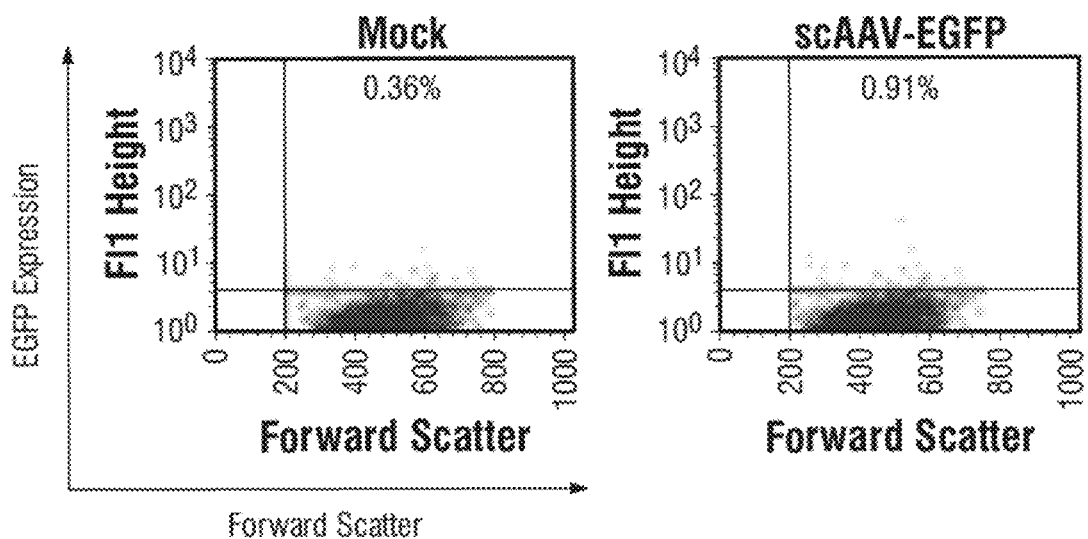
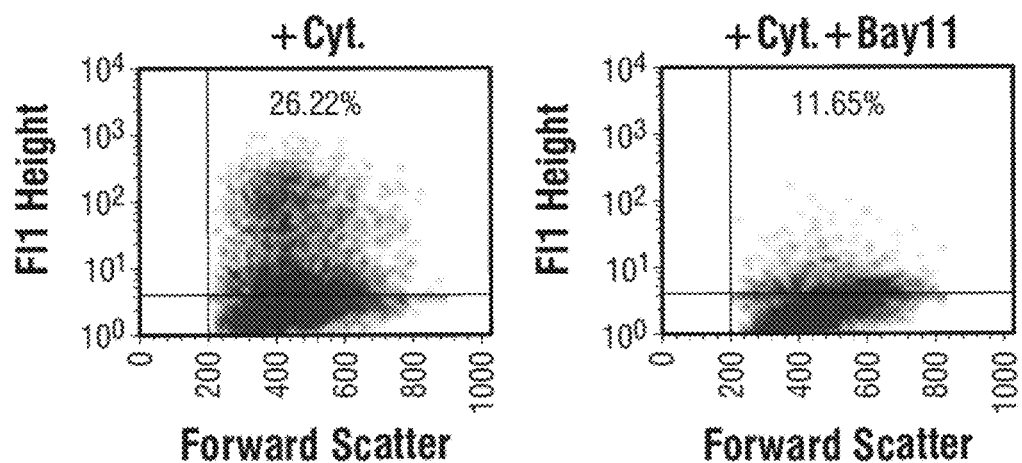
FIG. 2A

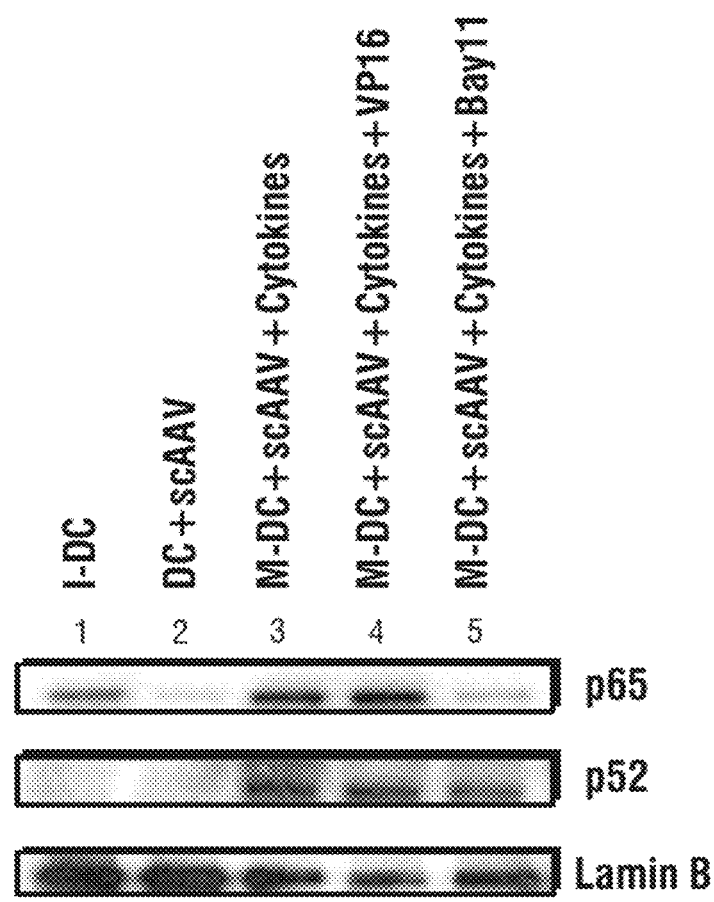

```
1                                                           25                                              50
AGGAACCCTAGTGATGGAGTTGGCCACTCCCTCTCTGCCTCGCTCACTGAGGCCGGGGCGACCAAAG
D-SEQUENCE 75                                                          100                         125                 145
GTCGCCCGAGCCCGGGCTTTGCCCGGGCGGCCTCAGTGAGGAGCGAGCCGCCAAGAGAGCCAGTGGCCAA
                                                                                                        SEQ ID NO: 22
```

| Transcription factor | No. of binding sites |
| --- | --- |
| p300 | 4 |
| TFIIB | 4 |
| SpII | 1 |

FIG. 5

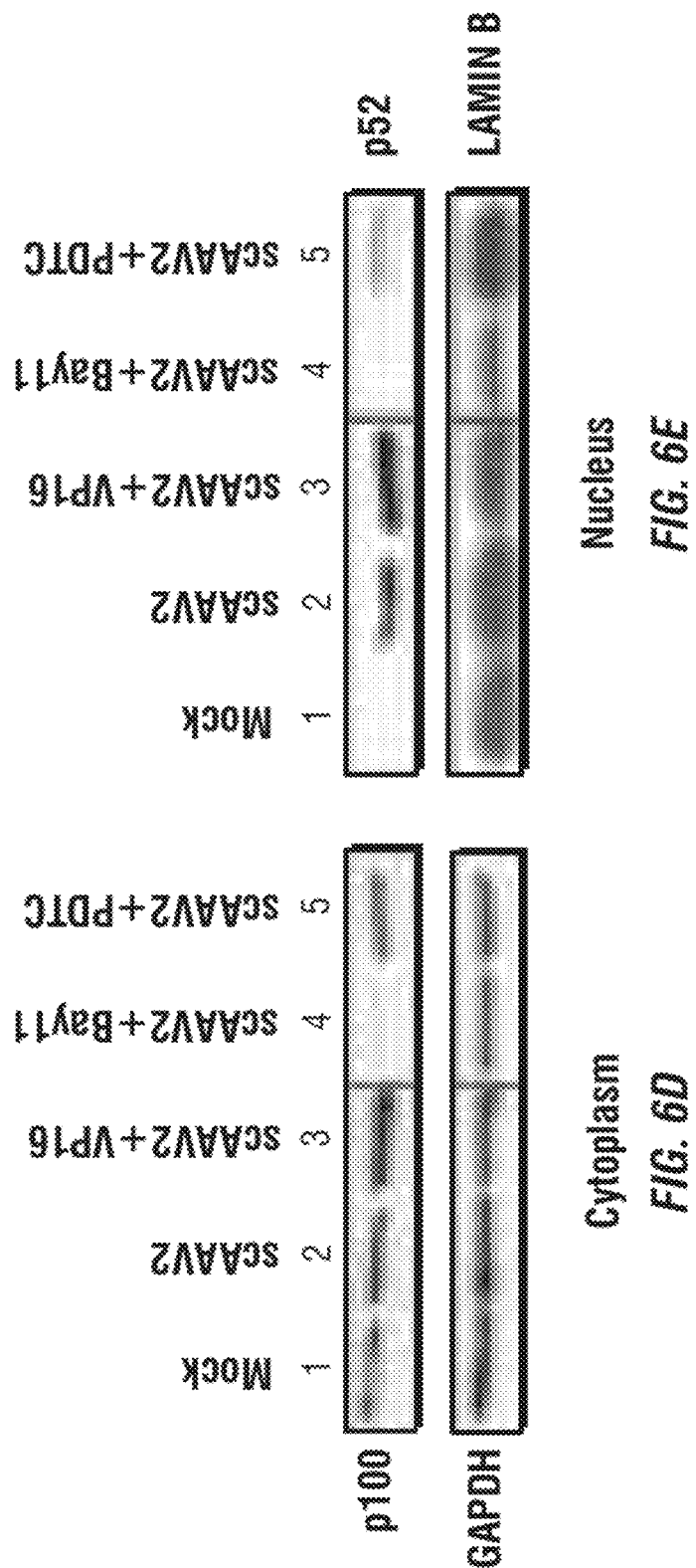

| Strand | Sequence | |
|---|---|---|
| ssD[-]: | 5'-CTC CA TCACTA G GGGT TCCT-3' | SEQ ID NO: 23 |
| dsD[±]: | 5'-CTC CA TCACTA G GGGT TCCT-3'<br>3'-GAGG TAGT GAT CCC AAGGA-5' | SEQ ID NO: 23<br>SEQ ID NO: 45 |
| ssD[+]: | 5'-GAGGTA GTGAT CC CCAAGGA-3' | SEQ ID NO: 25 |

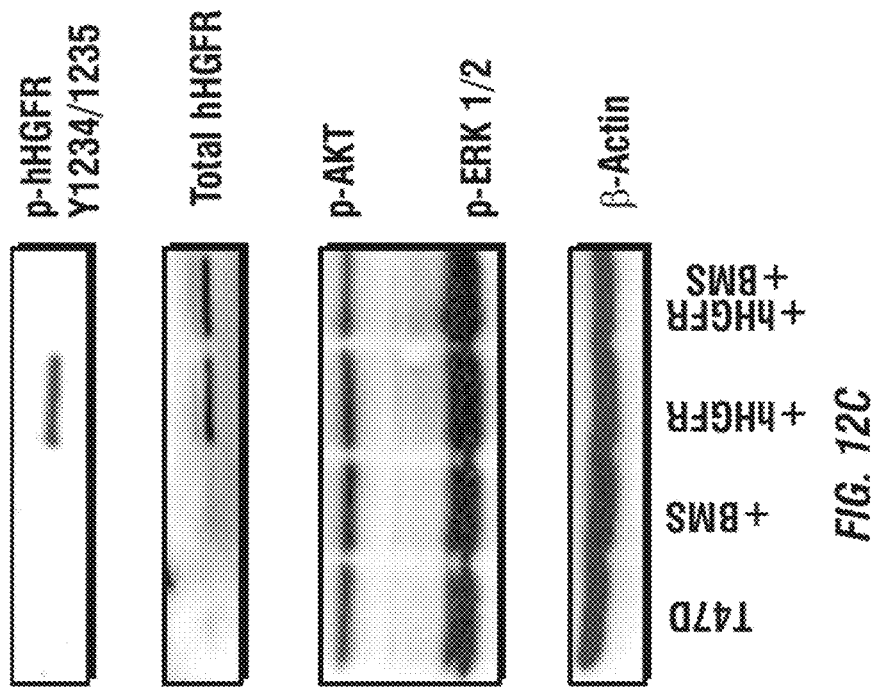
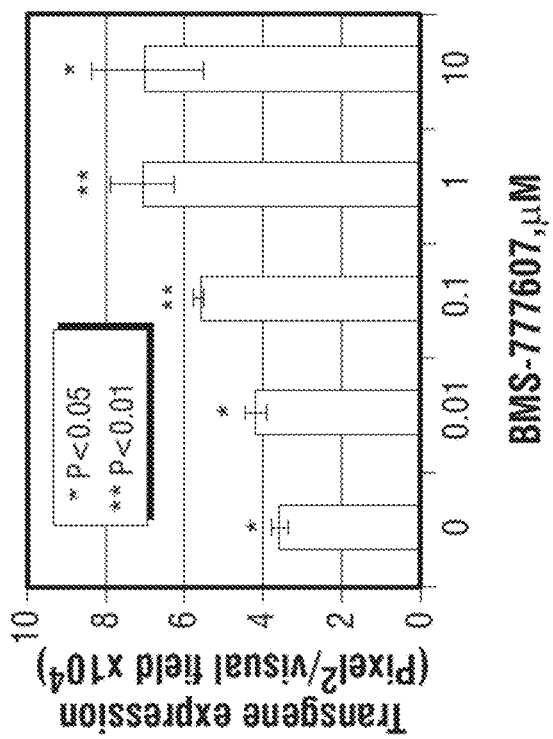
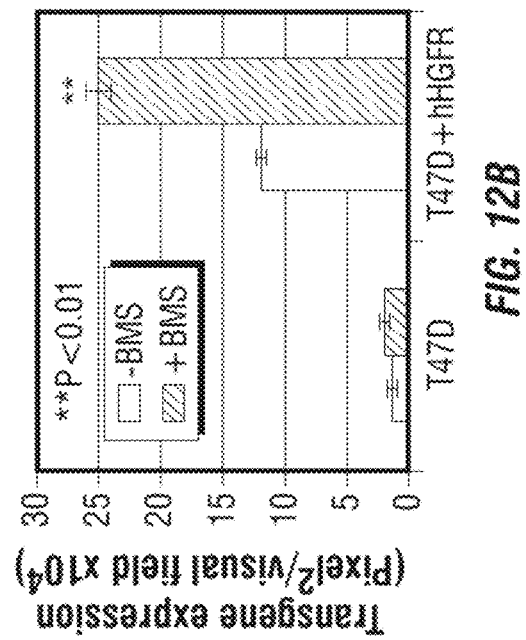
FIG. 12A
FIG. 12B
FIG. 12C

Huh7 Tumors

Hep293TT Tumors

WT-AAV3

Y705+731F-AAV3

WT 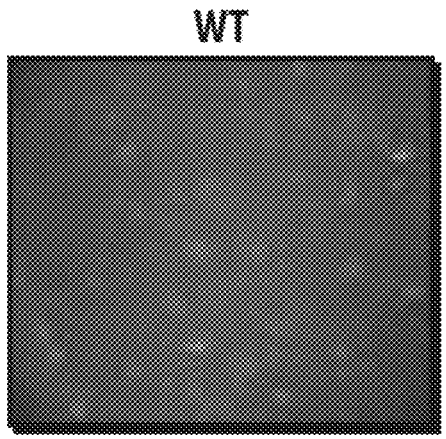 S458V 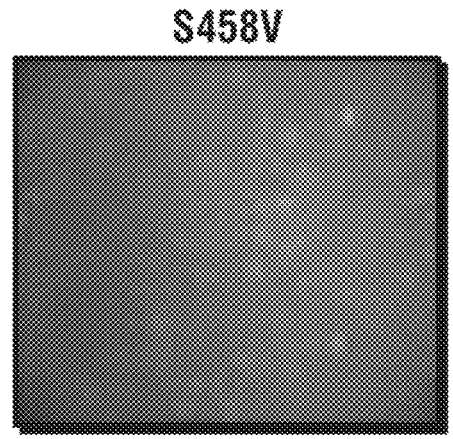
S578V 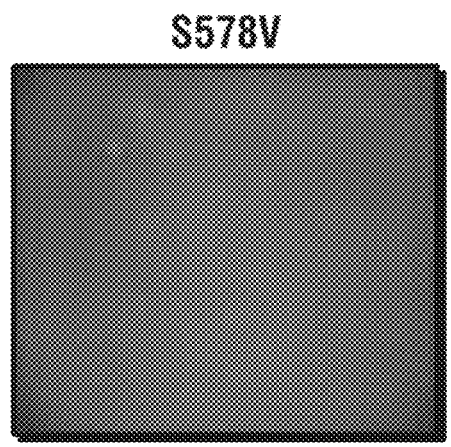
S662V 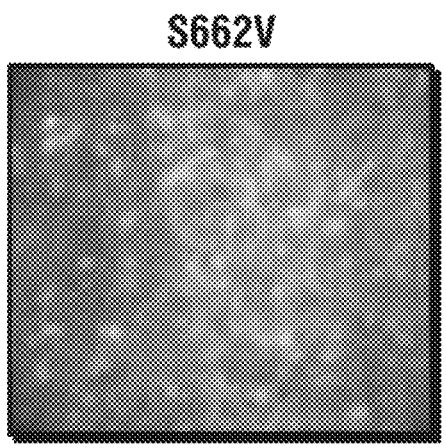 S658V 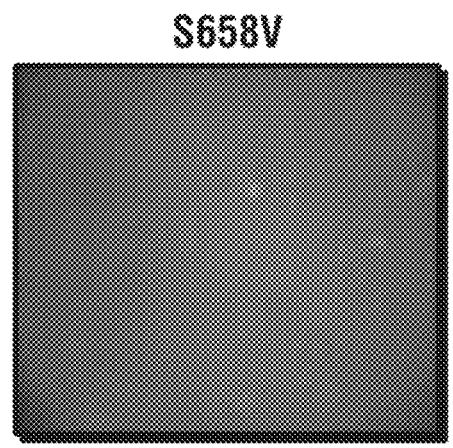
*FIG. 20A*

Color Key
- S458
- S492
- S662
- DE Loop(aa319-333) } PANEL B
- HI Loop(aa651-670) }

```
CAPSID            Serine and Threonine residue alignment in AAV serotype capsids                                100
AAV1    (1)   MAADGYLPDWLEDNLSEGIREWWDLKPGAPKPKANQQKQDDGRGLVLPGYKYLGPFNGLDKGEPVNAADAAALEHDKAYDQQLKAGDNPYLRYNHADAEF
AAV2    (1)   MAADGYLPDWLEDTLSEGIRQWWKLKPGPPPKPAERHKDDSRGLVLPGYKYLGPFNGLDKGEPVNEADAAALEHDKAYDRQLDSGDNPYLKYNHADAEF
AAV3    (1)   MAADGYLPDWLEDNLSEGIREWWALKPGVPQPKANQQHQDNRRGLVLPGYKYLGPGNGLDKGEPVNEADAAALEHDKAYDQQLKAGDNPYLKYNHADAEF
AAV4    (1)   -MTDGYLPDWLEDNLSEGIREWWALQPGAPKPKANQQHQDNARGLVLPGYKYLGPGNGLDRGEPVNRADEVAREHDISYNEQLEAGDNPYLKYNHADAEF
AAV5    (1)   MSFVDHPPDWLEEVG-EGLRRFLGLEAGPPKPKPNQQHQDQARGLVLPGYNYLGPGNGLDRGEPVNRADEVAREHDISYNEQLEAGDNPYLKYNHADAEF
AAV6    (1)   MAADGYLPDWLEDNLSEGIREWWDLKPGAPKPKANQQKQDDGRGLVLPGYKYLGPFNGLDKGEPVNAADAAALEHDKAYDQQLKAGDNPYLRYNHADAEF
AAV7    (1)   MAADGYLPDWLEDNLSEGIREWWALKPGAPKPKANQQKQDNGRGLVLPGYKYLGPFNGLDKGEPVNAADAAALEHDKAYDQQLQAGDNPYLRYNHADAEF
AAV8    (1)   MAADGYLPDWLEDNLSEGIREWWALKPGAPQPKANQQHQDNARGLVLPGYKYLGPGNGLDKGEPVNAADAAALEHDKAYDQQLKAGDNPYLKYNHADAEF
AAV9    (1)   MAADGYLPDWLEDNLSEGIREWWDLKPGAPKPKANQQHQDNGRGLVLPGYKYLGPFNGLDKGEPVNAADAAALEHDKAYDQQLKAGDNPYLKYNHADAEF
AAV10   (1)   MAADGYLPDWLEDNLSEGIREWWDLKPGAPKPKANQQKQDDGRGLVLPGYKYLGPFNGLDKGEPVNAADAAALEHDKAYDQQLKAGDNPYLRYNHADAEF 101                                                                                             200
AAV1    (101) QERLQEDTSFGGNLGRAVFQAKKRVLEPLGLVEEGAKTAPGKKRPVEQSPQE-PDSSSGIGKTGQQPAKKRLNFGQTGDSESVPDPQPLGEPPATPAAVG
AAV3    (101) QERLKEDTSFGGNLGRAVFQAKKRVLEPLGLVEEPVKTAPGKKRPVEHSPVE-PDSSSGTGKAGQQPARKRLNFGQTGDADSVPDPQPLGQPPAAPSGLG
AAV4    (100) QERLQEDTSFGGNLGRAVFQAKKRILEPLGLVEEAAKTAPGKKGAVDQSPQE-PDSSSGVGKSGKQPARKRLNFGQTGDSESVPDPQPLGEPPAAPTSLG
AAV5    (100) QQRLQGDTSFGGNLGRAVFQAKKRVLEPLGLVEQAGETAPGKKRPLIESPQQ-PDSSTGIGKKGKQPAKKKLVFEDETGAGDGP---PEGSTSGAMSDDS
AAV6    (101) QEKLADDTSFGGNLGKAVFQAKKRVLEPFGLVEEGAKTAPTGKRIDDHFPKR--------KKARTEEDSKPSTSSDAEAGPSGS-QQLQIPAQPASSLG
AAV7    (101) QERLQEDTSFGGNLGRAVFQAKKRVLEPFGLVEEGAKTAPGKKRPVEQSPQE-PDSSSGIGKTGQQPAKKRLNFGQTGDSESVPDPQPLGEPPATPAAVG
AAV8    (101) QERLQEDTSFGGNLGRAVFQAKKRVLEPLGLVEEGAKTAPAKKRPVEPSPQRSPDSSTGIGKKGQQPARKRLNFGQTGDSESVPDPQPLGEPPAAPSSVG
AAV9    (101) QERLKEDTSFGGNLGRAVFQAKKRVLEPLGLVEEGAKTAPGKKRPVEPSPQRSPDSSTGIGKKGQQPARKRLNFGQTGDSESVPDPQPLGEPPAAPSGVG
AAV10   (101) QERLQEDTSFGGNLGRAVFQAKKRLLEPLGLVEEAAKTAPGKKRPVEQSPQE-PDSSAGIGKSGAQPAKKRLNFGQTGDTESVPDPQPIGEPPAAPSGVG
              QERLQEDTSFGGNLGRAVFQAKKRVLEPLGLVEEAAKTAPGKKRPVEPSPQRSPDSSTGIGKKGQQPAKKRLNFGQTGDSESVPDPQPIGEPPAGPSGLG 201                                                                                             300
AAV1    (200) PTTMASGGGAPMADNNEGADGVGNASGNWHCDSTWLGDRVITTSTRTWALPTYNNHLYKQISSAST-GASNDNHYFGYSTPWGYFDFNRFHCHFSPRDWQ
AAV2    (200) TNTMATGSGAPMADNNEGADGVGNSSGNWHCDSTWMGDRVITTSTRTWALPTYNNHLYKQISSQS--GASNDNHYFGYSTPWGYFDFNRFHCHFSPRDWQ
AAV3    (200) SNTMASGGGAPMADNNEGADGVGNSSGNWHCDSQWLGDRVITTSTRTWALPTYNNHLYKQISSQS--GASNDNHYFGYSTPWGYFDFNRFHCHFSPRDWQ
AAV4    (196) EMRAAAGGAAVEGG--QGADGVGNASGDWHCDSTWSEGHVTTTSTRTWVLPTYNNHLYKRLGESLQ-----SNTYNGFSTPWGYFDFNRFHCHFSPRDWQ
AAV5    (190) ADTMASGGGGPLGDNNQGADGVGNASGDWHCDSTWMGDRVVTKSTRTWVLPSYNNHQYREIKSGS-VDGSNANAYFGYSTPWGYFDFNRFHSPRDWQ
AAV6    (200) PTTMASGGGAPMADNNEGADGVGNASGNWHCDSTWLGDRVITTSTRTWALPTYNNHLYKQISSAST-GASNDNHYFGYSTPWGYFDFNRFHCHFSPRDWQ
AAV7    (201) SGTVAAGGGAPMADNNEGADGVGSSSGNWHCDSTWLGDRVITTSTRTWALPTYNNHLYKQISSETAG-STNDNTYFGYSTPWGYFDFNRFHCHFSPRDWQ
AAV8    (201) PNTMAAGGGGAPMADNNEGADGVGSSSGNWHCDSTWLGDRVITTSTRTWALPTYNNHLYKQISNGTSGGATNDNTYFGYSTPWGYFDFNRFHCHFSPRDWQ
AAV9    (200) SLTMASGGGGAPVADNNEGADGVGSSSGNWHCDSQWLGDRVITTSTRTWALPTYNNHLYKQISNSTSGGSSNDNAYFGYSTPWGYFDFNRFHCHFSPRDWQ
AAV10   (201) SGTMAAGGGAPMADNNEGADGVGSSSGNWHCDSTWLGDRVITTSTRTWALPTYNNHLYKQISNGTSGGSTRDNTYFGYSTPWGYFDFNRFHCHFSPRDWQ
```

Tyrosine residue alignment in AAV serotype capsids

```
CAPSID      1                                                                                                   100
AAV1   (1)  MAADGYLPDWLEDNLSEGIREWWDLKPGAPKPKANQQKQDDGRGLVLPGYKYLGPFNGLDKGEPVNAADAAALEHDKAYDQQLKAGDNPYLRYNHADAEF
AAV2   (1)  MAADGYLPDWLEDTLSEGIREWWALKPGAPPPPKPAERHKDDSRGLVLPGYKYLGPFNGLDKGEPVNEADAAALEHDKAYDRQLDSGDNPYLKYNHADAEF
AAV3   (1)  MAADGYLPDWLEDNLSEGIRQWWKLKPGPPPPKPAERHKDDSRGLVLPGYKYLGPGLPGPGNLDKGEPVNEADAAALEHDKAYDQQLKAGDNPYLKYNHADAEF
AAV4   (1)  -MTDGYLPDWLEDNLSEGVREEWALQPGAPKPKPNQQHQDNARGLVLPGYKYLGPGNGLDKGEPVNRADEVAREHDISYNEQLEAGDNPYLKYNHADAEF
AAV5   (1)  MSFVDHPPDWLEEVG-EGLREFLGLEAGPPKPKPNQQHQDQARGLVLPGYNYLGPGNGLDRGEPVNRADEVAREHDISYNEQLEAGDNPYLRYNHADAEF
AAV6   (1)  MAADGYLPDWLEDNLSEGIREWWDLKPGAPKPKANQQKQDDGRGLVLPGYKYLGPFNGLDKGEPVNAADAAALEHDKAYDQQLKAGDNPYLRYNHADAEF
AAV7   (1)  MAADGYLPDWLEDNLSEGIREWWDLKPGAPKPKANQQKQDNGRGLVLPGYKYLGPFNGLDKGEPVNAADAAALRHDKAYDQQLQAGDNPYLRYNHADAEF
AAV8   (1)  MAADGYLPDWLEDNLSEGIREWWALKPGAPQPKANQQHQDNARGLVLPGYKYLGPGLPGNGLDKGEPVNAADAAALEHDKAYDQQLKAGDNPYLKYNHADAEF
AAV9   (1)  MAADGYLPDWLEDNLSEGIREWWDLKPGAPKPKANQQKQDDGRGLVLPGYKYLGPFNGLDKGEPVNAADAAALEHDKAYDQQLKAGDNPYLRYNHADAEF
AAV10  (1)  MAADGYLPDWLEDNLSEGIREWWDLKPGAPKPKANQQKQDDGRGLVLPGYKYLGPFNGLDKGEPVNAADAAALEHDKAYDQQLKAGDNPYLRYNHADAEF 101                                                                                                 200
AAV1   (101) QERLQEDTSFGGNLGRAVFQAKKRVLEPLGLVEEGAKTAPGKKRPVEQSPQE-PDSSSGIGKTGQQPAKKRLNFGQTGDSESVPDPQPLGEPPATPAAVG
AAV2   (101) QERLKEDTSFGGNLGRAVFQAKKRVLEPLGLVEEPVKTAPGKKRPVEHSPVE-PDSSSGTGKAGQQPARKRLNFGQTGDADSVPDPQPLGQPPAAPSGLG
AAV3   (100) QERLQEDTSFGGNLGRAVFQAKKRILEPLGLVEEAAKTAPGKKRPVEHSPVE-PDSSSGTGKAGQQPARKRLNFGQTGDSESVPDPQPLGEPPAAPTSLG
AAV4   (100) QQRLQEDTSFGGNLGRAVFQAKKRVLEPLGLVEQAGHETAPGKKRPLIESPQQ-PDSSTGIGKKGKQPAKKKLVFEDETGAGDGP---PEGSTSGAMSDDS
AAV5   (101) QEKLADDTSFGGNLGKAVFQAKKRVLEPFGLVEEGAKTAFTGKRTAPTGKRIDDHFPKR------KKARTEEDSKPSTSSDAEAGPSGS-QQLQIPAQPASSLG
AAV6   (101) QERLQEDTSFGGNLGRAVFQAKKRVLEPLGLVEEGAKTAPGKKRPVEQSPQE-PDSSSGIGKTGQQPAKKRLNFGQTGDSESVPDPQPLGEPPATPAAVG
AAV7   (101) QERLQEDTSFGGNLGRAVFQAKKRVLEEGAKTAPAKKRPVEPSPQRSPDSSTGIGKKGQPARKRLNFGQTGDSESVPDPQPLGEPPAAPSVG
AAV8   (101) QERLQEDTSFGGNLGRAVFQAKKRVLEEGAKTAPGKKRPVEPSPQRSPDSSTGIGKKGQQPARKRLNFGQTGDSESVPDPQPLGEPPAAPSGVG
AAV9   (101) QERLKEDTSFGGNLGRAVFQAKKRLLEPLGLVEEAAKTAPGKKRPVEQSPQE-PDSSAGIGKSGAQPAKKRLNFGQTGDTESVPDPQPIGEPPAAPSGVG
AAV10  (101) QERLQEDTSFGGNLGRAVFQAKKRVLEPLGLVEEGAKTAPGKKRPVEPSPQRSPDSSTGIGKKGQQPAKKRLNFGQTGDSESVPDPQPIGEPPAGPSGLG 201                                                                                                 300
AAV1   (200) PTTMASGGGAPMADNNEGADGVGNASGNWHCDSTWLGDRVITTSTRTWALPTYNNHLYKQISSAST-GASNDNHYFGYSTPWGYFDFNRFHCHFSPRDWQ
AAV2   (200) TNTMATGSGAPMADNNEGADGVGNSSGNWHCDSTWMGDRVITTSTRTWALPTYNNHLYKQISSQS--GASNDNHYFGYSTPWGYFDFNRFHCHFSPRDWQ
AAV3   (200) SNTMASGGGAPMADNNEGADGVGNSSGNWHCDSQWLGDRVITTSTRTWALPTYNNHLYKQISSQS--GASNDNHYFGYSTPWGYFDFNRFHCHFSPRDWQ
AAV4   (196) EMRAAAGGAAVEGG--QGADGVGNASGDWHCDSTWSEGHVTTSTRTWVLPSYNNHLYKRLGESLQ------SNTYNGFSTPWGYFDFNRFHCHFSPRDWQ
AAV5   (190) ADTMSAGGGGPLGDNNQGADGVGNASGDWHCDSTWMGDRVTKSTRTWVLPSYNNHQYREIKSGS-VDGSNANAYFGYSTPWGYFDFNRFHSHWSPRDWQ
AAV6   (200) PTTMASGGGAPMADNNEGADGVGNASGNWHCDSTWLGDRVITTSTRTWALPTYNNHLYKQISSAST-GASNDNHYFGYSTPWGYFDFNRFHCHFSPRDWQ
AAV7   (201) SGTVAAGGGGAPMADNNEGADGVGSSSGNWHCDSTWLGDRVITTSTRTWALPTYNNHLYKQISSETAG-STNDNTYFGYSTPWGYFDFNRFHCHFSPRDWQ
AAV8   (201) PNTMAAGGGAPMADNNEGADGVGSSSGNWHCDSQWLGDRVITTSTRTWALPTYNNHLYKQISNGTSGGATNDNTYFGYSTPWGYFDFNRFHCHFSPRDWQ
AAV9   (200) SLITMASGGGAPVADNNEGADGVGSSSGNWHCDSQWLGDRVITTSTRTWALPTYNNHLYKQISNDAYFGYSTPWGYFDFNRFHCHFSPRDWQ
AAV10  (201) SGTMAAGGGAPMADNNEGADGVGSSSGNWHCDSTWLGDRVITTSTRTWALPTYNNHLYKQISNGTSGGSTNDNTYFGYSTPWGYFDFNRFHCHFSPRDWQ
```

```
                601
AAV1  (587) SSTDPATGDVHAMGALPGMVWQDRDVYLQGPIWAKIPHTDGHFHPSPLMGGFGLKNPPPQILIKNTPVPANPPAEFSATKFASFITQYSTGQVSVEIEWE
AAV2  (586) GNRQAATADVNTQGVLPGMVWQDRDVYLQGPIWAKIPHTDGHFHPSPLMGGFGLKHPPPQILIKNTPVPANPSTTFSAAKFASFITQYSTGQVSVEIEWE
AAV3  (587) SNTAPTTGTVNHQGALPGMVWQDRDVYLQGPIWAKIPHTDGHFHPSPLMGGFGLKHPPPQIMIKNTPVPANPPTTFSPAKFASFITQYSTGQVSVEIEWE
AAV4  (585) NSNLPTGTVDRLTALGAVPGMVWQNRDIYYQGPIWAKIPHTDGHFHPSPLIGGFGLKHPPPQIFIKNTPVPANPATTFSSTPVNSFITQYSTGQVSVQIDWE
AAV5  (576) STTAPATGTYNLQEIVPGSVWMERDVYLQGPIWAKIPETGAHFHPSPAMGGFGLKHPPPMLIKNTPVPGN--ITSFSDVPVSSFITQYSTGQVTVEMEWE
AAV6  (587) SSTDPATGDVHVMGALPGMVWQDRDVYLQGPIWAKIPHTDGHFHPSPLMGGFGLKHPPPQILIKNTPVPANPPAEFSATKFASFITQYSTGQVSVEIEWE
AAV7  (588) ANTAAQTQVVNNQGALPGMVWQNRDVYLQGPIWAKIPHTDGNFHPSPLMGGFGLKHPPPQILIKNTPVPANPPEVFTPAKFASFITQYSTGQVSVEIEWE
AAV8  (589) QNTAPQIGTVNSQGALPGMVWQNRDVYLQGPIWAKIPHTDGNFHPSPLMGGFGLKHPPPQILIKNTPVPADPPTTFNQSKLNSFITQYSTGQVSVEIEWE
AAV9  (587) AQAQAQTGWVQNQGILPGMVWQNRDVYLQGPIWAKIPHTDGNFHPSPLMGGFGMKHPPPQILIKNTPVPADPPTAFNKDKLNSFITQYSTGQVSVEIEWE
AAV10 (589) QNAAPIVGAVNSQGALPGMVWQNRDVYLQGPIWAKIPHTDGNFHPSPLMGGFGLKHPPPQILIKNTPVPADPPTTFSQAKLASFITQYSTGQVSVEIEWE 701                                             751
AAV1  (687) LQKENSKRWNPEIQYTSNYAKSANVDFTVDNNGLYTEPRPIGTRYLTRPL-   SEQ ID NO:1
AAV2  (686) LQKENSKRWNPEIQYTSNYNKSVNVDFTVDTNGVYSEPRPIGTRYLTRNL-   SEQ ID NO:2
AAV3  (687) IQKERSKRWNPEIQYTSNYYKSVNVDFTVDTNGVYSEPRPIGTRYLTRNL-   SEQ ID NO:3
AAV4  (685) IQKENSKRWNPEVQYTSNYGQQNSLLWAPDAAAGKYTEPRAIGTRYLTHHL-  SEQ ID NO:4
AAV5  (675) LKKENSKRWNPEIQYTNNYNDPQFVDFAPDSTGEYRTTRPIGTRYLTRPL-   SEQ ID NO:5
AAV6  (687) LQKENSKRWNPEVQYTSNYAKSANVDFTVDNNGLYTEPRPIGTRYLTRPL-   SEQ ID NO:6
AAV7  (688) LQKENSKRWNPEIQYTSNFEKQTGVDFAVDSQGVYSEPRPIGTRYLTRNL-   SEQ ID NO:7
AAV8  (689) LQKENSKRWNPEIQYTSNYYKSTSVDFAVNTEGVYSEPRPIGTRYLTRNL-   SEQ ID NO:8
AAV9  (687) LQKENSKRWNPEIQYTSNYYKSNNVEFAVNTEGVYSEPRPIGTRYLTRNL-   SEQ ID NO:9
AAV10 (689) LQKENSKRWNPEIQYTSNYYKSTNVDFAVNTDGTYSEPRPIGTRYLTRNL-   SEQ ID NO:10
```

| MUTANT | PACKAGING EFFICIENCY | TRANSDUCTION EFFICIENCY |
|---|---|---|
| AAV2-S261V | ~10-FOLD LOWER | -* |
| AAV2-S264V | NO CHANGE | -* |
| AAV2-S267V | NO DNAse I- RESISTANT PARTICLES | -* |
| AAV2-S276V | ~10-FOLD LOWER | -* |
| AAV2-S384V | ~3-FOLD HIGHER | ~10-FOLD LOWER |
| AAV2-S458V | NO CHANGE | ~4-FOLD HIGHER |
| AAV2-S468V | ~5-FOLD HIGHER | NO CHANGE |
| AAV2-S492V | NO CHANGE | ~2-FOLD HIGHER |
| AAV2-S498V | NO CHANGE | ~10-FOLD LOWER |
| AAV2-S578V | NO CHANGE | ~10-FOLD LOWER |
| AAV2-S658V | ~10-FOLD LOWER | -* |
| AAV2-S662V | NO CHANGE | ~20-FOLD HIGHER |
| AAV2-S668V | NO DNAse I- RESISTANT PARTICLES | -* |
| AAV2-S707V | NO CHANGE | ~10-FOLD LOWER |
| AAV2-S721V | NO CHANGE | NO CHANGE |

*FIG. 34*

| MUTANT | PACKAGING EFFICIENCY | TRANSDUCTION EFFICIENCY |
|---|---|---|
| AAV2-S662V | NO CHANGE | ~20-FOLD HIGHER |
| AAV2-S662A | ~5-FOLD HIGHER | ~3-FOLD HIGHER |
| AAV2-S662D | NO CHANGE | ~8-FOLD HIGHER |
| AAV2-S662F | ~10-FOLD LOWER | NO CHANGE |
| AAV2-S662H | NO CHANGE | ~4-FOLD HIGHER |
| AAV2-S662N | ~10-FOLD LOWER | NO CHANGE |
| AAV2-S662L | ~10-FOLD LOWER | NO CHANGE |
| AAV2-S662I | ~10-FOLD LOWER | NO CHANGE |

*FIG. 35*

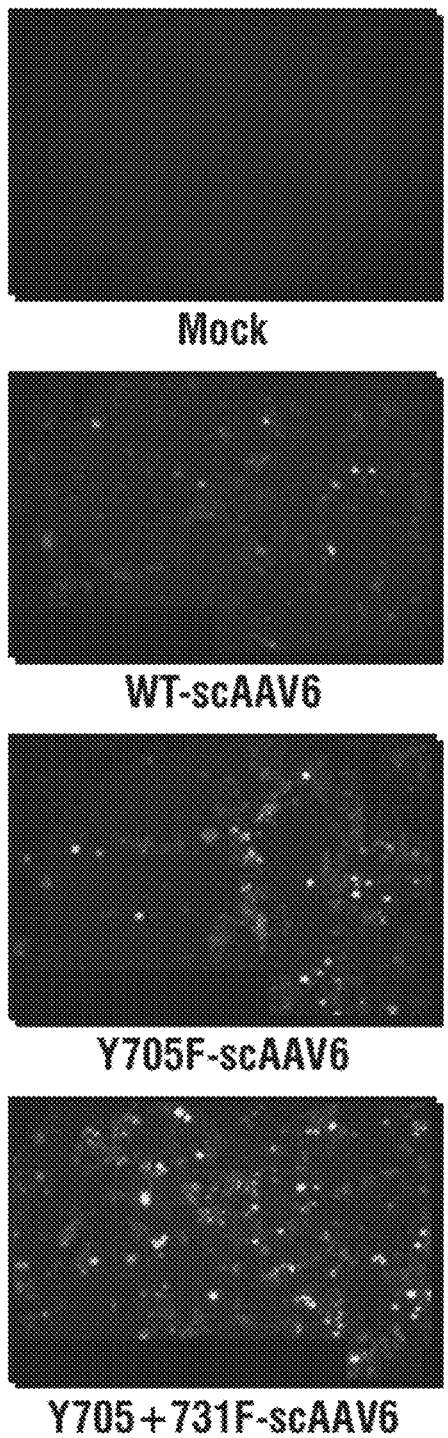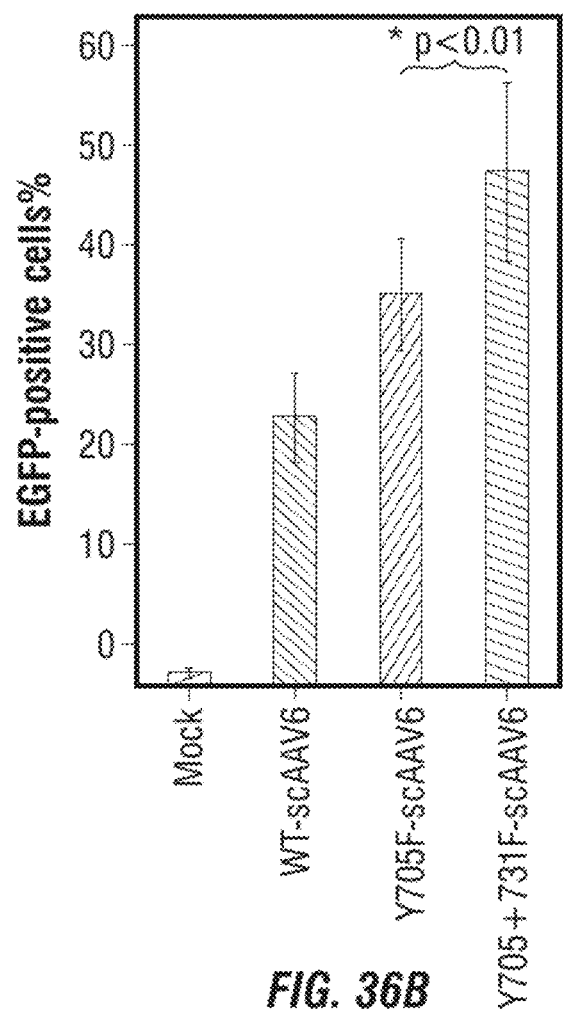
FIG. 36A
FIG. 36B

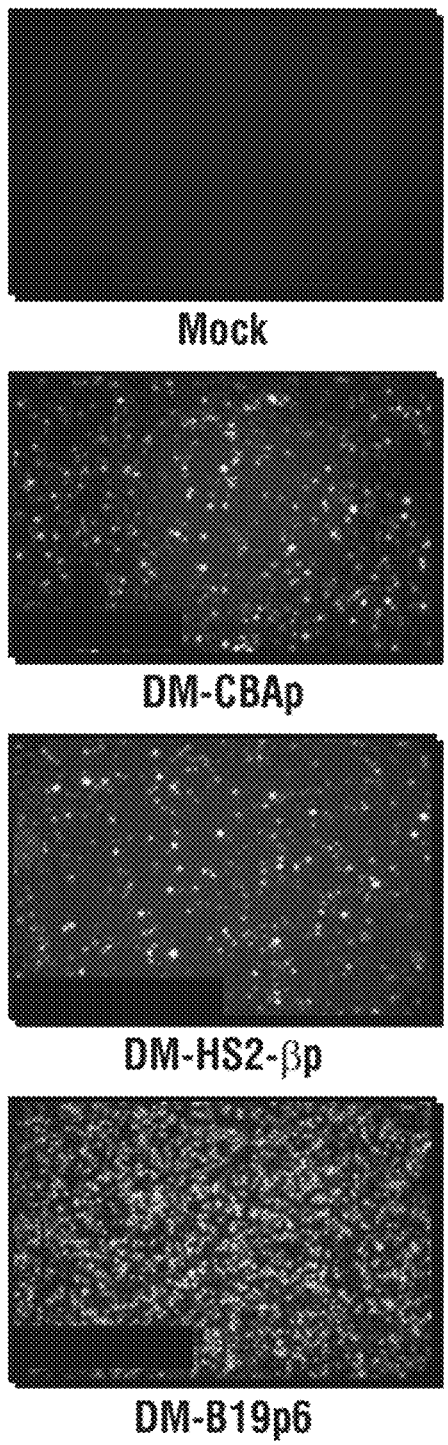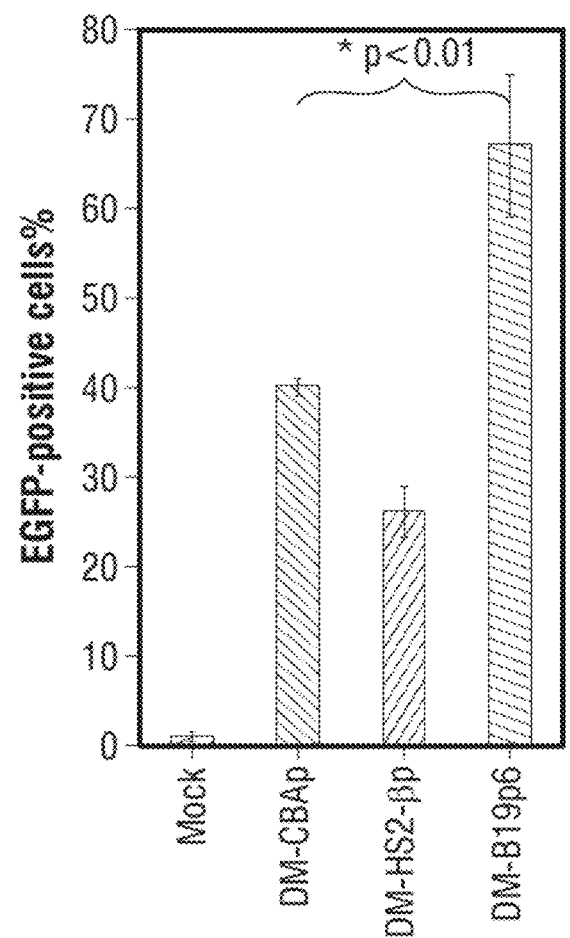
FIG. 37A
FIG. 37B

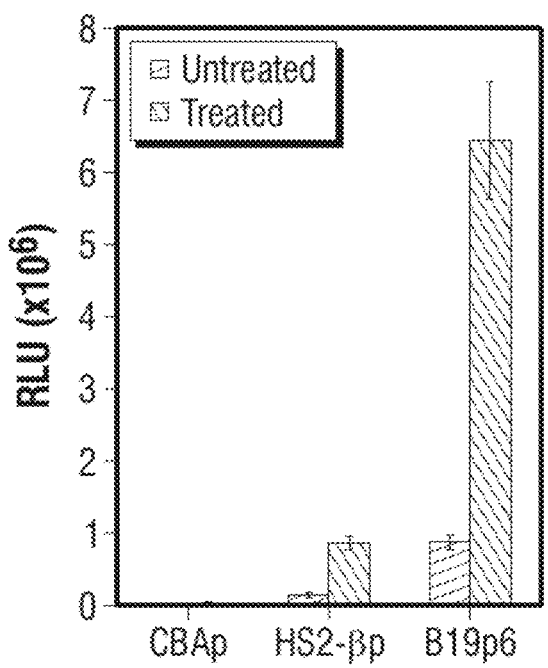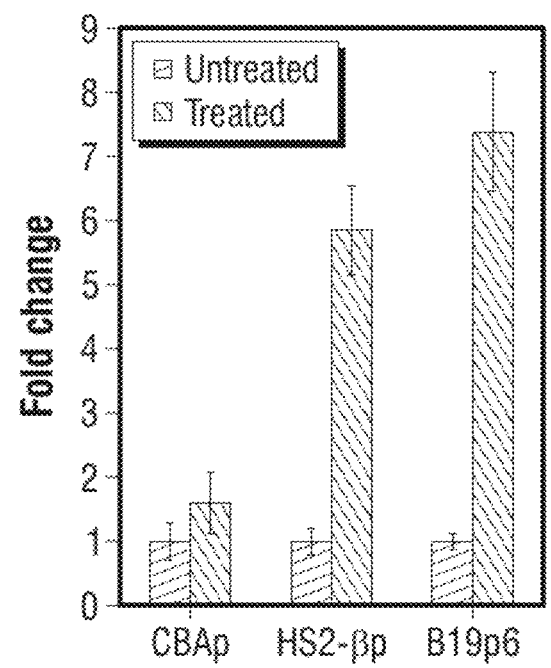
*FIG. 38A*  *FIG. 38B*

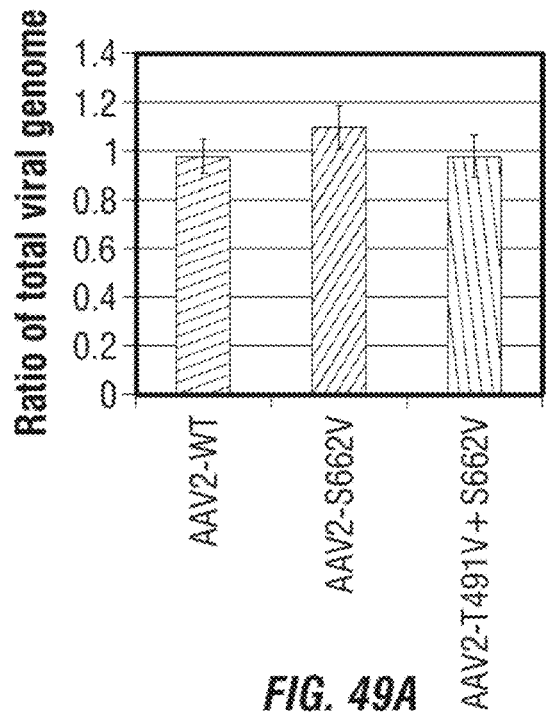
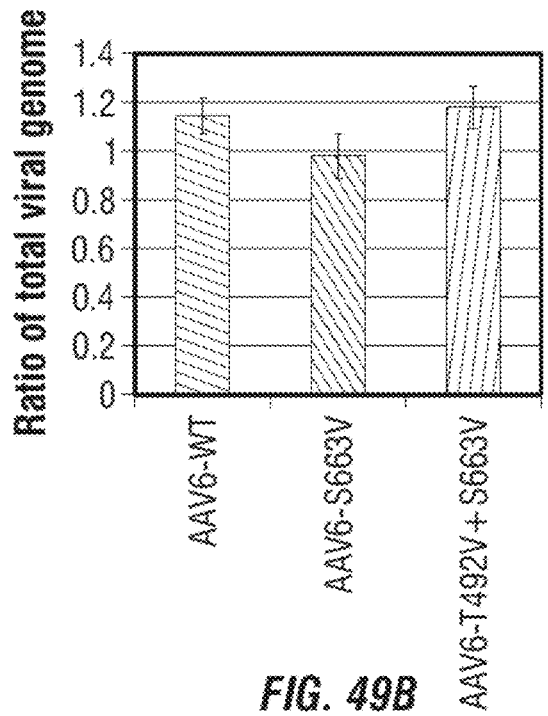
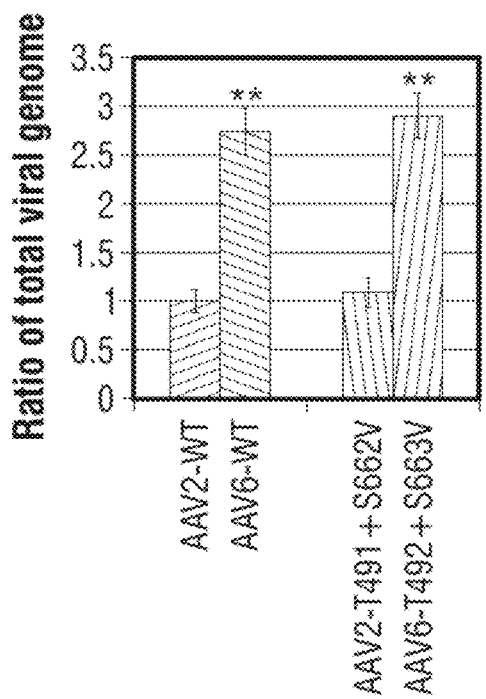
FIG. 49A
FIG. 49B
FIG. 49C

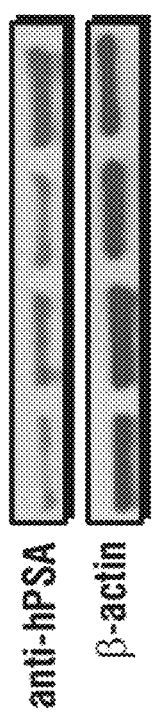
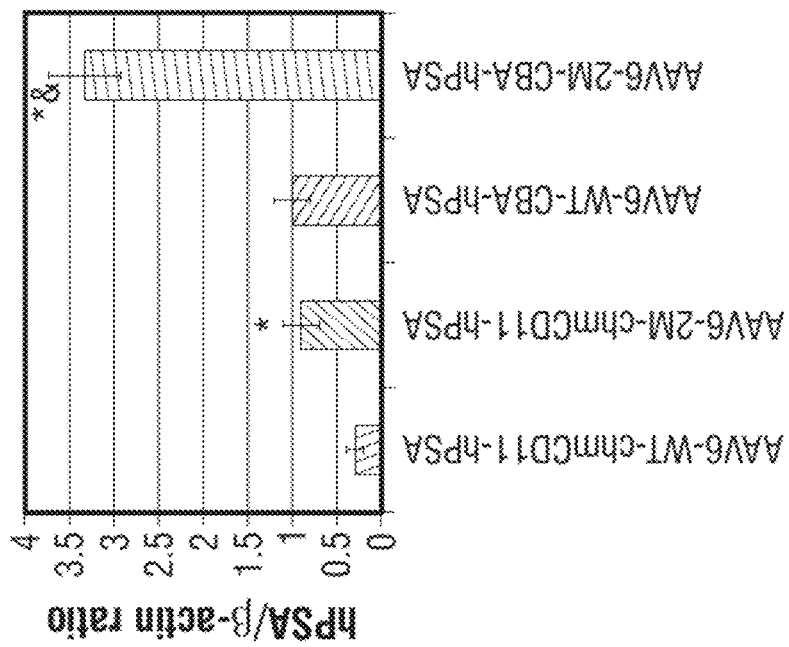
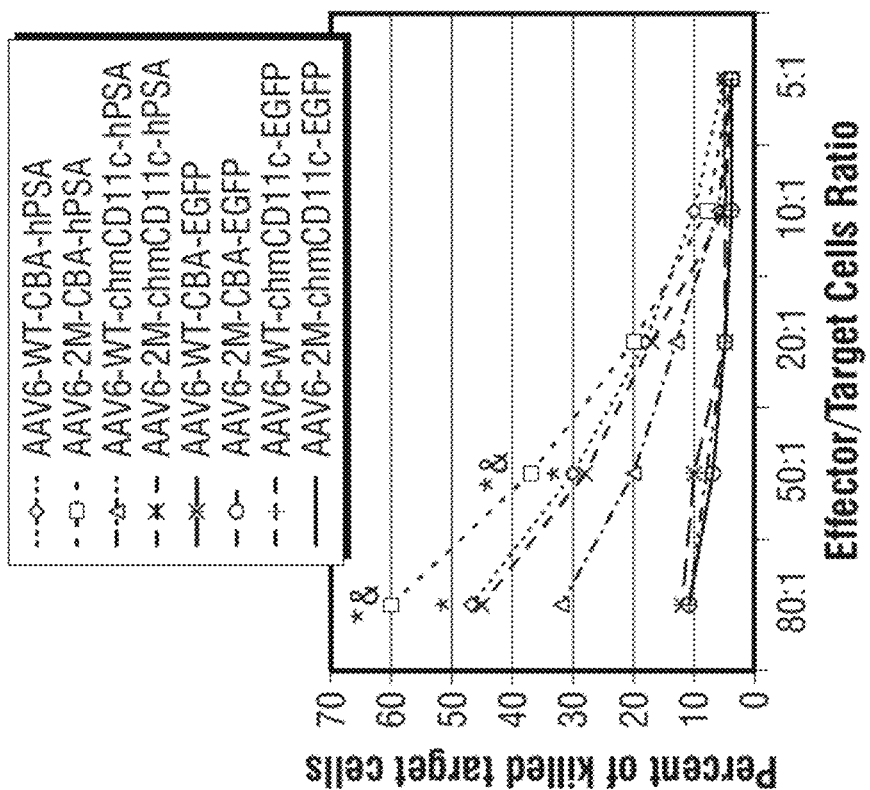

CAPSID-MODIFIED rAAV VECTOR COMPOSITIONS AND METHODS THEREFOR

CROSS-REFERENCE TO RELATED APPLICATIONS

The present application is a continuation of U.S. patent application Ser. No. 16/179,818, filed Nov. 2, 2018, which is a continuation of U.S. patent application Ser. No. 15/987,993, filed May 24, 2018, which is a continuation of U.S. patent application Ser. No. 14/214,011, filed Mar. 14, 2014, which is a continuation-in-part of U.S. patent application Ser. No. 13/899,481, filed May 21, 2013 (now U.S. Pat. No. 9,920,097). U.S. patent application Ser. No. 14/214,011 is also a continuation-in-part of PCT Intl. Patent Appl. No. PCT/US2013/041234 filed May 15, 2013, which is a continuation-in-part of U.S. patent application Ser. No. 13/840,224, filed Mar. 15, 2013 (now U.S. Pat. No. 9,725,485), which claims the benefit of U.S. Provisional Patent Appl. No. 61/647,318, filed May 15, 2012. The content of each of the aforementioned applications is specifically incorporated herein in its entirety by express reference thereto.

STATEMENT REGARDING FEDERALLY SPONSORED RESEARCH OR DEVELOPMENT

This invention was made with government support under Grant Nos. DK058327, HL051811, HL059412, HL078810, DK062302, EB002073, GM082946, HL065570, HL076901, HL097088 awarded by the National Institutes of Health. The government has certain rights in the invention.

REFERENCE TO AN ELECTRONIC SEQUENCE LISTING

The contents of the electronic sequence listing (U120270048US03-SEQ-COB.xml; Size: 62,092 bytes; and Date of Creation: Sep. 1, 2022) are herein incorporated by reference in their entirety.

NAMES OF THE PARTIES TO A JOINT RESEARCH AGREEMENT

Not Applicable.

FIELD OF THE INVENTION

The present invention relates generally to the fields of molecular biology and virology, and in particular, to the development of gene delivery vehicles. Also disclosed are improved rAAV vector compositions useful in delivering a variety of nucleic acid segments, including those encoding therapeutic proteins polypeptides, peptides, antisense oligonucleotides, and ribozyme constructs to selected host cells for use in various diagnostic and/or therapeutic regimens. Methods are also provided for preparing and using these modified rAAV-based vector constructs in a variety of viral-based gene therapies, and in particular, for the diagnosis, prevention, treatment and/or amelioration of symptoms of human diseases, disorders, dysfunctions, trauma, or injury. The invention also provides mutated rAAV-based viral vector delivery systems with increased transduction efficiency and/or improved viral infectivity of selected mammalian host cells. In particular, the invention provides improved rAAV vectors and virions having particles having amino acid substitutions in one or more surface-exposed residues of a viral capsid protein.

DESCRIPTION OF RELATED ART

Major advances in the field of gene therapy have been achieved by using viruses to deliver therapeutic genetic material. The adeno-associated virus (AAV) has attracted considerable attention as a highly effective viral vector for gene therapy due to its low immunogenicity and ability to effectively transduce non-dividing cells. AAV has been shown to infect a variety of cell and tissue types, and significant progress has been made over the last decade to adapt this viral system for use in human gene therapy.

In its normal "wild type" form, recombinant AAV (rAAV) DNA is packaged into the viral capsid as a single stranded molecule about 4600 nucleotides (nt) in length. Following infection of the cell by the virus, the molecular machinery of the cell converts the single DNA strand into a double-stranded form. Only the double-stranded DNA form is useful to the polypeptides of the cell that transcribe the contained gene or genes into RNA.

AAV has many properties that favor its use as a gene delivery vehicle: 1) the wild type virus is not associated with any pathologic human condition; 2) the recombinant form does not contain native viral coding sequences; and 3) persistent transgenic expression has been observed in many applications.

The transduction efficiency of recombinant adeno-associated virus 2 (AAV) vectors varies greatly in different cells and tissues in vitro and in vivo, which has limited the usefulness of many of them in potential gene therapy regimens. Systematic studies have been performed to elucidate the fundamental steps in the life cycle of AAV. For example, it has been documented that a cellular protein, FKBP52, phosphorylated at tyrosine residues by epidermal growth factor receptor protein tyrosine kinase (EGFR-PTK), inhibits AAV second-strand DNA synthesis and consequently, transgene expression in vitro as well as in vivo. It has also been demonstrated that EGFR-PTK signaling modulates the ubiquitin/proteasome pathway-mediated intracellular trafficking as well as FKBP52-mediated second-strand DNA synthesis of AAV vectors. In those studies, inhibition of EGFR-PTK signaling led to decreased ubiquitination of AAV capsid proteins, which in turn, facilitated nuclear transport by limiting proteasome-mediated degradation of AAV vectors, implicating EGFR-PTK-mediated phosphorylation of tyrosine residues on AAV capsids. What is lacking in the prior art are improved rAAV viral vectors that have enhanced transduction efficiency for infecting selected mammalian cells, and for targeted gene delivery to human cells in particular.

BRIEF SUMMARY OF THE INVENTION

The present invention overcomes limitations and deficiencies inherent in the prior art by providing novel improved rAAV-based genetic constructs that encode one or more therapeutic agents useful in the preparation of medicaments for the prevention, treatment, and/or amelioration of one or more diseases, disorders or dysfunctions resulting from a deficiency in one or more of such polypeptides. In particular, the invention provides VP3 capsid-protein-modified rAAV-based genetic constructs encoding one or more selected molecules, such as, for example, one or more diagnostic or therapeutic agents (including, e.g., proteins, polypeptides, peptides, antibodies, antigen binding fragments, siRNAs, RNAis, antisense oligo- and poly-nucleotides, ribozymes, and variants and/or active fragments thereof), for use in the diagnosis, prevention, treatment, and/or amelioration of symptoms of a variety of mammalian diseases, disorders, dysfunctions, trauma, injury, and such like.

The present invention provides mutated AAV VP3 capsid proteins that include modification of one or more surface-exposed amino acid resides (including, e.g., without limitation, lysine, serine, threonine, and/or tyrosine residues) as compared to wildtype. Also provided are infectious rAAV virions that comprise the mutated AAV capsid proteins of the present invention, as well as nucleic acid molecules and rAAV vectors encoding the mutant AAV capsid proteins of the present invention, and nucleic acids encoding one or more selected diagnostic and/or therapeutic agents for delivery to a selected population of mammalian cells.

Advantageously, the novel rAAV vectors, express constructs, and infectious virions and viral particles comprising them as disclosed herein preferably have an improved efficiency in transducing one or more of a variety of cells, tissues and organs of interest, when compared to wild-type, unmodified, expression constructs, and to the corresponding rAAV vectors and virions comprising them.

The improved rAAV vectors provided herein transduce one or more selected host cells at higher-efficiencies (and often much higher efficiencies) than conventional, wild-type, unmodified rAAV vector constructs. By performing extensive analysis and detailed experiments involved the site-directed mutagenesis of various individual and/or combinations of two, three, four, five, or even more surface-exposed amino acid residues on various AAV capsid proteins from a variety of AAV serotypes (including AAV1-AAV12), the inventors have developed a collection of single- and multi-mutated rAAV vectors having improved properties. The inventors have repeatedly demonstrated that substitution of one or more virion surface-presenting amino acid residues yields improved viral vectors that are capable of higher-efficiency transduction than the corresponding, non-substituted (i.e., unmodified) parent vectors from which the mutants were prepared.

The development of these new capsid-mutant rAAV viral vectors dramatically reduces the number of viral particles needed for conventional gene therapy regimens. In addition to having improved transduction efficiencies for various mammalian cells, the surface-exposed amino acid-modified rAAV vectors described herein are more stable, less immunogenic, and can be produced at much lower cost than the traditional viral vectors currently employed in mammalian gene therapy regimens.

In a particular embodiment the invention provides a modified AAV VP3 capsid protein, that includes: (a) a non-tyrosine amino acid residue at (i) one or more positions corresponding to Y445, Y705 and Y731 of the wild-type AAV6 capsid protein as set forth in SEQ ID NO:6; or (ii) one or more positions corresponding to Y444, Y500 and Y730 of the wild-type AAV2 capsid protein as set forth in SEQ ID NO:2; (b) a non-serine amino acid residue at a position corresponding to S663 of the wild-type AAV6 capsid protein as set forth in SEQ ID NO:6; (c) a non-threonine amino acid residue at a position corresponding to T492 of the wild-type AAV6 capsid protein as set forth in SEQ ID NO:6; (d) a combination of two or more amino acid substitutions listed in (a), (b), and (c); each with a non-native amino acid; or (e) a combination of tree or more amino acid substitutions listed in (a), (b), and (c); each with a non-native amino acid; or alternatively, wherein each of the amino acid substitutions is at an equivalent amino acid position corresponding thereto in any one of the other wild-type vector serotypes selected from the group consisting of AAV1, AAV3, AAV4, AAV5, AAV7, AAV9, and AAV10, as set forth in SEQ ID NO:1, SEQ ID NO:3, SEQ ID NO:4, SEQ ID NO:5, SEQ ID NO:7, SEQ ID NO:9, and SEQ ID NO:10, respectively.

In certain embodiments, the modified AAV VP3 capsid protein includes: (i) a non-tyrosine amino acid residue at one or more positions corresponding to Y445, Y705 and Y731 of the wild-type AAV6 capsid protein as set forth in SEQ ID NO:6; or (ii) one or more positions corresponding to Y444, Y500 and Y730 of the wild-type AAV2 capsid protein as set forth in SEQ ID NO:2; or at an equivalent amino acid position corresponding thereto in any one of the other wild-type vector serotypes selected from the group consisting of AAV1, AAV3, AAV4, AAV5, AAV7, AAV9, and AAV10, as set forth in SEQ ID NO:1, SEQ ID NO:3, SEQ ID NO:4, SEQ ID NO:5, SEQ ID NO:7, SEQ ID NO:9, and SEQ ID NO:10.

Similarly, in other embodiments, the modified AAV VP3 capsid protein includes a non-serine amino acid residue at a position corresponding to S663 of the wild-type AAV6 capsid protein as set forth in SEQ ID NO:6; or at an equivalent amino acid position corresponding thereto in any one of the other wild-type vector serotypes selected from the group consisting of AAV1, AAV3, AAV4, AAV5, AAV7, AAV9, and AAV10, as set forth in SEQ ID NO:1, SEQ ID NO:2, SEQ ID NO:3, SEQ ID NO:4, SEQ ID NO:5, SEQ ID NO:7, SEQ ID NO:9, and SEQ ID NO:10.

In further embodiments, the modified AAV VP3 capsid protein includes a non-threonine amino acid residue at a position corresponding to T492 of the wild-type AAV6 capsid protein as set forth in SEQ ID NO:6; or at an equivalent amino acid position corresponding thereto in any one of the other wild-type vector serotypes selected from the group consisting of AAV1, AAV3, AAV4, AAV5, AAV7, AAV9, and AAV10, as set forth in SEQ ID NO:1, SEQ ID NO:2, SEQ ID NO:3, SEQ ID NO:4, SEQ ID NO:5, SEQ ID NO:7, SEQ ID NO:9, and SEQ ID NO:10.

In the practice of the invention, (a) the non-tyrosine or non-threonine amino acid residue is preferably selected from one or more of serine (S), phenylalanine (F), valine (V), histidine (H), isoleucine (I), alanine (A), leucine (L) aspartic acid (D), asparagine (N), glutamic acid (E), arginine (R), and isoleucine (I); and (b) the non-serine amino acid residue is preferably selected from one or more of phenylalanine (F), valine (V), histidine (H), isoleucine (I), alanine (A), leucine (L) aspartic acid (D), asparagine (N), glutamic acid (E), arginine (R), and isoleucine (I).

In particular embodiments, the modified AAV VP3 capsid protein preferably includes (a) a phenylalanine residue at one or more positions corresponding to Y445, Y705 and Y731 of the wild-type AAV6 capsid protein as set forth in SEQ ID NO:6 or (b) a phenylalanine residue at one or more positions corresponding to Y444, Y500 and Y730 of the wild-type AAV2 capsid protein as set forth in SEQ ID NO:2.

In other embodiments, the modified AAV VP3 capsid protein preferably includes a valine residue at a position corresponding to S663 or to T492 of the wild-type AAV6 capsid protein as set forth in SEQ ID NO:6.

The invention also provides an isolated and purified polynucleotide that encodes one or more of the disclosed VP3 mutant proteins described herein, as well as recombinant adeno-associated viral (rAAV) vectors that include such a polynucleotide. Preferably, the vector constructs of the present invention further include at least one nucleic acid segment that encodes a diagnostic or therapeutic molecule operably linked to a promoter capable of expressing the nucleic acid segment in a suitable host cell comprising the vector. In the practice of the invention, the transduction efficiency of a virion comprising the modified AAV VP3 capsid protein will be higher than that of the corresponding, unmodified, wild-type protein, and as such, will preferably possess a transduction efficiency in a mammalian cell that is at least 2-fold, at least about 4-fold, at least about 6-fold, at least about 8-fold, at least about 10-fold, or at least about 12-fold or higher in a selected mammalian host cell than that of a virion that comprises a corresponding, unmodified, capsid protein. In certain embodiments, the transduction efficiency of the rAAV vectors provided herein will be at least about 15-fold higher, at least about 20-fold higher, at least about 25-fold higher, at least about 30-fold higher, or at least about 40, 45, or 50-fold or more greater than that of a virion that comprises a corresponding, unmodified, capsid protein. Moreover, the infectious virions of the present invention that include one or more modified AAV VP3 capsid proteins are preferably less susceptible to ubiquitination when introduced into a mammalian cell than that of a virion that comprises a corresponding, unmodified, capsid protein.

The present invention also concerns rAAV vectors, wherein the nucleic acid segment further includes one or more promoters, one or more enhancers, one or more post-transcriptional regulatory sequences, one or more polyadenylation signals, or any combination thereof, operably linked to the nucleic acid segment that encodes the selected diagnostic and/or therapeutic polynucleotide of interest.

Preferably, the promoter is a homologous promoter, a heterologous promoter, an exogenous promoter, an endogenous promoter, a tissue-specific promoter, a cell-specific promoter, a constitutive promoter, an inducible promoter, or any combination thereof.

In certain embodiments, the nucleic acid segments cloned into the rAAV expression vectors described herein will express or encode one or more polypeptides, peptides, ribozymes, peptide nucleic acids, siRNAs, RNAis, antisense oligonucleotides, antisense polynucleotides, antibodies, antigen binding fragments, or any combination thereof when the vector is introduced into one or more suitable mammalian cells.

As noted herein, the therapeutic agents useful in the invention may include one or more agonists, antagonists, anti-apoptosis factors, inhibitors, receptors, cytokines, cytotoxins, erythropoietic agents, glycoproteins, growth factors, growth factor receptors, hormones, hormone receptors, interferons, interleukins, interleukin receptors, nerve growth factors, neuroactive peptides, neuroactive peptide receptors, proteases, protease inhibitors, protein decarboxylases, protein kinases, protein kinase inhibitors, enzymes, receptor binding proteins, transport proteins or one or more inhibitors thereof, serotonin receptors, or one or more uptake inhibitors thereof, serpins, serpin receptors, tumor suppressors, diagnostic molecules, chemotherapeutic agents, cytotoxins, or any combination thereof.

The rAAV vectors of the present invention may be comprised within a virion having a serotype that is selected from the group consisting of AAV serotype 1 (AAV1), AAV serotype 2 (AAV2), AAV serotype 3 (AAV3), AAV serotype 4 (AAV4), AAV serotype 5 (AAV5), AAV serotype 6 (AAV6), AAV serotype 7 (AAV7), AAV serotype 8 (AAV8), AAV serotype 9 (AAV9), AAV serotype 10 (AAV10), AAV serotype 11 (AAV11), or AAV serotype 12 (AAV12), or any other serotype as known to one of ordinary skill in the viral arts.

In related embodiments, the invention further provides populations and pluralities of rAAV vectors, virions, infectious viral particles, or host cells that include one or more nucleic acid segments that encode a modified VP3 protein that comprises one or more amino acid deletions, insertions, or substitutions, or any combination thereof.

Preferably, the promoter host cells will be human host cells, including, for example blood cells, stem cells, hematopoietic cells, CD34$^+$ cells, liver cells, cancer cells, vascular cells, pancreatic cells, neural cells, ocular or retinal cells, epithelial or endothelial cells, dendritic cells, fibroblasts, or any other cell of mammalian origin, including, for example a cell from the liver, the lung, the heart, the pancreas, the intestines, the kidney, or the brain of a mammal.

The invention further provides composition and formulations that include one or more of the proteins nucleic acid segments viral vectors, host cells, or viral particles of the present invention together with one or more pharmaceutically-acceptable buffers, diluents, or excipients. Such compositions may be included in one or more diagnostic or therapeutic kits, for diagnosing, preventing, treating or ameliorating one or more symptoms of a mammalian disease, injury, disorder, trauma or dysfunction.

The invention further includes a method for providing a mammal in need thereof with a diagnostically- or therapeutically-effective amount of a selected biological molecule, the method comprising providing to a cell, tissue or organ of a mammal in need thereof, an amount of an rAAV vector; and for a time effective to provide the mammal with a diagnostically- or a therapeutically-effective amount of the selected biological molecule.

The invention further provides a method for diagnosing, preventing, treating, or ameliorating at least one or more symptoms of a disease, a disorder, a dysfunction, an injury, an abnormal condition, or trauma in a mammal. In an overall and general sense, the method includes at least the step of administering to a mammal in need thereof one or more of the disclosed rAAV vectors, in an amount and for a time sufficient to diagnose, prevent, treat or ameliorate the one or more symptoms of the disease, disorder, dysfunction, injury, abnormal condition, or trauma in the mammal. In the case of rAAV8 vectors, such disease may preferably include one or more diseases or dysfunctions of the mammalian eye, and in the case of rAAV6 vectors, one or more diseases of stem cells, blood cells, hematopoietic cells, or CD35+ cells, including for example, sickle cell disease, β-thalassemia, and such like.

In particular embodiments, the invention provides a method for providing a mammal in need thereof with a therapeutically-effective amount of a mammalian protein or peptide such as an $\alpha_1$-antitrypsin or a β-globin protein or peptide. This method generally involves providing to a cell, tissue or organ of a mammal in need thereof, an amount of one of the disclosed capsid-modified rAAV vectors and for a time effective to provide the mammal with a therapeutically-beneficial amount of the protein or peptide.

The invention also provides a method for preventing, treating, or ameliorating one or more symptoms of a hemoglobinopathy, such as β-thalassemia or sickle cell disease, in a mammal, and in a human in particular. Such method generally includes the step of administering to a mammal in need thereof one or more of the disclosed rAAV vectors comprising a nucleic acid segment encoding a suitable hemoglobinopathy therapeutic agent, in an amount and for a time sufficient to prevent, treat or ameliorate the one or more symptoms of the hemoglobinopathy in the mammal. In the practice of the invention, the population of mammalian cells to which the vector constructs of the invention are preferably administered include, without limitation, a CD34+ cell, a hematopoietic stem cell, a stem cell, a mesenchymal stem cell, an erythroid cell, a bone marrow cell, an endothelial cell, an epithelial cell, a vascular cell, a dendritic cell, a blood cell, a fibroblast, a cancer cell, a liver cell, a lung cell, a cardiac cell, a pancreatic cell, an intestinal cell, a renal cell, a neural cell, or any combination thereof.

The invention also provides a method of transducing a population of mammalian cells. In an overall and general sense, the method includes at least the step of introducing into one or more cells of the population, a composition that comprises an effective amount of one or more of the rAAV vectors disclosed herein.

In a further embodiment, the invention also provides isolated nucleic acid segments that encode one or more of the VP3 mutant capsid proteins as described herein, and provides recombinant vectors, virus particles, infectious virions, and isolated host cells that comprise one or more of the improved vector sequences described and tested herein.

Additionally, the present invention provides compositions, as well as therapeutic and/or diagnostic kits that include one or more of the disclosed vectors or AAv compositions, formulated with one or more additional ingredients, or prepared with one or more instructions for their use.

The invention also demonstrates methods for making, as well as methods of using the disclosed improved rAAV capsid-mutated vectors in a variety of ways, including, for example, ex situ, in vitro and in vivo applications, methodologies, diagnostic procedures, and/or gene therapy treatment methods. Because many of the improved vectors are resistant to proteasomal degradation, they possess significantly increased transduction efficiencies in vivo making them particularly suited for viral vector-based human gene therapy regimens, and for delivering one or more genetic constructs to selected mammalian cells in vivo and/or in vitro.

In addition to a variety of single mutation vectors described herein that possess improved properties making them useful in a number of embodiments, the inventors have also surprisingly found that mutation of two or more amino acid residues (and preferably those on or near the outer surface of the capsid proteins) confers even greater transduction efficiency, making them even more suited as delivery vehicles. Exemplary amino acid residues that have been mutated include, for example, but are not limited to, amino acids such as tyrosines, lysine, serine, and threonine found in the surface exposed regions of VP3 protein.

In one aspect, the invention provides compositions comprising recombinant adeno-associated viral (AAV) vectors, virions, viral particles, and pharmaceutical formulations thereof, useful in methods for delivering genetic material encoding one or more beneficial or therapeutic product(s) to mammalian cells and tissues. In particular, the compositions and methods of the invention provide a significant advancement in the art through their use in the treatment, prevention, and/or amelioration of symptoms of one or more mammalian diseases. It is contemplated that human gene therapy will particularly benefit from the present teachings by providing new and improved viral vector constructs for use in the treatment of a number of diverse diseases, disorders, and dysfunctions.

In another aspect, the invention concerns modified rAAV vector that encode one or more mammalian therapeutic agents for the prevention, treatment, and/or amelioration of one or more disorders in the mammal into which the vector construct is delivered.

In particular, the invention provides rAAV-based expression constructs that encode one or more mammalian therapeutic agent(s) (including, but not limited to, for example, protein(s), polypeptide(s), peptide(s), enzyme(s), antibodies, antigen binding fragments, as well as variants, and/or active fragments thereof, for use in the treatment, prophylaxis, and/or amelioration of one or more symptoms of a mammalian disease, dysfunction, injury, and/or disorder.

In one embodiment, the invention provides an rAAV vector that comprises at least a first capsid protein comprising at least a first amino acid substitution to a non-native amino acid at one or more surface exposed amino acid residues in an rAAV capid protein, and wherein the vector further additionally includes at least a first nucleic acid segment that encodes at least a first diagnostic or therapeutic agent operably linked to a promoter capable of expressing the segment in a host cell that contains the expression vector construct.

The surface-exposed amino acid-modified rAAV vectors of the present invention may optionally further include one or more enhancer sequences that are each operably linked to the nucleic acid segment. Exemplary enhancer sequences include, but are not limited to, one or more selected from the group consisting of a CMV enhancer, a synthetic enhancer, a liver-specific enhancer, an vascular-specific enhancer, a brain-specific enhancer, a neural cell-specific enhancer, a lung-specific enhancer, a muscle-specific enhancer, a kidney-specific enhancer, a pancreas-specific enhancer, and an islet cell-specific enhancer.

Exemplary promoters useful in the practice of the invention include, without limitation, one or more heterologous, tissue-specific, constitutive or inducible promoters, including, for example, but not limited to, a promoter selected from the group consisting of a CMV promoter, a β-globin promoter, a β-actin promoter, an insulin promoter, an enolase promoter, a BDNF promoter, an NGF promoter, an EGF promoter, a growth factor promoter, an axon-specific promoter, a dendrite-specific promoter, a brain-specific promoter, a hippocampal-specific promoter, a kidney-specific promoter, an elafin promoter, a cytokine promoter, an interferon promoter, a growth factor promoter, an alpha-1 antitrypsin promoter, a brain-specific promoter, a neural cell-specific promoter, a central nervous system cell-specific promoter, a peripheral nervous system cell-specific promoter, an interleukin promoter, a serpin promoter, a hybrid CMV promoter, a hybrid β-actin promoter, an EF1 promoter, a U1a promoter, a U1b promoter, a Tet-inducible promoter, a human parvovirus promoter, and a VP16-LexA promoter. In exemplary embodiments, the promoter is a mammalian or avian β-globin or an erythroid cell-dendrite-cell, or tumor-cell-specific promoter.

The first nucleic acid segment may also further include one or more post-transcriptional regulatory sequences or one or more polyadenylation signals, including, for example, but not limited to, a woodchuck hepatitis virus post-transcription regulatory element, a polyadenylation signal sequence, or any combination thereof.

Exemplary diagnostic or therapeutic agents deliverable to host cells by the present vector constructs include, but are not limited to, an agent selected from the group consisting of a polypeptide, a peptide, an antibody, an antigen binding fragment, a ribozyme, a peptide nucleic acid, a siRNA, an RNAi, an antisense oligonucleotide, an antisense polynucleotide, and any combination thereof.

In exemplary embodiments, the improved rAAV vectors of the invention will preferably encode at least one diagnostic or therapeutic protein or polypeptide selected from the group consisting of a molecular marker, an adrenergic agonist, an anti-apoptosis factor, an apoptosis inhibitor, a cytokine receptor, a cytokine, a cytotoxin, an erythropoietic agent, a glutamic acid decarboxylase, a glycoprotein, a growth factor, a growth factor receptor, a hormone, a hormone receptor, an interferon, an interleukin, an interleukin receptor, a kinase, a kinase inhibitor, a nerve growth factor, a netrin, a neuroactive peptide, a neuroactive peptide receptor, a neurogenic factor, a neurogenic factor receptor, a neuropilin, a neurotrophic factor, a neurotrophin, a neurotrophin receptor, an N-methyl-D-aspartate antagonist, a plexin, a protease, a protease inhibitor, a protein decarboxylase, a protein kinase, a protein kinase inhibitor, a proteolytic protein, a proteolytic protein inhibitor, a semaphorin, a semaphorin receptor, a serotonin transport protein, a serotonin uptake inhibitor, a serotonin receptor, a serpin, a serpin receptor, a tumor suppressor, and any combination thereof.

In certain applications, the capsid-modified rAAV vectors of the present invention may include one or more nucleic acid segments that encode a polypeptide selected from the group consisting of BDNF, CNTF, CSF, EGF, FGF, G-SCF, GM-CSF, gonadotropin, IFN, IFG-1, M-CSF, NGF, PDGF, PEDF, TGF, TGF-B2, TNF, VEGF, prolactin, somatotropin, XIAP1, IL-1, IL-2, IL-3, IL-4, IL-5, IL-6, IL-7, IL-8, IL-9, IL-10, IL-10(I87A), viral IL-10, IL-11, IL-12, IL-13, IL-14, IL-15, IL-16, IL-17, IL-18, and any combination thereof.

In another embodiment, the invention concerns genetically-modified improved transduction-efficiency rAAV vectors that include at least a first nucleic acid segment that encodes one or more therapeutic agents that alter, inhibit, reduce, prevent, eliminate, or impair the activity of one or more endogenous biological processes in the cell. In particular embodiments, such therapeutic agents may be those that selectively inhibit or reduce the effects of one or more metabolic processes, dysfunctions, disorders, or diseases. In certain embodiments, the defect may be caused by injury or trauma to the mammal for which treatment is desired. In other embodiments, the defect may be caused the over-expression of an endogenous biological compound, while in other embodiments still; the defect may be caused by the under-expression or even lack of one or more endogenous biological compounds.

The genetically-modified rAAV vectors and expression systems of the present invention may also further include a second nucleic acid segment that comprises, consists essentially of, or consists of, one or more enhancers, one or more regulatory elements, one or more transcriptional elements, or any combination thereof, that alter, improve, regulate, and/or affect the transcription of the nucleotide sequence of interest expressed by the modified rAAV vectors.

For example, the rAAV vectors of the present invention may further include a second nucleic acid segment that comprises, consists essentially of, or consists of, an HS2 enhancer, a CMV enhancer, a synthetic enhancer, a dendrite cell-specific enhancer, an erythroid cell-specific enhancer, a stem cell-specific enhancer, a tissue-specific enhancer, or any combination thereof. The second nucleic acid segment may also further comprise, consist essentially of, or consist of, one or more intron sequences, one or more post-transcriptional regulatory elements, or any combination thereof.

The improved vectors and expression systems of the present invention may also optionally further include a polynucleotide that comprises, consists essentially of, or consists of, one or more polylinkers, restriction sites, and/or multiple cloning region(s) to facilitate insertion (cloning) of one or more selected genetic elements, genes of interest, or therapeutic or diagnostic constructs into the rAAV vector at a selected site within the vector.

In other embodiments, the invention also provides capsid-modified rAAV vectors that are comprised within an infectious adeno-associated viral particle or a virion, as well as pluralities of such virions or infectious particles. Such vectors and virions may be comprised within one or more diluents, buffers, physiological solutions or pharmaceutical vehicles, or formulated for administration to a mammal in one or more diagnostic, therapeutic, and/or prophylactic regimens. The vectors, virus particles, virions, and pluralities thereof of the present invention may also be provided in excipient formulations that are acceptable for veterinary administration to selected livestock, exotics, domesticated animals, and companion animals (including pets and such like), as well as to non-human primates, zoological or otherwise captive specimens, and such like.

The invention also concerns host cells that comprise at least one of the disclosed capsid protein-modified rAAV expression vectors, or one or more virus particles or virions that comprise such an expression vector. Such host cells are particularly mammalian host cells, with human host cells being particularly highly preferred, and may be either isolated, in cell or tissue culture. In the case of genetically modified animal models, the transformed host cells may even be comprised within the body of a non-human animal itself.

In certain embodiments, the creation of recombinant non-human host cells, and/or isolated recombinant human host cells that comprise one or more of the disclosed rAAV vectors is also contemplated to be useful for a variety of diagnostic, and laboratory protocols, including, for example, means for the production of large-scale quantities of the rAAV vectors described herein. Such virus production methods are particularly contemplated to be an improvement over existing methodologies including in particular, those that require very high titers of the viral stocks in order to be useful as a gene therapy tool. The inventors contemplate that one very significant advantage of the present methods will be the ability to utilize lower titers of viral particles in mammalian transduction protocols, yet still retain transfection rates at a suitable level.

Compositions comprising one or more of the disclosed capsid-modified, improved transduction-efficiency rAAV vectors, expression systems, infectious AAV particles, or host cells also form part of the present invention, and particularly those compositions that further comprise at least a first pharmaceutically-acceptable excipient for use in therapy, and for use in the manufacture of medicaments for the treatment of one or more mammalian diseases, disorders, dysfunctions, or trauma. Such pharmaceutical compositions may optionally further comprise one or more diluents, buffers, liposomes, a lipid, a lipid complex; or the tyrosine-modified rAAV vectors may be comprised within a microsphere or a nanoparticle. Pharmaceutical formulations suitable for intramuscular, intravenous, or direct injection into an organ or tissue or a plurality of cells or tissues of a human or other mammal are particularly preferred, however, the compositions disclosed herein may also find utility in administration to discreet areas of the mammalian body, including for example, formulations that are suitable for direct injection into one or more organs, tissues, or cell types in the body. Such injection sites include, but are not limited to, the brain, a joint or joint capsule, a synovium or sub-synovium tissue, tendons, ligaments, cartilages, bone, peri-articular muscle or an articular space of a mammalian joint, as well as direct administration to an organ such as the heart, liver, lung, pancreas, intestine, brain, bladder, kidney, or other site within the patient's body, including, for example, introduction of the viral vectors via intraabdominal, intrathoracic, intravascular, or intracerebroventricular delivery.

Other aspects of the invention concern recombinant adeno-associated virus virion particles, compositions, and host cells that comprise, consist essentially of, or consist of, one or more of the capsid-modified, improved transduction efficiency, rAAV vectors disclosed herein, such as for example pharmaceutical formulations of the vectors intended for administration to a mammal through suitable means, such as, by intramuscular, intravenous, intra-articular, or direct injection to one or more cells, tissues, or organs of a selected mammal. Typically, such compositions may be formulated with pharmaceutically-acceptable excipients as described hereinbelow, and may comprise one or more liposomes, lipids, lipid complexes, microspheres or nanoparticle formulations to facilitate administration to the selected organs, tissues, and cells for which therapy is desired.

Kits comprising one or more of the disclosed capsid-modified rAAV vectors (as well as one or more virions, viral particles, transformed host cells or pharmaceutical compositions comprising such vectors); and instructions for using such kits in one or more therapeutic, diagnostic, and/or prophylactic clinical embodiments are also provided by the present invention. Such kits may further comprise one or more reagents, restriction enzymes, peptides, therapeutics, pharmaceutical compounds, or means for delivery of the composition(s) to host cells, or to an animal (e.g., syringes, injectables, and the like). Exemplary kits include those for treating, preventing, or ameliorating the symptoms of a disease, deficiency, dysfunction, and/or injury, or may include components for the large-scale production of the viral vectors themselves, such as for commercial sale, or for use by others, including e.g., virologists, medical professionals, and the like.

Another important aspect of the present invention concerns methods of use of the disclosed rAAV vectors, virions, expression systems, compositions, and host cells described herein in the preparation of medicaments for diagnosing, preventing, treating or ameliorating at least one or more symptoms of a disease, a dysfunction, a disorder, an abnormal condition, a deficiency, injury, or trauma in an animal, and in particular, in a vertebrate mammal. Such methods generally involve administration to a mammal in need thereof, one or more of the disclosed vectors, virions, viral particles, host cells, compositions, or pluralities thereof, in an amount and for a time sufficient to diagnose, prevent, treat, or lessen one or more symptoms of such a disease, dysfunction, disorder, abnormal condition, deficiency, injury, or trauma in the affected animal. The methods may also encompass prophylactic treatment of animals suspected of having such conditions, or administration of such compositions to those animals at risk for developing such conditions either following diagnosis, or prior to the onset of symptoms.

As described above, the exogenous polynucleotide will preferably encode one or more proteins, polypeptides, peptides, ribozymes, or antisense oligonucleotides, or a combination of these. In fact, the exogenous polynucleotide may encode two or more such molecules, or a plurality of such molecules as may be desired. When combinational gene therapies are desired, two or more different molecules may be produced from a single rAAV expression system, or alternatively, a selected host cell may be transfected with two or more unique rAAV expression systems, each of which will provide unique heterologous polynucleotides encoding at least two different such molecules.

Compositions comprising one or more of the disclosed rAAV vectors, expression systems, infectious AAV particles, host cells also form part of the present invention, and particularly those compositions that further comprise at least a first pharmaceutically-acceptable excipient for use in the manufacture of medicaments and methods involving therapeutic administration of such rAAV vectors. Such pharmaceutical compositions may optionally further comprise liposomes, a lipid, a lipid complex; or the rAAV vectors may be comprised within a microsphere or a nanoparticle. Pharmaceutical formulations suitable for intramuscular, intravenous, or direct injection into an organ or tissue of a human are particularly preferred.

Another important aspect of the present invention concerns methods of use of the disclosed vectors, virions, expression systems, compositions, and host cells described herein in the preparation of medicaments for treating or ameliorating the symptoms of various polypeptide deficiencies in a mammal. Such methods generally involve administration to a mammal, or human in need thereof, one or more of the disclosed vectors, virions, host cells, or compositions, in an amount and for a time sufficient to treat or ameliorate the symptoms of such a deficiency in the affected mammal. The methods may also encompass prophylactic treatment of animals suspected of having such conditions, or administration of such compositions to those animals at risk for developing such conditions either following diagnosis, or prior to the onset of symptoms.

BRIEF DESCRIPTION OF THE DRAWINGS

For promoting an understanding of the principles of the invention, reference will now be made to the embodiments, or examples, illustrated in the drawings and specific language will be used to describe the same. It will, nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates.

The following drawings form part of the present specification and are included to demonstrate certain aspects of the present invention. The invention may be better understood by reference to the following description taken in conjunction with the accompanying drawings, in which like reference numerals identify like elements, and in which:

FIG. 1A, FIG. 1B, and FIG. 1C show the effect of NF-κB pathway inhibitors and activator on AAV vector-mediated EGFP expression in HeLa cells in vitro. Cells were pre-treated with various concentrations of inhibitors and activators for 12 hrs and transduced with $2\times10^3$ AAV-EGFP vgs per cell. FIG. 1A: Transgene expression was detected by fluorescence microscopy 48 hrs post-infection. Representative images are shown. FIG. 1B: Quantitative analyses of the data from FIG. 1A. Images from five visual fields were analyzed as described. *P<0.001. FIG. 1C: Western blot analysis of HeLa cell extracts transduced with scAAV vectors and in the presence of NF-κB modulators. The samples were analyzed by using anti-p65 and anti-IκB antibodies [classical pathway], anti-p100/p52 antibody [non-canonical pathway] for detection NF-κB signaling in response to AAV exposure. These results are representative of two independent experiments;

FIG. 2A and FIG. 2B show AAV-EGFP vector-mediated transduction of primary human monocytes-derived dendritic cells in the presence of NF-κB modulators. FIG. 2A: Transgene expression was detected by flow cytometry 48 hrs post-transduction. FIG. 2B: Western blot analysis for components of classical and non-canonical pathway of NF-κB activation in nuclear extracts from dendritic cells, mock-transduced or transduced with 2,000 vgs/cell of scAAV vectors and in the presence of NF-κB modulators;

FIG. 4A: Representative images are shown. Original magnification: ×400. FIG. 4B: Quantitative analyses of the data from FIG. 4A. Images from five visual fields were analyzed quantitatively as described in the legend to FIG. 1A;

FIG. 5 demonstrates that AAV genome contains putative binding sites for NF-κB-responsive transcription factors within the inverted terminal repeats (ITRs). The putative NF-κB-responsive transcription factor-binding sites in the AAV-ITRs were identified by in silico analysis using the TRANSFAC database [alggen.lsi.upc.es/]. The binding sites for p300, TFIIB, and SpII transcriptions factors are denoted by green, red, and blue underlined fonts, respectively. The boxed sequence represents the 20-nucleotide single-stranded D-sequence within the ITR;

FIG. 6A, FIG. 6B, FIG. 6C, FIG. 6D and FIG. 6E show the effect of NF-κB activators and inhibitors on transgene expression from an AAV2-EGFP vector in HeLa cells in vitro. Cells were either mock-treated or pretreated with various combinations of inhibitors and activators for 12 hr. Washed cells were infected with $2 \times 10^3$ vg/cell of scAAV2-EGFP (FIG. 6A), ssAAV2-EGFP (FIG. 6B), or TM-scAAV2-EGFP (FIG. 6C). Transgene expression was detected by fluorescence microscopy 48 hrs' postinfection. Representative images are shown; FIG. 6D shows a Western blot analysis of cytoplasmic and nuclear extracts from HeLa cells transduced with scAAV vectors and in the presence of NF-κB modulators. The samples were analyzed by using anti-p100/p52 antibody for detection of NF-κB signaling. Anti-GAPDH and lamin B antibodies were used as appropriate controls. These results are representative of two independent experiments;

FIG. 8A: IL-1α; FIG. 8B: IL-6; FIG. 8C: TNF-α; FIG. 8D: IL-12α, FIG. 8E: KC; and FIG. 8F: RANTES. Values are significant above 2.6 and below 0.38; calculated by determining the variability in the 96-well plates used to measure specific gene expression;

FIG. 11A: Equivalent numbers of T47D and T47D+hHGFR cells were infected with various indicated multiplicity-of-infection (MOI) of scAAV3-CBAp-EGFP vectors under identical conditions. Transgene expression was determined by fluorescence microscopy 72 hrs post-infection. FIG. 11B: T47D+hHGFR cells were transduced with 2,000 vgs/cell of scAAV3 vectors in the absence or the presence of 5 μg/mL of hHGF. Transgene expression was determined by fluorescence microscopy 72 hrs' post-infection;

FIG. 12A, FIG. 12B and FIG. 12C show the effect of BMS-777607 on AAV3-mediated transgene expression. FIG. 12A: T47D+hHGFR cells, either mock-treated or treated with various concentration of BMS-777607, were infected with 2,000 vgs/cell of scAAV3-CBAp-EGFP vectors. Transgene expression was determined by fluorescence microscopy 72 hrs' post-infection. FIG. 12B: T47D and T47D+hHGFR cells were infected with 10,000 vgs/cell of scAAV3-CBAp-EGFP vectors in the absence or the presence of 1 μM of BMS-777607. FIG. 12C: T47D and T47D+hHGFR cells were mock-treated or pretreated with BMS-777607 for 2 hrs. Whole-cell lysates were prepared and analyzed on Western blots using various indicated primary antibodies. β-actin was used as a loading control;

FIG. 13A: T47D+hHGFR cells, either mock-treated or treated with 1 μM of BMS-777607, were infected with 2,000 vgs/cell of either scAAV2-, scAAV3- or scAAV4-CBAp-EGFP vectors. FIG. 13B: T47D+hHGFR cells, either mock-treated or treated with 1 μM of BMS-777607, were infected with 2,000 vgs/cell of either scAAV5-, scAAV7-, scAAV8- or scAAV9-CBAp-EGFP vectors. Transgene expression was determined by fluorescence microscopy 72 hrs post-infection;

FIG. 14A: HeLa cells, either mock-treated or treated with 5 μM of MG132, were infected with scAAV2-CBAp-EGFP vectors. FIG. 14B: Huh7 and Hep293TT cells, either mock-treated or treated with various concentration of MG132, were infected with scAAV3-WT-CBAp-EGFP vectors. FIG. 14C: HeLa cells, either mock-treated or treated with 200 µM of Tyr23, were infected by scAAV2-CBAp-EGFP vectors. FIG. 14D: Hep293TT cells, either mock-treated or treated with Tyr23, were infected by scAAV3-CBAp-EGFP vectors. Transgene expression was determined 72 hrs' post-transduction;

FIG. 16A: Huh7 cells were transduced with WT or various indicated Y-F mutant scAAV3-CBAp-EGFP vectors under identical conditions. Transgene expression was determined 72 hrs post-transduction. FIG. 16B: Huh7 cells were transduced with 5,000 vgs/cell of WT or Y-F mutant scAAV3 vectors in the absence or the presence of 5 µg/mL of hHGF. Transgene expression was determined by fluorescence microscopy 72 hrs post-infection (FIG. 16C);

FIG. 19A: Transgene expression was detected by fluorescence microscopy 48 hrs post infection. FIG. 19B: Images from three visual fields were analyzed as described. *$P<0.005$, **$P<0.001$ vs. WT AAV2;

FIG. 20A and FIG. 20B show the analysis of EGFP expression after transduction of HEK293 cells with individual site-directed scAAV2 capsid mutants. Each of the 15 surface-exposed serines (S) in AAV2 capsid was substituted with valine (V) and evaluated for its efficiency to mediate transgene expression. FIG. 20A: EGFP expression analysis at 48 hrs post-infection at an MOI of $1 \times 10^3$ vgs/cell. FIG. 20B: Quantitation of transduction efficiency of each of the serine-mutant AAV2 vectors. *$P<0.005$, **$P<0.001$ vs. WT AAV2;

FIG. 21A: A trimer of the AAV2 VP3 shown in ribbon representation and viewed down the icosahedral threefold axis (left) and rotated 90° (right) with VP monomers colored in blue, purple and light blue showing the location of serine residues 458, 492, and 662 in the yellow, green, and red spheres, respectively. The approximate positions of the icosahedral two-, three-, and five-fold axes are depicted by the filled oval, triangle, and pentagon, respectively. FIG. 21B: The capsid surface of AAV2 shown in blue with serine residues 458, 492, and 662 highlighted in the same colors as in FIG. 3A. S458 and 492 are located adjacent to each other on the outer surface of the protrusions facing the depression surrounding the two-fold axes. S662 is located on the HI loop (colored white) (between the β-H and β-I strands of the core eight-stranded beta-barrel) which lie on the floor of the depression surrounding the icosahedral five-fold axes. The five-fold symmetry related DE loops (between the β-D and β-E strands), which form the channel at the icosahedral 5-fold axes, are colored in brown. The approximate positions of an icosahedral two-fold (2F), three-fold (3F), and five-fold (5F) axes are indicated by the open arrows;

FIG. 22A: EGFP expression analysis at 48 h after infection of 293 cells at an MOI of $1 \times 10^3$ vgs/cell. FIG. 22B: Quantitation of the transduction efficiency of each of the serine-mutant AAV2 vectors. *$P<0.005$, **$P<0.001$ vs. WT AAV2;

FIG. 23A: Quantitation of the transduction efficiency of WT- and S662V-AAV2 vectors in HEK293, HeLa, NIH3T3, H2.35 and moDCs. FIG. 23B: Western blot analysis of lysates from different cell lines for p-p38 MAPK expression levels. Total p38 MAPK and GAPDH levels were measured and used as loading controls. *$P<0.005$, **$P<0.001$ vs. WT AAV2;

FIG. 24A: Effect of JNK and p38 MAPK inhibitors, and site-directed substitution of the serine residue at position 662 on EGFP expression. FIG. 24B: Quantitation of the data in FIG. 24A at 48 hrs after infection and initiation of maturation. FIG. 24C: Analysis of expression of co-stimulatory markers such as CD80, CD83, CD86 in moDCs infected with scAAV2-S662V vectors at an MOI of $5 \times 10^4$ vgs/cell. iDCs—immature dendritic cells, and mDCs—mature dendritic cells, stimulated with cytokines, generated as described herein, were used as negative and positive controls, respectively. A representative example is shown. *$P<0.005$, **$P<0.001$ vs. WT AAV2;

FIG. 26A: EGFP expression analysis at 48 h post-infection at MOI of $1\times10^3$ vg/cell. FIG. 26B: Quantification of transduction efficiency of each of the threonine-mutant scAAV2 vectors. *P<0.005, **P<0.001 vs. WT AAV2;

FIG. 27A: EGFP expression analysis at 48 hrs' post-infection at MOI of $1\times10^3$ vg/cell. FIG. 27B: Quantification of transduction efficiency of each of the threonine-mutant AAV2 vectors. *P<0.005, **P<0.001 vs. WT AAV2;

FIG. 28A: EGFP expression analysis at 48 hrs' post-infection at MOI of $1\times10^3$ vg/cell. FIG. 28B: Quantification of transduction efficiency of each of the optimized scAAV2 vectors. *P<0.005, **P<0.001 vs. WT AAV2;

FIG. 29A: EGFP expression analysis at 16, 24 and 48 hrs' post-infection at MOI of $1\times10^3$ vg/cell. FIG. 29B: Quantification of transduction efficiency of each of the optimized scAAV2 vectors. *P<0.005, **P<0.001 vs. WT AAV2;

FIG. 32A: The capsid surface of AAV2 (grey) with the 17 surface threonine residues mutated in blue (251, 329, 330, 454, 503, 581, 592, 597, 660, 671, 701, 713, 716), green (455), yellow (491), brown (550), and pink (659). The surface location of T329, T330, T713 and T716 are indicated by arrows. The five-fold symmetry related DE loops (between the RD and PE strands) are colored in orange. The HI loops (between the PH and RI strands) are colored white and S662 located in this loop is in red. The white dashed triangle in FIG. 32A depicts a viral asymmetric unit bounded by a five-fold axis and two three-fold axes with a two-fold axis between the three-folds. Dashed ovals delineate the approximate footprints (2/60) of threonine residues that affect transduction when mutated. FIG. 32B: A "Roadmap" projection of the AAV2 capsid surface residues within a viral asymmetric unit. The areas covered by AAV2 surface threonines and S662 are colored as in FIG. 32A. The residues in the tyrosine triple mutant residues, 444, 500, and 730 are shown in shades of purple. Dashed ovals are as described in FIG. 23A. Dashed rectangle (blue) shows residues previously determined to be important in heparin sulfate receptor binding for AAV2 and AAV6 (Wu et al., 2006; Opie et al., 2003);

Figure 33A:
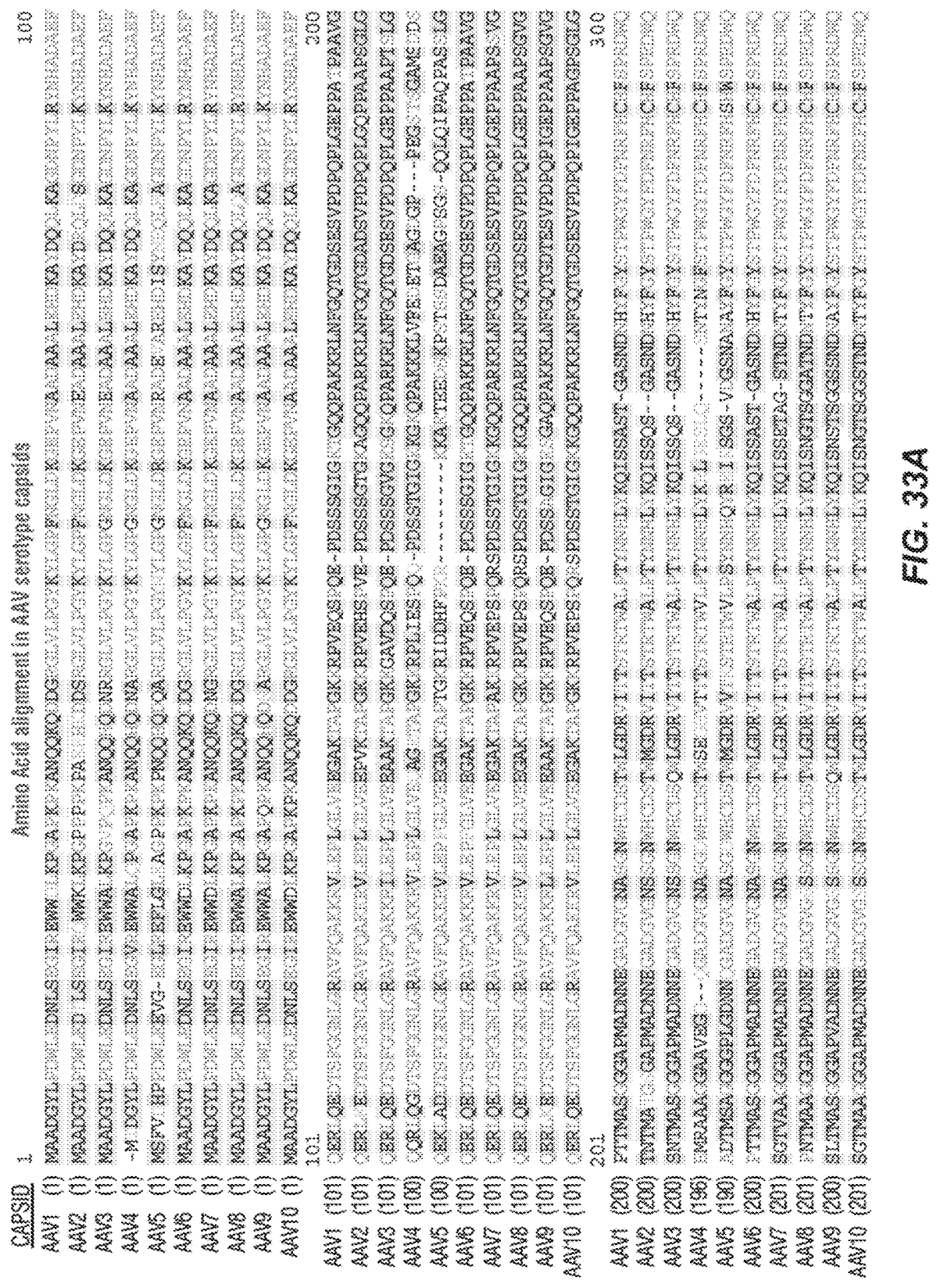
Figure 33A:
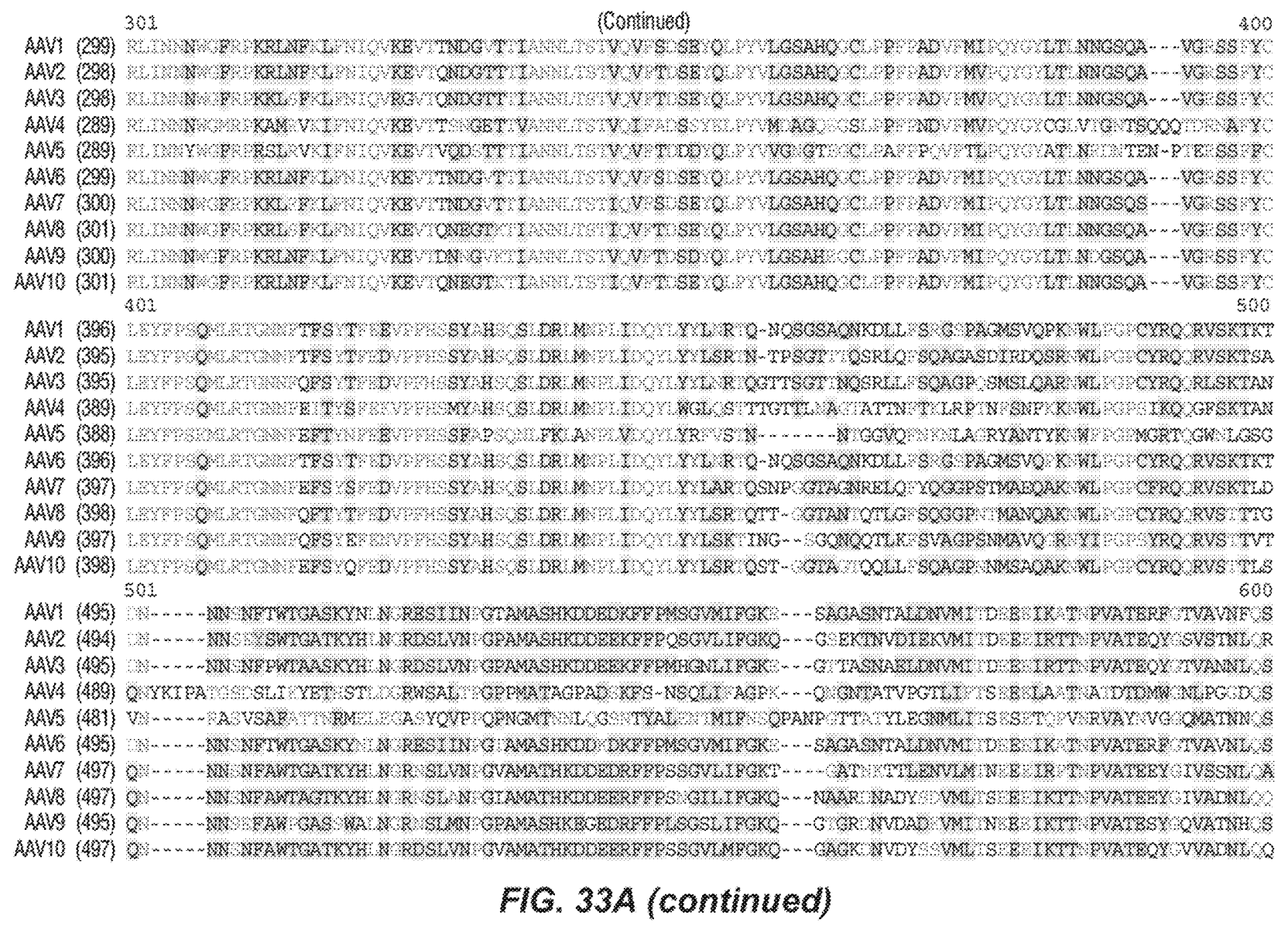
Figure 33A:
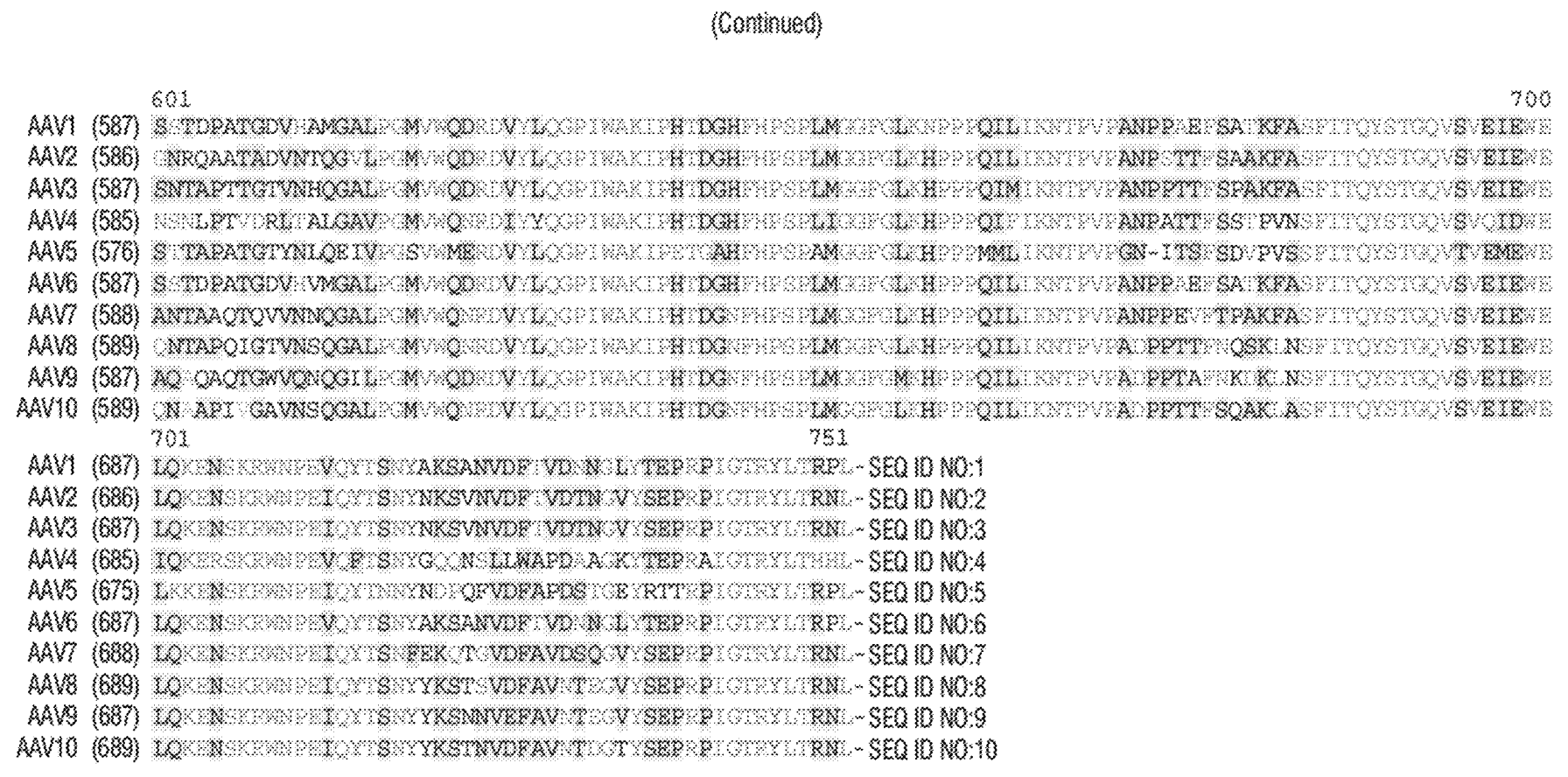
Figure 33B:
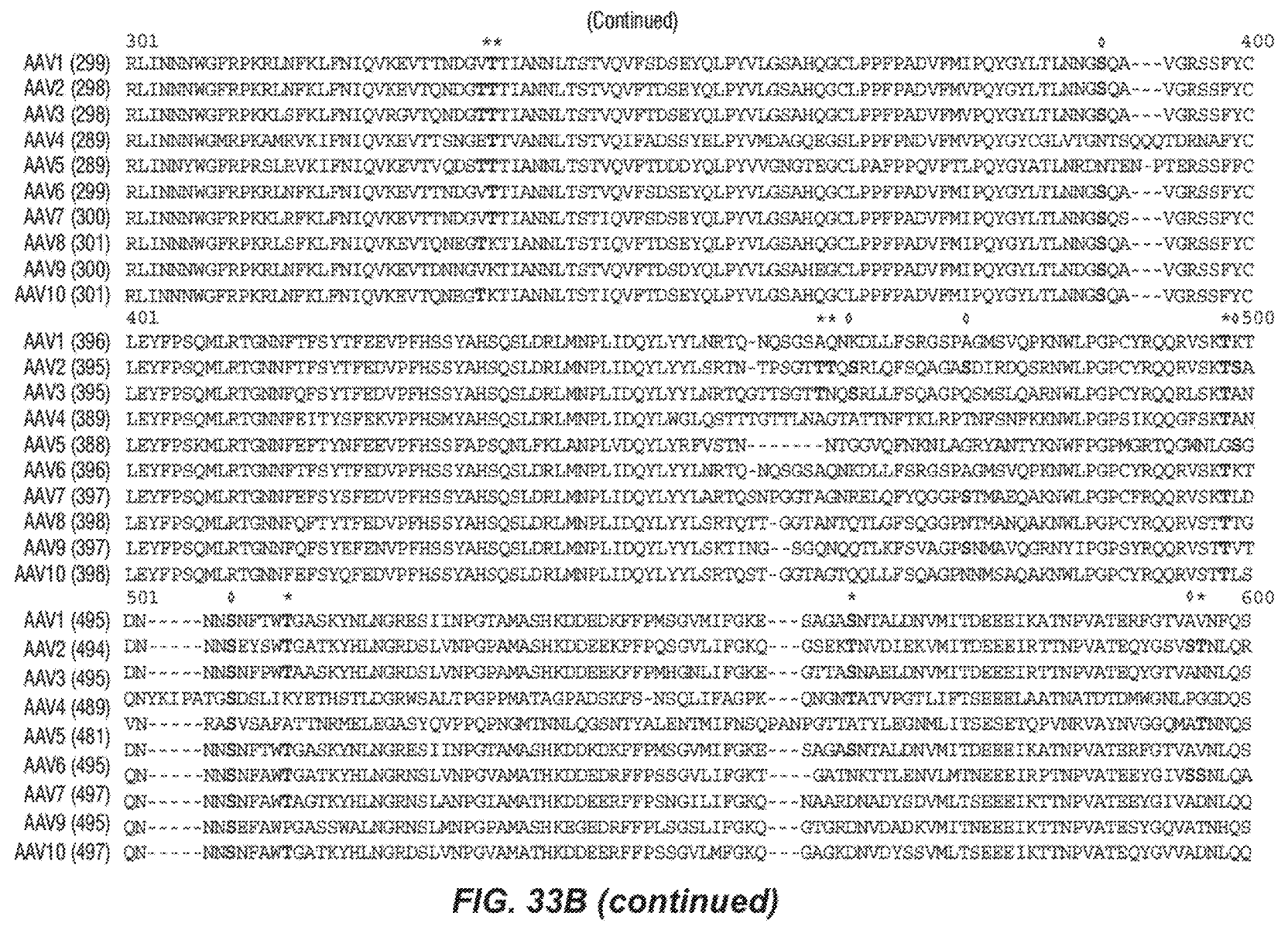
Figure 33B:
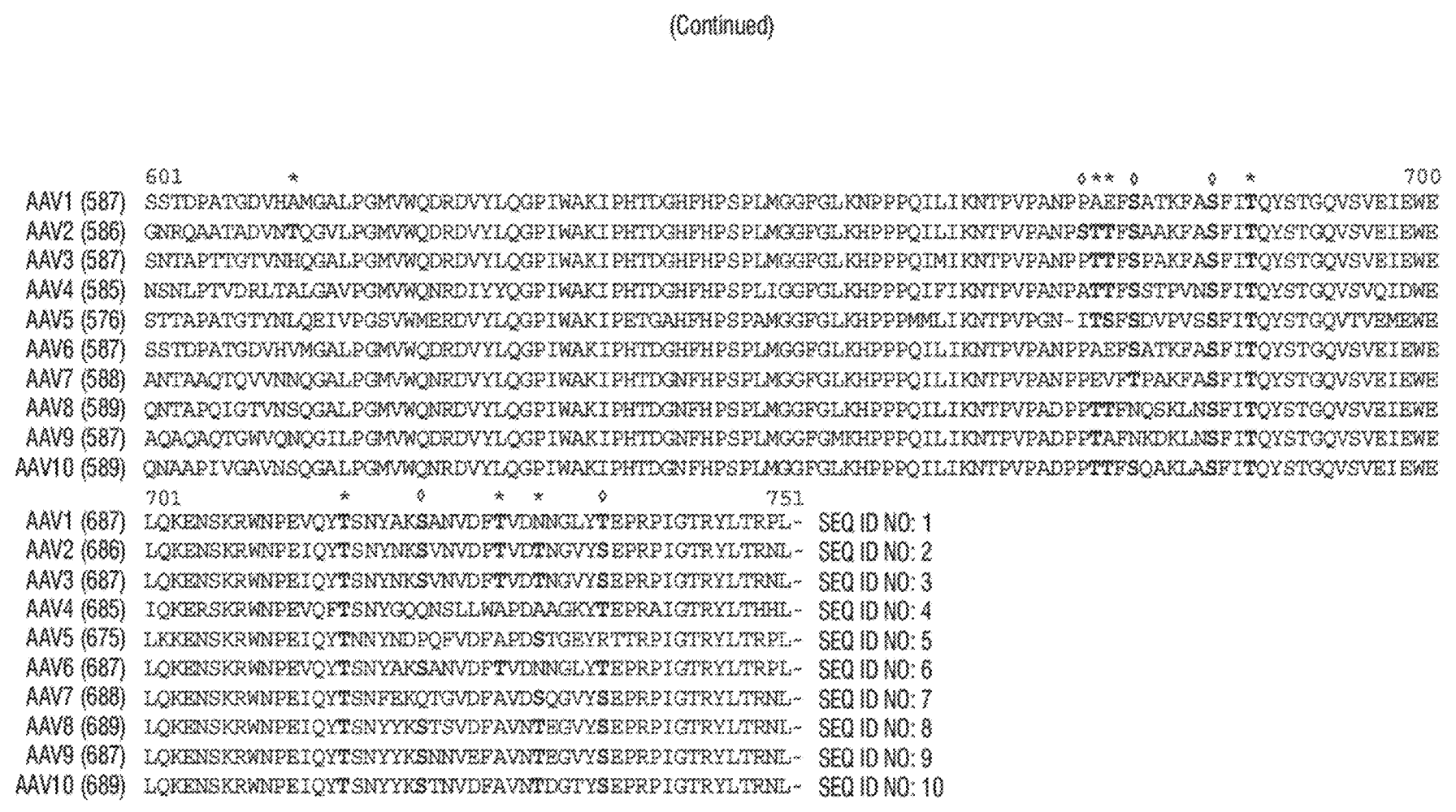
Figure 33C:
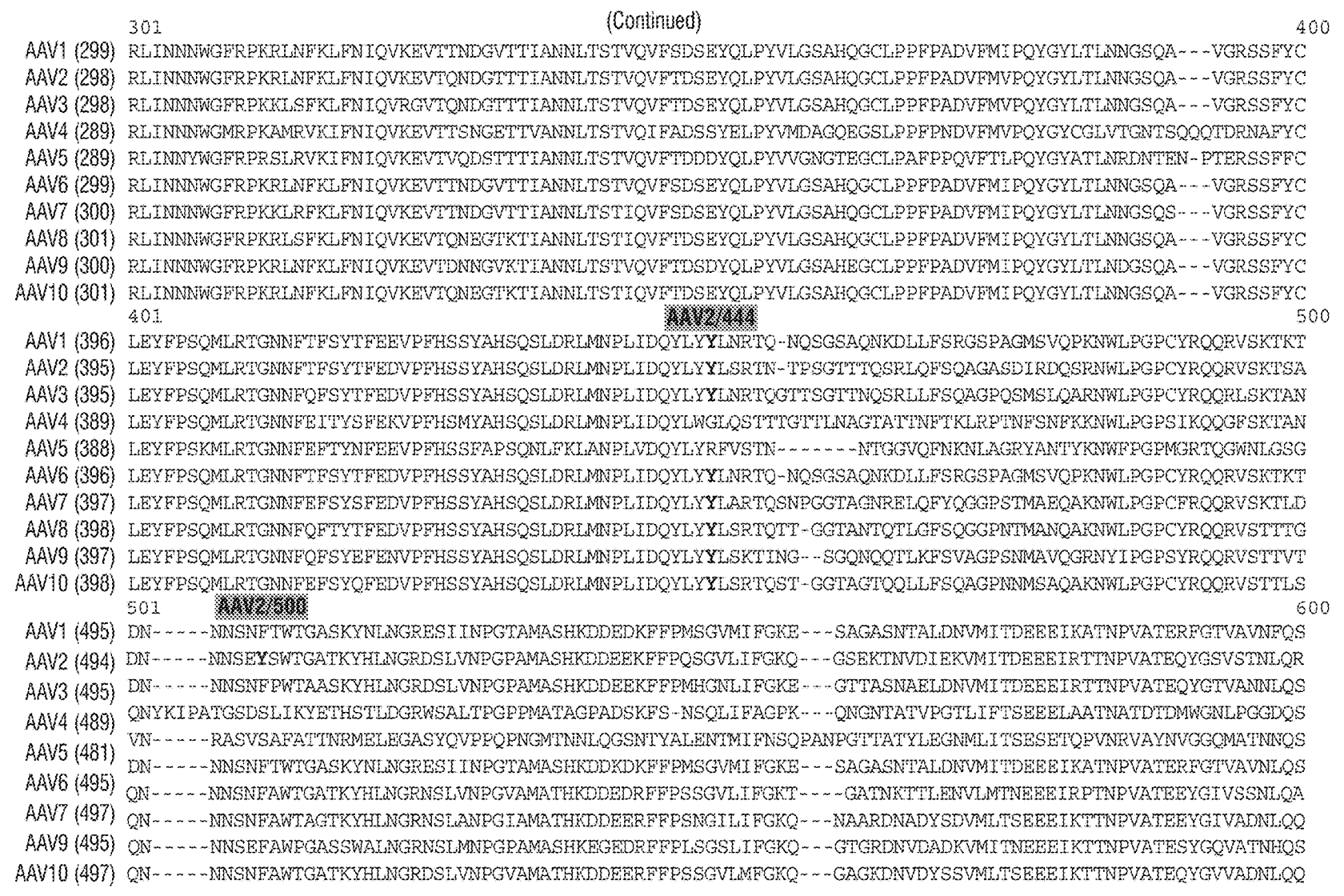

FIG. 33A, FIG. 33B, and FIG. 33C show amino acid alignment of the wild-type AAV1-10 capsids. FIG. 33A shows amino acid alignment of the wild-type AAV1-10 serotype capsids (SEQ ID NO:1 through SEQ ID NO:10). FIG. 33B shows amino acid alignment of the wild-type AAV1-10 serotype capsids, as well as surface-exposed serine and threonine residues that are conserved in among AAV1-10 capsids (conserved, surface-exposed residues are shown in bold); and FIG. 33C shows conserved, surface-exposed tyrosine residues in the wild-type AAV1-12 capsids, as well as embodiments of amino acid modifications. The tyrosine residues conserved among AAV1-12 are shown in bold;

FIG. 34 show packaging and transduction efficiencies of various serine-valine mutant AAV2 vectors relative to WT AAV2 vectors amino acid alignment of the wild-type AAV1-10 capsids;

FIG. 35 shows packaging and transduction efficiencies of serine-mutant vectors replaced with various amino acids relative to WT AAV2 vectors;

FIG. 36A, FIG. 36B, FIG. 36C, and FIG. 36D show the transduction efficiency of WT and tyrosine-mutant scAAV6 vectors in human hematopoietic cells. Approximately $5\times10^3$ K562 cells were either mock-infected, or infected with $5\times10^3$ vgs/cell of WT or various tyrosine-mutant scAAV6-CBAp-EGFP vectors, and transgene expression was determined 48 hrs post-infection using a Zeiss fluorescence microscope (FIG. 36A), and Accuri C6 flow cytometer (FIG. 36B) (Original magnification, 100×). Approximately $1\times10^4$ primary human CD34$^+$ cells were either mock-infected, or infected with $2\times10^4$ vgs/cell of WT or various tyrosine-mutant scAAV6-CBAp-EGFP vectors under identical conditions, and transgene expression was determined 72 hrs post-infection by fluorescence microscopy (FIG. 36C) (Original magnification, 200×), and quantified by fluorescence-activated cell sorting (FACS) using a BD FACS Aria Flow Cytometer followed by processing with software FCS Express 4 (FIG. 36D). *Y705+731F-scAAV6 vs. WT-scAAV6 vectors, p<0.01;

FIG. 37A, FIG. 37B, FIG. 37C and FIG. 37D show the transcriptional potential of CBAp, HS2-βp, and B19p6 promoters in human hematopoietic cells. Approximately $1\times10^4$ cells were either infected with DM scAAV6 vectors (K562 cells) or WT scAAV6 vectors (human CD34$^+$ cells) expressing the EGFP gene under the control of the three different promoters at $5\times10^3$ vgs/cell (K562 cells) or $2\times10^4$ vgs/cell (human CD34$^+$ cells), respectively. Transgene expression in K562 cells (FIG. 37A and FIG. 37B) and human CD34$^+$ cells (FIG. 37C and FIG. 37D) was determined 72 hrs' post-infection by fluorescence microscopy and quantitated by the flow cytometry as described above. The original image magnifications were 100× (FIG. 37A) and 200× (FIG. 37B). *DM-scB19p6-EGFP vs. DM-scAAV6-HS2-βp-EGFP vectors, p<0.01;

FIG. 38A and FIG. 38B show transcriptional potential of CBAp, HS2-βp and B19p6 promoters in human erythroleukemia cells following erythroid differentiation. Equivalent numbers of mock-treated, or Epo-induced erythroid-differentiated K562 cells were infected with $5\times10^3$ vgs/cell of scAAV6-Gluc vectors, and transgene expression was determined 18 hrs' post-infection (FIG. 38A). Fold changes in transgene expression from the three promoters were calculated from untreated vs. Epo-treated groups (FIG. 38B);

(FIG. 45A) Equivalent numbers of cells from various donors were infected with $2\times10^4$ vgs/cell of scAAV2 or AAV6 vectors, and transgene expression was evaluated as described in the text. The boxes represent the upper quartile and lower quartile of the values; the horizontal lines indicate the median values; and different markers represent individual experiments. (FIG. 45B and FIG. 45C) Equivalent numbers of CD34$^b$ cells from the same lots were transduced with scAAV2 or scAAV6 vectors as described in the text, either in the absence or the presence of 10% FBS. Transgene expression was evaluated 72 hrs after transduction by fluorescence microscopy and quantitated by flow cytometry;

(FIG. 46A and FIG. 46B) Equivalent numbers of CD34$^b$ cells were transduced with scAAV2 or scAAV6 vectors in the presence of 10 ng/mL of rhFlt3, 10 ng/mL of rhTPO and 1 ng/mL of rhSCF for 2 hrs (condition 1) or in the presence of 10 ng/mL of rhIL6, 10 ng/mL of rhIL3 and 1 ng/mL of rhSCF for 2 hrs (condition 2). Transgene expression was evaluated 72 hrs after transduction by fluorescence microscopy and quantitated as described in the text. (FIG. 46C) Equivalent numbers of CD34$^b$ cells either were mock-infected, or were infected with scAAV6 vectors for either 2 hrs or 16 hrs. Transgene expression was evaluated 72 hrs after infection by flow cytometry as described in the text;

(FIG. 48A and FIG. 48C) EGFP expression analysis at 48 hrs' post infection at a multiplicity of infection (MOI) of 2000 vgs per cell. (FIG. 48B and FIG. 48D) Quantitation of transduction efficiency of each of the AAV vectors. Scale bar is 200-mm. * P<0.005, ** P<0.001 vs. WT-AAV. Data from a representative experiment are shown. Similar results were obtained on samples from three different donors;

FIG. 49A, FIG. 49B, FIG. 49C, FIG. 49D, and FIG. 49E show the analysis of intracellular trafficking of AAV vectors to the nucleus. Ratio of total viral genomes in cytoplasm 2 hrs' post infection: (FIG. 49A) capsid-optimized AAV2 and WT-AAV2 vectors, (FIG. 49B) capsid-optimized AAV6 and WT-AAV6 vectors, (FIG. 49C) AAV6 and AAV2 vectors; AAV2 and AAV6 viral genome distribution within cell at 16 hrs' (FIG. 49D) and 48 hrs' (FIG. 49E) post infection. Cytoplasm-purple, nucleus-yellow. ** P<0.001 considered as significant. Similar results were observed on samples from three independent donors;

(FIG. 50A) EGFP expression analysis at 48 hrs' post infection. (FIG. 50B) Quantitation of transduction efficiency of teach of the AAV vectors; and FIG. 51A, FIG. 51B, and FIG. 51C show the analysis of CTLs killing activity on LNCaP cells. FIG. 51A and FIG. 51B: Western blot analysis of hPSA expression driven by cmCD11c (SV40-CD11c-3/5) or CBA promoters in moDCs transduced with AAV6-WT and AAV6-T492V T492VbS663V S663V (DM) vectors. FIG. 51C: FACS analysis of percentages of killed LNCaP cells co-incubated with hPSA-CTLs at different ratios. Non-specific CTLs were stimulated with same vectors expressing GFP. *P<0.005 between same promoter and different capsids, and &P<0.005 between same capsid and different promoters, considered as significant. A representative example of experiments on samples from three different donors is shown.

BRIEF DESCRIPTION OF THE SEQUENCES

Figure 3A:
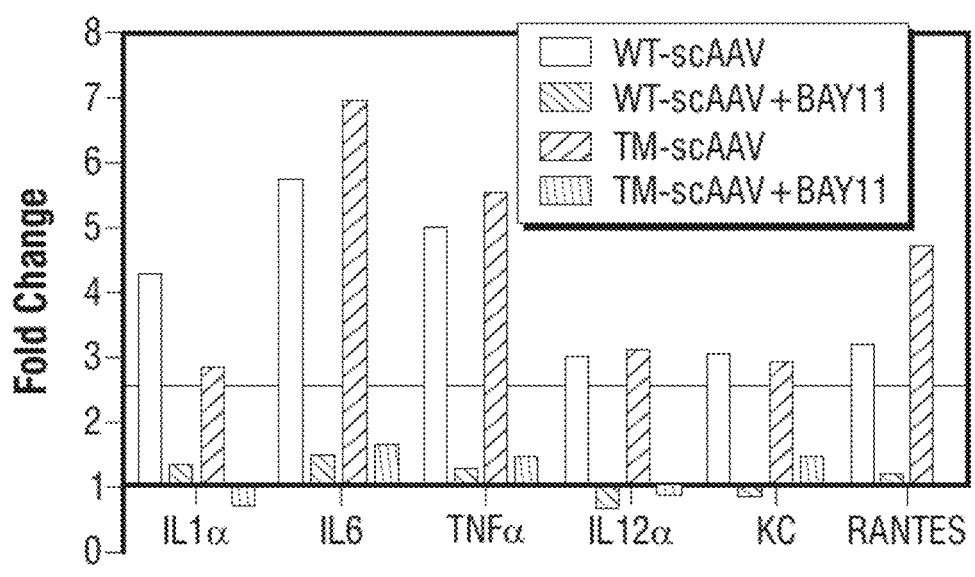
FIG. 3A and FIG. 3B show AAV vector-induced innate immune and NF-κB response in mice in vivo. Gene expression profiling of innate immune mediators (FIG. 3A) or NF-κB activation (FIG. 3B) was performed as described. The data for fold changes in gene expression at the 2 hrs time-point comparing AAV vectors with Bay11 (hatched or open bars) with AAV vectors without Bay11 (black or grey bars) are shown. The minimal threshold fold-increase (horizontal black line) was 2.5 (FIG. 3A) or 3.0 (FIG. 3B) by measuring the variability of duplicate ΔCT (compared to GAPDH, $2^{-\Delta CT(variability)}$)

SEQ ID NO:1 is an amino acid sequence of the capsid protein of the wild-type adeno-associated virus serotype 1 (AAV1);

SEQ ID NO:2 is an amino acid sequence of the capsid protein of the wild-type adeno-associated virus serotype 2 (AAV2);

SEQ ID NO:3 is an amino acid sequence of the capsid protein of the wild-type adeno-associated virus serotype 3 (AAV3);

SEQ ID NO:4 is an amino acid sequence of the capsid protein of the wild-type adeno-associated virus serotype 4 (AAV4);

SEQ ID NO:5 is an amino acid sequence of the capsid protein of the wild-type adeno-associated virus serotype 5 (AAV5);

SEQ ID NO:6 is an amino acid sequence of the capsid protein of the wild-type adeno-associated virus serotype 6 (AAV6);

SEQ ID NO:7 is an amino acid sequence of the capsid protein of the wild-type adeno-associated virus serotype 7 (AAV7);

SEQ ID NO:8 is an amino acid sequence of the capsid protein of the wild-type adeno-associated virus serotype 8 (AAV8);

SEQ ID NO:9 is an amino acid sequence of the capsid protein of the wild-type adeno-associated virus serotype 9 (AAV9);

SEQ ID NO:10 is an amino acid sequence of the capsid protein of the wild-type adeno-associated virus serotype 10 (AAV10);

SEQ ID NO:11 through SEQ ID NO:21 are oligonucleotide primer sequences useful in accordance with certain aspects of the present invention;

SEQ ID NO:22 is a nucleic acid sequence containing the putative binding site for NF-kB-responsive transcription factors (See FIG. 5);

SEQ ID NO:23 is a single-stranded nucleic acid sequence probe useful in accordance with certain aspects of the present invention (See FIG. 10);

SEQ ID NO:24 is a double-stranded nucleic acid sequence probe useful in accordance with certain aspects of the present invention (See FIG. 10);

SEQ ID NO:25 through SEQ ID NO:27 are oligonucleotide primer sequences useful in accordance with certain aspects of the present invention;

SEQ ID NO:28 is a single-stranded nucleic acid sequence TAMRA probe useful in accordance with certain aspects of the present invention; and SEQ ID NO:29 through SEQ ID NO:44 are oligonucleotide primer sequences useful in accordance with certain aspects of the present invention.

DESCRIPTION OF ILLUSTRATIVE EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would be a routine undertaking for those of ordinary skill in the art having the benefit of this disclosure.

Recombinant adeno-associated virus (AAV) vectors have been used successfully for in vivo gene transfer in numerous pre-clinical animal models of human disease, and have been used successfully for long-term expression of a wide variety of therapeutic genes (Daya and Berns, 2008; Niemeyer et al., 2009; Owen et al., 2002; Keen-Rhinehart et al., 2005; Scallan et al., 2003; Song et al., 2004). AAV vectors have also generated long-term clinical benefit in humans when targeted to immune-privileged sites, i.e., ocular delivery for Leber's congenital amaurosis (Bainbridge et al., 2008; Maguire et al., 2008; Cideciyan et al., 2008). A major advantage of this vector is its comparatively low immune profile, eliciting only limited inflammatory responses and, in some cases, even directing immune tolerance to transgene products (LoDuca et al., 2009). Nonetheless, the therapeutic efficiency, when targeted to non-immune privileged organs, has been limited in humans due to antibody and CD8+ T cell responses against the viral capsid, while in animal models, adaptive responses to the transgene product have also been reported (Manno et al., 2006; Mingozzi et al., 2007; Muruve et al., 2008; Vandenberghe and Wilson, 2007; Mingozzi and High, 2007). These results suggested that immune responses remain a concern for AAV vector-mediated gene transfer.

Based on pre-clinical data from murine models (Snyder et al., 1999), AAV was considered as minimally immunogenic for years, due to absence of prior exposure of these antigens in these models and the presence of variety of tolerance-inducing mechanisms against the vector (Dobrzynski et al., 2004; Cao et al., 2007). This was best illustrated in gene transfer studies in murine and canine models of hemophilia B, which showed remarkable therapeutic efficiency (5-25% of F.IX levels) and long-term (2-8 years) and stable F.IX expression (Snyder et al., 1999). In the first clinical trial using AAV to deliver the human F.IX gene to the liver in subjects with hemophilia B, therapeutic levels (~11.8%) of F.IX expression were observed at a high dose of vector ($2\times10^{12}$ vgs/kg body weight) (Manno et al., 2006).

However, 4-6 weeks after gene transfer, an AAV capsid-specific T cell response was observed that coincided with a rise in liver transaminases and a drop in F.IX transgene expression to baseline levels. This CD8+ T cell-mediated immune response was unexpected (Mingozzi et al., 2007), as this had not been observed in any pre-clinical animal models. This study and several others have implicated the host inflammatory and innate immune responses for cytotoxic T-lymphocyte mediated elimination of transduced hepatocytes (Zhu et al., 2009; Li et al., 2009; Madsen et al., 2009). Subsequently, a great deal of effort has been devoted to circumvent the host immune response to AAV vectors. These include the use of alternate naturally occurring AAV serotypes such as AAV1 (Brantly et al., 2009; Cohn et al., 2007) or AAV8 (Nathwani et al., 2006), the use of shuffled capsids (Gray et al., 2010), or surface-exposed tyrosine-mutant AAV2 (Markusic et al., 2010) vectors. In addition, strategies to counter the risks associated with the immune response have included the use of transgene constructs which have targeted expression in the host tissue (Wang et al., 2010), or the development of transient immune-suppression protocols (Jiang et al., 2006).

Although such strategies have incrementally improved the safety of AAV gene transfer, their efficacy in humans remains to be seen. For example, immune suppression with cyclosporine and MMF was effective at lower AAV1 vector dose ($3\times10^{11}$ vg/kg) but failed to prevent IFN-α CD8+ T cell responses against capsid at high doses ($1\times10^{12}$ vg/kg) during muscle-directed gene transfer in patients with lipoprotein lipase deficiency (Ross et al., 2006). These data underscore the importance of pursuing further studies on the biology of the virus-host cell interactions to identify the first "danger signal" in response to AAV infection. It was reasoned that understanding how the potential activity and the selectivity of proteins associated with inflammatory and innate immune response are regulated in host cells upon transduction with AAV might offer clues to address obstacles of the host immune response against the capsid and/or the transgene product. Although compared with other viral vectors, AAV vectors are inefficient in transducing professional APCs such as DCs, additional signals that activate NF-κB would lead to increased transgene expression in these cells, thereby increasing the risk of adaptive responses to the transgene product.

Recombinant vectors based on AAV serotype 2 are currently in use in a number of gene therapy clinical trials (Daya and Berns, 2008), and have recently shown remarkable efficacy in the treatment of Leber's congenital amaurosis (Bainbridge et al., 2008; Cideciyan et al., 2008; Maguire et al., 2008). However, concerns have been raised with reference to the humoral response to AAV2 vectors based on the high prevalence of sero-positivity in the general population (~80 to 90%) (Boutin et al., 2010; Mendell et al., 2012; Manno et al., 2006). The discovery of many novel AAV serotypes has prompted the development of AAV vectors to circumvent this potential problem (Muramatsu et al., 1996; Chiorini et al., 1997; Chiorini et al., 199; Rutledge et al., 1998; Gao et al., 2002; Gao et al., 2004).

For example, recombinant AAV8 vectors were recently reported to be therapeutic in a mouse model of liver cancer. (Kato et al., 2006) However, several groups have described various strategies to target human liver cancer cells in murine models using AAV2 vectors. (Su et al., 1996; Peng et al., 2000; Su et al., 2000; Ma et al., 2005; Wang et al., 2005; Tse et al., 2008; Zhang et al., 2008; Malecki et al., 2009; Wang et al.) To identify the most efficient AAV serotype to target human liver cancer cells, three different human liver cancer cell lines were shown to be transduced extremely efficiently by AAV3 vectors (Glushakova et al., 2009). Human hepatocyte growth factor receptor (hHGFR) was subsequently identified as a cellular co-receptor for AAV3 infection (Ling et al., 2010). However, the precise role of hHGFR, especially the role of tyrosine kinase activity associated with the intracellular domain of hHGFR, in AAV3-mediated transduction remained unclear. Data in Example 5, below, provide a more-detailed explanation of AAV3-hHGFR interactions, and demonstrate the development of optimized AAV3 vector for use in targeting human liver cancer cells.

RAAV Capsid Proteins

Supramolecular assembly of 60 individual capsid protein subunits into a non-enveloped, T-1 icosahedral lattice capable of protecting a 4.7-kb single-stranded DNA genome is a critical step in the life-cycle of the helper-dependent human parvovirus, adeno-associated virus2 (AAV2). The mature 20-nm diameter AAV2 particle is composed of three structural proteins designated VP1, VP2, and VP3 (molecular masses of 87-, 73-, and 62-kDa, respectively) in a ratio of 1:1:18. Based on its symmetry and these molecular weight estimates, of the 60 capsid proteins comprising the particle, three are VP1 proteins, three are VP2 proteins, and fifty-four are VP3 proteins. The employment of three structural proteins makes AAV serotypes unique among parvoviruses, as all others known package their genomes within icosahedral particles composed of only two capsid proteins. The anti-parallel β-strand barreloid arrangement of these 60 capsid proteins results in a particle with a defined tropism that is highly resistant to degradation. Modification of one or more tyrosine residues in one or more of the capsid proteins has been shown by the inventors to achieve superior transfection at lower dose and lower cost than conventional protocols. By site-specifically modifying one or more tyrosine residues on the surface of the capsid, the inventors have achieved significant improvement in transduction efficiency.

Uses for Improved, Capsid-Modified RAAV Vectors

The present invention provides compositions including one or more of the disclosed tyrosine-modified rAAV vectors comprised within a kit for diagnosing, preventing, treating or ameliorating one or more symptoms of a mammalian disease, injury, disorder, trauma or dysfunction. Such kits may be useful in diagnosis, prophylaxis, and/or therapy, and particularly useful in the treatment, prevention, and/or amelioration of one or more symptoms of cancer, diabetes, autoimmune disease, kidney disease, cardiovascular disease, pancreatic disease, intestinal disease, liver disease, neurological disease, neuromuscular disorder, neuromotor deficit, neuroskeletal impairment, neurological disability, neurosensory dysfunction, stroke, ischemia, eating disorder, $\alpha_1$-antitrypsin (AAT) deficiency, Batten's disease, Alzheimer's disease, sickle cell disease, β-thalassemia, β-globin deficiency, Huntington's disease, Parkinson's disease, skeletal disease, pulmonary disease, injury, trauma, or any combination thereof.

The invention also provides for the use of a composition disclosed herein in the manufacture of a medicament for treating, preventing or ameliorating the symptoms of a disease, disorder, dysfunction, injury or trauma, including, but not limited to, the treatment, prevention, and/or prophylaxis of a disease, disorder or dysfunction, and/or the amelioration of one or more symptoms of such a disease, disorder or dysfunction. Exemplary conditions for which rAAV viral based gene therapy may find particular utility include, but are not limited to, cancer, diabetes, sickle cell disease, β-thalassemia, autoimmune disease, kidney disease, cardiovascular disease, pancreatic disease, diseases of the eye, intestinal disease, liver disease, neurological disease, neuromuscular disorder, neuromotor deficit, neuroskeletal impairment, neurological disability, neurosensory dysfunction, stroke, $\alpha_1$-antitrypsin (AAT) deficiency, Batten's disease, ischemia, an eating disorder, Alzheimer's disease, Huntington's disease, Parkinson's disease, skeletal disease, pulmonary disease, and any combinations thereof.

The invention also provides a method for treating or ameliorating the symptoms of such a disease, injury, disorder, or dysfunction in a mammal. Such methods generally involve at least the step of administering to a mammal in need thereof, one or more of the tyrosine-modified rAAV vectors as disclosed herein, in an amount and for a time sufficient to treat or ameliorate the symptoms of such a disease, injury, disorder, or dysfunction in the mammal.

Such treatment regimens are particularly contemplated in human therapy, via administration of one or more compositions either intramuscularly, intravenously, subcutaneously, intrathecally, intraperitoneally, or by direct injection into an organ or a tissue of the mammal under care.

The invention also provides a method for providing to a mammal in need thereof, a therapeutically-effective amount of the rAAV compositions of the present invention, in an amount, and for a time effective to provide the patient with a therapeutically-effective amount of the desired therapeutic agent(s) encoded by one or more nucleic acid segments comprised within the rAAV vector. Preferably, the therapeutic agent is selected from the group consisting of a polypeptide, a peptide, an antibody, an antigen-binding fragment, a ribozyme, a peptide nucleic acid, an siRNA, an RNAi, an antisense oligonucleotide, an antisense polynucleotide, a diagnostic marker, a diagnostic molecule, a reporter molecule, and any combination thereof.

AAV Vector Compositions

One important aspect of the present methodology is the fact that the improved rAAV vectors described herein permit the delivery of smaller titers of viral particles in order to achieve the same transduction efficiency as that obtained using higher levels of conventional, non-surface capsid modified rAAV vectors. To that end, the amount of AAV compositions and time of administration of such compositions will be within the purview of the skilled artisan having benefit of the present teachings. In fact, the inventors contemplate that the administration of therapeutically-effective amounts of the disclosed compositions may be achieved by a single administration, such as for example, a single injection of sufficient numbers of infectious particles to provide therapeutic benefit to the patient undergoing such treatment. Alternatively, in some circumstances, it may be desirable to provide multiple, or successive administrations of the AAV vector compositions, either over a relatively short, or over a relatively prolonged period, as may be determined by the medical practitioner overseeing the administration of such compositions. For example, the number of infectious particles administered to a mammal may be approximately $10^7$, $10^8$, $10^9$, $10^{10}$, $10^{11}$, $10^{12}$, $10^{13}$, or even higher, infectious particles/mL, given either as a single dose (or divided into two or more administrations, etc.) as may be required to achieve therapy of the particular disease or disorder being treated. In fact, in certain embodiments, it may be desirable to administer two or more different rAAV vector-based compositions, either alone, or in combination with one or more other diagnostic agents, drugs, bioactives, or such like, to achieve the desired effects of a particular regimen or therapy. In most rAAV-vectored, gene therapy-based regimens, the inventors contemplate that lower titers of infectious particles will be required when using the modified-capsid rAAV vectors described herein, as compared to the use of equivalent wild-type, or corresponding "un-modified" rAAV vectors.

As used herein, the terms "engineered" and "recombinant" cells are intended to refer to a cell into which an exogenous polynucleotide segment (such as DNA segment that leads to the transcription of a biologically active molecule) has been introduced. Therefore, engineered cells are distinguishable from naturally occurring cells, which do not contain a recombinantly introduced exogenous DNA segment. Engineered cells are, therefore, cells that comprise at least one or more heterologous polynucleotide segments introduced through the hand of man.

To express a therapeutic agent in accordance with the present invention one may prepare a tyrosine-modified rAAV expression vector that comprises a therapeutic agent-encoding nucleic acid segment under the control of one or more promoters. To bring a sequence "under the control of" a promoter, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded polypeptide. This is the meaning of "recombinant expression" in this context. Particularly preferred recombinant vector constructs are those that comprise an rAAV vector. Such vectors are described in detail herein.

When the use of such vectors is contemplated for introduction of one or more exogenous proteins, polypeptides, peptides, ribozymes, and/or antisense oligonucleotides, to a particular cell transfected with the vector, one may employ the capsid-modified rAAV vectors disclosed herein to deliver one or more exogenous polynucleotides to a selected host cell.

Pharmaceutical Compositions

The genetic constructs of the present invention may be prepared in a variety of compositions, and may be formulated in appropriate pharmaceutical vehicles for administration to human or animal subjects. The rAAV molecules of the present invention and compositions comprising them provide new and useful therapeutics for the treatment, control, and amelioration of symptoms of a variety of disorders, and in particular, articular diseases, disorders, and dysfunctions, including for example osteoarthritis, rheumatoid arthritis, and related disorders.

The invention also provides compositions comprising one or more of the disclosed capsid-modified rAAV vectors, expression systems, virions, viral particles, mammalian cells, or combinations thereof. In certain embodiments, the present invention provides pharmaceutical formulations of one or more capsid-modified rAAV vectors disclosed herein for administration to a cell or an animal, either alone or in combination with one or more other modalities of therapy, and in particular, for therapy of human cells, tissues, and diseases affecting man. Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, intra-articular, intramuscular administration and formulation.

Exemplary Definitions

Unless defined otherwise, all technical and scientific terms used herein have the same meaning as commonly understood by one of ordinary skill in the art to which this invention belongs. Although any methods and compositions similar or equivalent to those described herein can be used in the practice or testing of the present invention, the preferred methods and compositions are described herein. For purposes of the present invention, the following terms are defined below:

In accordance with the present invention, polynucleotides, nucleic acid segments, nucleic acid sequences, and the like, include, but are not limited to, DNAs (including and not limited to genomic or extragenomic DNAs), genes, peptide nucleic acids (PNAs) RNAs (including, but not limited to, rRNAs, mRNAs and tRNAs), nucleosides, and suitable nucleic acid segments either obtained from natural sources, chemically synthesized, modified, or otherwise prepared or synthesized in whole or in part by the hand of man.

The term "effective amount," as used herein, refers to an amount that is capable of treating or ameliorating a disease or condition or otherwise capable of producing an intended therapeutic effect.

As used herein, the terms "engineered" and "recombinant" cells are intended to refer to a cell into which an exogenous polynucleotide segment (such as DNA segment that leads to the transcription of a biologically active molecule) has been introduced. Therefore, engineered cells are distinguishable from naturally occurring cells, which do not contain a recombinantly introduced exogenous DNA segment. Engineered cells are, therefore, cells that comprise at least one or more heterologous polynucleotide segments introduced through the hand of man.

The term "effective amount," as used herein, refers to an amount that is capable of treating or ameliorating a disease or condition or otherwise capable of producing an intended therapeutic effect.

The term "operably linked," as used herein, refers to that the nucleic acid sequences being linked are typically contiguous, or substantially contiguous, and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

Polypeptide", as used herein, refers to a polymer of amino acids and/or amino acid analogs that may or may not be modified. Various amino acid analogs and modifications are described herein. A polypeptide may be cyclic or linear and may be branched or unbranched. The term "amino acid sequence" or "polypeptide sequence" as used herein can refer to the polypeptide material itself and is not restricted to the sequence information (i.e. the succession of letters or three letter codes chosen among the letters and codes used as abbreviations for amino acid names) that biochemically characterizes a polypeptide. For purposes of the disclosure the use of the term "polypeptide" and "protein" are interchangeable unless specifically noted otherwise.

The term "promoter," as used herein refers to a region or regions of a nucleic acid sequence that regulates transcription.

"Purified," as used herein, means separated from many other compounds or entities. A compound or entity may be partially purified, substantially purified, or pure. A compound or entity is considered pure when it is removed from substantially all other compounds or entities, i.e., is preferably at least about 90%, more preferably at least about 91%, 92%, 93%, 94%, 95%, 96%, 97%, 98%, 99%, or greater than 99% pure. A partially or substantially purified compound or entity may be removed from at least 50%, at least 60%, at least 70%, or at least 80% of the material with which it is naturally found, e.g., cellular material such as cellular proteins and/or nucleic acids.

The term "regulatory element," as used herein, refers to a region or regions of a nucleic acid sequence that regulates transcription. Exemplary regulatory elements include, but are not limited to, enhancers, post-transcriptional elements, transcriptional control sequences, and such like.

The term "subject," as used herein, describes an organism, including mammals such as primates, to which treatment with the compositions according to the present invention can be provided. Mammalian species that can benefit from the disclosed methods of treatment include, but are not limited to, apes; chimpanzees; orangutans; humans; monkeys; domesticated animals such as dogs and cats; livestock such as horses, cattle, pigs, sheep, goats, and chickens; and other animals such as mice, rats, guinea pigs, and hamsters.

The term "substantially corresponds to," "substantially homologous," or "substantial identity," as used herein, denote a characteristic of a nucleic acid or an amino acid sequence, wherein a selected nucleic acid or amino acid sequence has at least about 70 or about 75 percent sequence identity as compared to a selected reference nucleic acid or amino acid sequence. More typically, the selected sequence and the reference sequence will have at least about 76, 77, 78, 79, 80, 81, 82, 83, 84 or even 85 percent sequence identity, and more preferably, at least about 86, 87, 88, 89, 90, 91, 92, 93, 94, or 95 percent sequence identity. More preferably still, highly homologous sequences often share greater than at least about 96, 97, 98, or 99 percent sequence identity between the selected sequence and the reference sequence to which it was compared.

The percentage of sequence identity may be calculated over the entire length of the sequences to be compared, or may be calculated by excluding small deletions or additions which total less than about 25 percent or so of the chosen reference sequence. The reference sequence may be a subset of a larger sequence, such as a portion of a gene or flanking sequence, or a repetitive portion of a chromosome. However, in the case of sequence homology of two or more polynucleotide sequences, the reference sequence will typically comprise at least about 18-25 nucleotides, more typically at least about 26 to 35 nucleotides, and even more typically at least about 40, 50, 60, 70, 80, 90, or even 100 or so nucleotides.

When highly-homologous fragments are desired, the extent of percent identity between the two sequences will be at least about 80%, preferably at least about 85%, and more preferably about 90% or 95% or higher, as readily determined by one or more of the sequence comparison algorithms well-known to those of skill in the art, such as e.g., the FASTA program analysis described by Pearson and Lipman (1988).

The term "treatment" or any grammatical variation thereof (e.g., treat, treating, and treatment, etc.), as used herein, includes but is not limited to, alleviating a symptom of a disease or condition; and/or reducing, suppressing, inhibiting, lessening, ameliorating or affecting the progression, severity, and/or scope of a disease or condition.

The term "vector," as used herein, refers to a nucleic acid molecule (typically comprised of DNA) capable of replication in a host cell and/or to which another nucleic acid segment can be operatively linked so as to bring about replication of the attached segment. A plasmid, cosmid, or a virus is an exemplary vector.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Next Generation RAAV2 Vectors: Point Mutations in Tyrosines Lead to High-Efficiency Transduction at Lower Doses The present example demonstrates that mutations of surface-exposed tyrosine residues on AAV2 capsids circumvents the ubiquitination step, thereby avoiding proteasome-mediated degradation, and resulting in high-efficiency transduction by these vectors in human cells in vitro and murine hepatocytes in vivo, leading to the production of therapeutic levels of human coagulation factor at reduced vector doses. The increased transduction efficiency observed for tyrosine-mutant vectors is due to lack of ubiquitination, and improved intracellular trafficking to the nucleus. In addition to yielding insights into the role of tyrosine phosphorylation of AAV2 capsid in various steps in the life cycle of AAV2, these studies have resulted in the development of novel AAV2 vectors that are capable of high-efficiency transduction at lower doses.

Materials and Methods

Recombinant AAV2 Vectors. Highly purified stocks of scAAV2 vectors containing the enhanced green fluorescence protein (EGFP) gene driven by the chicken β-actin (CBA) promoter (scAAV2-EGFP), and ssAAV2 vectors containing the factor IX (F.IX) gene under the control of the apolipoprotein enhancer/human α-1 antitrypsin (ApoE/hAAT) promoter (ssAAV2-F.IX) were generated using published methods.

Localization of Surface-Tyrosines on the AAV2 Capsid. The crystal structure of AAV2 (PDB accession number 1lp3) was used to localize the tyrosine residues on the AAV2 capsid surface. The icosahedral two-, three- and five-fold related VP3 monomers were generated by applying icosahedral symmetry operators to a reference monomer using Program O on a Silicon graphics Octane workstation. The position of the tyrosine residues were then visualized and analyzed in the context of a viral asymmetric unit using the program COOT, and graphically presented using the program PyMOL Molecular Graphics System (DeLano Scientific, San Carlos, Calif., USA).

Construction of Surface-Exposed Tyrosine Residue Mutant AAV2 Capsid Plasmids. A two-stage procedure, based on QuikChange II® site-directed mutagenesis (Stratagene, La Jolla, Calif., USA) was performed using plasmid pACG-2. Briefly, in stage one, two PCR extension reactions were performed in separate tubes for each mutant. One tube contained the forward PCR primer and the other contained the reverse primer. In stage two, the two reactions were mixed and a standard PCR mutagenesis assay was carried out as per the manufacturer's instructions. PCR primers were designed to introduce changes from tyrosine to phenylalanine residues as well as a silent change to create a new restriction endonuclease site for screening purposes. All mutants were screened with the appropriate restriction enzyme and were sequenced prior to use.

Preparation of Whole Cell Lysates (WCL) and Co-Immunoprecipitations. Approximately $2 \times 10^6$ HeLa cells, mock-treated or treated with MG132, were also subjected to mock-infection or infection with the WT scAAV2-EGFP or Y730F mutant vectors at $5 \times 10^3$ particles/cell for 2 hr at 37° C. For immunoprecipitations, cells were treated with 0.01% trypsin and washed extensively with PBS. WCL were cleared of non-specific binding by incubation with 0.25 mg of normal mouse IgG together with 20 [1 of protein G-agarose beads. After preclearing, 2 µg of capsid antibody against intact AAV2 particles (mouse monoclonal IgG3, clone A20; Research Diagnostics, Inc. (Flanders, N.J., USA), or 2 µg of normal mouse IgG (as a negative control) were added and incubated at 4° C. for 1 hr, followed by precipitation with protein G-agarose beads. For immunoprecipitations, resuspended pellet solutions were used for SDS-PAGE. Membranes were treated with monoclonal HRP-conjugated anti-Ub antibody (1:2,000 dilution) specific for ubiquitin (Ub) (mouse monoclonal immunoglobulin $G_1$ γIgG$_1$], clone P4D1; Santa Cruz, Calif., USA). Immunoreactive bands were visualized using chemiluminescence (ECL-plus, Amersham Pharmacia Biotech, Piscataway, N.J., USA).

Isolation of Nuclear and Cytoplasmic Fractions from HeLa Cells. Nuclear and cytoplasmic fractions from HeLa cells were isolated and mock-infected or recombinant wt scAAV2-EGFP or Y700F vector-infected cells were used to isolate the cytoplasmic and nuclear fractions. The purity of each fraction was determined to be >95%.

Southern Blot Analysis for AAV2 Trafficking. Low-$M_r$ DNA samples from nuclear and cytoplasmic fractions were isolated and electrophoresed on 1% agarose gels or 1% alkaline-agarose gels followed by Southern blot hybridization using a $^{32}$P-labeled EGFP-specific DNA probe.

Recombinant AAV2 Vector Transduction Assays in Vitro. Approximately $1 \times 10^5$ HeLa cells were used for transductions with recombinant AAV2 vectors. The transduction efficiency was measured 48-hr post-transduction by EGFP imaging using fluorescence microscopy. Images from three to five visual fields were analyzed quantitatively by ImageJ analysis software (NIH, Bethesda, Md., USA). Transgene expression was assessed as total area of green fluorescence (pixel$^2$) per visual field (mean±SD). Analysis of variance (ANOVA) was used to compare between test results and the control and they were determined to be statistically significant.

Recombinant AAV2 Vector Transduction Studies in Vivo. scAAV2-EGFP vectors were injected intravenously via the tail vein into C57BL/6 mice at $1 \times 10^{10}$ virus particles per animal. Liver sections from three hepatic lobes of the mock-injected and injected mice 2 weeks after injection were mounted on slides. The transduction efficiency was measured by EGFP imaging as described. ssAAV2-FI.X vectors were injected intravenously (via the tail vein) or into the portal vein of C57BL/6, BALB/c, and C3H/HeJ mice at $1 \times 10^{10}$ or $1 \times 10^{11}$ virus particles per animal. Plasma samples were obtained by retro-orbital bleed and analyzed for hF.IX expression by ELISA.

Results

Mutations in Surface-Exposed Tyrosine Residues Significantly Improve Transduction Efficiency of AAV2 Vectors. To demonstrate that tyrosine-phosphorylation of AAV2 capsids leads to increased ubiquitination and results in impaired intracellular trafficking, and is therefore unfavorable to viral transduction, surface-exposed tyrosine residues were modified on AAV2 capsids. Inspection of the capsid surface of the AAV2 structure revealed seven surface-exposed tyrosine residues (Y252, Y272, Y444, Y500, Y700, Y704, and Y730). Site-directed mutagenesis was performed for each of the seven tyrosine residues, which were conservatively substituted with phenylalanine residues (tyrosine-phenylalanine, Y-F) (Table 1). scAAV2-EGFP genomes encapsidated in each of the tyrosine-mutant capsids were successfully packaged, and mutations of the surface-exposed tyrosine residues did not lead to reduced vector stability.

TABLE 1

Titers of Wildtype (WT) and Tyrosine-Modified (Y-F Mutants) AAV2 Vectors

| AAV Vectors | $1^{st}$ packaging titers (vgs/mL) | $2^{nd}$ packaging titers (vgs/mL) | $3^{rd}$ packaging titers (vgs/mL) | $4^{th}$ packaging titers (vgs/mL) |
|---|---|---|---|---|
| WT scAAV2-EGFP | $3.4 \times 10^{11}$ | $1.0 \times 10^{12}$ | $3.2 \times 10^{11}$ | $3.0 \times 10^{11}$ |
| Y252F scAAV2-EGFP | $3.8 \times 10^{11}$ | $4.0 \times 10^{11}$ | ND | ND |
| Y272 scAAV2-EGFP | $7.7 \times 10^{11}$ | $1.0 \times 10^{11}$ | ND | ND |
| Y444F scAAV2-EGFP | $9.7 \times 10^{10}$ | $4.0 \times 10^{10}$ | $6.0 \times 10^{9}$ | $5.0 \times 10^{10}$ |
| Y500F scAAV2-EGFP | $8.8 \times 10^{10}$ | $2.0 \times 10^{9}$ | $4.0 \times 10^{10}$ | $6.0 \times 10^{10}$ |
| Y700F scAAV2-EGFP | $1.0 \times 10^{11}$ | $4.0 \times 10^{11}$ | ND | ND |
| Y704F scAAV2-EGFP | $6.0 \times 10^{11}$ | $2.0 \times 10^{11}$ | ND | ND |
| Y730F scAAV2-EGFP | $1.2 \times 10^{11}$ | $5.0 \times 10^{11}$ | $1.2 \times 10^{11}$ | $4.0 \times 10^{11}$ |

ND = Not done.

The transduction efficiency of each of the tyrosine-mutant vectors was analyzed and compared with the WT scAAV2-EGFP vector in HeLa cells in vitro under identical conditions. From the results, it was evident that whereas mock-infected cells showed no green fluorescence, the transduction efficiency of each of the tyrosine-mutant vectors was significantly higher compared with the WT scAAV2-EGFP vector at 2,000 viral particles/cell. Specifically, the transduction efficiency of Y444F, Y500F, Y730F vectors was ~8- to 11-fold higher than the WT vector.
Mutations in Surface-Exposed Tyrosine Residues Dramatically Improve Transduction Efficiency of AAV2 Vectors in Murine Hepatocytes In Vivo The efficacy of WT and tyrosine-mutant scAAV2-EGFP vectors was also evaluated in a mouse model in vivo. The transduction efficiency of tyrosine-mutant vectors was significantly higher, and ranged between 4-29-fold, compared with the WT vector. When other tissues, such as heart, lung, kidney, spleen, pancreas, GI tract (jejunum, colon), testis, skeletal muscle, and brain were harvested from mice injected with $1 \times 10^{10}$ particles of the tyrosine-mutant vectors and analyzed, no evidence of EGFP gene expression was seen. Thus, mutations in the surface-exposed tyrosine residues did not appear to alter the liver-tropism following tail vein injection of these vectors in vivo.
Increased Transduction Efficiency of Tyrosine-Mutant Vectors is Due to Lack of Ubiquitination, and Improved Intracellular Trafficking to the Nucleus To further confirm the hypothesis that EGFR-PTK-mediated phosphorylation of capsid proteins at tyrosine residues is a pre-requisite for ubiquitination of AAV2 capsids, and that ubiquitinated virions are recognized and degraded by cytoplasmic proteasome on their way to the nucleus, leading to inefficient nuclear transport, a series of experiments were performed as follows.

In the first study, HeLa C12 cells, carrying adenovirus-inducible AAV2 rep and cap genes, were mock infected, or infected with WT, Y444F or Y730F scAAV2-EGFP vectors. Whereas mock-infected cells showed no green fluorescence, and ~15% of cells were transduced with the WT scAAV2-EGFP vectors in the absence of co-infection with adenovirus, the transduction efficiency of Y444F and Y730F scAAV2-EGFP vectors was increased by ~9 and ~18-fold, respectively, compared with the WT vector. Interestingly, whereas co-infection with adenovirus led to ~11-fold increase, the transduction efficiency of Y444F and Y730F scAAV2-EGFP vectors was not further enhanced by co-infection with adenovirus. Since adenovirus can improve AAV2 vector nuclear transport in HeLa cells, these data suggested that the surface-exposed tyrosine residues play a role in intracellular trafficking of AAV2, and that their removal leads to efficient nuclear transport of AAV2 vectors.

In a second study, HeLa cells, either mock-treated or treated with Tyr23, a specific inhibitor of EGFR-PTK, or MG132, a proteasome inhibitor, both known to increase the transduction efficiency of AAV vectors, were mock-infected or infected with the WT or Y730F scAAV2-EGFP vectors. Whereas mock-infected cells showed no green fluorescence, and ~5% of cells were transduced with the WT scAAV2-EGFP vectors in mock-treated cells, pretreatment with Tyr23 or MG132 led to an ~9-fold and ~6-fold increase in the transduction efficiency, respectively. Although the transduction efficiency of Y730F scAAV2-EGFP vectors was increased by ~14-fold compared with the WT vectors, it was not further enhanced by pretreatment with either Tyr23 or MG132. These data strongly suggest that the absence of surface-exposed tyrosine residues, which prevented phosphorylation of the mutant vectors, likely prevented ubiquitination of the capsid proteins, and these vectors could not be recognized on their way to the nucleus and degraded by the proteasome, which led to their efficient nuclear translocation.

In a third study, HeLa cells, either mock-treated or treated with MG132, were mock-infected or infected with the WT, Y730F, or Y444F scAAV2-EGFP vectors. WCL were prepared 4 hrs post-infection and equivalent amounts of proteins were immunoprecipitated first with anti-AAV2 capsid antibody (A20) followed by Western blot analyses with anti-Ub monoclonal antibody. Whereas ubiquitinated AAV2 capsid proteins (Ub-AAV2 Cap) were undetectable in mock-infected cells, the signal of ubiquitinated AAV2 capsid proteins was weaker in untreated cells, and a significant accumulation of ubiquitinated AAV2 capsid proteins occurred following treatment with MG132. Interestingly, infections with Y730F or Y444F vectors dramatically decreased the extent of accumulation of MG132-induced ubiquitinated AAV2 capsid proteins. These results substantiate that mutation in tyrosine residues circumvents proteasome-mediated degradation of the vectors.

In a fourth study, the fate of the input WT, Y444F, and Y730F vector viral DNA was determined in HeLa cells. Southern blot analysis of low-$M_r$ DNA samples isolated from cytoplasmic [C] and nuclear [N] fractions and densitometric scanning of autoradiographs, revealed that ~36% of the input scAAV2 DNA was present in the nuclear fraction in cells infected with the WT vector. Interestingly, however, the amount of input Y730F and Y444F scAAV2 vector DNA in the nuclear fraction was increased to ~72% and ~70%, respectively. These results further documented that mutations in the surface-exposed tyrosine residues prevent ubiquitination of AAV2 capsids, resulting in a decrease of proteasome-mediated degradation, and in turn, facilitate nuclear transport of AAV2 vectors.

Tyrosine-Mutant Vectors Express Therapeutic Levels of Human Factor IX Protein at ~10-Fold Reduced Vector Dose in Mice It was important to examine whether tyrosine-mutant AAV2 vectors were capable of delivering a therapeutic gene efficiently at a reduced vector dose in vivo. To this end, a single-stranded, hepatocyte-specific human Factor IX (h.FIX) expression cassette was encapsidated in the Y730F vector, and the efficacy of this vector was tested in three different strains of mice (BALB/c, C3H/HeJ, and C57BL/6). Consistently in all three strains, Y730F vector achieved ~10-fold higher circulating hF.IX levels compared with the WT vector following tail vein or portal vein administration, with the latter being the more effective route. These results clearly indicated that the Y730F vectors expressed therapeutic levels of human F.IX protein (~50 ng/mL) at ~10-fold reduced vector dose ($10^{10}$ particles/mouse) in C57BL/6 mice by port vein injection. It should be noted that hepatic viral gene transfer in C57BL/6 mice is generally more efficient than in the other two strains.

These results demonstrated here are consistent with the interpretation that EGFR-PTK-induced tyrosine phosphorylation of AAV2 capsid proteins promotes ubiquitination and degradation of AAV2, thus leading to impairment of viral nuclear transport and decrease in transduction efficiency. Mutational analyses of each of the seven surface-exposed tyrosine residues yield AAV2 vectors with significantly increased transduction efficiency in vitro as well as in vivo. Specifically, Y444F and Y730F mutant vectors bypass the ubiquitination step, which results in a significantly improved intracellular trafficking and delivery of the viral genome to the nucleus.

Despite long-term therapeutic expression achieved in preclinical animal models by AAV2 vectors composed of the WT capsid proteins, in a recent gene therapy trial, two patients with severe hemophilia B developed vector dose-dependent transaminitis that limited duration of hepatocyte-derived hF.IX expression to <8 weeks. Subsequent analyses demonstrated presence of memory CD8$^+$ T cells to AAV capsids in humans and an MHC I-restricted, capsid-specific cytotoxic T lymphocyte (CTL) response in one of the hemophilia B patients, which mirrored the time course of the transaminitis. It was concluded that this CD8$^+$ T cell response to input capsid eliminated AAV2-transduced hepatocytes. These data demonstrated that a lower capsid antigen dose is sufficient for efficient gene transfer with the Y730F vector, and show much-reduced ubiquitination of AAV-Y730F compared to WT capsid, a prerequisite for MHC I presentation. Thus, the T-cell response to AAV2 capsid (a serious hurdle for therapeutic gene transfer in the liver), may be avoided by using the surface-exposed tyrosine-mutant AAV2 vectors.

Dramatically increased transduction efficiency of tyrosine-mutant vectors have also been observed in primary human neuronal and hematopoietic stem cells in vitro and in various tissues and organs in mice in vivo. Double, triple, and quadruple tyrosine-mutants have also been constructed to examine whether such multiple mutants are viable, and whether the transduction efficiency of these vectors can be augmented further. It is noteworthy that with a few exceptions (Y444 positioned equivalent to a glycine in AAV5; Y700 positioned equivalent to phenylalanine in AAV4 and AAV5; and Y704 positioned equivalent to a phenylalanine in AAV7), these tyrosine residues are highly conserved in AAV serotypes 1 through 10.

Example 2—Activation of the NF-κB Pathway by RAAV Vectors

Since the in silico analysis with human transcription factor database demonstrated the presence of several binding sites for NF-κB, a central regulator of cellular immune and inflammatory responses, in the adeno-associated virus (AAV) genome, the present example investigates whether AAV utilizes NF-κB during its life cycle. Small molecule modulators of NF-κB were used in HeLa cells transduced with recombinant AAV vectors. VP16, an NF-κB activator, augmented AAV vector-mediated transgene expression up to 25-fold. Of the two NF-κB inhibitors (Bay11), which blocks both the canonical and the non-canonical NF-κB pathways, totally ablated the transgene expression, whereas pyrrolidone dithiocarbamate (PDTC), which interferes with the classical NF-κB pathway, had no effect. Western blot analyses confirmed the abundance of the nuclear p52 protein component of the non-canonical NF-κB pathway in the presence of VP16, which was ablated by Bay11, suggesting that the non-canonical NF-κB pathway is triggered during AAV infection. Similar results were obtained with primary human dendritic cells (DCs) in vitro, in which cytokines-induced expression of DC maturation markers, CD83 and CD86, was also inhibited by Bay11. Administration of Bay11 prior to gene transfer in normal C57BL/6 mice in vivo resulted in up to 7-fold decrease in AAV vector-induced production of pro-inflammatory cytokines and chemokines such as, IL-1β, IL-6, TNFα, IL-12β, KC, and RANTES. These studies suggested that transient immuno-suppression with NF-κB inhibitors prior to transduction with AAV vectors leads to a dampened immune response, which has significant implications in the optimal use of AAV vectors in human gene therapy.

Recent studies have begun to define the initial activation signals that result from AAV gene transfer. One study found AAV-induced signaling through the Toll-like receptor 9 (TLR9)-myeloid differentiation factor 88 (MyD88) pathway to induce a type I interferon response in plasmacytoid dendritic cells (pDCs), thereby driving subsequent adaptive immune responses to the vector and transgene product upon gene transfer to murine skeletal muscle (Zhu et al., 2009). These data indicate sensing of the DNA genome by the endosomal TLR9 receptor in pDCs. No evidence for induction of pro-inflammatory cytokines following in vitro pulsing of DCs or macrophages with AAV was found. Still, earlier reports demonstrated a rapid, albeit highly transient, Kupffer cell-dependent innate response to AAV vectors in the liver, which included expression of several inflammatory cytokines (Zaiss and Muruve, 2008; Zaiss et al., 2008; Zaiss and Muruve, 2005; Zaiss et al., 2002).

Interestingly, the role of NF-κB, a key cellular responder to many stress- and pathogen-derived signals and regulator of pro-inflammatory cytokine expression (Hayden and Ghosh, 2004; Hiscott et al., 2006; Li and Verma, 2002), has not been previously studied in the AAV life cycle. In this example, it is shown that infection of human cells with AAV can lead to activation of the non-canonical NF-κB pathway. In addition, activation of NF-κB substantially increases transgene expression (including in DCs), while inhibition of NF-κB blunts expression. Prevention of inflammatory cytokine induction by transient inhibition of NF-κB reveals a role for NF-κB in the innate response to AAV in vivo, and importantly, does not interfere with long-term transgene expression.

Results

AAV-ITRS Contain Binding Sites for NF-κB-Responsive Transcription Factors

The existence of a cellular protein which interacts specifically with the single-stranded D[−]-sequence in the left inverted terminal repeat (ITR) of the AAV2 genome has been previously described (Qing et al., 1997). Since the ssD[+]-sequence in the right ITR is complementary to the ssD[−]-sequence in the left ITR, it was reasoned that a putative cellular protein might also exist, and interact with the ssD[+]-sequence in the right ITR. In electrophoretic mobility-shift assays, using the ssD[+]-sequence probe, a distinct cellular protein was indeed detected, which was designated as ssD[+]-sequence binding protein (ssD[+]-BP) (Qing et al., 1997). Following purification and mass spectrometry, ssD[+]-BP was found to have partial amino acid homology to a cellular NF-κB repressing factor, a negative regulator of transcription. Additional in silico analysis with human transcription factor database [TRANSFAC, algen.lsi.upc.es/] demonstrated the presence of several binding sites for NF-κB binding co-factors, such as p300, TFIIB, and SplI. One of these is the p300/CREB transcription factor that has been recently shown to be associated with the AAV genome (Dean et al., 2009). Although it is not known whether the NF-κB signaling is activated by AAV binding to the cell surface receptors/co-receptors, recent studies have demonstrated that the innate immune response could be triggered either a) through the Toll like receptor 9 (TLR9)-myeloid differentiation factor 88 (MYD88) pathway, or b) through the activation of the CD40 ligand on the cell surface in mouse models in vivo (Zhu et al., 2009; Mays et al., 2009). Both of these ligands are known to interact downstream with NF-κB transcription factors during their biological activation (Mineva et al., 2007; Loiarro et al., 2005). The following data demonstrated that the NF-κB is involved in the AAV life cycle.

AAV Infection Activates Non-Canonical NF-κB Pathway in Human Cells

Figure 6A:
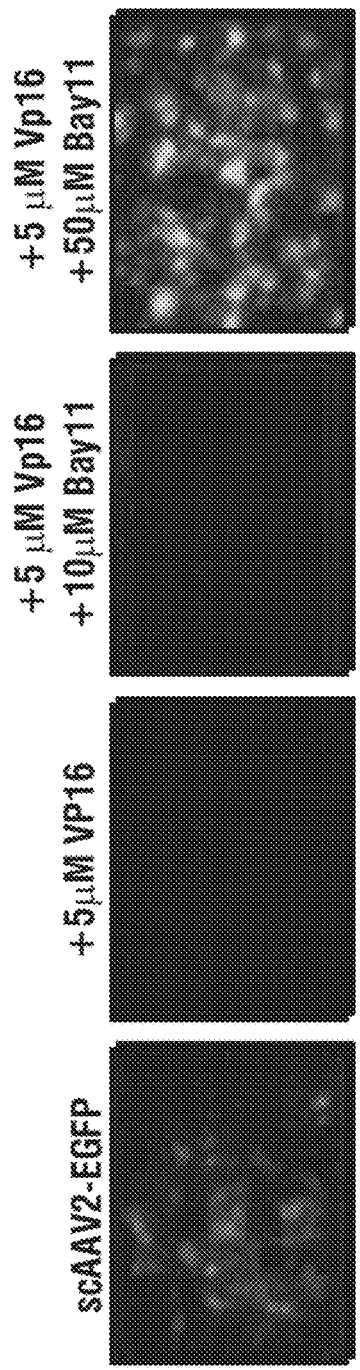
Figure 6B:
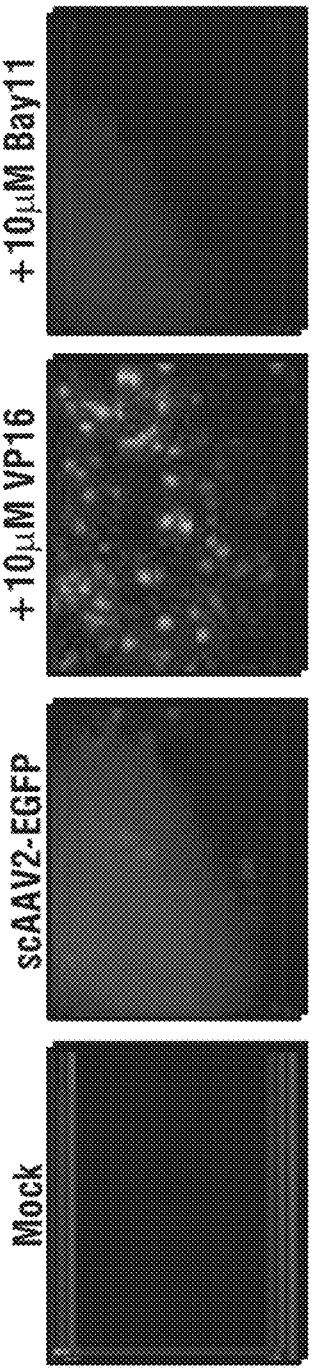
Figure 6C:
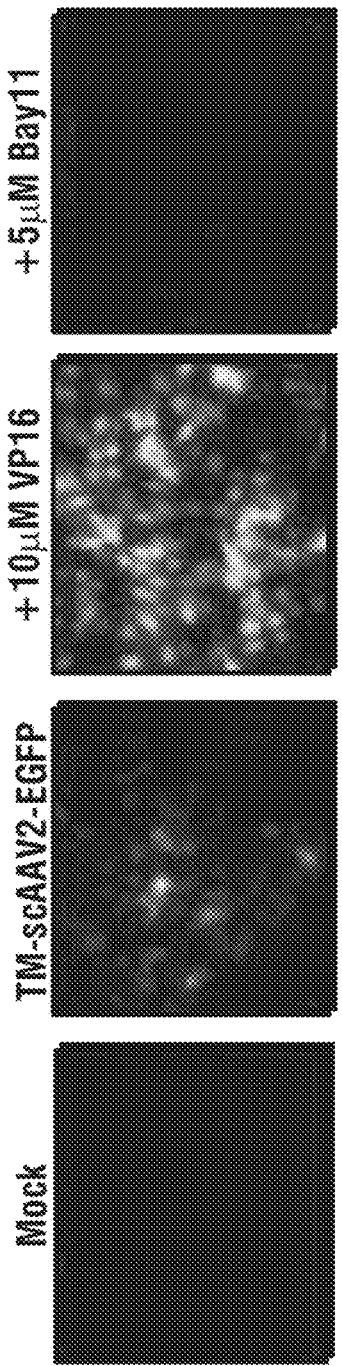

Small molecule activators and inhibitors of NF-κB signaling were used in HeLa cells transduced with a self-complementary serotype 2 vector expressing EGFP (scAAV-EGFP). VP16, an NF-κB activator (Wu and Miyamoto, 2008), augmented EGFP expression by ~25-fold (FIG. 1A and FIG. 1B). Between the two inhibitors tested, Bay11, that blocks the activity of both IKKκ and IKKκ, totally ablated EGFP expression, whereas PDTC, which inhibits IKB degradation by blocking IKB ubiquitin ligase in the classical pathway (Cuzzocrea et al., 2002), had no noticeable effect on EGFP expression (FIG. 1A and FIG. 1B). Furthermore, VP16-mediated augmented transgene expression was completely ablated by Bay11, but not by PDTC (FIG. 6A). Similar results were obtained with both ssAAV vectors (FIG. 6B) and with the tyrosine triple-mutant scAAV vector (Y730+500+444F; TM-AAV), which were described in the previous examples (Markusic et al., 2010) (FIG. 6C). It was concluded, therefore, that transgene expression from the AAV vector was regulated by the alternative (non-canonical) pathway of NF-κB. This conclusion was confirmed by Western blot analysis (FIG. 6D and FIG. 6E), which revealed an increase in the cytosolic p100 and the nuclear p52 protein components of the non-canonical NF-κB pathway by ~3- to 6-fold in the presence of VP16. Moreover, transduction with AAV vector by itself (i.e., in the absence of activator) increased p100 and p52 (FIG. 1C), indicating that infection of the cell activated the alternative NF-κB pathway. This increase was ablated by Bay11 treatment, while p65, the marker used for the classical NF-κB pathway, was unaffected (FIG. 1C).

Figure 7:
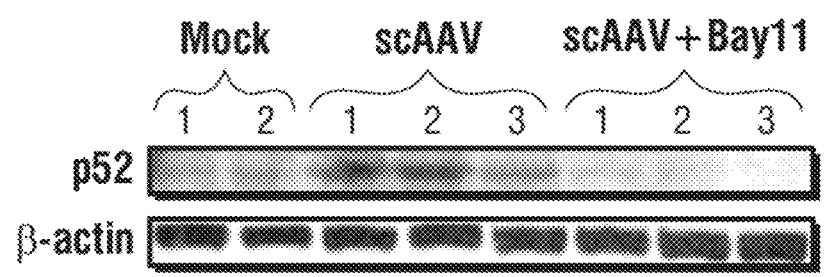
FIG. 7 is a Western blot analysis of liver homogenates from mice following mock-injections (n=2), or injections with scAAV vectors, with and without prior administration of Bay11 (n=3 each). The samples were analyzed by using anti-p52 antibody for detection NF-κB signaling in response to AAV exposure. Anti-β-actin antibody was used as a loading control.
Figure 8A:
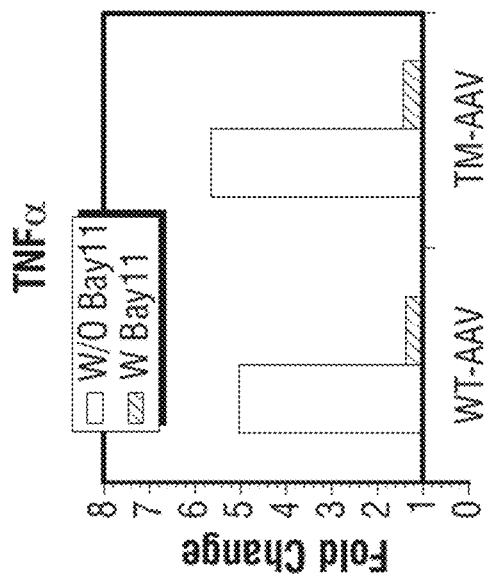
FIG. 8A, FIG. 8B, FIG. 8C, FIG. 8D, FIG. 8E, and FIG. 8F show fold changes in gene expression of various cytokines/chemokines from total mRNA collected from liver samples from animals injected with the WT-AAV or the TM-AAV vectors, following PBS- or Bay11-pre-treatment.
Figure 8B:
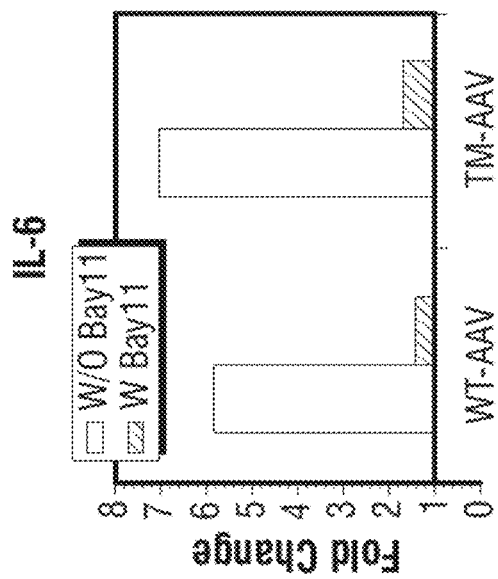
Figure 8C:
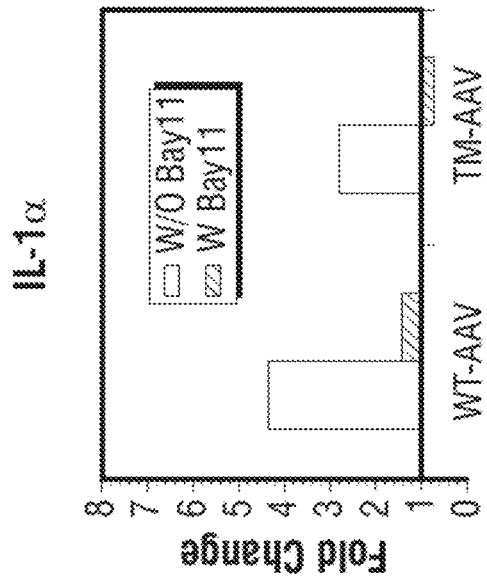
Figure 8D:
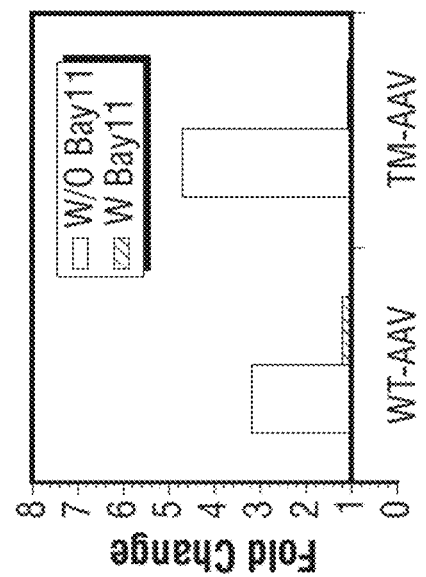
Figure 8E:
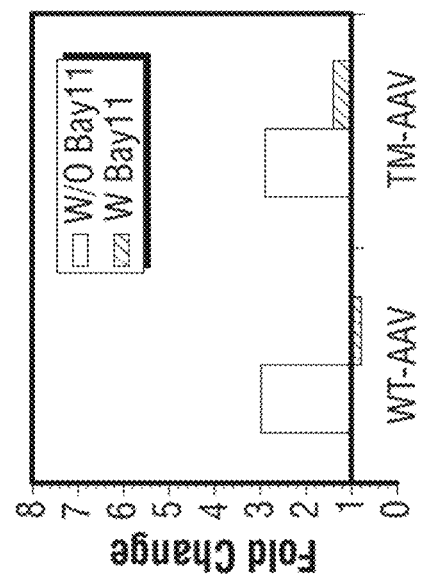
Figure 8F:
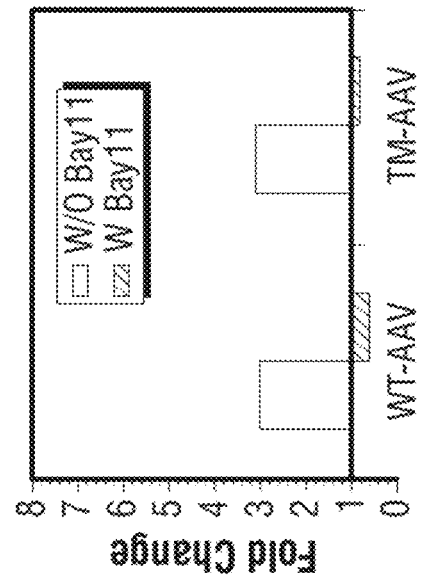

NF-κB Pathway is Operational in Primary Human Antigen-Presenting Cells Following AAV Infection In primary human dendritic cells (DCs), on the other hand, while transgene expression was again substantially increased with the NF-κB activator (FIG. 2A), AAV infection by itself did not activate NF-κB (FIG. 2B). In the presence of VP16, ~20-fold increase in EGFP expression was observed compared with scAAV vector-transduced DCs. Treatment with cytokines (TNF-α, IL-6, IL-1β, PGE2), known to activate the NF-κB pathway, led to a further increase in transgene expression to ~26%, which was reduced to ~12% following treatment with Bay11 (FIG. 2A). Western blot analyses of nuclear fractions further corroborated that the alternative pathway of NF-κB activation (accumulation of p52 proteins) was operational (FIG. 2B). Similar results were obtained following scAAV vector-mediated gene delivery to murine livers in vivo (FIG. 7). The inventors also tested the capability of NF-κB modulators to induce phenotypic changes in DCs. Flow cytometric analyses of two DC maturation markers, CD83 and CD86 indicated that VP16 alone was not able to induce maturation or enhance the expression of co-stimulatory molecules when used together with the cytokines cocktail. However, treatment with Bay11 led to inhibition of cytokine-mediated maturation of APCs, further implicating the involvement of NF-κB (Table 2). This reduction of maturation markers expression diminishes the main function of DCs to process antigenic material and reduces T-cell activation and proliferation. Thus, it was hypothesized that suppression of NF-κB activation prior to vector administration might lead to a dampened innate immune response against AAV.

TABLE 2

FACS Analyses of Markers of Maturation of Primary Human Dendritic Cells

| Group | Geometric means of levels of expression in cells expressing | |
|---|---|---|
| | CD83 | CD86 |
| Immature DCs | 10.38 | 7.04 |
| DCs - No maturation supplement | 18.08 | 13.63 |
| Mature DCs + Cytokines | 20.60 | 26.80 |
| DCs + AAV | 18.29 | 12.65 |
| DCs + VP16 | 16.48 | 13.70 |
| Mature DCs + AAV + Cytokines | 24.25 | 23.75 |
| Mature DCs + AAV + Cytokines + VP16 | 19.92 | 21.92 |
| Mature DCs + AAV + Cytokines + Bay11 | 16.88 | 10.11 |

Data from a representative experiment are shown (n = 3).

Figure 3B:
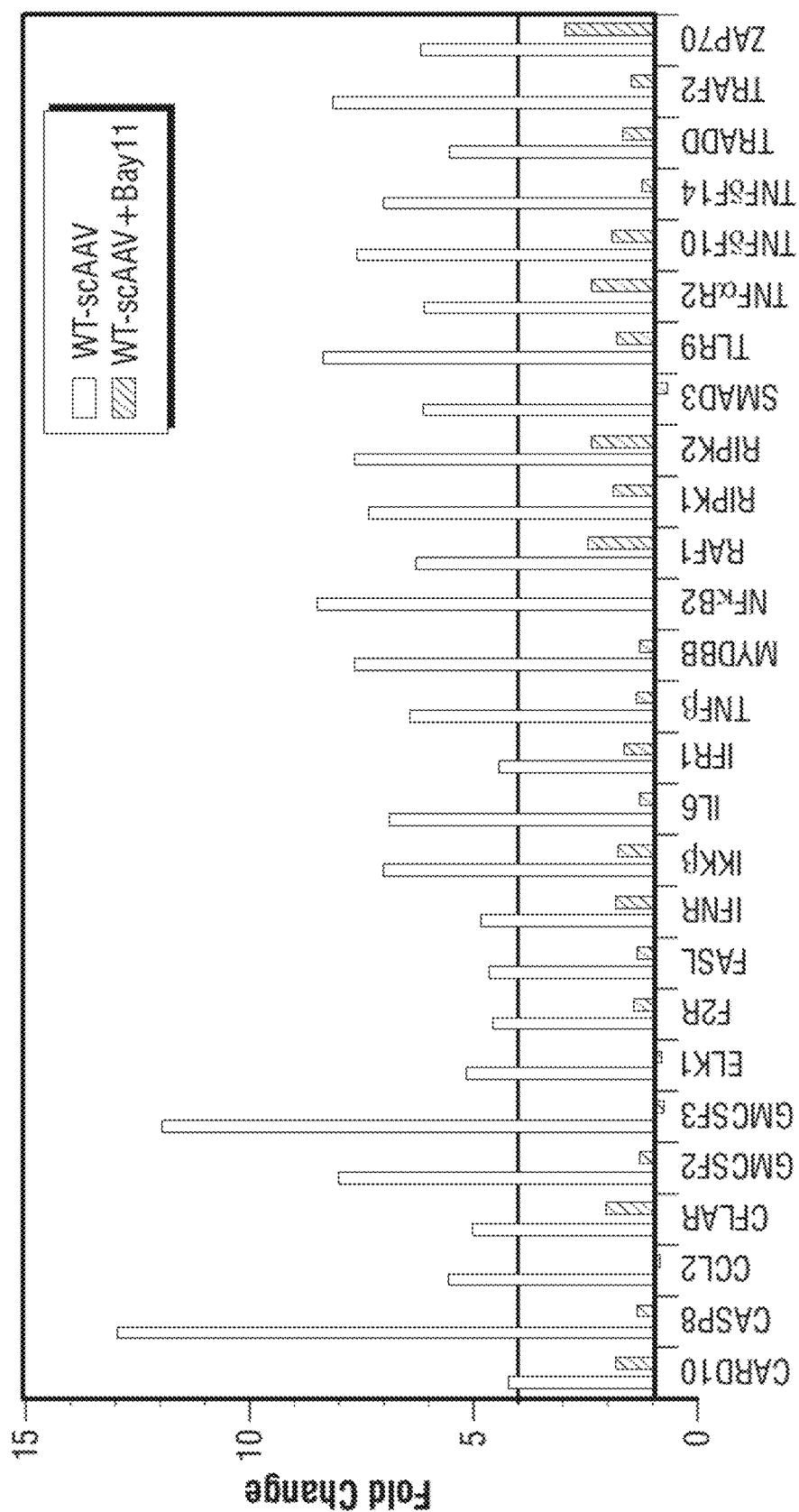
Figure 9:
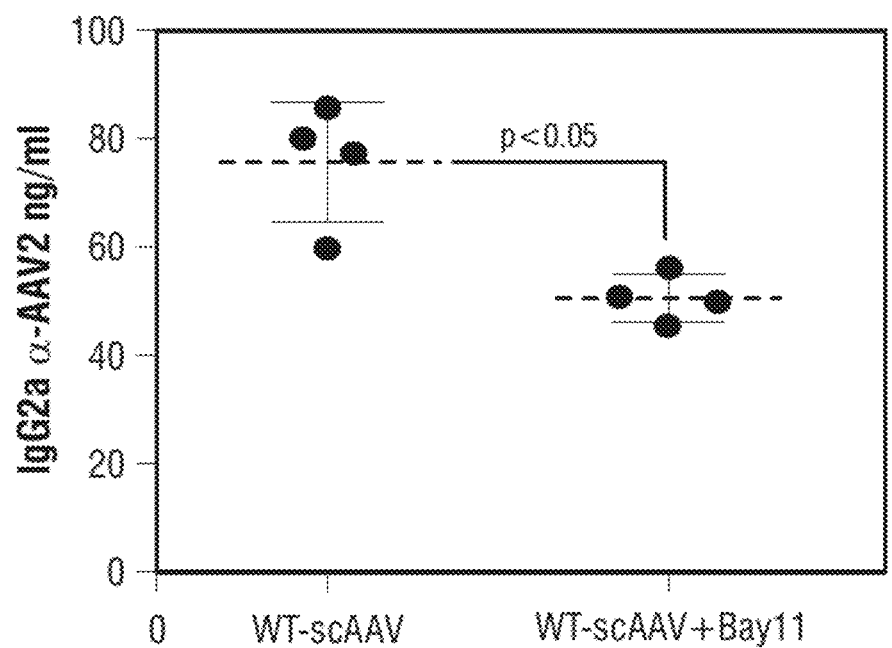
FIG. 9 demonstrates humoral response to AAV vectors in the absence or presence of NF-kB inhibitor. Anti-AAV2 IgG2a levels were determined in peripheral blood from mice at day 10 following injections with scAAV vectors, with and without prior administration of Bay11 (n=4 each)

Inhibition of NF-κB Activation Leads to Suppression of Pro-Inflammatory Cytokine Production Prior to AAV Vector-Mediated Gene Transfer in Mice in Vivo. In in vivo studies, a single dose of Bay11 at 20 mg/kg body weight was administered intra-peritoneally (i.p.) 12 hrs prior to vector administration in C57BL/6 mice. Transcript levels from liver homogenates of innate immune mediators (FIG. 3A) or for activation of NF-κB (FIG. 3B) genes were measured from Bay11- and vector-injected groups and compared with sham-injected mice. These data revealed that 2 hrs post-vector administration, mice injected with Bay11+AAV vector had significantly reduced levels of pro-inflammatory cytokines or chemokines including IL-1α, IL-6, TNFα, IL-12α, KC, and RANTES, compared with sham- and AAV vector-injected animals (FIG. 3A), and additionally, the up-regulation of the NF-κB gene expression profile was prevented (FIG. 3B). A similar down-regulation trend of these innate immune response markers was seen in mice injected with the more efficacious tyrosine triple-mutant AAV vector (Y730+500+444F; TM-AAV). The up-regulation of type I interferon expression by both wild-type (WT-AAV) and TM-AAV vectors was unaffected by Bay11 (FIG. 8A, FIG. 8B, FIG. 8C, FIG. 8D, FIG. 8E, and FIG. 8F). Administration of Bay11 also significantly reduced the anti-AAV2 antibody response in these mice (FIG. 9). The sum of these results implies that the transient inflammatory cytokine response, typically seen during in vivo hepatic AAV gene transfer, is mediated by NF-κB activation.

Figure 4A:
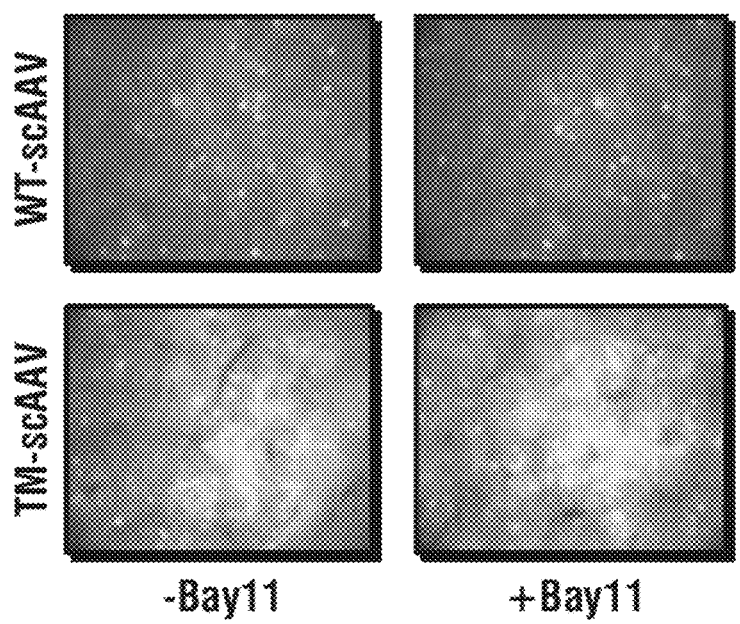
FIG. 4A and FIG. 4B illustrate transgene expression in murine hepatocytes 10 days post-injection of $1 \times 10^{11}$ vgs each of WT-scAAV-EGFP or TM-scAAV-EFGP vectors/animal via the tail-vein.
Figure 4B:
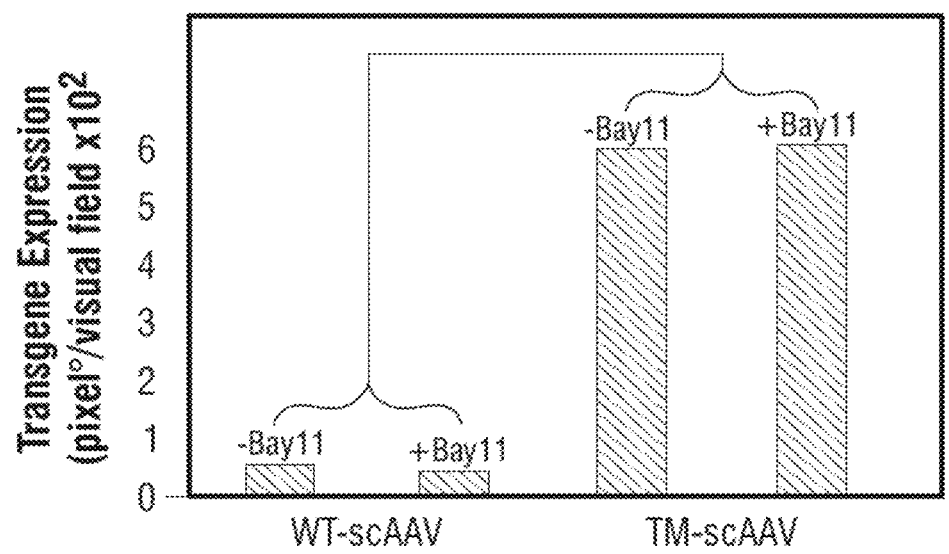

AAV Vector-Mediated Transgene Expression in Murine Hepatocytes. In view of the observation that Bay11 strongly inhibits AAV-mediated transgene expression in HeLa cells in vitro 48 hrs post-transduction (FIG. 1A and FIG. 1B), which would be counter-productive to achieve long-term transgene expression in vivo, it was important to examine the effect of Bay11 in mice. As can be seen in FIG. 4A, animals injected with or without Bay11 had similar levels of EGFP expression from either vector when analyzed 2 weeks after gene transfer. Transduction efficiency of the TM-AAV vector was ~12-fold higher than that of the WT-AAV vector (FIG. 4B), consistent with recently published studies (Markusic et al., 2010). These data suggested that Bay11 administration could safely and effectively down-regulate mediators of innate immune response without compromising long-term transgene expression.

Materials and Methods

Recombinant AAV Vectors. Highly purified stocks of self-complementary (sc) AAV2 vectors were generated containing either the wild-type (WT) plasmid or the triple tyrosine-mutant (TM; Y730+500+444F) plasmid and the enhanced green fluorescence protein (EGFP) gene driven by the chicken β-actin (CBA) promoter (WT-scAAV2-EGFP, TM-scAAV2-EGFP) by triple transfection of HEK-293 cells. The vectors were then purified by CsCl gradient centrifugation, filter sterilized, and quantified by slot-blot hybridization as described (Liu et al., 2003; Kube and Srivastava, 1997). The tyrosine-mutant pACG2-Y730+500+444F-Rep/Cap plasmid has been described recently (Markusic et al., 2010).

Recombinant AAV Vector Transduction Assays in Vitro. Optimal concentration of NF-κB-modulating compounds was determined by a cell viability assay with tenfold-dilutions from the $IC_{50}$ or were used as described previously (Wu and Miyamoto, 2008; Kumar et al., 2008). VP16 or Bay11 (10 or 5 μM, final concentration), and PDTC (50 or 25 μM final concentration) were used either alone or in activator/inhibitor combinations. For transduction experiments, approximately $1 \times 10^5$ HeLa cells were either pre-treated with these compounds 24 hrs prior to vector infection. Cells were transduced with 500 or 2,000 vector genomes (vgs) per cell of recombinant WT-AAV or TM-AAV vectors encoding the EGFP transgene as described previously (Markusic et al., 2010). After 7 days of culture, primary human dendritic cells were transduced with AAV vectors at 2000 vgs/cell and incubated for 48 hrs. Transgene expression was assessed as total area of green fluorescence ($pixel^2$) per visual field (mean±SD), or by flow cytometry. Analysis of variance (ANOVA) was used to compare between test results and the control and they were determined to be statistically significant.

Recombinant AAV Vector Transduction Studies in Vivo. Groups of 6-weeks old normal C57BL/6J mice (Jackson Laboratories, Bar Harbor, Me., USA) were administered intra-peritoneally, with a single dose (20 mg/kg) of NF-κB inhibitor Bay11, in a 200-μL volume diluted in DMSO (day 0). Animals injected with only the DMSO carrier solvent were considered as baseline (mock) group (n=75) and animals injected with Bay11 were the test group (n=75). At this point, the animals from mock and Bay11 groups were randomized to receive either phosphate buffered saline (PBS, pH 7.4) or WT-AAV or TM-AAV vectors (n=25 mice each group). On day 1, $\sim 1 \times 10^{11}$ viral genome (vg) particles of WT-AAV2-EGFP or TM-AAV2-EGFP vectors or PBS were administered intravenously via the tail vein. To measure the modulation of immune response to AAV, 5 animals each from PBS-, WT-AAV-, or TM-AAV vector-injected groups were sacrificed by carbon-dioxide inhalation at different time points post-vector administration (2, 6, 10, 24 hrs and day 10). Hepatic lobes were collected, cross-sectioned and mounted on slides to study the effect of Bay11 on AAV-mediated EGFP expression (from day 10 mice). All animal studies were conducted in accordance with institutional animal care and use committee guidelines.

Gene-Expression Analysis of Innate Immune Response by RT-PCR Assay. Groups of 6-weeks old normal C57BL/6J mice were administered intra-peritoneally, with a single dose (20 mg/kg) of NF-κB inhibitor, Bay11, in a 200-μL volume diluted in DMSO (day 0). On day 1, mice were injected with either phosphate-buffered saline (PBS, pH 7.4), or with $\sim 1 \times 10^{11}$ vgs of the wild-type (WT) AAV-EGFP vectors, or the tyrosine triple-Mutant™ AAV-EGFP vectors intravenously via the tail-vein (n=5 mice each group). At 2 hr post-vector administration, gene expression profiling of the innate immune response was performed that included Toll-like receptors 1-9, MyD88, MIP-1, IL-1α, IL-1β, IL-12α, IL6, KC, TNFα, RANTES, MCP-1, IFNα, IFNβ, and IP-10. Data were captured and analyzed using an ABI Prism 7500 Sequence Detection System with v1.1 Software (Applied Biosystems). The baseline was determined automatically for the 18S rRNA and for other genes. Thresholds were determined manually for all genes. Gene expression was measured by the comparative threshold cycle (Ct) method. The parameter threshold cycle (Ct) was defined as the cycle number at which the reporter fluorescence generated by the cleavage of the probe passed a fixed threshold above baseline. Cytokine gene expression was normalized using the endogenous reference 18S rRNA gene and mock-infected murine mRNA were used as reference sample. Relative gene expression was determined for each group of treated and untreated animals and values >2.6 and <0.38 were considered as significant up-regulations and down-regulations between the groups and was calculated by assessing the variability in the 96 well plates used to measure specific gene expression.

Cells, Antibodies and Chemicals. HeLa cells were obtained from the American Type Culture Collection (Rockville, Md., USA) and maintained as monolayer cultures in Iscove's-modified Dulbecco's medium (IMDM, Invitrogen, Inc., Carlsbad, Calif., USA) supplemented with 10% newborn calf serum (NCS) (Lonza, Inc., Basel, SWITZERLAND) and antibiotics. Leukapheresis-derived PBMCs were resuspended in serum-free AIM-V medium (Lonza, Inc.) and semi-adherent cell fractions were incubated in serum-free AIM-V medium supplemented with recombinant human IL-4 (500 U/mL) and GM-CSF (800 U/mL) (R&D Systems, MN, USA). Cells were treated with NF-κB modulators (10 mM VP16 or 10 mM Bay11), and cytokines cocktail including 10 ng/mL TNF-α, 10 ng/mL IL-1, 10 ng/mL IL-6, 1 mg/mL PGE2 (R&D Systems) for 20 hr. Cells were harvested, characterized to ensure they met the typical phenotype of mature DCs (CD83, RPE, murine IgG1, CD86, FITC, murine IgG1; Invitrogen, Inc.). All primary and secondary antibodies were purchased from Cell Signaling Technology, Inc. (Danvers, Mass., USA) or Santa Cruz Biotechnology, Inc (Santa Cruz, Calif., USA). NF-kB activators [Etoposide (VP16), Aphidicolin, Hydroxyurea (HU)] and NF-kB inhibitors [Bay11-7082 (Bay11), Pyrrolidine dithiocarbamate (PDTC)] were purchased from Sigma-Aldrich Co. (St. Louis, Mo., USA). These compounds were re-suspended in either DMSO (Sigma-Aldrich Co.) or in sterile, DNAase-, RNAase-free water (Invitrogen, Inc.) as per the manufacturer's instructions.

Western Blot Analyses. Homogenized lysates of the cell pellets from ~2×10$^6$ HeLa cells or DCs, mock or pre-treated with the optimal concentration of NF-κB activators or inhibitors were used for sample preparation. Whole cell proteins were isolated using the RIPA lysis buffer (Sigma-Aldrich Co.) and cytoplasmic and nuclear proteins were extracted using a commercial kit (NE-PER Extraction Reagent Kit, Pierce Biotech, Rockford, Ill., USA) as per the manufacturer's protocol in the presence of a protease inhibitor cocktail (Halt™ Protease Inhibitor Cocktail Kit, Pierce Biotech). The protein extracts were boiled for 5 min under reducing conditions [SDS-sample buffer containing 62.5 mM Tris-HCl (pH 6.8 at 25° C.), 2% wt./vol. SDS, 10% glycerol, 50 mM DTT, 0.01% wt./vol. bromo-phenol blue (Cell Signaling Technology, Inc.)] and stored at −86° C. until further analysis. Equal volumes of samples were run on 4-15% SDS-PAGE (Bio-Rad, Hercules, Calif., USA). Gels were transferred onto a 0.2-μm nitrocellulose membrane (Bio-Rad) and typically incubated overnight with 1:1000 dilution of primary antibodies [p100/52, p65, inhibitory kinase-IκBκ, glyceraldehyde 3-phosphate dehydrogenase (GAPDH), Lamin B (Cell Signaling Technology, Inc.), β-actin (Santa Cruz Biotechnology)]. The next day, blots were incubated with 1:2,000-1:5,000 of the appropriate anti-idiotypic HRP labeled IgG secondary antibody (Santa Cruz Biotechnology). Immunoblot detection was performed using the ECL plus Western blotting detection kit (Amersham Biosciences, Piscataway, N.J., USA). The intensity of the protein bands was measured with Adobe Photoshop CS3 Software® and normalized to proteins levels from the housekeeping gene products used as loading controls.

Figures 10A, 10B:
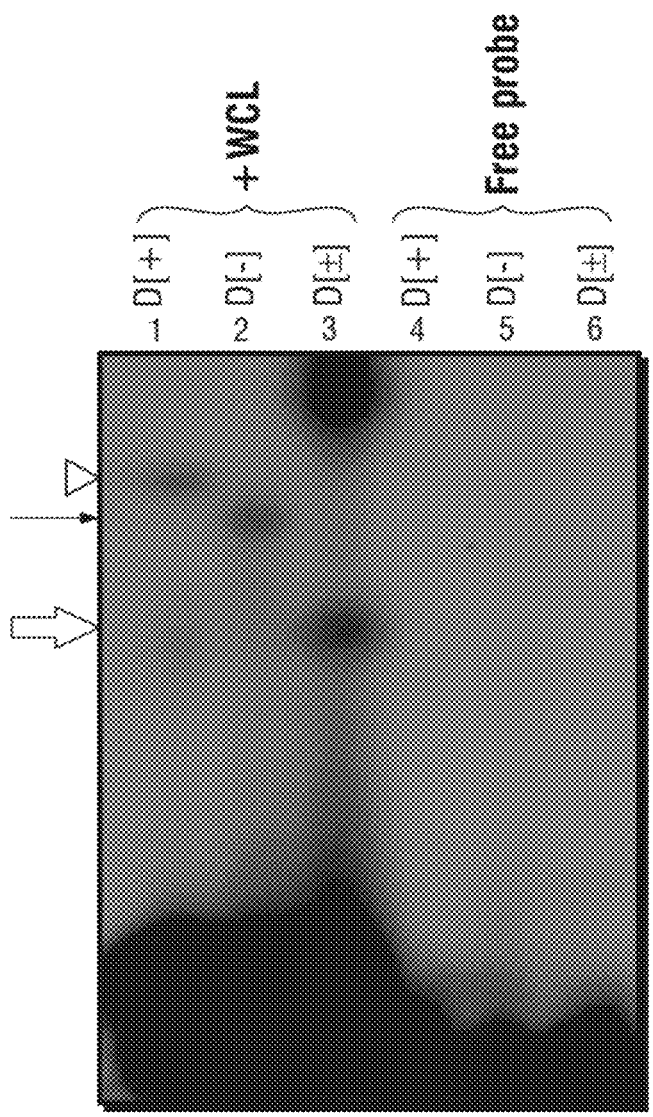
FIG. 10A and FIG. 10B illustrate electrophoretic mobility-shift assays carried out with whole-cell extracts prepared from HeLa cells and $^{32}$P-labeled single-stranded D[+]-sequence probe (lane 1), which interacted with a host cell protein (lane 3, arrowhead). Single-stranded D[−]-sequence (lane 2) probe was used as an appropriate control, which also interacted with a cellular protein, FKBP52 (lane 4, arrow). Binding assays were also carried out using biotin-labeled ssD[+]-sequence probe followed by selection with streptavidin-beads, and fractionation by SDS-polyacrylamide gel electrophoresis. The relevant protein band was visualized by silver staining, excised from the gel, and subjected to mass spectrometry, and one of the unique peptides was found to share homology with the NF-κB-repressing factor (NRF)

The basis for the present study was the finding that the host cellular NF-κB can bind to the 20-bp D-sequence present in the AAV inverted terminal repeats (ITRs) (Qing et al., 1997), which was identified by electrophoretic mobility-shift assays followed by mass-spectrometry (FIG. 10A and FIG. 10B). The data presented in this example provide the first evidence of the involvement of NF-κB in AAV infection. Using a variety of pharmacological modulators, which have been extensively used by other investigators (Wu and Miyamoto, 2008; Kumar et al., 2008) to study the NF-κB signaling pathway, it was shown that the non-canonical NF-κB pathway is up-regulated following AAV infection. This is significant considering that activation of the NF-κB transcriptional program is a fundamental immediate early step of inflammatory and immune activation (Li and Verma, 2002), and NF-κB signaling represents a prime candidate for viral susceptibility or interference (Hiscott et al., 2006). Viruses which activate NF-κB have been shown to be susceptible to innate immune response through an interferon response (Vesicular stomatitis virus, Measles virus) (Hiscott et al., 2003), toll-like receptor (TLR) dependent (Ebola virus, Respiratory syncytial virus) (Okumura et al., 2010; Lizundia et al., 2008), and TLR-independent signaling pathway (Cytomegalovirus, Hepatitis C virus) (Castanier et al., 2010; Gourzi et al., 2007). On the other hand, many viruses disrupt the innate immune responses and NF-κB using multifunctional viral decoy proteins that target specific aspects of the NF-κB pathway. Viruses, including human immunodeficiency virus type I (HIV-I), human T-cell leukemia virus type 1 (HTLV-1), Human herpesvirus 8 (HHV8) and Epstein-Barr virus (EBV), have incorporated aspects of NF-κB signaling into their life cycle and pathogenicity, and thus utilize NF-κB activation to promote their survival (Hiscott et al., 2006).

In contrast, it stands to reason that the non-canonical pathway of NF-κB is activated following AAV infection both because the non-canonical NF-κB activation is known to be important for innate and adaptive immune response (Gilmore, 2006), and AAV vectors lack complex structural gene elements necessary to develop any NF-κB-like decoy proteins. The exacerbated activation of the non-canonical pathway has been associated to a wide range of inflammatory disorders like rheumatoid arthritis, ulcerative colitis or B cell lymphomas (Dejardin, 2006). Monarch-1, a pyrin-containing protein expressed exclusively in cells of myeloid lineage suppresses pro-inflammatory cytokines and chemokines through inhibition of NF-κB inducing kinase (NIK) necessary to activate non-canonical NF-κB pathway (Lich et al., 2007). The activation of non-canonical pathway of NF-κB activation has been shown to result in maturation and T-cell priming activity of DCs over-expressing a mutated IκBκ which blocks activation of the classical pathway (Lind et al., 2008). In alymphoplasia (Aly) mouse deficient in NIK, the cross-priming of CD8+ T cells to exogenous antigens in DCs is affected suggesting the importance of this pathway in adaptive immunity (Lind et al., 2008). Mice deficient in non-canonical pathway components are also deficient in secondary lymphoid organ development and homeostasis (Guo et al., 2008). It is not known whether AAV-binding activates the NF-κB signaling to a cell surface receptor. Recent studies have demonstrated that the innate immune response to AAV could be triggered through the TLR9-MYD88 pathway or through activation of the CD40 ligand on cell surface in murine models in vivo (Zhu et al., 2009; Mays et al., 2009). It is interesting to note that while both rely on NF-κB signaling down-stream for mounting an innate immune response (Mineva et al., 2007; Loiarro et al., 2005), activation of TNF super family receptors such as CD40L can activate the non-canonical NF-κB pathway (Qing et al., 2005).

Based on the evidence that the first "danger-signal" or "trigger" to immune surveillance directed against AAV vectors may be the activation of alternative NF-κB signaling pathway, it was reasoned that transient blocking of NF-κB during AAV vector administration could dampen the host immune response. One possible strategy to negate the NF-κB-priming by AAV is to generate targeted mutations against the NF-κB responsive transcription factor binding sites in the AAV-ITRs. However, given the pleiotropic functions of NF-κB proteins in cellular physiology (Hayden and Ghosh, 2004), it is possible that different NF-κB-responsive cytokine promoter-binding transcription factors might be operational in different cell types. Alternatively, a protocol for transient immuno-suppression by targeting the NF-κB pathway might be universally applicable. The selective NF-κB inhibitor, Bay11, can markedly reduce markers of inflammation and innate immune response to AAV vectors yet does not affect its transgene expression in vivo. Bay11 was able to down-regulate the activity of several key regulators namely, IL-1α, IL-6, TNFα, IL-12α, KC and RANTES, suggesting the benefit of using this pharmacologic modulator to selectively down-regulate the inflammatory and innate immune response against AAV vectors. Interestingly, NIK that is critical for activation of the non-canonical NF-κB pathway, is also known induce activation of IL-1α, IL-6, IL-12α, TNFα and RANTES in response to a variety of viral infections (DiPaolo et al., 2009; Yanagawa and Onoe, 2006; Andreakos et al., 2006; Habib et al., 2001). In addition, it is well recognized that NIK is pivotal to the activation and function of the quiescent professional antigen presenting cells, the DCs, whose activity is critical for priming of the antigen specific CD4+ helper T cells, leading to immune responses to relevant targets such as the delivery vector (Andreakos et al., 2006; Habib et al., 2001; Martin et al., 2003; Brown and Lillicrap, 2002). In vitro, NIK increases DC antigen presentation by potently activating NF-κB and consequently up-regulating the expression of cytokines (TNFα, IL-6, IL-12, IL-15, and IL-18), chemokines {IL-8, RANTES, macrophage inflammatory protein-1α, monocyte chemo-attractant protein-1, and monocyte chemo-attractant protein-3}, MHC antigen-presenting molecules (class I and II), and co-stimulatory molecules (CD80 and CD86) (Andreakos et al., 2006). In vivo, NIK enhances immune responses against a vector-encoded antigen and shifts them toward a T helper 1 immune response with increased IgG2a levels, T-cell proliferation, IFN-γ production, and cytotoxic T lymphocyte responses more potently than complete Freund's adjuvant (Andreakos et al., 2006). Bay11, used in this study, prevents the activity of IKKα and β, which are the substrates for NIK in the non-canonical pathway (Pierce et al., 1997). These data indicate the high specificity of Bay11 in targeting the non-canonical NF-κB pathway as well as its ability to prevent the activation of major modulators of immune response.

A protocol for transient immuno-suppression by targeting the NF-κB pathway might be universally applicable to limit immuno-toxicities. Indeed, a recent report showed decreased AAV capsid antigen presentation by the use of a proteasomal inhibitor, Bortezomib [Velcade®] (Finn et al., 2010). Bortezomib has a considerable anti-myeloma efficacy (Kube and Srivastava, 1997), which is likely in large part due to repression of NF-κB signaling. It may therefore be possible to simultaneously block MHC I presentation of capsid and inflammatory signals or use more selective NF-κB-targeted therapies, such as Bay11 in this study, or the newer IKK inhibitors in order to further enhance the safety and therapeutic efficacy of AAV vectors.

Example 3—Development of Optimized AAV3 Serotype Vectors: Mechanism of High-Efficiency Transduction of Human Liver Cancer Cells Adeno-associated virus 2 (AAV2), a non-pathogenic human parvovirus, contains a single-stranded DNA genome, and possesses a wide tissue-tropism that transcends the species barrier (Muzyczka, 1992). Recombinant AAV2 vectors have gained attention as a promising vector system for the potential gene therapy of a variety of human diseases, and are currently in use in a number of gene therapy clinical trials (Daya and Berns, 2008). More recently, several additional AAV serotypes have been isolated, and have been shown to transduce specific cell types efficiently (Muramatsu et al., 1996; Chiorini et al., 1997; Chiorini et al., 1999; Rutledge et al., 1998; Gao G P et al., 2002; Vandenberghe et al., 2004). Whereas various steps in the life cycle of AAV2 are reasonably well understood (Summerford and Samulski 1998; Qing et al., 1999; Summerford et al. 1999; Hansen et al., 2000; Hansen et al., 2001; Sanlioglu et al., 2000; Douar et al., 2001; Zhao et al., 2006; Thomas et al. 2004; Zhong et al. 2004; Ferrari et al., 1996; Fisher et al. 1996; Qing et al., 2004; Zhong et al., 2004; Zhong et al., 2004; Zhong et al., 2008; McCarty et al., 2004; Bainbridge et al., 2008), less is known about the other serotypes.

Of the 10 commonly used AAV serotypes, AAV3 has been reported to transduce cells and tissues poorly (Zincarelli et al.; Zincarelli et al., 2008). However, recent studies revealed that AAV3 vectors transduce established human hepatoblastoma (HB) and human hepatocellular carcinoma (HCC) cell lines as well as primary human hepatocytes extremely efficiently (Glushakova et al., 2009). Subsequently, it was documented that AAV3 infection was strongly inhibited by hepatocyte growth factor (HGF), HGF receptor (HGFR) specific siRNA, and anti-HGFR antibody, which suggested that AAV3 utilizes HGFR as a cellular receptor/co-receptor for viral entry (Ling et al., 2010).

The ubiquitin-proteasome pathway plays a crucial role in intracellular trafficking of AAV vectors (Douar et al., 2001; Zhong et al., 2007; Duan et al., 2000). Intact AAV2 capsids can be phosphorylated at tyrosine residues by epidermal growth factor receptor protein tyrosine kinase (EGFR-PTK), and that tyrosine-phosphorylation of AAV capsids negatively affects viral intracellular trafficking and transgene expression. These observations led to the suggestion that tyrosine-phosphorylation is a signal for ubiquitination of AAV capsids followed by proteasome-mediated degradation (Duan et al., 2000; Zhong et al., 2008). This led to the hypothesis that mutations of the surface-exposed tyrosine residues (Y) to phenylalanine (F) might allow the vectors to evade phosphorylation, ubiquitination and proteasome-mediated degradation. Indeed, mutations of the surface-exposed tyrosine residues in AAV2 vectors led to high-efficiency transduction at lower doses both in HeLa cells in vitro and murine hepatocytes in vivo (Zhong et al., 2008). Therapeutic levels of expression of human factor IX have been obtained in several different strains of mice using the single and multiple tyrosine-mutant AAV2 vectors (Zhong et al., 2008; Markusic et al., 2010). Additional studies have corroborated that similar Y-to-F mutations in AAV serotypes 6, 8 and 9 also lead to augmented transgene expression (Petrs-Silva et al., 2009; Qiao et al., 2010; Taylor and Ussher, 2010). Six of seven surface-exposed tyrosine residues in AAV2 are also conserved in AAV3, but their involvement in AAV3-mediated transduction has not been evaluated.

This example demonstrates that: (i) AAV3 vector-mediated transduction is dramatically increased in T47D cells, a human breast cancer cell line that expresses undetectable levels of the endogenous hHGFR (Abella et al., 2005), following stable transfection and over-expression of hHGFR; (ii) the tyrosine kinase activity associated with hHGFR negatively affects the transduction efficiency of AAV3 vectors; (iii) the use of proteasome inhibitors significantly improves AAV3 vector-mediated transduction; (iv) site-directed mutagenesis of three surface-exposed tyrosine residues on the AAV3 capsid leads to improved transduction efficiency; (v) a specific combination of two tyrosine-mutations further improves the extent of transgene expression; and (vi) AAV3 vectors efficiently transduce human HB and HCC tumors in a murine xenograft model in vivo, following both intratumoral or systemic administration. These optimized AAV3 vectors provide improved tools for gene therapy, and particularly for the therapy of liver cancer in humans.

Materials and Methods

Cell Lines and Cultures. Human cervical cancer (HeLa) and hepatocellular carcinoma (Huh7) cell lines were purchased from American Type Culture Collection (Manassas, Va., USA), and maintained in complete DMEM medium (Mediatech, Inc., Manassas, Va., USA) supplemented with 10% heat-inactivated fetal bovine serum (FBS, Sigma-Aldrich Co.), 1% penicillin and streptomycin (P/S, Lonza, Inc.). A newly established human hepatoblastoma (Hep293TT) cell line (Chen et al., 2009) was maintained in complete RPMI medium 1640 (Invitrogen, Inc.) supplemented with 15% heat-inactivated FBS (Sigma-Aldrich Co.), 1% penicillin and streptomycin (P/S, Lonza, Inc.). Cells were grown as adherent cultures in a humidified atmosphere at 37° C. in 5% $CO_2$ and were sub-cultured after treatment with trypsin-versene mixture (Lonza, Inc.) for 2-5 min at room temperature, washed and re-suspended in complete medium. A human breast cancer cell line, T47D, and T47D cells stably transfected with a hHGFR expression plasmid (T47D+hHGFR), were maintained in complete DMEM medium (Mediatech, Inc.) with or without 600 µg/mL of G418, supplemented with 10% heat-inactivated fetal bovine serum (FBS, Sigma-Aldrich Co.), 1% penicillin and streptomycin (Lonza, Inc.).

Recombinant AAV Plasmids and Vectors. Recombinant AAV3 packaging plasmid and recombinant AAV2-CBAp-EGFP vector plasmid were generously provided respectively by Drs. R. Jude Samulski and Xiao Xiao, University of North Carolina at Chapel Hill, Chapel Hill, N.C. Highly purified stocks of scAAV2 and scAAV3 vectors containing the enhanced green fluorescence protein (EGFP) gene driven by the chicken β-actin promoter (CBAp) were packaged by the calcium phosphate triple-plasmid transfection protocol described previously (Wu et al., 2007; Kube and Srivastava, 1997). The physical particle titers of recombinant vector stocks were determined by quantitative DNA slot-blot analyses (Kube and Srivastava, 1997).

Construction of Surface-Exposed Tyrosine Residue Mutant AAV3 Capsid Plasmids A two-stage procedure, based on QuikChange II® site-directed mutagenesis (Stratagene) was performed by using plasmid pAAV3 as described previously (Glushakova et al., 2009; Ling et al., 2010). Briefly, in stage one, two PCR extension reactions were performed in separate tubes for each mutant. One tube contained the forward PCR primer and the other contained the reverse primer (Table 3).

In stage two, the two reactions were mixed and a standard PCR mutagenesis assay was carried out as the manufacturer's instructions. PCR primers were designed to introduce changes from tyrosine to phenylalanine residues and a silent change to create a new restriction endonuclease site for screening purposes (Table 3). All mutants were screened with the appropriate restriction enzyme and were sequenced before use.

TABLE 3

NUCLEOTIDE SEQUENCES OF PRIMERS USED FOR SITE-DIRECTED MUTAGENESIS

| Mutants | Primer Sequences (5' to 3') |
|---|---|
| Y252F | ACCGAACCTGGGCTCTGCCCACTTT<br>CAACAACCATCTCTACAAG (SEQ ID NO: 11)<br>- *ApaI*      Tyr→Phe |
| Y272F | CAATCAGGAGCTTCGAACGACAACCACT<br>CTTTGGCTACAGCACC (SEQ ID NO: 12)<br>+BstBI      Tyr→Phe |
| Y444F | CTTATCGATCAGTATCTGTACTT<br>CCTGAACAGAACGCAAGGAACA (SEQ ID NO: 13)<br>+ClaI      Tyr→Phe |
| F501Y | *GCTAACGACAACAACAACAGTAACTATCCA<br>TGGA**CAGCGGCCAGCAAA* (SEQ ID NO: 14)<br>Phe→Tyr +NcoI |
| Y701F | TGGAATCCAGAGATTCAGTTCAC G<br>TCCAACTACAACAAGTCTGTT (SEQ ID NO: 15)<br>Tyr→Phe +BmgBI |
| Y705F | GAGATTCAGTACACGTCCAACTT<br>CAACAAGTCTGTTAATGTGGAC (SEQ ID NO: 16)<br>+AflIII Tyr→Phe |
| Y731F | GTGAACCTCGCCCTATTGGAACCCGGTT<br>TCTCACACGAAACTTG (SEQ ID NO: 17)<br>Tyr→Phe |

The codon triplets are shown in bold; italicized fonts denote the mutations from tyrosine to phenylalanine residues, and bold, italic, and underlined fonts indicate the silent mutations to eliminate/create the restriction enzyme sites (underlined), which were used to identify the desired clones.

AAV Vector Transduction Assays. Huh7 or HeLa cells were seeded in 96-well plates at a concentration of 5,000 cells per well in complete DMEM medium. AAV infections were performed in serum- and antibiotic-free DMEM medium. Hep293TT cells were seeded in 96-well plates at a concentration of 10,000 cells per well in complete RPMI medium. The infections were performed in serum- and antibiotic-free RPMI medium. The expression of EGFP was analyzed by direct fluorescence imaging 72 hrs' post-transduction.

Western Blot Analyses. Cells were harvested and disrupted in a radio-immunoprecipitation assay (RIPA) lysis buffer (50 mM Tris-HCl, pH 8.0, 150 mM NaCl, 0.1% SDS, 1% NP-40, 0.25% sodium deoxycholate and 1 mM EDTA with protease inhibitor cocktail, 1 mM NaF and 1 mM $Na_3VO_4$). Total protein concentration was measured using a Bradford reagent (Bio-Rad) and equal amounts (50 µg) of whole cell lysates were resolved by SDS-PAGE. After electrophoresis, samples were electro-transferred to a nitrocellulose membrane (Bio-Rad), probed with relevant primary antibodies at 4° C. overnight, incubated with horseradish peroxidase-conjugated secondary antibodies (Jackson ImmunoResearch, West Grove, Pa., USA), and detected with an enhanced chemi-luminescence substrate (Amersham). Antibodies against phospho-c-Met (Y1234/1235), total c-Met, phospho-Akt (S473) and phospho-ERK (T202/Y204) were purchased from Cell Signaling, and anti-β-actin (AC-74) antibody was obtained from Sigma-Aldrich Co.

Recombinant AAV3 Vector Transduction Studies in Mouse Xenograft Models. Groups of 6-weeks old NSG mice (Jackson Laboratories) were injected subcutaneously with $5 \times 10^6$ Hep293TT or Huh7 cells. Four-week post-injection, indicated numbers of AAV3 vector genomes (vgs) were administered either intratumorally or through tail-vein. Four days post-vector administration, tumors were resected, cross-sectioned and evaluated for EGFP expression using a fluorescent microscope. Sections were also stained with DAPI to visualize the cell nucleus. All animal studies were conducted in accordance with approved institutional guidelines.

Statistical Analysis. Results are presented as mean±standard deviation (SD). Differences between groups were identified using a grouped-unpaired two-tailed distribution of Student's T test. P values <0.05 were considered statistically significant.

Results

Figure 11A:
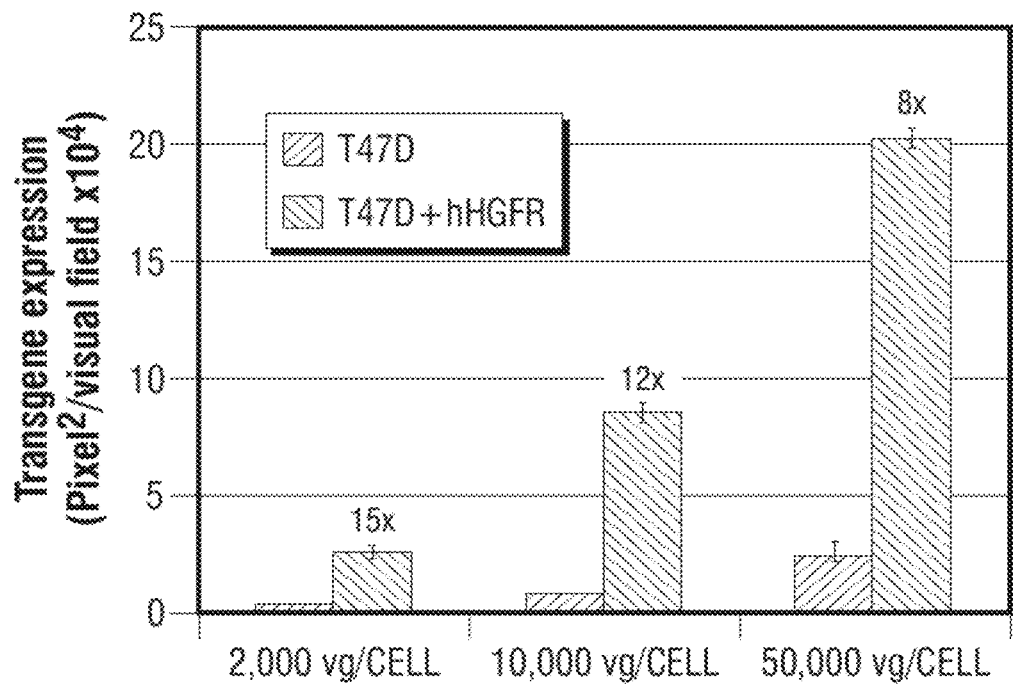
FIG. 11A and FIG. 11B show the analysis of AAV3-mediated transgene expression in T47D and T47D+hHGFR cells.
Figure 11B:
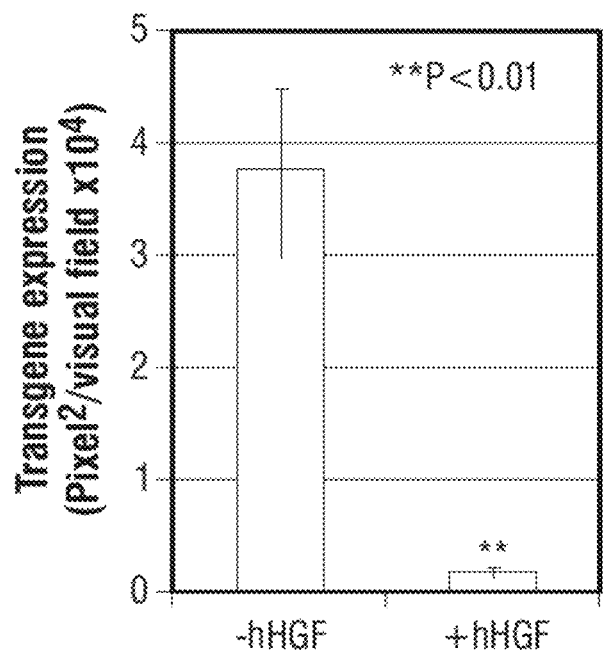

Human HGFR is required for AAV3 infectivity. AAV3 utilizes human hepatocyte growth factor receptor (HGFR) as a cellular co-receptor (Ling et al., 2010). To unequivocally corroborate this finding, a human breast cancer cell line, T47D, was used that expresses undetectable levels of hHGFR (Abella et al., 2005), as well as T47D cells stably transfected with hHGFR expression plasmids (T47D+hHGFR) (Abella et al., 2005). The expression of hHGFR protein in the established cell line T47D+hHGFR was confirmed by Western blot analysis (see FIG. 12C). Equivalent numbers of T47D and T47D+hHGFR cells were transduced with various multiplicities-of-infection (MOI) of self-complementary (sc) AAV3-CBAp-EGFP vectors under identical conditions and transgene expression was determined 72 hr post-transduction. These results, shown in FIG. 11A, document that the transduction efficiency of AAV3 vectors is ~8-13-fold higher in cells that express hHGFR than those that do not. AAV3 vector-mediated transduction of T47D+hHGFR cells could be completely blocked in the presence of 5 µg/mL of hHGF (FIG. 11B). Taken together, these data provide conclusive evidence that cell surface expression of hHGFR is required for successful transduction by AAV3 vectors.

Inhibition of HGFR Protein Tyrosine Kinase Activity Enhances Transduction Efficiency of AAV3 Vectors. To examine whether in addition to the extracellular domain, the intracellular domain of HGFR, which contains protein tyrosine kinase activity, is also involved in AAV3 infection, a further study was performed. Binding of its ligand, HGF, results in dimerization of the receptor and intermolecular trans-phosphorylation of multiple tyrosine residues in the intracellular domain (Nguyen et al., 1997). T47D+hHGFR cells were treated for two hrs with increasing concentrations of a specific HGFR kinase inhibitor, BMS-77760707 (BMS) (Schroeder et al., 2009; Dai and Siemann, 2010). Cells were subsequently infected with scAAV3 vectors at 2,000 vgs/cell. These results are shown in FIG. 12A. It is evident that BMS-777607-treatment led to ~2-fold increase in AAV3 transduction efficiency. Although the p-value is higher when BMS-777607 was used at the highest concentration of 10 µM, compared with the lower concentration of 1 µM, this change is most likely due to drug toxicity. In previous studies, it was reported that BMS-777607 treatment had no significant effect on cell growth at doses ≤1 µM. However, doses of 10 µM did result in significant reduction in cell proliferation, which suggests that this concentration is toxic to cells (Dai and Siemann, 2010). In the next experiment, to rule out any possible non-specific nature of this drug, the parental T47D cells were included as a control. Both cell types were treated with 1 µM BMS-777607 for 2 hr and then infected with scAAV3 vectors at 10,000 vg/cell. The results, shown in FIG. 12B, indicated that whereas BMS-777607-treatment significantly enhanced AAV3 infectivity in T47D+hHGFR cells, it had no effect in T47D cells that lack expression of hHGFR.

To examine whether inhibition of the HGFR kinase led to alterations in the phosphorylation status of specific cellular proteins involved in the downstream signaling pathway total and phosphorylation levels of the HGFR protein in both T47D and T47D+hHGFR lysates were determined following a 2-hr drug-incubation period. Activation of signaling pathways downstream from HGFR kinase, ERK1/2 and Akt, were analyzed using phosphorylation-specific antibodies. These results, shown in FIG. 12C, confirmed that whereas little expression of hHGFR occurs in T47D cells, the level of expression is significantly higher in T47D+hHGFR cells for both total HGFR and phosphorylated HGFR, which is consistent with previously published reports (Abella et al., 2005). Treatment of T47D+hHGFR cells with BMS-777607 completely blocked the phosphorylation of HGFR, but not total HGFR. In addition, BMS-777607-treatment had no effect on the expression of phosphorylated AKT and ERK1/2. These results suggest that the enhancement of AAV3 vector infectivity by the BMS-777607-treatment is due to inhibition of HGFR kinase.

Figure 13A:
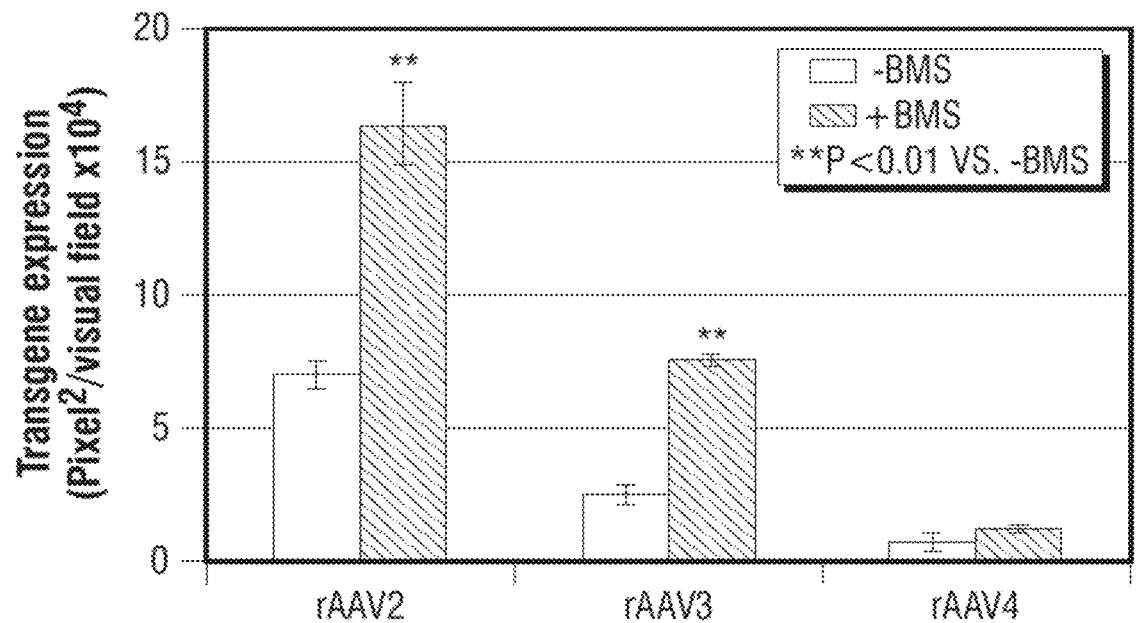
FIG. 13A and FIG. 13B show the effect of BMS-777607 on various AAV serotype-mediated transgene expression.
Figure 13B:
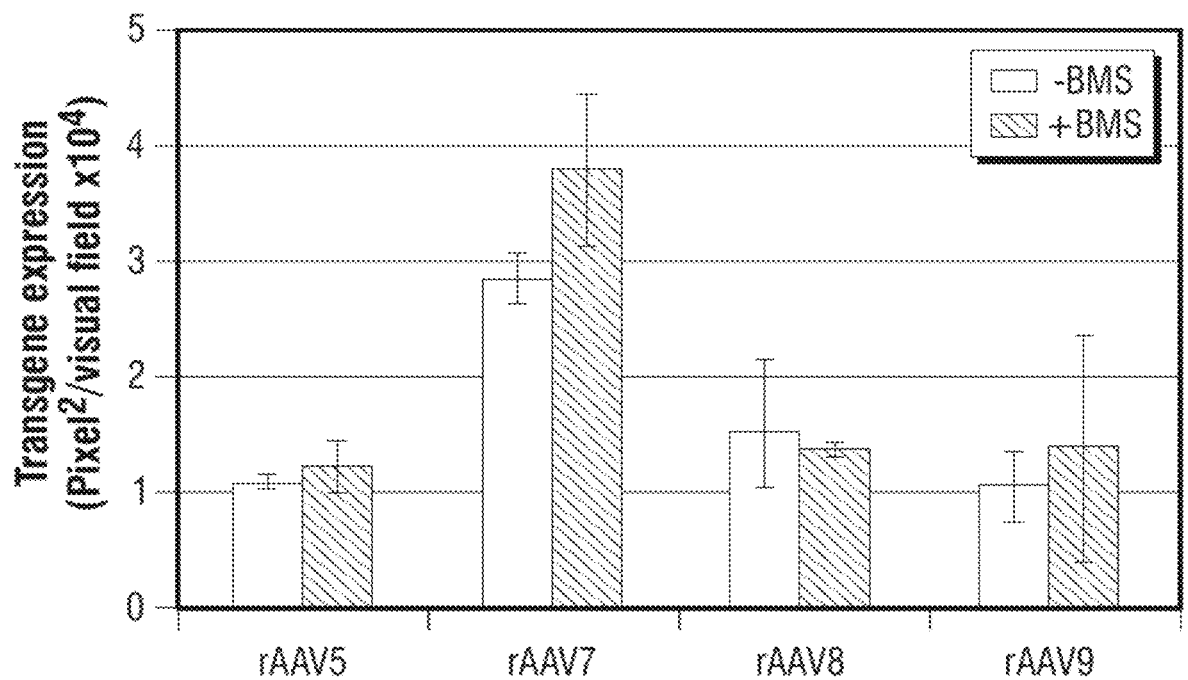

To date, only AAV2 has been reported to use hHGFR as a co-receptor (Yan et al., 2002). The roles of hHGFR and hHGFR kinase inhibitor on other AAV serotypes are not known. To rule out any non-specific enhancement of transduction by BMS-777607, other serotypes of AAV, which are not dependent on HGFR, as well as AAV2 vectors, were compared for transduction efficiency following treatment of cells with BMS-777607. These results, shown in FIG. 13, indicate that whereas AAV2 and AAV3 vectors can efficiently transduce T47D+hHGFR cells, other serotypes (AAV4-AAV9) can only transduce these cells at a very low efficiency. This result suggests that hHGFR is not involved in the life cycle of these AAV serotypes. Treatment of cells with BMS-777607 significantly increased the transduction efficiency of both AAV2 and AAV3 vectors, but not the other AAV serotypes, which suggested that the effect of the BMS-777607-treatment is AAV serotype-specific.

Figure 14A:
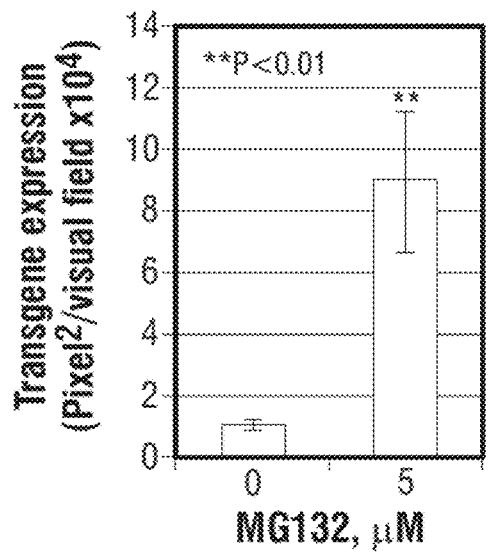
FIG. 14A, FIG. 14B, FIG. 14C and FIG. 14D show the comparative analyses of AAV3-mediated transduction efficiency in Huh7 and Hep293TT cells with or without treatment with MG132.
Figure 14B:
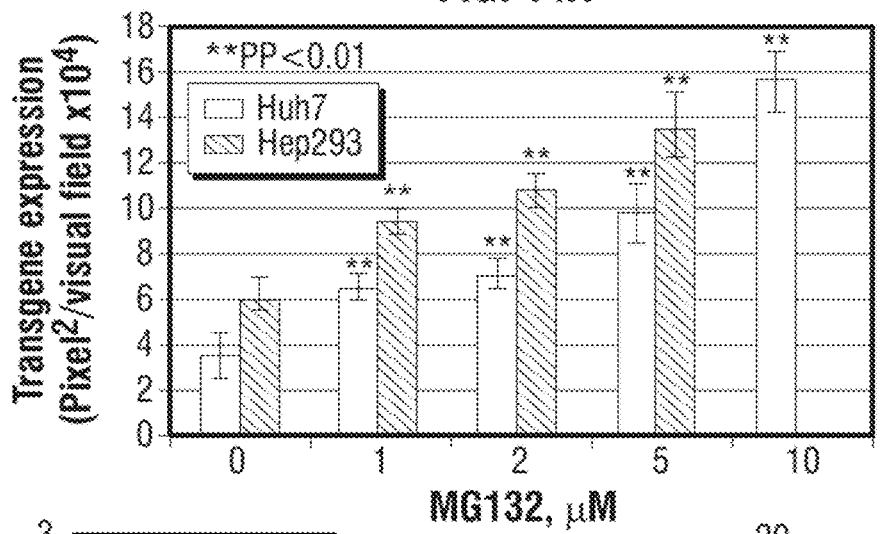

Proteasome Inhibitors Increase the Transduction Efficiency of AAV3 Vectors. Previous studies have shown that proteasome inhibitors, such as MG132, can significantly enhance the transduction efficiency of AAV2 vectors by facilitating intracellular trafficking (Zhong et al., 2007; Yan et al., 2002). To evaluate whether MG132 can also improve AAV3 trafficking in target cells, Huh7, a well-established human hepatocellular carcinoma cell line (Nakabayashi et al., 1982), and Hep293TT, a recently established human hepatoblastoma cell line (Chen et al., 2009), were either mock-treated or treated with increasing concentrations of MG132. Following a two-hour treatment, cells were infected with scAAV3-EGFP vectors. HeLa cells, treated with 5 µM MG132 and transduced with scAAV2 vectors, were included as a positive control. Transgene expression was determined by fluorescence microscopy 72 hrs post-transduction. These data are shown in FIG. 14A and FIG. 14B. As can be seen, pretreatment with MG132 significantly increased the transduction efficiency of scAAV2 vectors in HeLa cells, which is consistent with previously results (Zhong et al., 2008). Interestingly, a dose-dependent increase in the transduction efficiency of scAAV3 vectors in both Huh7 and Hep293TT cells occurred following MG132-treatment, suggesting that AAV3 vectors also undergo ubiquitination followed by proteasome-mediated degradation.

Figure 14C:
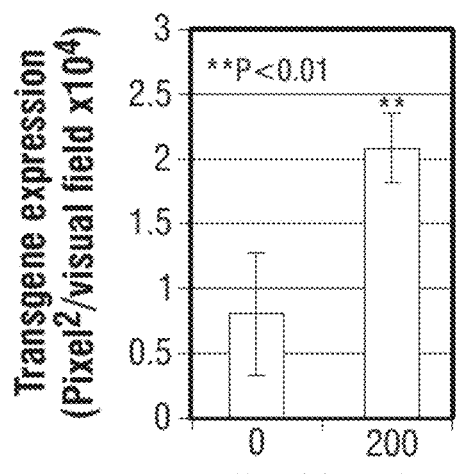
Figure 14D:
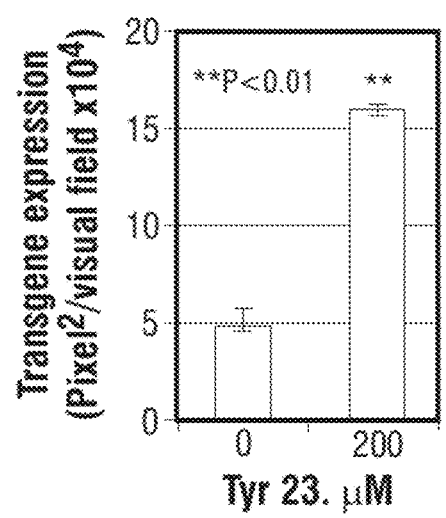

Previous studies have also shown that inhibition of EGFR-PTK signaling by Tyrphostin 23 (Tyr23), a specific inhibitor of EGFR-PTK (May et al., 1998), modulates the Ub/proteasome pathway, which in turn, facilitates intracellular trafficking and transgene expression mediated by AAV2 vectors (Zhong et al., 2007). Hep293TT cells were mock-treated or treated with Tyr23 for 2 hr and transduced with scAAV3 vectors. HeLa cells, pretreated with Tyr23 and transduced with scAAV2 vectors, were included as appropriate controls. Transgene expression was determined 72 hr post-transduction. These results, shown in FIG. 14C and FIG. 14D, indicate that Tyr23-treatment led to a significant increase in the transduction efficiency of both scAAV2 and scAAV3 vectors. The increased transgene expression was independent of vector entry, since there was no significant difference in the amounts of internalized viral DNA in the presence or absence of either MG132 or Tyr23. These results further corroborate the involvement of the host cell Ub/proteasome machinery in the life cycle of AAV3 vectors as well.

Site-directed Mutagenesis of Surface-Exposed Tyr Residues Significantly Improves Transduction Efficiency of scAAV3 Vectors. In the preceding examples, the inventors have demonstrated that there are seven surface-exposed tyrosine residues (Y252, Y272, Y444, Y500, Y700, Y704 and Y730) on AAV2 capsids that are phosphorylated by EGFR-PTK and negatively affect the transduction efficiency of AAV2 vectors (Zhong et al., 2008). Alignment of amino acid sequences from AAV2 and AAV3 capsids indicated that six of seven tyrosine residues (Y252, Y272, Y444, Y701, Y705 and Y731) are conserved in AAV3 capsid (Table 4).

TABLE 4

Surface-Exposed Tyr Residues on AAV Capsids, & Site-Directed Mutagenesis to Convert Them to Phenylalanine Residues

| AAV2 | AAV3 |
| --- | --- |
| Y252 | Y252→F |
| Y272 | Y272→F |
| Y444 | Y444→F |
| Y500 | F501 |
| Y700 | Y701→F |
| Y704 | Y705→F |
| Y730 | Y731→F |

The surface-exposed tyrosine (Y) residues on AAV2 and AAV3 capsids are shown; arrows denote the site-directed mutations from Y to phenylalanine (F) residues on AAV3 capsids.

Figure 15A:
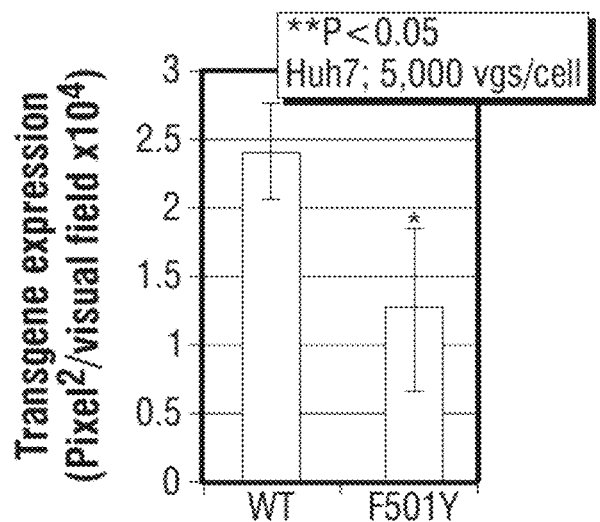
FIG. 15A, FIG. 15B and FIG. 15C show the site-directed mutational analyses of surface-exposed tyrosine residues on AAV3 capsids. Huh7 cells were transduced with WT or F501Y scAAV3-CBAp-EGFP vectors under identical conditions, and transgene expression was determined 72 hrs' post-transduction. Transduction efficiency of WT (FIG. 15A) and various Y-F scAAV3-mediated transgene expression in Huh7 (FIG. 15B) and Hep293TT (FIG. 15C) cells. Transgene expression was determined 72 hrs post-transduction.

One tyrosine residue, Y500 in AAV2, is present as F501 in AAV3. Since it has been shown that Y to F mutations in several AAV serotypes enhance transgene expression by circumventing ubiquitination and proteasome-mediated degradation (Zhong et al., 2008; Petrs-Silva et al., 2009; Qiao et al., 2010; Taylor and Ussher et al., 2010), it was reasoned that mutation of F501 back to a tyrosine residue would reduce the transduction efficiency of AAV3 vectors. This hypothesis was tested by generating a mutant AAV3 vector in which the phenylalanine residue was substituted with a tyrosine residue (F501Y). The transduction efficiency of the mutant vector was compared with its wild-type (WT) AAV3 counterpart using Huh7 cells under identical conditions. As can be seen in FIG. 15A, the extent of the transgene expression mediated by the F501Y mutant vector was reduced by ~50% compared with the WT AAV3 vector.

Figure 15B:
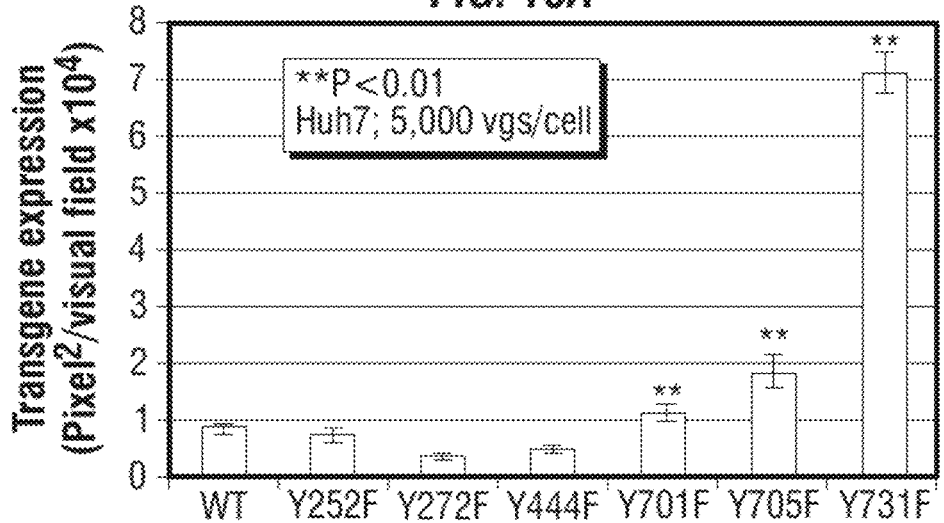
Figure 15C:
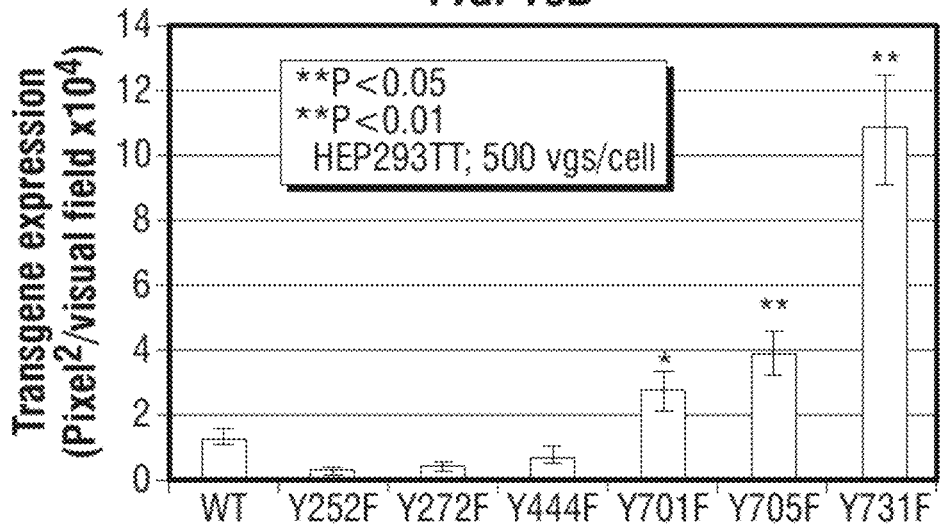

To further test the hypothesis that tyrosine-mutations on AAV3 capsids would lead to decreased EGFR-PTK-mediated phosphorylation followed by reduced ubiquitination and impaired proteasome-mediated degradation resulting in increased transgene expression, all six surface-exposed tyrosine residues on AAV3 capsids were modified and substituted with phenylalanine residues (tyrosine-phenylalanine, Y-F). Each of the single tyrosine-mutant vectors encapsidating scAAV2-CBAp-EGFP genomes could be successfully packaged. Vector titers for each of the mutants were determined by both quantitative DNA slot blots and qPCR, and no significant differences in the packaging efficiency were observed. The transduction efficiency of each of the tyrosine-mutant vectors was analyzed and compared with the WT scAAV3-CBAp-EGFP vector in both Huh7 (FIG. 15B) and Hep293TT (FIG. 15C) cells under identical conditions. From these results, it is evident that, the transduction efficiency of three of the tyrosine-mutant vectors (Y701F, Y705F and Y731F) is significantly higher compared with the WT scAAV3 vector. Specifically, the transduction efficiency of Y731F vector was ~8-fold higher than the WT vector, followed by Y705F (~3-fold) and Y701F (~2-fold) vectors.

Figure 16A:
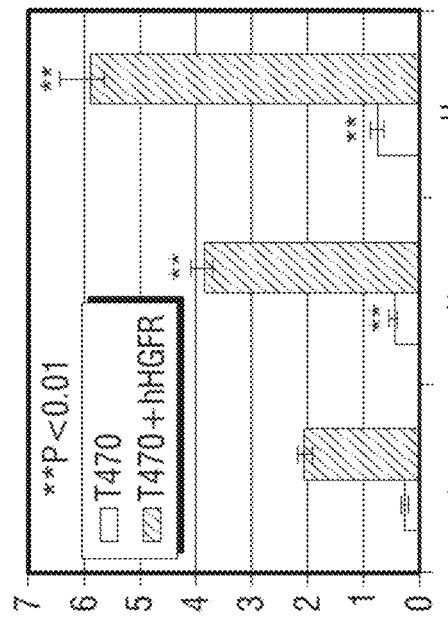
FIG. 16A, FIG. 16B, and FIG. 16C illustrate the transduction efficiency of WT and single, double, and triple tyrosine-mutant AAV3 vectors.
Figure 16B:
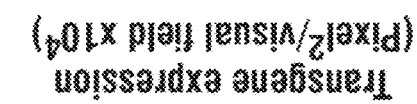

Multiple-Mutations in Surface-Exposed Tyrosine Residues Further Improve the Transduction Efficiency of AAV3 Vectors. In the prior examples involving Y-F mutant AAV2 vectors, it was observed that specific combinations of the most efficient single-mutations of surface-exposed tyrosine residues further augmented the transduction efficiency of AAV2 vectors (Markusic et al., 2010). To examine whether a similar enhancement could be achieved with AAV3 vectors, the following double- and triple-mutant AAV3 vectors were constructed: Y701+731F, Y705+731F, and Y701+705+731F. Each of these mutant vectors was packaged to similar titers, as determined by both quantitative DNA slot blots and qPCR. The transduction efficiency of these multiple-mutants was compared with the WT and the Y731F single-mutant AAV3 vectors in Huh7 cells under identical conditions. These results are shown in FIG. 16A. As can be seen, whereas the Y731F mutation significantly increased the transduction efficiency of AAV3 vectors, as observed before, only one of the double-mutations (Y705+731F) led to an additional significant increase in transgene expression. Interestingly, the transduction efficiency of both the double mutant (Y701+731F) and the triple mutant (Y701+705+731F) vectors was reduced to levels similar to the WT AAV3 vector. The best-performing single and multiple tyrosine-mutants on human liver cancer cells were then evaluated for transduction of T47D and T74D+hHGFR cells (FIG. 16B). Similar to human liver cancer cells, the tyrosine-mutant rAAV3 vectors led to high-efficiency transduction of both cell types, with or without hHGFR expression.

Figure 16C:
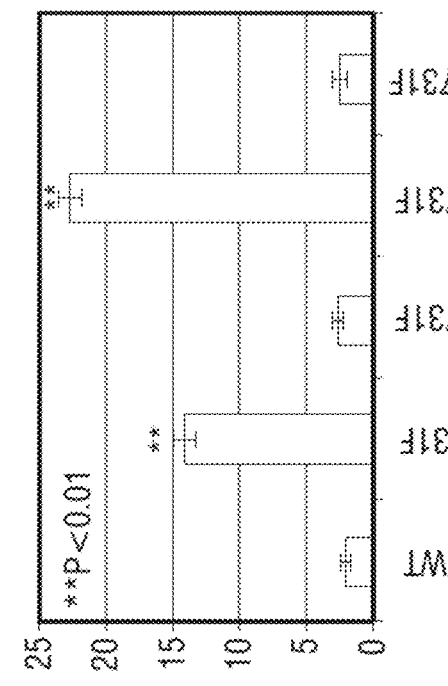

To examine the possibility whether the observed enhanced transduction efficiency of the Y-F mutant vectors was due to the involvement of one or more additional putative cellular receptor/co-receptor functions, the WT, Y731F, and Y705+731F mutant scAAV3-CBAp-EGFP vectors were used to transduce Huh7 cells in the absence or the presence of 5 μg/mL hHGF under identical conditions. These results are shown in FIG. 16C. As is evident, the presence of hHGF dramatically inhibited the transduction efficiency and transgene expression of all three AAV3 vectors, which is consistent with the interpretation that the tyrosine-mutant vectors also utilize hHGFR as a cellular receptor/co-receptor for viral entry.

Figure 17A:
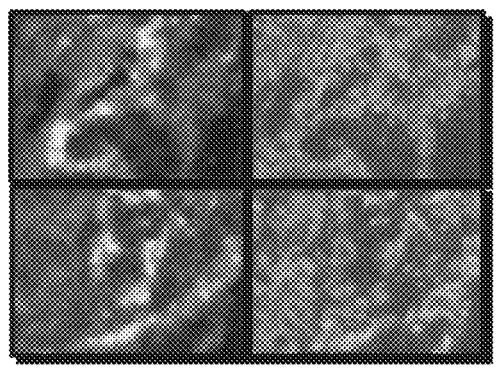
FIG. 17A, FIG. 17B, FIG. 17C and FIG. 17D show the transduction efficiency of AAV3 vectors in vivo following direct intra-tumor injections. Transduction efficiency of WT-AAV3 vectors in Huh7- (FIG. 17A) and Hep293TT- (FIG. 17B) derived tumors in NSG mice. Transduction efficiency of WT- (FIG. 17C) and Y705+731F-AAV3 (FIG. 17D) vectors in Hep293TT-derived tumors in NSG mice. EGFP fluorescence (green) and DAPI staining (blue) of two representative tumor sections from each set of mice is shown.
Figure 17B:
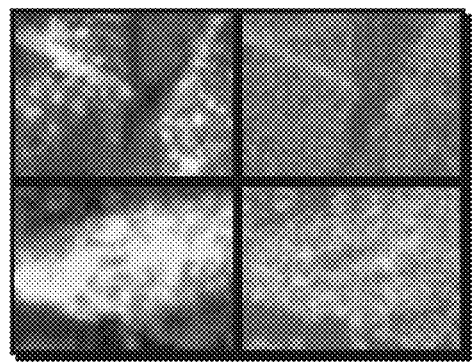

AAV3 Vectors Transduce Human Liver Tumors in Murine Xenograft Models. To demonstrate AAV3 vectors could also transduce human HB and HCC tumors in a xenograft mouse model in vivo, ~5×10$^6$ HCC (Huh7) or HB (Hep293TT) cells were injected sub-cutaneously in NOD/Scid gamma (NSG) mice. Four-weeks later, when tumors were clearly visible and palpable in both groups of animals, ~2×10$^{10}$ vgs of scAAV3-CBAp-EGFP vectors were injected directly into tumors. Four-days post-vector injections, tumors were excised and thin sections were examined under a fluorescence microscope. These results indicated that AAV3 vectors were effective to transduce both human HCC (FIG. 17A) and HB (FIG. 17B) tumors in vivo. Consistent with the in vitro data, the transduction efficiency of AAV3 vectors was higher in Hep293TT cell-derived tumors than that in Huh7 cell-derived tumors.

Figure 17C:
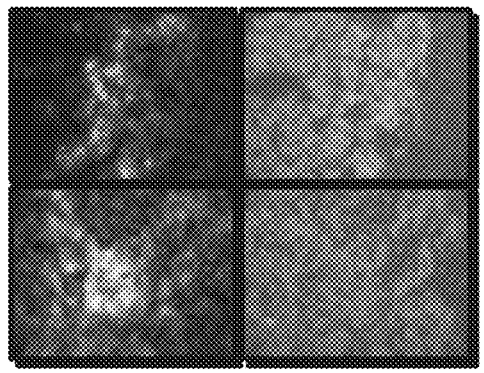
Figure 17D:
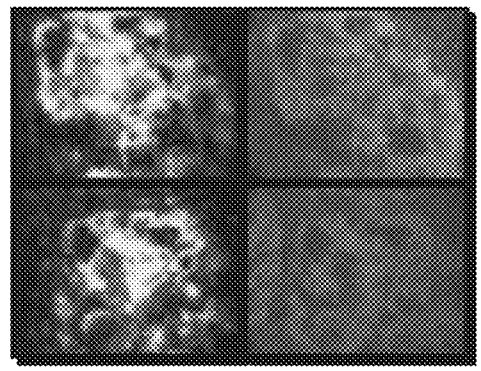

Optimized Tyrosine-Mutant AAV3 Vectors are Highly Efficient in Transducing Human Liver Tumors in Murine Xenografts. Next, the best performing double tyrosine-mutant AAV3 vectors were further evaluated in vivo for xenograft human liver tumors gene transfer. In the first set of studies, ~$5 \times 10^{10}$ vgs of either the wild-type (WT) scAAV3- or Y705+731F-AAV3-CBAp-EGFP vectors were intratumorally injected in NSG mice bearing human HB (Hep293TT) tumors. Four-days post-vector injections, tumors were excised, and thin sections were examined under a fluorescence microscope (FIG. 17C). As can be seen, tumors injected with the WT-AAV3 vectors exhibited detectable levels expression of EGFP. The transduction efficiency of the double tyrosine-mutant AAV3 vectors was significantly higher compared with the WT AAV3 vectors, which is consistent with the in vitro data.

Figures 18A, 18B, 18C:
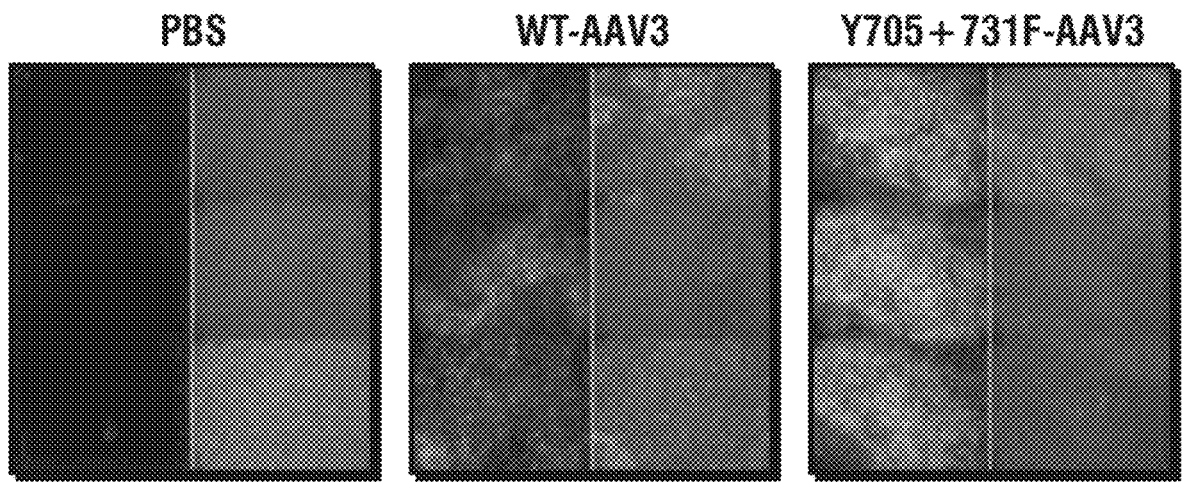
FIG. 18A, FIG. 18B and FIG. 18C show the transduction efficiency of WT- and Y705+731F-AAV3 vectors in Hep293TT-derived tumors in NSG mice following tail-vein injections. EGFP fluorescence (green) and DAPI staining (blue) of tumor in three representative tumor sections from each set of mice injected with PBS (FIG. 18A), WT-AAV3 (FIG. 18B), or Y705+731F-AAV3 (FIG. 18C) vectors is shown.

In the second set of studies, ~$5 \times 10^{11}$ vgs of either the WT-scAAV3- or the Y705+731F-scAAV3-CBAp-EGFP vectors were injected via the tail-vein in NSG mice bearing human HB (Hep293TT) tumors. Phosphate-buffered saline (PBS) injections were used as an appropriate control. Whereas little transgene expression occurred in tumors from mice injected with pBS (FIG. 18A), direct tumor-targeting could be achieved following systemic administration of AAV3 vectors. The transduction efficiency of the optimized tyrosine-mutant AAV3 vectors (FIG. 18C), once again, was significantly higher than that of the WT AAV3 vectors (FIG. 18B). These data suggest that the observed increased transduction efficiency of tyrosine-mutant AAV3 vectors was independent of viral administration route.

HGFR is a trans-membrane receptor tyrosine kinase, and binding of its ligand, HGF, results in dimerization of the receptor and intermolecular trans-phosphorylation of multiple tyrosine residues in the intracellular domain. (Liu et al., 2008) Whereas it is clear that AAV3 capsid interacts with the extracellular domain of hHGFR, it is less clear, whether AAV3-binding to hHGFR also triggers its activation and phosphorylation of the downstream target proteins. The data does indeed demonstrate that suppression of the hHGFR-PTK activity leads to a modest increase in AAV3 vector-mediated transgene expression. In this context, it is of interest to note that the transduction efficiency of AAV3 vectors is significantly higher in a more recently established human hepatoblastoma (HB) cell line, Hep293TT, compared with that in a HB cell line, Huh6, which was established nearly three decades ago. Although subtle differences might exist between the two cell lines, specific mutations have been identified in the tyrosine kinase domain of hHGFR in Hep293TT cells, which render it inactive, and that the hHGFR-specific kinase inhibitor, BMS-777607, which augments the transduction efficiency in Huh6 cells, has little effect on AAV3 transduction efficiency in Hep293TT cells.

Despite the utilization of two distinct cellular growth factor receptors as co-receptors by AAV2 (hFGFR1) and AAV3 (hHGFR), the two serotypes appear to share certain post-receptor entry and intracellular trafficking pathways. For example, both capsids become phosphorylated at tyrosine residues by EGFR-PTK, presumably in the late endosomes, followed by ubiquitination, which leads to proteasome-mediated degradation. (Zhong et al., 2008) However, although 6 of 7 surface-exposed tyrosines in AAV2 are conserved in AAV3, the patterns of behavior of the corresponding Y-F mutants are somewhat divergent. For example, Y730F (for AAV2) and Y731F (for AAV3) are the most efficient single-mutants, followed by Y444F (for AAV2), and Y705F (for AAV3), the transduction efficiency of Y444F (for AAV3) remains unaltered. Similarly, whereas the transduction efficiency of the Y730+444F double-mutant (for AAV2) is not significantly different from that of Y730F, the transduction efficiency of the Y705+731F double-mutant (for AAV3) is significantly higher than Y731F. Furthermore, the Y730+500+444F triple-mutant (for AAV2) is the most efficient, the Y731+501+705F triple-mutant (for AAV3) is the most efficient, the Y501 residue having already been mutated in the WT AAV3 capsid. Interestingly, even the WT AAV3 vectors were able to transduce human liver tumors reasonably well in a mouse xenograft model in vivo following intratumor injection. However, evidence that the tyrosine-mutant vector resulted in higher gene transfer efficiency in vivo has been demonstrated.

Human liver cancer, especially hepatocellular carcinoma (HCC), is one of the most aggressive malignant tumors. The major obstacle to survival with HCC is recurrence after HCC resection. (Tang, 2005) Thus, transduction of 100% of target cells is desirable in order to completely eliminate the tumor. In previous studies, it was observed that melittin, a toxic peptide derived from bee venom, inhibits the viability and motility of HCC cells both in vitro and in vivo via the suppression of Rac1-dependent pathway (Liu et al, 2008) and up-regulation of mitochondria membrane protein 7A6. (Zhang et al., 2007) Melittin has been shown to induce apoptosis of HCC cells potentially by activating CaMKII/TAK1/JNK/p38 signaling pathway. (Wang et al., 2009)

Based on previous studies with recombinant adenovirus vectors containing the melittin gene driven by a liver cancer cell-specific promoter to achieve specific killing of liver cancer cells both in vitro and in vivo (Ling et al., 2005), this example provides optimized tyrosine-mutant AAV3-melittin vectors under the control of a liver cancer cell-specific promoter that can be used to selectively target both primary and metastatic liver cancer.

Example 4—High-Efficiency Transduction of Human Monocyte-Derived Dendritic Cells by Capsid-Modified Recombinant AAV2 Vectors Dendritic cells (DCs) are antigen-presenting cells (APCs), which play a critical role in the regulation of the adaptive immune response. DCs are unique APCs and have been referred to as "professional" APCs, since the principal function of DCs is to present antigens, and because only DCs have the ability to induce a primary immune response in resting naïve T lymphocytes. (Banchereau and Steinman, 1998) Although a naturally occurring anti-tumor immune response is detectable in patients, this response fails to control tumor growth. On the other hand, monocyte-derived DCs (moDCs) generated ex vivo in the presence of granulocyte-macrophage colony-stimulating factor (GM-CSF) and interleukin 4 (IL-4) possess the capacity to stimulate antigen-specific T-cells after endogenous expression of antigens. (Chapuis et al., 1997; den Brok et al., 2005) For this reason, genetically-modified DCs have been extensively studied and numerous Phase I and II clinical trials evaluating the efficacy of DCs in patients with cancer have been initiated. (Figdor et al., 2004; Palucka et al., 2011) However, current methods for DC loading are inadequate in terms of cell viability, uncertainty regarding the longevity of antigen presentation, and the restriction by the patient's haplotype. (Palucka et al., 2011)

The possibility of manipulating viral genomes by biotechnological techniques, together with the recent identification of many tumor-associated antigens (TAAs), has sparked an interest in using recombinant viruses to express TAAs in the hope of inducing a protective antitumor immune response in patients. (Liu, 2010; Robert-Guroff, 2007) Among different methods for gene delivery, vectors based on a human parvovirus, the adeno-associated virus serotype 2 (AAV2), have attracted much attention mainly because of the non-pathogenic nature of this virus, and its ability to mediate long-term, sustained therapeutic gene expression. (Daya and Berns, 2008; Mueller and Flotte, 2008; Srivastava, 2008) Successful transduction of different subsets of DCs by different commonly used serotypes of AAV vectors has been demonstrated and the potential advantage of an AAV-based antitumor vaccine discussed. (Pannazhagan et al., 2001; Veron et al., 2007; Mahadevan et al., 2007; Shin et al., 2008; Taylor and Ussher, 2010) However, further improvements in gene transfer by recombinant AAV vectors to DCs in terms of specificity and transduction efficiency are warranted to achieve a significant impact when used as an anti-tumor vaccine.

Cellular epidermal growth factor receptor protein tyrosine kinase (EGFR-PTK) negatively impacts nuclear transport and subsequent transgene expression by recombinant AAV2 vectors primarily due to phosphorylation of capsids at surface tyrosine residues. (Zhong et al., 2007) These studies resulted in the development of next generation recombinant AAV2 vectors containing point mutations in surface exposed tyrosine residues that transduce various cells and tissues with high-efficiency at lower doses compared to the wild-type (WT) vector. (Zhong et al., 2008) However, such single or multiple tyrosine-mutant AAV vectors failed to increase the transduction efficiency of monocyte-derived DCs (moDCs) more than 2-fold, most likely due to lower levels of expression and/or activity of EGFR-PTK compared with that in HeLa cells or hepatocytes. (Taylor and Ussher, 2010)

Serine/threonine protein kinases are involved in a wide variety of cellular processes such as differentiation, transcription regulation, and development of many cell types including immune cells. Such kinases can also negatively regulate the efficiency of recombinant AAV vector-mediated gene transfer by phosphorylating the surface-exposed serine and/or threonine residues on the viral capsid and target the vectors for proteasome-mediated degradation. In the present example, the following were documented: (i) Site-directed mutagenesis of the 15 surface-exposed serine (S) residues on the AAV2 capsid to valine (V) residues leads to improved transduction efficiency of S458V, S492V, and S662V mutant vectors compared with the WT AAV2 vector; (ii) The S662V mutant vector efficiently transduces human monocyte-derived dendritic cells (moDCs), a cell type not readily amenable to transduction by the conventional AAV vectors; (iii) High-efficiency transduction of moDCs by S662V mutant does not induce any phenotypic changes in these cells; and (iv) Recombinant S662V-vectors encoding a truncated human telomerase (hTERT) gene, used to transduced DCs result in rapid, specific T-cell clone proliferation and generation of robust CTLs, which leads to specific cell lysis of K562 cells.

Materials and Methods

Cells and Antibodies. HEK293, HeLa and NIH3T3 cells were obtained from the American Type Culture Collection and maintained as monolayer cultures in DMEM (Invitrogen, Inc.) supplemented with 10% FBS (Sigma-Aldrich Co.) and antibiotics (Lonza, Inc.). Leukapheresis-derived peripheral blood mononuclear cells (PBMCs) (AllCells) were purified on Ficoll-Paque (GEHeathCare), resuspended in serum-free AIM-V medium (Lonza, Inc.), and semi-adherent cell fractions were incubated for 7 days with recombinant human IL-4 (500 U/mL) and GM-CSF (800 U/mL) (R&D Systems). Cell maturation was initiated with a cytokine mixture including 10 ng/mL TNF-α, 10 ng/mL IL-1, 10 ng/mL IL-6, and 1 mg/mL PGE2 (R&D Systems) for 48 hrs. Prior to EGFP expression cells were characterized for co-stimulatory molecules expression to ensure that they met the typical phenotype of mature dendritic cells (mDC) (CD80, RPE, murine IgG1; CD83, RPE, murine IgG1; CD86, FITC, murine IgG1; Invitrogen, Inc.). (Jayandharan et al., 2011)

Site-Directed Mutagenesis. A two-stage PCR was performed with plasmid pACG2 as described previously (Wang and Malcolm, 1999) using Turbo Pfu Polymerase (Stratagene). Briefly, in stage one, two PCR extension reactions were performed in separate tubes for the forward and reverse PCR primer for 3 cycles. In stage two, the two reactions were mixed and a PCR reaction was performed for an additional 15 cycles, followed by DpnI digestion for 1 hr. Primers were designed to introduce changes from serine (TCA or AGC) to valine (GTA or GTC) for each of the residues mutated.

Production of Recombinant AAV Vectors. Recombinant AAV2 vectors containing the EGFP gene driven by the chicken β-actin promoter were generated as described previously (Zologukhin et al., 2002). Briefly, HEK293 cells were transfected using polyethylenimine (PEI, linear, MW 25,000, Polysciences, Inc.). Seventy-two hrs post transfection, cells were harvested and vectors were purified by iodixanol (Sigma-Aldrich Co.) gradient centrifugation and ion exchange column chromatography (HiTrap Sp Hp 5 mL, GE Healthcare, Piscataway, N.J., USA). Virus was then concentrated and the buffer exchanged in three cycles to lactated Ringer's using centrifugal spin concentrators (Apollo, 150-kDa cut-off, 20-mL capacity, CLP) (Cheng et al., 2011). Ten L of purified virus was treated with DNAse I (Invitrogen, Inc.) for 2 hrx at 37° C., then an additional 2 hr with proteinase K (Invitrogen, Inc.) at 56° C. The reaction mixture was purified by phenol/chloroform, followed by chloroform treatment. Packaged DNA was precipitated with ethanol in the presence of 20 μg glycogen (Invitrogen, Inc.). DNAse I-resistant AAV particle titers were determined by RT-PCR with the following primer-pair, specific for the CBA promoter:

Forward 5'-TCCCATAGTAACGCCAATAGG-3' (SEQ ID NO:18),

Reverse 5'-CTTGGCATATGATACACTTGATG-3' (SEQ ID NO:19), and SYBR Green PCR Master Mix (Invitrogen, Inc.). (Aslanidi et al., 2009).

Recombinant AAV Vector Transduction Assays In Vitro. HEK293 or monocyte-derived dendritic cells (moDCs), were transduced with AAV2 vectors with 1,000 vgs/cell or 2,000 vgs/cell respectively, and incubated for 48 hr. Alternatively, cells were pretreated with 50 μM of selective serine/threonine kinase inhibitors 2-(2-hydroxyethylamino)-6-aminohexylcarbamic acid tert-butyl ester-9-isopropylpurine (for CaMK-II), anthra[1,9-cd]pyrazol-6(2H)-one, 1,9-pyrazoloanthrone (for JNK), and 4-(4-fluorophenyl)-2-(4-methylsulfinylphenyl)-5-(4-pyridyl)1H-imidazole (for MAPK) (CK59, JNK inhibitor 2, PD 98059, Calbiochem), 1 hr before transduction. Transgene expression was assessed as the total area of green fluorescence (pixel2) per visual field (mean±SD) as described previously (Markusic et al., 2011; Jayandharan et al., 2011). Analysis of variance was used to compare test results and the control, which were determined to be statistically significant.

Western Blot Analysis. Western blot analysis was performed as described previously. (Akache et al., 2006) Cells were harvested by centrifugation, washed with PBS, and resuspended in lysis buffer containing 50 mM TrisHCl, pH 7.5, 120 mM NaCl, 1% Nonidet P-40, 10% glycerol, 10 mM Na4P2O7, 1 mM phenylmethylsulfonyl fluoride (PMSF), 1 mM EDTA, and 1 mM EGTA supplemented with protease and phosphotase inhibitors mixture (Set 2 and 3, Calbiochem). The suspension was incubated on ice for 1 hr and clarified by centrifugation for 30 min at 14,000 rpm at 4° C. Following normalization for protein concentration, samples were separated using 12% polyacrylamide/SDS electrophoresis, transferred to a nitrocellulose membrane, and probed with primary antibodies, anti p-p38 MAPK (Thr180/Tyr182) rabbit mAb, total p38 MAPK rabbit mAb and GAPDH rabbit mAb (1:1000, CellSignaling), followed by secondary horseradish peroxidase-linked linked antibodies (1:1000, CellSignaling).

Specific Cytotoxic T-Lymphocytes Generation and Cytotoxicity Assay. Monocyte-derived dendritic cells (moDCs) were generated as described above. Immature DCs were infected with AAV2-S662V vectors encoding human telomerase cDNA, separated into two overlapping ORF— hTERT838-2229 and hTERT2042-3454 at MOI 2,000 vgs/cell of each. Cells were then allowed to undergo stimulation with supplements to induce maturation. After 48 hr, the mature DCs expressing hTERT were harvested and mixed with the PBMCs at a ratio of 20:1. CTLs were cultured in AIM-V medium containing recombinant human IL-15 (20 IU/mL) and IL-7 (20 ng/mL) at 20×10$^6$ cells in 25 cm$^2$ flasks. Fresh cytokines were added every 2 days. After 7 days post-priming, the cells were harvested and used for killing assays (Heiser et al., 2002). A killing curve was generated and specific cell lysis was determined by FACS analysis of live/dead cell ratios as described previously (Mattis et al., 1997). Human immortalized myelogenous leukemia cell line, K562, was used as a target.

Statistical Analysis. Results are presented as mean±S.D. Differences between groups were identified using a grouped-unpaired two-tailed distribution of Student's T-test. P-values <0.05 were considered statistically significant.

Results

Figure 19A:
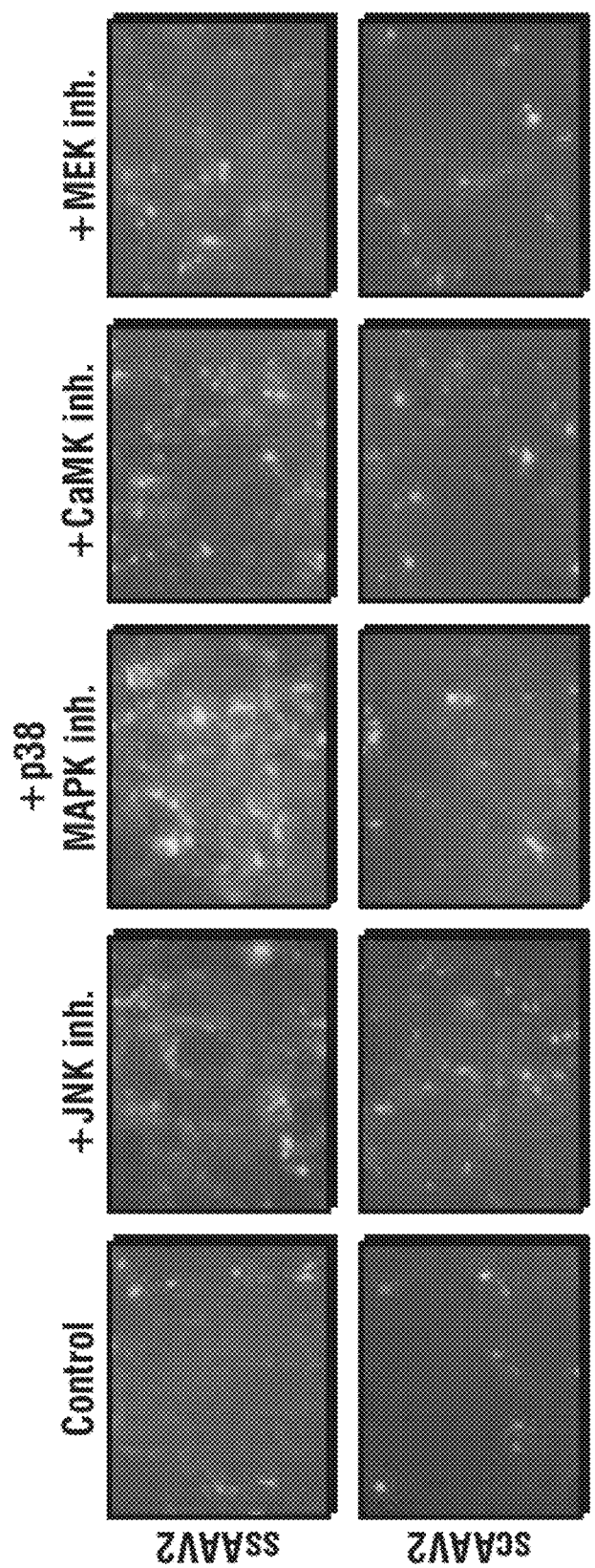
FIG. 19A and FIG. 19B show the effect of various kinase inhibitors on ssAAV and scAAV mediated EGFP expression in HEK293 cells. Cells were pretreated with inhibitors for 1 hr before infection then transduced with $1 \times 10^3$ vgs/cell.
Figure 19B:
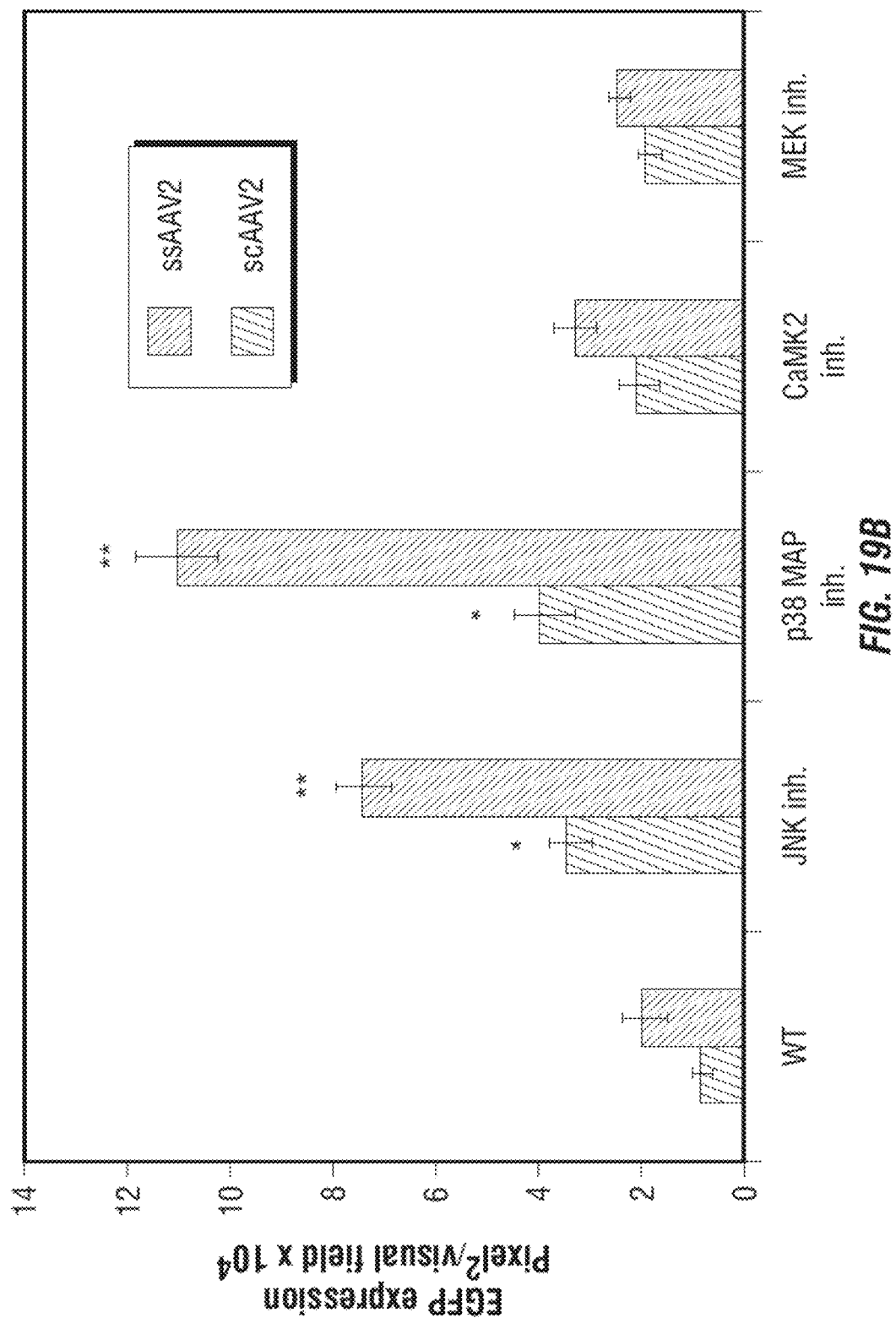

Inhibition of Specific Cellular Serine/Threonine Kinase Increases Transduction Efficiency of rAAV2 Vectors. In previous studies, inhibition of cellular epidermal growth factor receptor protein tyrosine kinase (EGFR-PTK) activity and site-directed mutagenesis of the 7 surface-exposed tyrosine residues was shown to significantly increase to the transduction efficiency of AAV2 vectors by preventing phosphorylation of these residues, thereby circumventing ubiquitination and subsequent proteasome-mediated degradation of the vectors (Zhong et al., 2008). However, AAV2 capsids also contain 15 surface-exposed serine residues, which can potentially be phosphorylated by cellular serine/threonine kinases widely expressed in various cell types and tissues. To test the hypothesis that inhibition of such kinase activity can prevent phosphorylation of surface-exposed serine residues and thus improve intracellular trafficking and nuclear transport of AAV2 vectors, several commercially available specific inhibitors of cellular serine/threonine kinases were used, including calmodulin-dependent protein kinase II (CamK-II), c-Jun N-terminal kinase (JNK); and mitogen-activated protein kinase (p38 MAPK). HEK293 cells were pre-treated with specific inhibitors, such as 2-(2-hydroxyethylamino)-6-aminohexylcarbamic acid tert-butyl ester-9-isopropylpurine (for CaMK-II), anthra[1,9-cd]pyrazol-6 (2H)-one, 1,9-pyrazoloanthrone (for JNK), and 4-(4-fluorophenyl)-2-(4-methylsulfinylphenyl)-5-(4-pyridyl)1H-imidazole (for p38 MAPK) for 1 hr at various concentrations. Cells were subsequently transduced with either single-stranded (ss) or self-complementary (sc) AAV2 vectors at 1,000 vector genomes (vgs) per cell. These results indicated that all inhibitors at an optimal concentration of 50 µM significantly increased the transduction efficiency of ssAAV2 and scAAV2 vectors, the p38 MAPK inhibitor being the most effective (FIG. 19A and FIG. 19B). This observation suggests, albeit does not prove, that the increase in the transduction efficiency was most likely due to prevention of phosphorylation of vector capsids rather than improved viral second-strand DNA synthesis.

Figure 20B:
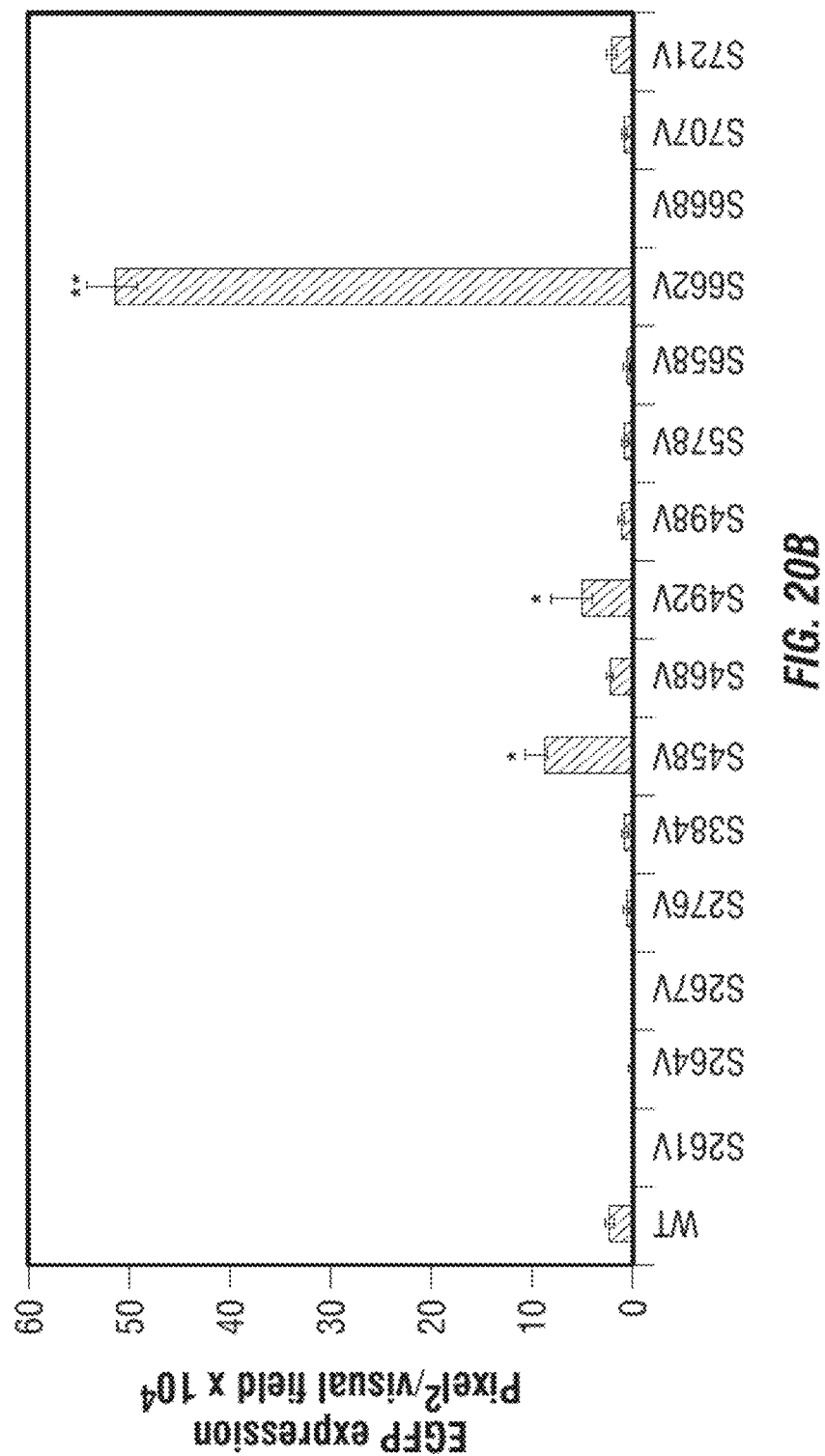
Figure 21A:
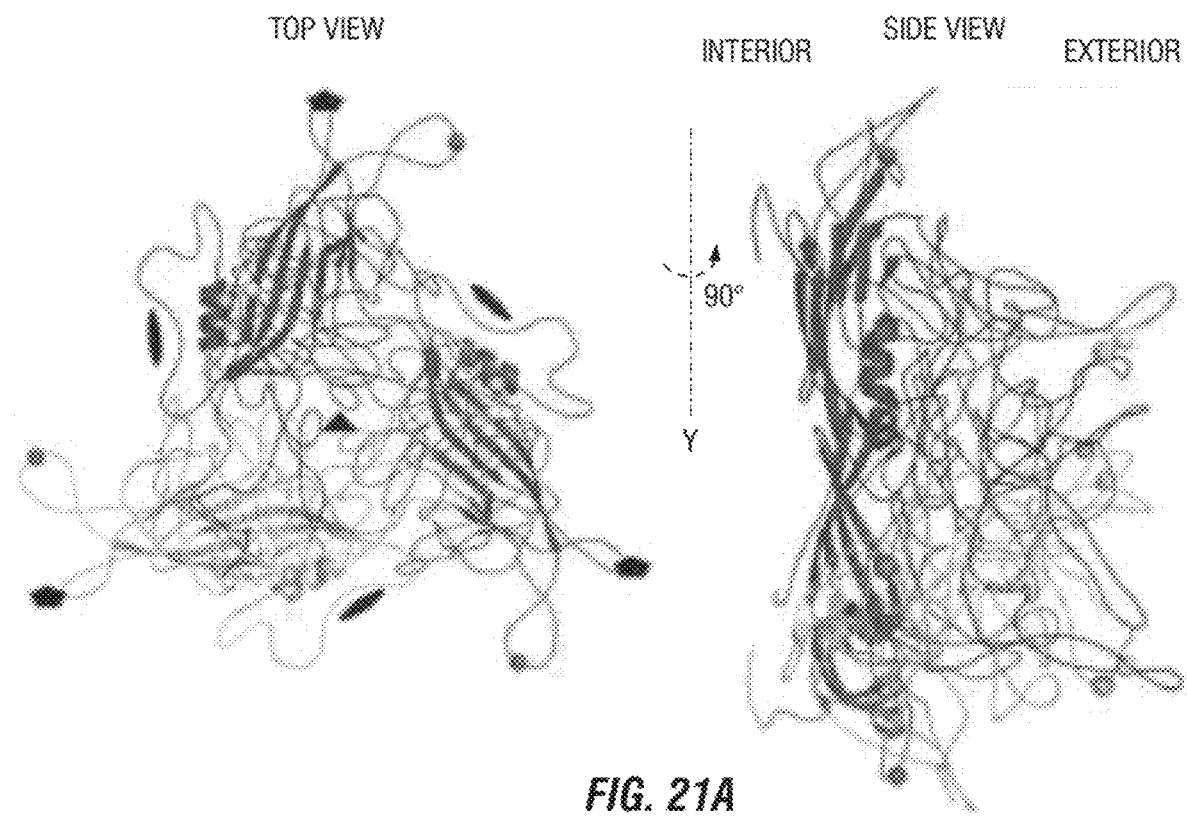
FIG. 21A and FIG. 21B illustrate the structure of AAV2.
Figure 21B:
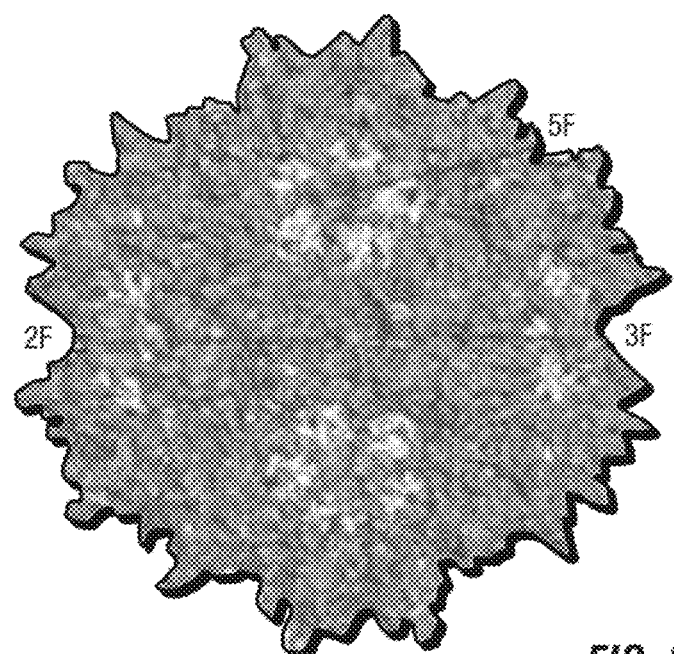

Site-Directed Mutagenesis of Surface-Exposed Serine Residues on AAV2 Capsid Improves AAV2 Vector-Mediated Transgene Expression. The AAV2 capsid contains 50 serine (S) residues in the viral protein 3 (VP3) common region of the three capsid VPs, of which 15 (S261, S264, S267, S276, S384, S458, S468, S492, S498, 5578, S658, S662, S668, S707, S721) are surface-exposed. (Xie et al., 2002) Each of the 15 S residues was substituted with valine (V) by site-directed mutagenesis as described (Zhong et al., 2008). Most mutants could be generated at titers similar to the WT AAV2 vectors, with the exception of S261V, S276V, and S658V, which were produced at ~10 times lower titers, and S267V and S668V, which produced no detectable levels of DNAse I-resistant vector particles. The titers of S468V and S384V mutants were ~3-5 times higher than the WT AAV2 vectors. Each of the S—V mutant vectors was evaluated for transduction efficiency in HEK293 cells. These results, shown in FIG. 20, indicate that of the 15 mutants, the S662V mutant transduced HEK293 cells ~20-fold more efficiently than its WT counterpart did. The transduction efficiency of the S458V and the S492V mutant vectors was increased by ~4- and 2-fold, respectively. The positions of these three critical surface exposed serine residues on the AAV2 capsid are shown in FIG. 21A and FIG. 21B. No further increase in transduction efficiency was observed with the double-mutants (S458+662V and S492+662V), or the triple-mutant (5458+492+662V), indicating that unlike some of the tyrosine-mutants, combining multiple mutations in the serine residues was neither additive nor synergistic. Interestingly, the transduction efficiency of the S468V and the S384V mutants, which were produced at titers higher than the WT AAV2 vectors, remained unchanged (S468V) or were reduced ~10-fold (S384V) at the same multiplicity of infection (MOI). These data are summarized in FIG. 34.

Figure 22A:
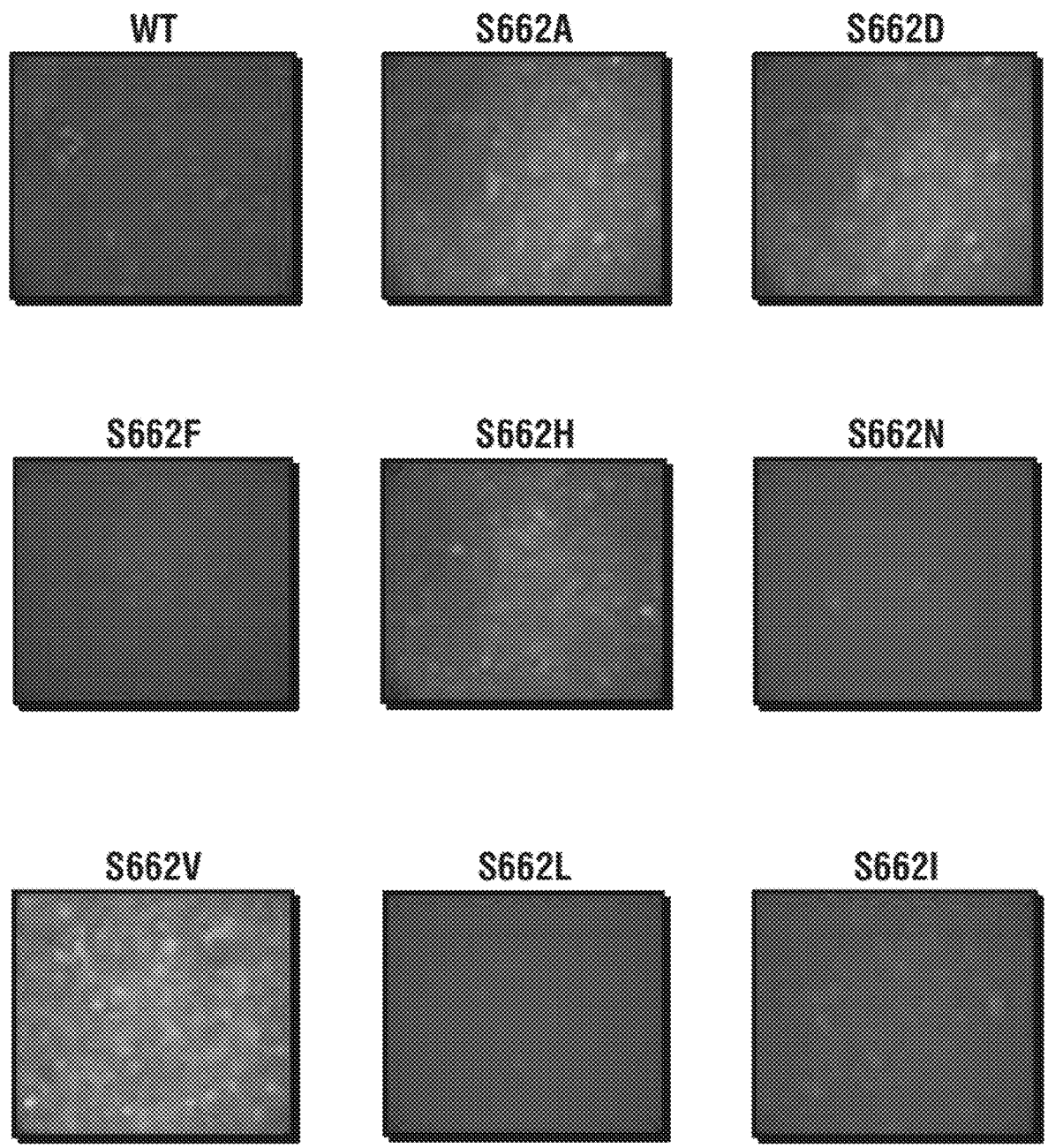
FIG. 22A and FIG. 22B show the evaluation of the effect of serine substitution at position 662 in the scAAV2 capsid with different amino acids in mediating transgene expression. The following 8 serine mutants were generated with different amino acids: S662→Valine (V), S662→Alanine (A), S662→Asparagine (N), S662→Aspartic acid (D), S662→Histidine (H), S662→Isoleucine (I), S662→Leucine (L), and S662→Phenylalanine (F), and their transduction efficiency in 293 cells was analyzed.
Figure 22B:
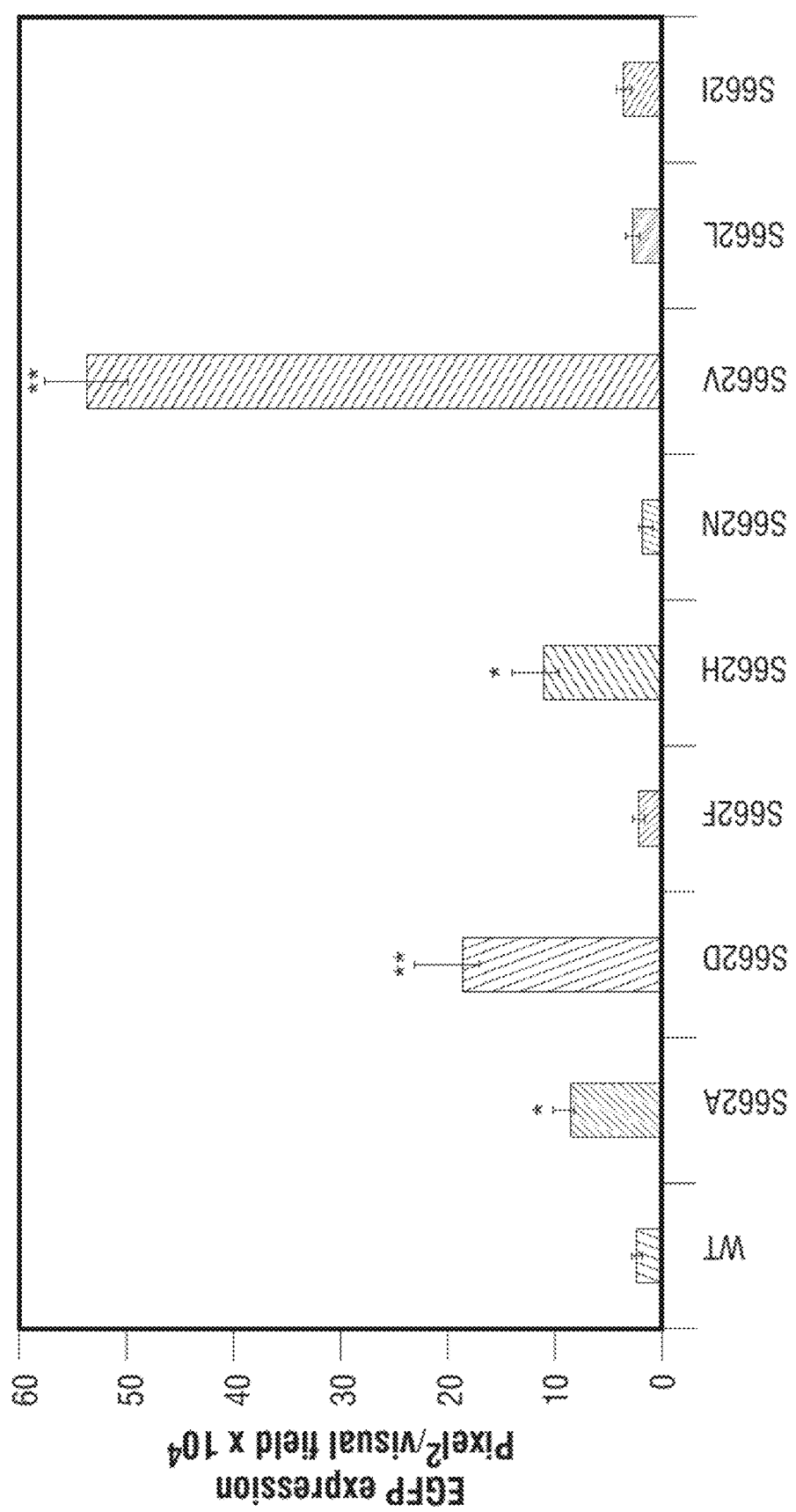

Substitution of S662 with Different Amino Acids has Diverse Effects on AAV2 Capsid Assembly and AAV2 Vector-Mediated Transgene Expression. In addition to S-to-V substitution at position 662, the following 7 mutants with different amino acids were also generated: 5662→Alanine (A), 5662→Asparagine (N), 5662→Aspartic acid (D), 5662→Histidine (H), 5662→Isoleucine (I), 5662→Leucine (L), and 5662→Phenylalanine (F), and evaluated their transduction efficiency in 293 cells. These results, shown in FIG. 22 and summarized in FIG. 35, demonstrate that the substitution of S with V led to the production of the most efficient mutant without any change in vector titers. Replacement of S with N, I, L, or F decreased the packaging efficiency ~10-fold with no significant effect on the transduction efficiency, whereas substitution with D or H increased the transduction efficiency ~8-fold and ~4-fold, respectively, with no effect on vector titers. Interestingly, substitution of S to A increased the viral titer up to ~5-fold, and enhanced the transgene expression ~3-fold compared with the WT AAV2 vector. The observed variability in titers and infectivity of the serine-mutants at position 662 suggests the critical role each of the amino acids plays in modulating both AAV2 packaging efficiency and biological activity.

Figure 23A:
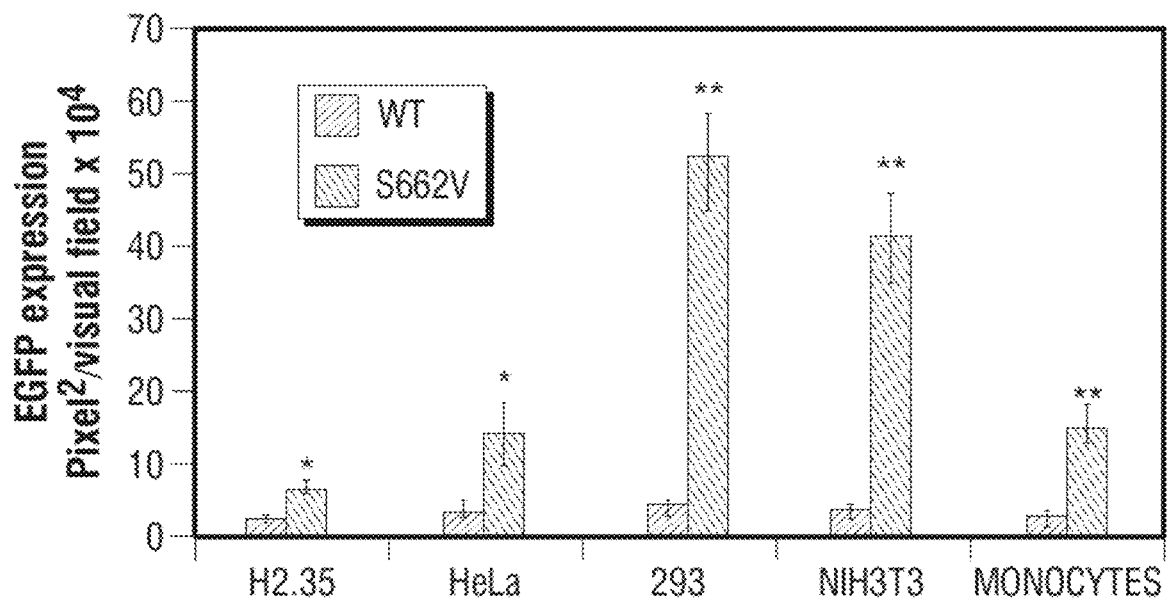
FIG. 23A and FIG. 23B show the analysis of correlation of transduction efficiency of scAAV2-S662V vectors with p38 MAPK activity in various cell types.
Figure 23B:
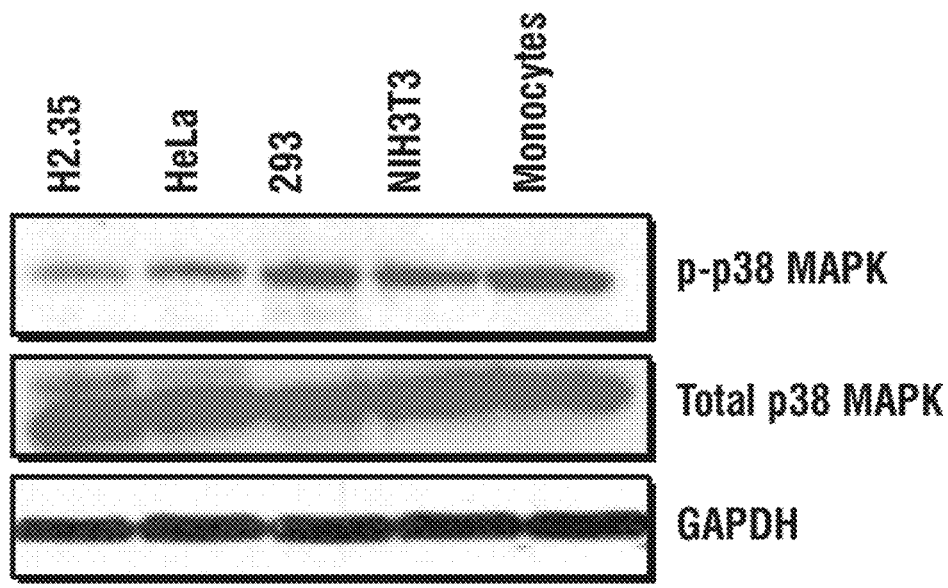

Transduction Efficiency of S662V Vectors Correlate with p38 MAPK Activity. Since all of the S662V vector-mediated transgene expression data thus far were derived using 293 cells, these studies were extended to include the following cells types: (i) NIH3T3 (mouse embryonic fibroblasts), (ii) H2.35 (mouse fetal hepatocytes), (iii) HeLa (human cervical cancer cells), and (iv) primary human monocyte-derived dendritic cells (moDCs). These cell types were transduced with WT scAAV2-EGFP or S662V scAAV2-EGFP vectors at an MOI of 2,000 vgs per cell under identical conditions. EGFP gene expression was evaluated 48 hrs post-infection (p.i.) for HeLa, 293 and moDCs, and 5 days p.i. for H2.35 and NIH3T3 cells. These results are shown in FIG. 23A. As can be seen, although the absolute differences in the transduction efficiency between WT and S662V mutant vectors ranged from ~3-fold (in H2.35 cells) to ~20-fold (in 293 cells) the mutant vector was consistently more efficient in each cell type tested. Since pre-treatment of cells with an inhibitor of cellular p38 MAPK was the most effective in increasing the transduction efficiency (FIG. 19A and FIG. 19B), the inventors examined whether or not the observed differences in the transduction efficiency of the WT and the mutant vectors was due to variations in the levels of expression and/or activity of the cellular p38 MAPK. Cell lysates prepared from each cell type were analyzed on Western blots probed with specific antibodies to detect both total p38 MAPK and phospho-p38 MAPK levels. GAPDH was used as a loading control. These results, shown in FIG. 23B, indicate that whereas the p38 MAPK protein levels were similar, the kinase activity, as determined by the level of phosphorylation, varied significantly among different cell types, and the transduction efficiency of the S662V mutant vector correlated roughly with the p38 MAPK activity. These approximate correlations between p38 MAPK activity and the efficiency of the S662V mutant vector can probably be explained by different cell susceptibilities for AAV infection, the overall number of viral particles entered cell after primary infection. It remains unclear as to which precise steps in the life cycle of AAV are modulated by p38 MAPK-mediated phosphorylation. It is also possible that other serine/threonine kinases contributing to the difference in efficiency of transduction by S662V and WT vectors. Interestingly, however, transduction by the WT-AAV2 vectors did not lead to up regulation of phosphorylation of p38 MAPK in 293 cells or in moDC, further supporting a previous report that AAV does not induce robust phenotypic changes in moDCs (Markusic et al., 2011).

Figure 24A:
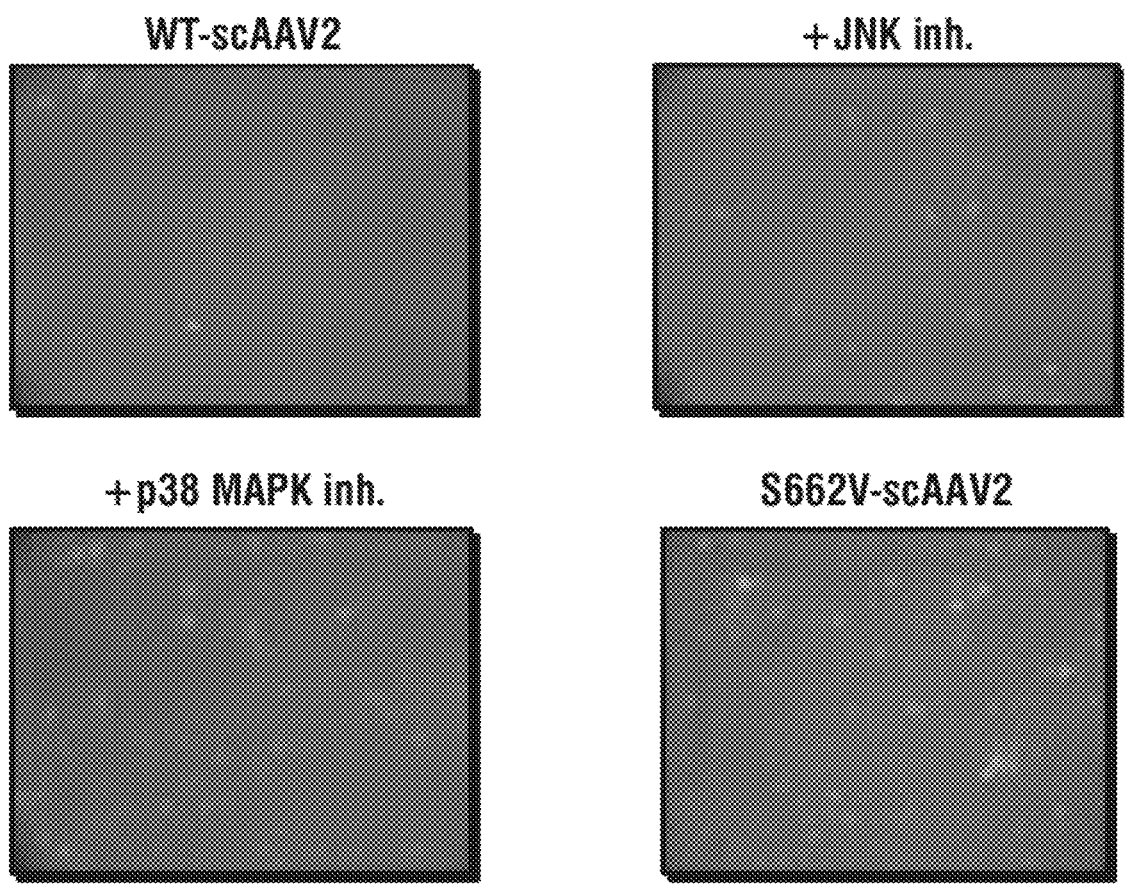
FIG. 24A, FIG. 24B, and FIG. 24C illustrate scAAV vector-mediated transgene expression in monocyte-derived dendritic cells (moDCs).
Figure 24B:
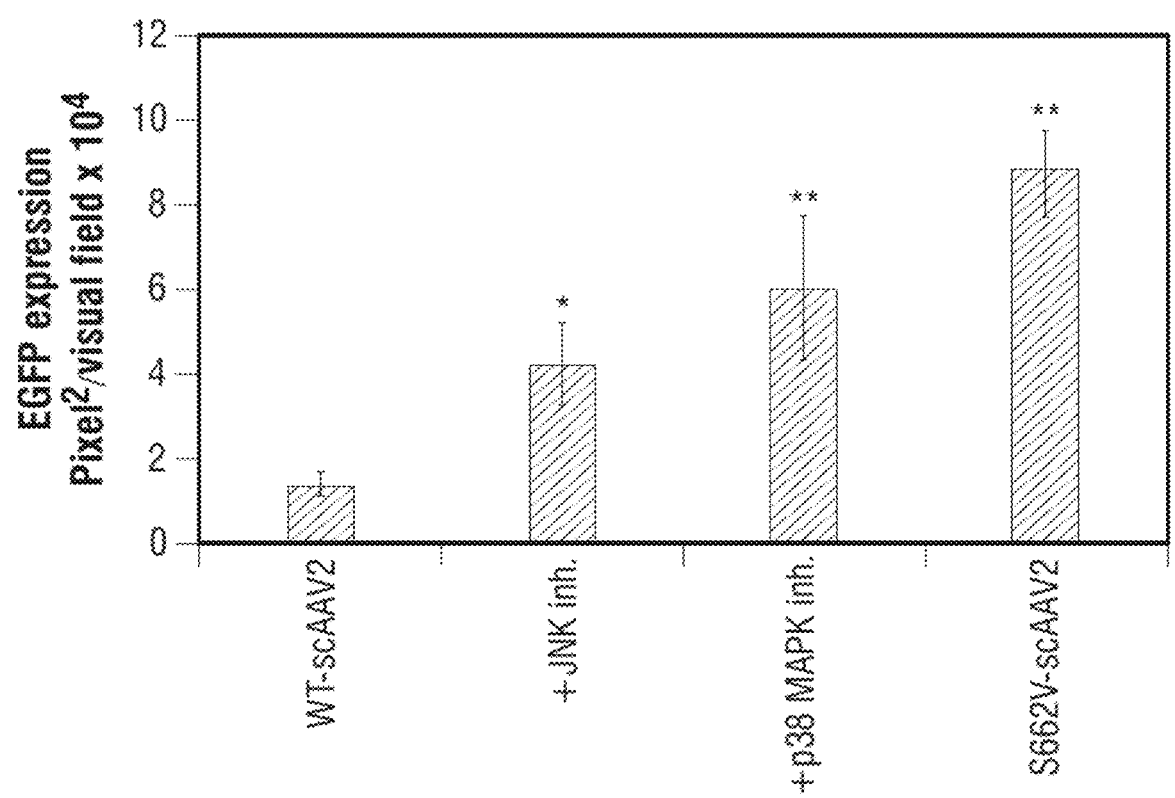
Figure 24C:
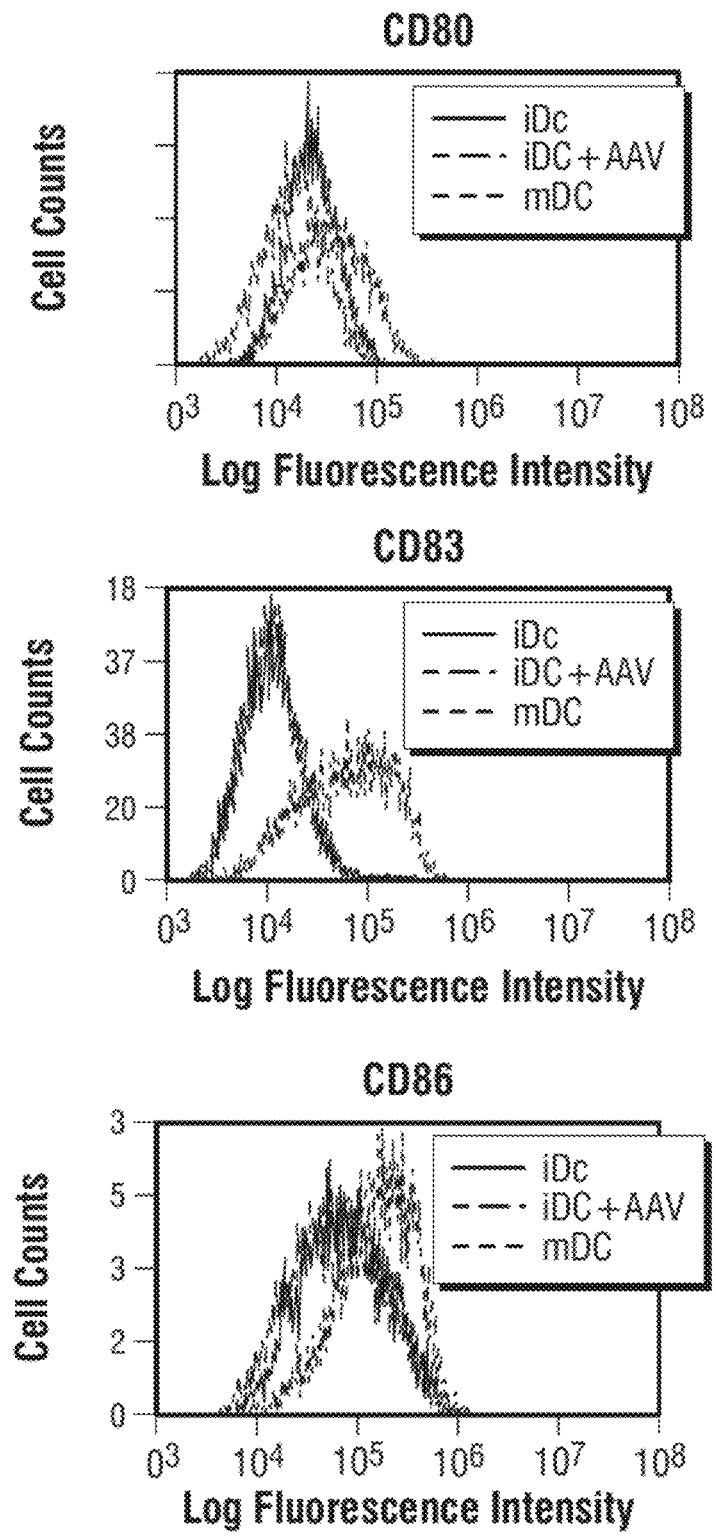
Figure 25:
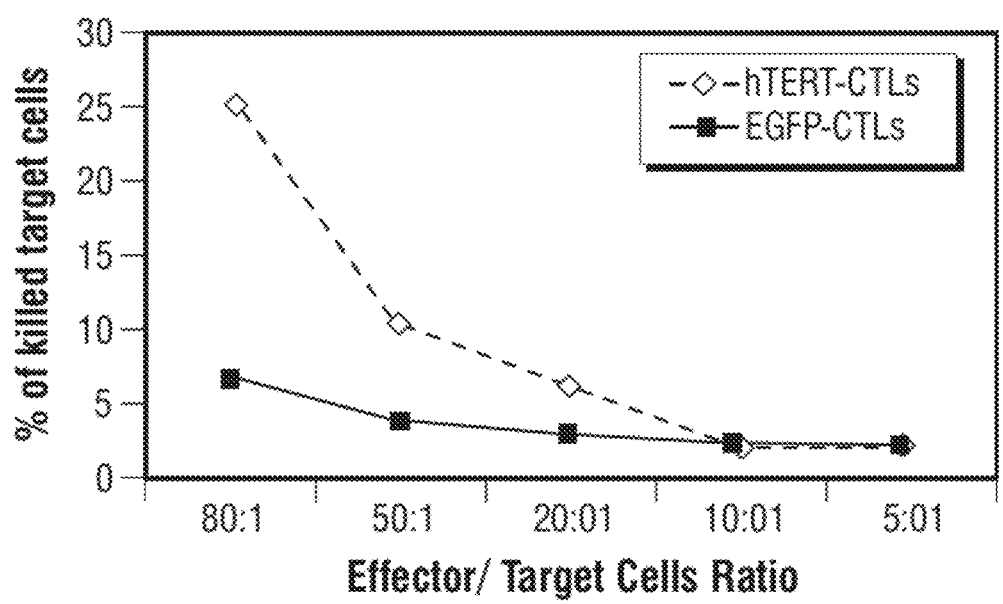
FIG. 25 shows the analysis of hTERT-specific cytotoxic T-lymphocytes (CTLs) killing activity on K562 cells. CTLs were generated after transduction of moDCs by scAAV2-S662V vectors encoding the truncated human telomerase (hTERT). scAAV2-S662V-EGFP vector-traduced moDCs were used to generate non-specific CTLs. Pre-stained with 3,3-dioctadecyloxacarbocyanine (DiOC18(3)), a green fluorescent membrane stain, $1 \times 10^5$ target K562 cells were co-cultured overnight with different ratios of CTLs (80:1, 50:1, 20:1, 10:1, 5:1). Membrane-permeable nucleic acid counter-stain, propidium iodide, was added to label the cells with compromised plasma membranes. Percentages of killed, double stain-positive cells were analyzed by flow cytometry.

S662V Vector-Mediated Transduction of Primary Human moDCs Does Not Lead to Phenotypic Alterations. MAPK family members play important roles in the development and maturation of APCs. moDCs, isolated from healthy donor leukapheresis, were treated with 50 μM selective kinase inhibitors as described above and then transduced with WT scAAV2-EGFP vectors. Two hrs p.i., cells were treated with supplements (TNF-α, IL-1β, Il-6, PGE2) to induce maturation. EGFP transgene expression was evaluated 48 hrs p.i. by fluorescence microscopy. Pre-treatment of moDCs with specific inhibitors of JNK and p38 MAPK increased EGFP expression levels ~2-fold and ~3-fold, respectively, and the transduction efficiency was enhanced by ~5-fold with the S662V mutant vectors (FIG. 24). Since inhibition of these kinases has previously been reported to prevent maturation of dendritic cells (Beisleve et al., 2005; Nakahara et al., 2006; Nakahara et al., 2004; Harley, 2008), the capability of S662V mutant to induce phenotypic changes in DCs also was evaluated. moDC were infected with an increasingly higher MOI up to 50,000 vgs per cell, harvested at 48 hrs p.i., and analyzed by fluorescence-activated cell sorting (FACS) for up regulation of surface co-stimulatory molecules. Flow cytometric analyses of DC maturation markers such as CD80, CD83 and CD86 indicated that, similar to WT AAV2 vectors, the S662V mutant vectors also did not induce the maturation of moDCs (FIG. 24C). This observation supports the previously described low immunogenicity of AAV vectors. (Shin et al., 2008; Jayandharan et al., 2011).

hTERT-Specific CTL Generation by moDC Transduced with AAV2-S662V Vectors. Since the serine-mutant AAV2 vector-mediated transgene expression in moDC was significantly improved compared with the WT-AAV2 vectors, the ability of S662V-loaded moDCs to stimulate the generation of cytotoxic T-lymphocytes and effect specific killing of the target cell was examined. Given that human telomerase is recognized as a unique anti-cancer target (Harley, 2008; Beatty and Vonderheide, 2008) commonly expressed in most cancer cells, a truncated human telomerase (hTERT) gene was cloned under the control of the chicken β-actin promoter and packaged the DNA into the AAV2 S662V mutant. Non-adherent peripheral blood mononuclear cells (PBMC) containing up to 25% of CD8 positive cells were stimulated once with moDC/hTERT delivered by the S662V vector. An immortalized myelogenous leukemia cell line, K562, was used for a two-color fluorescence assay of cell-mediated cytotoxicity to generate a killing curve with subsequently reduced effector to target cell ratio. Result of these experiments, shown in FIG. 25, suggest that moDC loaded with hTERT can effectively stimulate specific T cell clone proliferation and killing activity compared with moDC expressing GFP. Thus, since immunization strategies that generate rapid and potent effector responses are essential for effective immunotherapy, these results support the efficacy of AAV-based delivery methods for vaccination studies.

Discussion

Although the possibility of genetically-modified dendritic cells stimulating a specific anti-tumor cytotoxic T cell response has been proven in a number of clinical trials, a reliable method for therapeutic antigen loading, control of expression, and antigen presentation has not yet been previously developed (O'Neill and Bhardwaj, 2007; Tacken et al., 2007). Since the first attempts to transduce dendritic cells with conventional ssAAV vectors nearly a decade ago (Pannazhagan et al., 2001), significant progress has been made in increasing the transduction efficiency of these vectors. For example, the development of self-complementary AAV (scAAV) vectors has circumvented a major rate-limiting step of viral second-strand DNA synthesis, which dramatically increases transgene expression levels in different subsets of dendritic cells. (Shin et al., 2008; Aldrich et al., 2006; Wang et al., 2003) AAV vector-based antigen delivery to dendritic cells has successfully been utilized for several cancer models. (Mahadevan et al., 2007; Eisold et al., 2007; Yu et al., 2008)

The natural flexibility of AAV structural and regulatory viral components promotes rapid molecular evolution and formation of numerous serologically distinct serotypes (Gao et al., 2003; Vandenberghe et al., 2009; Wu et al., 2006). Several studies have shown that one can take advantage of such plasticity of AAV to generate new vectors with different cell and tissue tropism (Wu et al., 2000; Girod et al., 1999). Other studies revealed that substitution of a single amino acid on the viral capsid can strongly affect viral titer, interaction with cellular receptor, tissue-tropism and trafficking from endosome to the nucleolus (Zhong et al., 2008; Wu et al., 2006). Wu et al. (2006) have reported that replacement of lysine to glutamine at position 531 (K531E) on AAV6 capsid reduces gene transfer to mouse hepatocytes in vivo and affinity for heparin. The reverse mutation (E531K) on AAV1 capsid increased liver transduction and imparted heparin binding.

Data with AAV2 serotype vectors indicate that a single substitution of tyrosine to phenylalanine (Y→F) dramatically improves viral trafficking from endosome to the nucleolus by preventing capsid phosphorylation, subsequent ubiquitination and degradation via proteasome (Zhong et al., 2008). These studies have led to the generation of a number of vectors with increased transduction efficiency in different cell types and tissues. Such vectors were used to improve F.IX gene transfer to murine hepatocytes for the phenotypic correction of hemophilia B (Markusic et al., 2011). These tyrosine-mutant AAV vectors also led to high efficiency transduction of mouse retina for the potential treatment of ocular diseases (Petrs-Zilva et al., 2009). Although AAV6 serotype has shown higher transduction efficiency than AAV2 in dendritic cells (Veron et al., 2007; Taylor and Ussher, 2010), these studies have focused on AAV2 because these vectors have been studied more extensively in both basic research and clinical settings, however AAV6 vectors may be developed with a similar strategy as described herein.

It has become abundantly clear that phosphorylation of surface-exposed tyrosine-residues on AAV2 capsids negatively impacts the transduction efficiency of these vectors, which can be dramatically augmented by the use of specific inhibitors of cellular EGFR-PTK, known to phosphorylate these residues (Zhong et al., 2008). In the present example, the role of phosphorylation of serine residues in the life cycle of AAV2 vectors was more fully delineated.

Indeed, the transduction efficiency of both ssAAV and scAAV vectors could be augmented by pre-treatment of cells with specific inhibitors of JNK and p38 MAPK, implying that one or more surface-exposed serine and/threonine residues on the AAV2 capsid becomes phosphorylated inside the host cell and that this modification is detrimental to capsid trafficking to the nucleus.

Next, each of 15 surface-exposed serine residues was mutated individually, but only three of these mutations led to an increase in transduction efficiency in different cell types, which ranged from ~2-fold to ~20-fold. However, unlike the tyrosine-mutants (Markusic et al., 2011), combining multiple mutations did not augment the transduction efficiency of either the double-mutants (S458+662V and S492+662V), or the triple-mutant (S458+492+662V) AAV2 vectors in vitro. In this context, it is noteworthy that in a report by DiPrimio et al., (DiPrimio et al., 2008), in which the HI loop located between the H and I strands of the conserved core β-barrel and contains residue S662 was characterized, both site-directed mutagenesis and peptide substitutions showed that this capsid region plays a crucial role in AAV capsid assembly and viral genome packaging (FIG. 22A and FIG. 22B) (Xie et al., 2002). Although the S662 residue was not specifically targeted in those studies, the transduction efficiency of most of these mutants was either unchanged, or was reduced by up to 27-fold. The HI loop, which forms interactions between icosahedral five-fold symmetry related VPs and lies on the floor of the depression surrounding this axis, was also proposed to undergo a conformational re-arrangement that opens up the channel located at the icosahedral fivefold axis following heparin binding by AAV2 (Levy et al., 2009). Residues S458 and 492 are located adjacent to each other (contributed from symmetry related VPs) on the outer surface of the protrusions (surrounding the icosahedral three-fold axes) facing the depression at the two-fold axes. Previous mutation of residues adjacent to S458A, S492A and S492T had no effect on capsid assembly and resulted in no effect on transduction efficiency (Lochrie et al., 2006), which confirms the critical role that particular amino acids plays in packaging efficiency and biological activity of AAV. Additional structural analyses of these data revealed the following: For the three mutants with low yields, the side-chain of the residues interact with main-chain atoms from the same VP monomer, and S267V with a low titer, interacts with D269 from the same monomer. For another capsid mutant, S668V, which is located in the HI loop and shown to play a role in capsid assembly (DiPrimio et al., 2008), no obvious disruption of interaction was observed with the substitution. Interestingly, all of these residues, regardless of assembly phenotype, are at interface positions but only 458 and 492 involved in inter-VP interactions. The other residues are only involved in intra-VP interactions, if any. Thus, it is possible that the changes in the no capsid or low capsid yield mutants result in misfolding for their VPs or the abrogation of formation of multimers formation required for assembly when changed to alanine.

In the setting of tumor immunotherapy, the time of T cell activation and the potency and longevity of CD8 T cell responses are crucial factors in determining therapeutic outcome. Thus, the investors further evaluated whether increased transduction efficiency of moDC by the serine-mutant AAV2 vectors correlated with superior priming of T cells. Human telomerase was used as a specific target since it has been shown in numerous studies and clinical trials to be an attractive candidate for a broadly expressed rejection antigen for many cancer patients (Harley, 2008; Beatty and Vonderheide, 2008). These results suggest that modification of the AAV2 capsid might be beneficial in terms of producing more specific and effective vectors for gene delivery.

It is also important that one of the main obstacles, the induction of immuno-competition in cellular immune responses against vector-derived and transgene-derived epitopes, can probably be overcome not only by the replication-deficiency and lack of viral proteins expressed by recombinant AAV2, but also the fact that less capsid of modified viral particles will be degraded by host proteasomes and thus, provide less material for presentation.

Example 5→Optimization of the Capsid of RAAV2 Vectors

Adeno-associated virus (AAV) vectors are currently in use in a number of Phase I/II clinical trials as delivery vehicles to target a variety of tissues to achieve sustained expression of therapeutic genes (Daya and Berns 2008; Mueller and Flotte 2008; Srivastava 2008; Asokan et al., 2012; Flotte et al., 2012). However, large vector doses are needed to achieve therapeutic benefits. The requirements for sufficient amounts of the vector pose a production challenge, as well as the risk of initiating the host immune response to the vector (High and Aubourg, 2011; Mendell et al., 2012, Mingozzi and High, 2011). More specifically, recombinant vectors based on AAV2 serotype were initially used in a clinical trial for the potential gene therapy of hemophilia B, but in this trial, therapeutic level of expression of human Factor IX (hF.IX) was not achieved at lower vector doses, and at higher vector doses, the therapeutic level of expression of hF.IX was short-lived due to a cytotoxic T cell (CTL) response against AAV2 capsids (Manno et al., 2006; Mingozzi and High, 2007; Mingozzi et al., 2007).

In a more recent trial with recombinant vectors based on AAV8 serotype, therapeutic levels of expression of hF.IX were been achieved, but an immune response to AAV8 capsid proteins was observed (Aslanidi et al., 2012). Thus, it is critical to develop novel AAV vectors with high transduction efficiency that can be used at lower doses. Cellular epidermal growth factor receptor protein tyrosine kinase (EGFR-PTK) negatively affects transgene expression from recombinant AAV2 vectors primarily due to phosphorylation of AAV2 capsids at tyrosine residues, and tyrosine-phosphorylated capsids are subsequently degraded by the host proteasome machinery (Zhong et al., 2008; Markusic et al., 2010). Selective inhibitors of JNK and p38 MAPK serine/threonine kinases also improved the transduction efficiency of AAV2 vectors, suggesting that phosphorylation of certain surface-exposed serine and/or threonine residues might also decrease the transduction efficiency of these vectors. These studies led to the development of tyrosine- and serine-mutant AAV2 vectors, which has been shown to transduce various cell types with significantly higher efficiency than the WT vectors. (Aslanidi et al., 2012; Zhong et al., 2008; Markusic et al., 2010; Petrs-Silva et al., 2009) In addition to the tyrosine and serine residues, the elimination of surface-exposed threonine residues by site-directed mutagenesis also led to an increase in the transduction efficiency at lower vector doses. In this example, each of the 17 surface-exposed threonine residues was substituted with valine (V) residues by site-directed mutagenesis, and four of these mutants, T455V, T491V, T550V, T659V, were shown to increase the transduction efficiency between ~2-4-fold in human HEK293 cells. Because the tyrosine triple-mutant (Y730F+500+444F) vector transduced murine hepatocytes most efficiently than WT (Aslanidi et al., 2012; Zhong et al., 2008; Markusic et al., 2010; Petrs-Silva et al., 2009), these mutations were subsequently combined with the best-performing single serine-mutant (S662V) and single threonine-mutant (T491V) to generate the following vectors: two quadruple (Y444+500+730F+S662V; Y730+500+44F+T491V) and one quintuple (Y444+500+730F+S662V+T491V). The quadruple-mutant (Y444+500+730F+T491V) vector efficiently transduced a murine hepatocyte cell line in vitro as well as primary murine hepatocytes in vivo at reduced doses, which implicated the use of these vectors in human gene therapy in general, and hemophilia in particular.

Materials and Methods

Cells Human embryonic kidney cell line, HEK293, and murine hepatocyte cell line, H2.35, cells were obtained from the American Type Culture Collection (Manassas, Va., USA), and maintained as monolayer cultures in DMEM (Invitrogen, Inc.) supplemented with 10% fetal bovine serum (FBS; Sigma-Aldrich Co.) and antibiotics (Lonza, Inc.).

Production of Recombinant Vectors. Recombinant AAV2 vectors containing either EGFP (scAAV2-GFP) or firefly luciferase gene (Fluc) (ssAAV2-Fluc) driven by the chicken β-actin promoter (CBA) were generated as described previously (Aslanidi et al., 2012; Aslanidi et al., 2009; Zolotukhin et al., 2002; Kohlbrenner et al., 2005). Briefly, HEK293 cells were transfected using polyethylenimine (PEI, linear, MW 25,000, Polysciences, Inc.). Seventy-two hrs' posttransfection, cells were harvested and vectors were purified by iodixanol (Sigma-Aldrich Co.) gradient centrifugation and ion exchange column chromatography (HiTrap Sp Hp 5 mL, GE Healthcare). Virus was then concentrated and buffer exchanged into Lactated Ringer's solution in three cycles using centrifugal spin concentrators (Apollo, 150-kDa cut-off, 20-mL capacity, CLP). To determine genome titers, ten µl of purified virus were incubated with DNase I (Invitrogen, Inc.) at 37° C. for 2 hr, then with Proteinase K (Invitrogen, Inc.) at 55° C. for an additional 2 hr. The reaction mixture was purified by phenol/chloroform, followed by chloroform extraction. Packaged DNA was precipitated O/N with ethanol in the presence of 20 µg glycogen (Invitrogen, Inc.). DNase I-resistant AAV2 particle titers were determined by qPCR with the following primer-pairs specific for the CBA promoter:

```
Forward:
                                    (SEQ ID NO: 20)
5'-TCCCATAGTAACGCCAATAGG-3', Reverse:
                                    (SEQ ID NO: 21)
5'-CTTGGCATATGATACACTTGATG-3',
``` and SYBR GreenER PCR Master Mix (Invitrogen, Inc.) (Aslanidi et al., 2012; Aslanidi et al., 2009).

Site-Directed Mutagenesis. A two-stage PCR was performed with plasmid pACG2 as described previously (Aslanidi et al., 2012; Wang and Malcolm, 1999) using Turbo Pfu Polymerase (Stratagene). Briefly, in stage one, two PCR extension reactions were performed in separate tubes for the forward and reverse PCR primers for 3 cycles. In stage two, the two reactions were mixed and a PCR reaction was performed for an additional 15 cycles, followed by DpnI digestion for 1 hr. Primers were designed to introduce changes from threonine (ACA) to valine (GTA) for each of the residues mutated.

Recombinant AAV Vector Transduction Assays In Vitro. Human HEK293 were transduced with $1 \times 10^3$ vgs/cell, and murine hepatocytes H2.35 cells were transduced with $2 \times 10^3$ vgs/cell with WT and mutant scAAV2-GFP vectors, respectively, and incubated for 48 hr. Transgene expression was assessed as the total area of green fluorescence (pixel2) per visual field (mean±SD) as described previously (Aslanidi et al., 2012; Zhong et al., 2008; Markusic et al., 2010). Analysis of variance was used to compare test results and the control, which were determined to be statistically significant.

Analysis of Vector Genome Distribution In Cytoplasm and Nuclear Fractions. Approximately $1 \times 10^6$ H2.35 cells were infected by either WT or mutant scAAV2-GFP vectors with MOI $1 \times 10^4$ vgs/cell. Cells were collected at various time points by trypsin treatment to remove any adsorbed and un-adsorbed viral particles and then washed extensively with PBS. Nuclear and cytoplasmic fractions were separated with Nuclear and Cytoplasmic Extraction Reagents kit (Thermo Scientific) according to manufacturer instruction. Viral genome was extracted and detected by qPCR analysis with the CBA specific primers described above. The difference in amount of viral genome between cytoplasmic and nuclear fractions was determined by the following rule: $C_T$ values for each sample from cells treated with virus were normalized to corresponding $C_T$ from mock treated cells ($\Delta C_T$). For each pairwise set of samples, fold change in packaged genome presence was calculated as fold change=$2^{-(\Delta CT\text{-}cytoplasm - \Delta CT\text{-}nucleus)}$. Data from three independent experiments were presented as a percentage of the total amount of packaged genome in the nuclear and cytoplasmic fractions.

In Vivo Bioluminescence Imaging. All animal experiments were performed per institutional policies, and all procedures were done in accordance with the principles of the National Research Council's Guide for the Care and Use of Laboratory Animals. All efforts were made to minimize suffering. Ten-week-old C57BL/6 male mice (Jackson Laboratory, Bar Harbor, Me.) were injected intravenously with 1×10$^{10}$ vgs/animal of WT and mutant ssAAV2-Fluc vectors (n=3). Luciferase activity was analyzed two weeks post injection using a Xenogen IVIS Lumina System (Caliper Life Sciences). Briefly, mice were anesthetized with 2% isofluorane and injected intraperitoneally with luciferin substrate (Beetle luciferin, Caliper Life Sciences) at a dose of 150 µg/g of body weight. Mice were placed in a light-tight chamber and images were collected at 5 min after the substrate injection. Images were analyzed by the Living Image 3.2 software (Caliper Life Sciences) to determine relative signal intensity.

Visualization of the Position of the Mutant Residues on the AAV2 Capsid. The atomic coordinates for the AAV2 VP3 crystal structure (residues 217 to 735, VP1 numbering) (Protein Data Bank (PDB) accession no. 1lp3; [Xie et al., 2002]) was downloaded and used to generate a complete capsid model using the Oligomer generator application in VIPERdb (Carrillo-Trip et al., 2009). This generates 60 VP3 copies for creating the T=1 icosahedral capsid via matrix multiplication. The structure was viewed with the program COOT (Xie et al., 2002) and figures were generated using either of the computer programs, PyMOL (Schrodinger, LLC) and RIVEM (Xiao and Rossman, 2007).

Statistical Analysis. Results are presented as mean±S.D. Differences between groups were identified using a grouped-unpaired two-tailed distribution of Student's t-test. P-values <0.05 were considered statistically significant.

Results

Figure 26A:
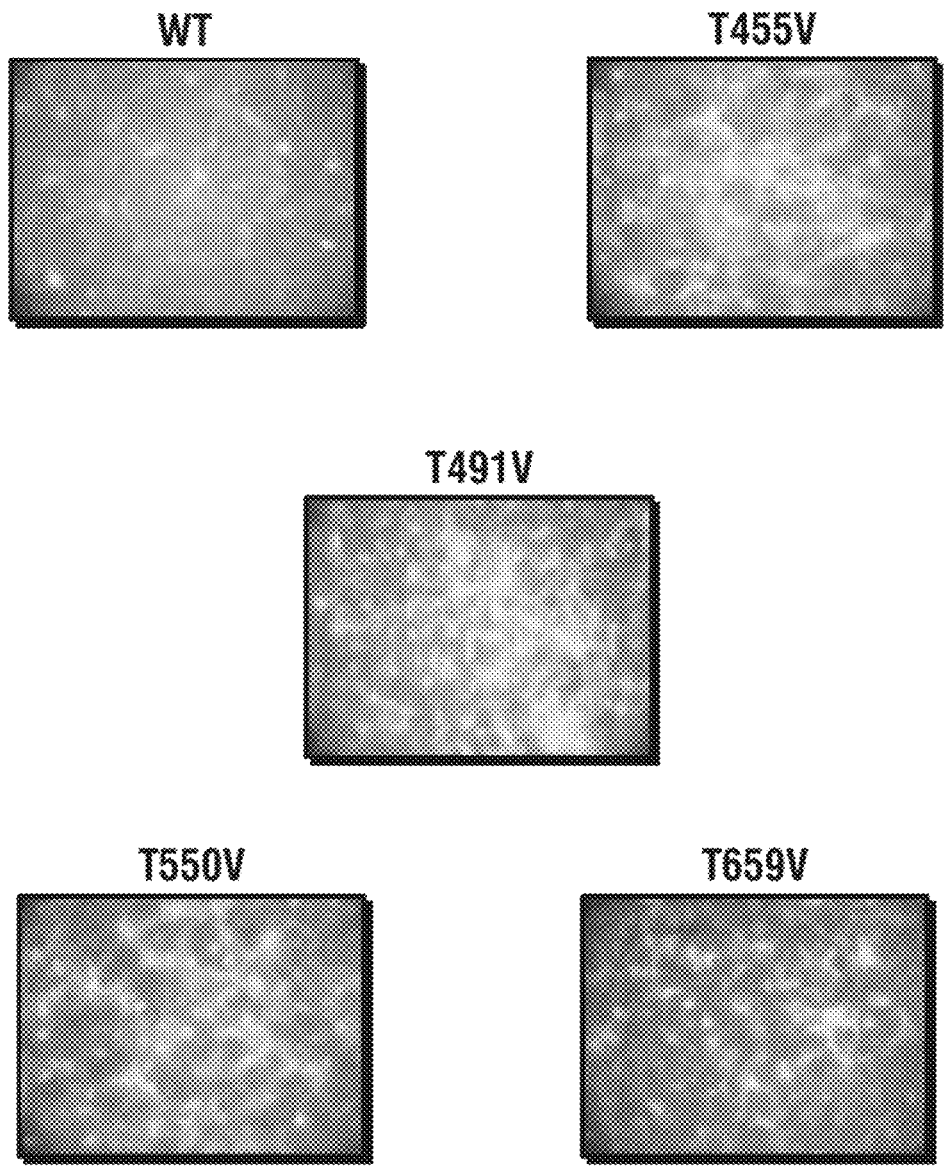
FIG. 26A and FIG. 26B show the analysis of EGFP expression after transduction of HEK293 cells with individual site-directed AAV2 capsid mutants. Each of the 17 surface-exposed threonine (T) residues in AAV2 capsid was substituted with valine (V) and evaluated for its efficiency to mediate transgene expression.
Figure 26B:
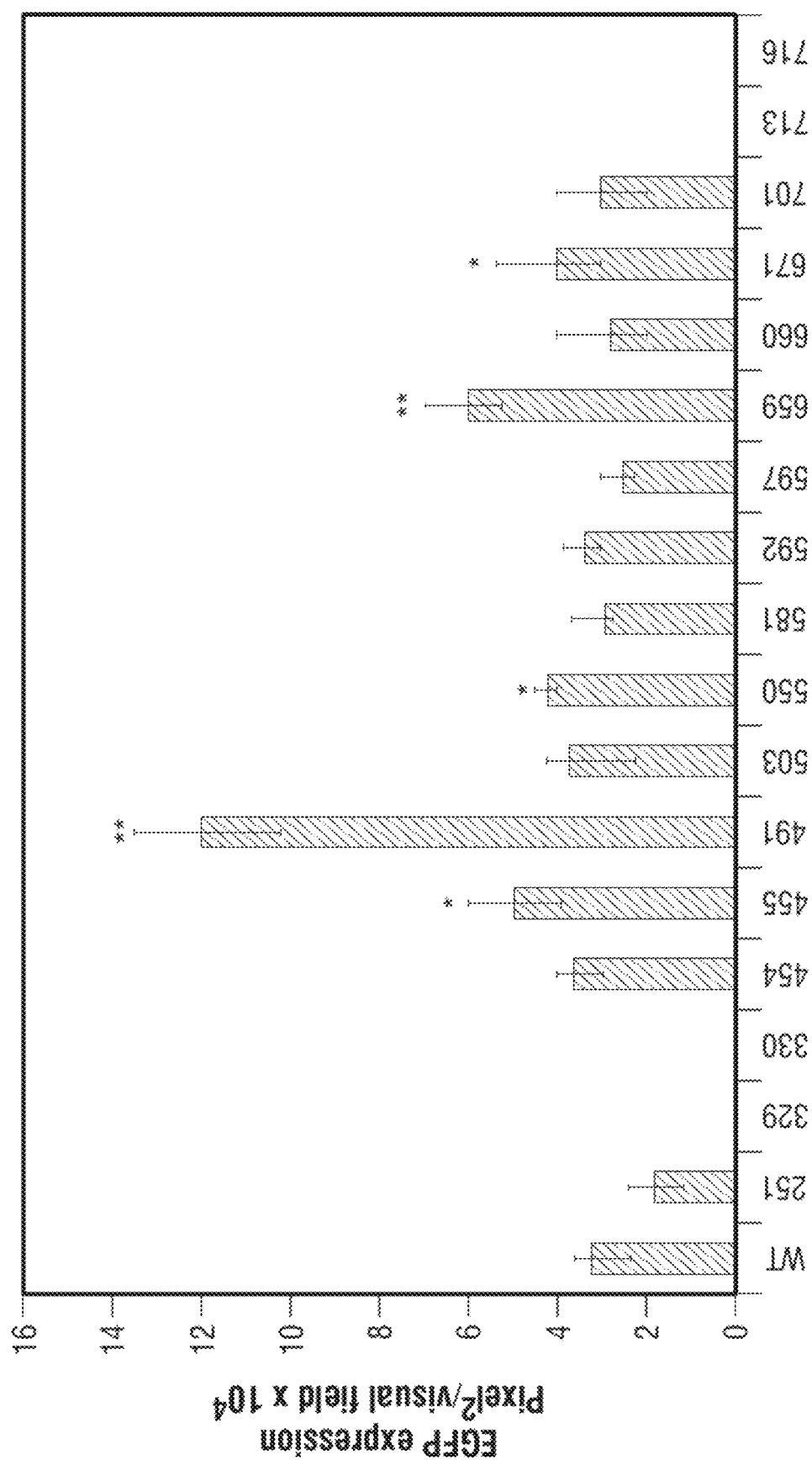

Site-Directed Mutagenesis of Surface-Exposed Threonine Residues on AAV2 Capsid. The AAV2 capsid contains 45 threonine (T) residues in the capsid viral protein 3 (VP3) common region of the three capsid VPs, VP1, VP2, and VP3. Seventeen of these (251, 329, 330, 454, 455, 503, 550, 592, 581, 597, 491, 671, 659, 660, 701, 713, 716) are surface-exposed. (Xie et al., 2002) Each of the 17 T residues was substituted with valine (V) by site-directed mutagenesis as described previously (Aslanidi et al., 2012; Zhong et al., 2008). Most mutants could be generated at titers similar to the WT AAV2 vectors, with the exception of T329V and T330V that were produced at ~10-fold lower titers, and T713V and T716V, which produced no detectable levels of DNase I-resistant vector particles. Each of the T-V mutant vectors was evaluated for transduction efficiency in HEK293 cells. These results, shown in FIG. 26A and FIG. 26B, indicate that of the 17 mutants, the T491V mutant transduced HEK293 cells ~4-fold more efficiently than its WT counterpart did. The transduction efficiency of the T455V, T550V, T659V mutant vectors were increased by ~2-fold. These data indicated that phosphorylation of specific tyrosine, serine, and threonine residues on AAV2 capsid by cellular kinases is a critical determinant of the transduction efficiency of these vectors.

Figure 27A:
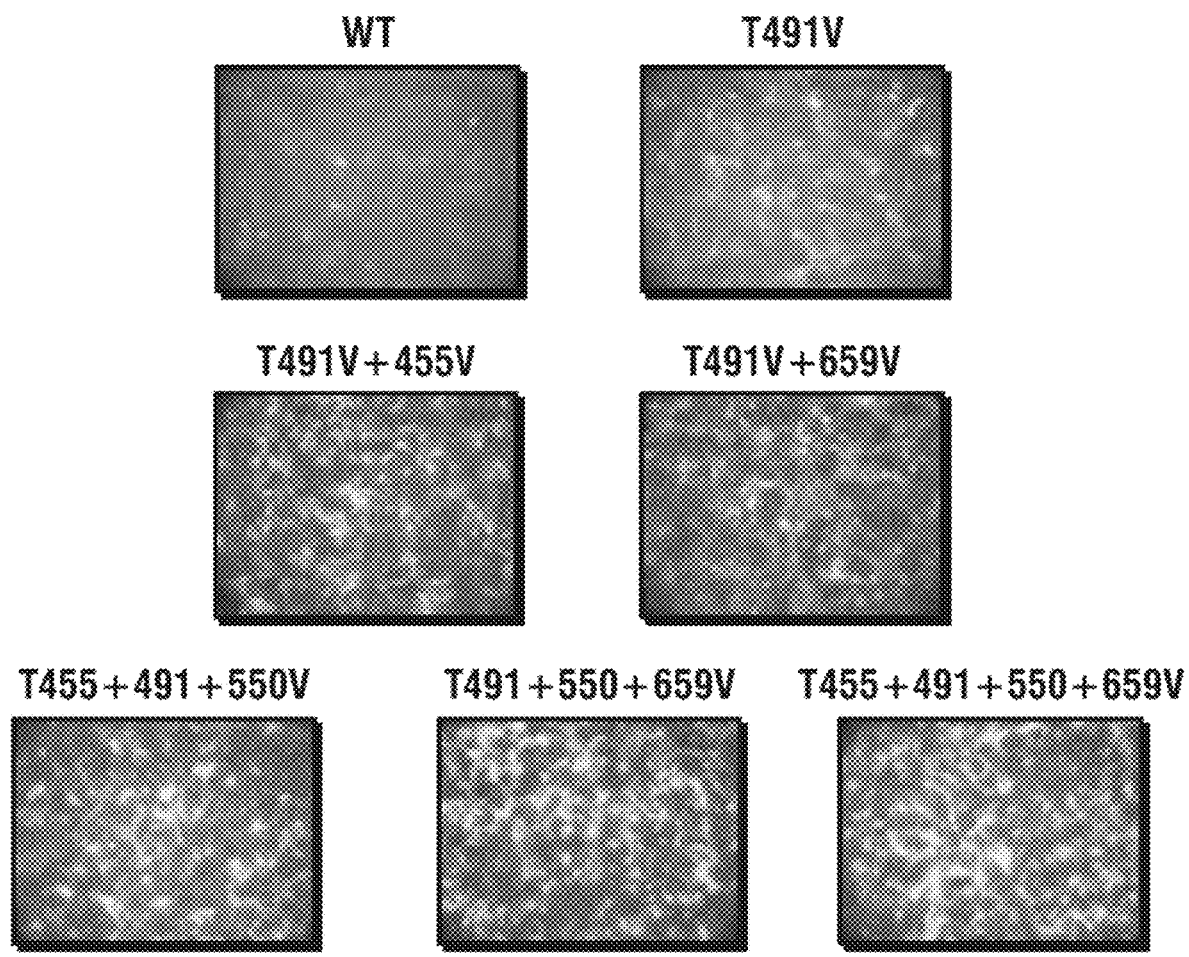
FIG. 27A and FIG. 27B show the analysis of EGFP expression in HEK293 cells infected with multiple site-directed AAV2 capsid mutants. Several most efficient threonine mutations were combined on single AAV2 capsid to produce double- and triple-mutant and efficiency of each vector was evaluated.
Figure 27B:
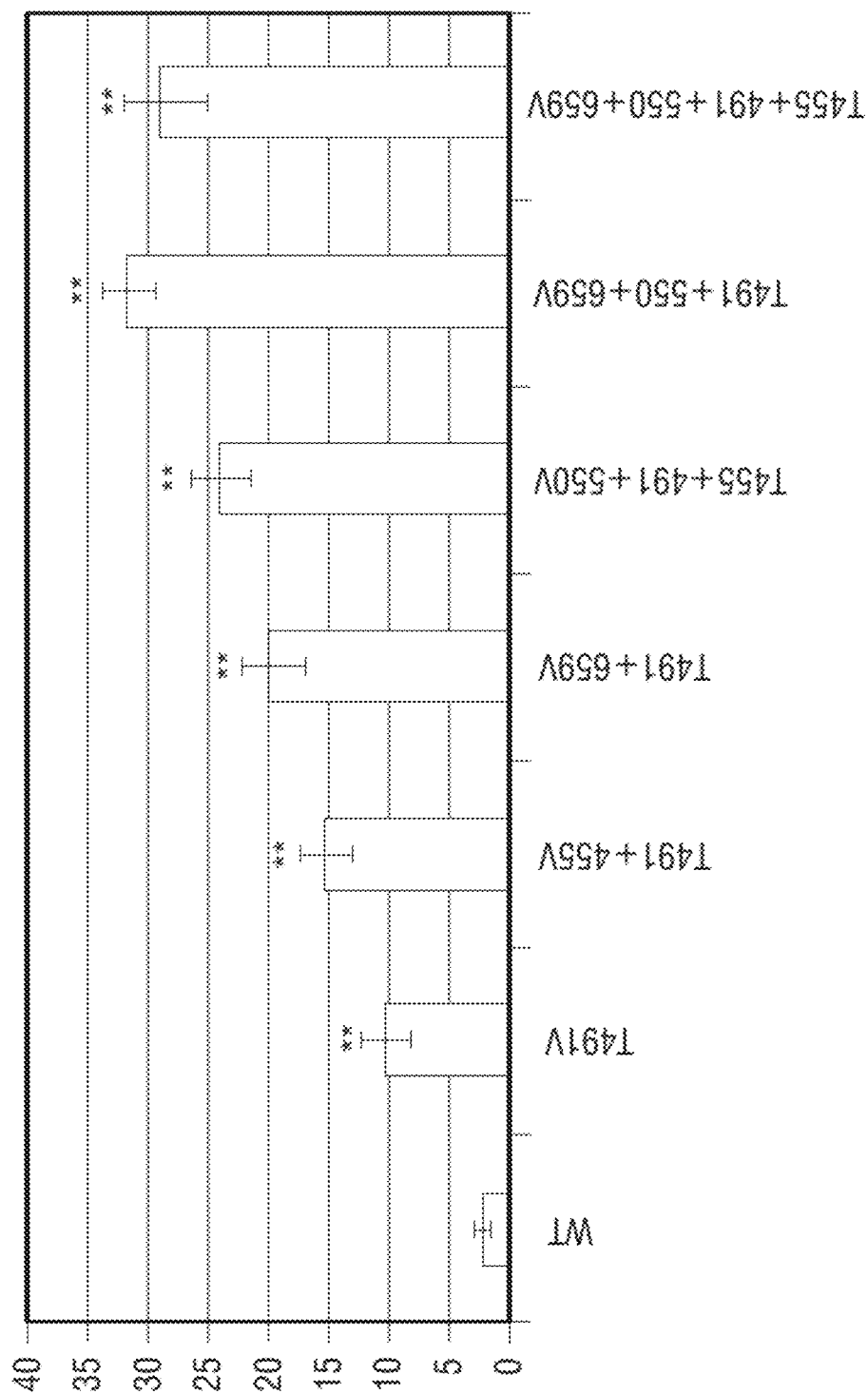

Multiple Mutations of Surface-Exposed Threonine Residues Further Improve Transduction Efficiency of AAV2 Vectors. To evaluate whether the transduction efficiency of the threonine-mutant AAV2 vectors could be enhanced further, the following multiple-mutant vectors were generated: three double-mutants (T455+491V; T550+491V; T659+491V), two triple-mutants (T455+491+550V; T491+550+659V), and one quadruple-mutant (T455+491+550+659V). Each of the multiple-mutant vectors packaged genome titers similar to the WT AAV2 vectors. In side-by-side comparisons, each of the multiple-mutant vectors was shown to transduce HEK293 more efficiently than the WT and the single-threonine mutant AAV2 vectors (FIG. 27A and FIG. 27B). The best performing vector was identified to be the triple-mutant (T491+550+659V), with the transduction efficiency ~10-fold higher than the WT vector, and ~3-fold higher than the best single-mutant (T491V) vector. These data confirmed that combining several threonine-mutations on a single viral capsid led to a synergetic effect in augmenting the transduction efficiency.

Optimized Threonine-Mutant AAV2 Vectors Efficiently Transduce Murine Hepatocytes in Vitro. The tyrosine triple-mutant (Y444+550+730F) vector described in previous examples has been shown to be efficient in transducing murine hepatocytes in a comparison of vectors containing up to 7 surface tyrosine to phenylalanine changes (Markusic et al. 2010; Jayandharan et al., 2011). Thus, it was of interest to evaluate whether combining the best performing single-serine (S662V) and single-threonine (T491V) mutations with the triple-tyrosine mutant could further increase the transduction efficiency of these vectors to produce even further improved expression vectors in accordance with the methods described herein.

Figure 28A:
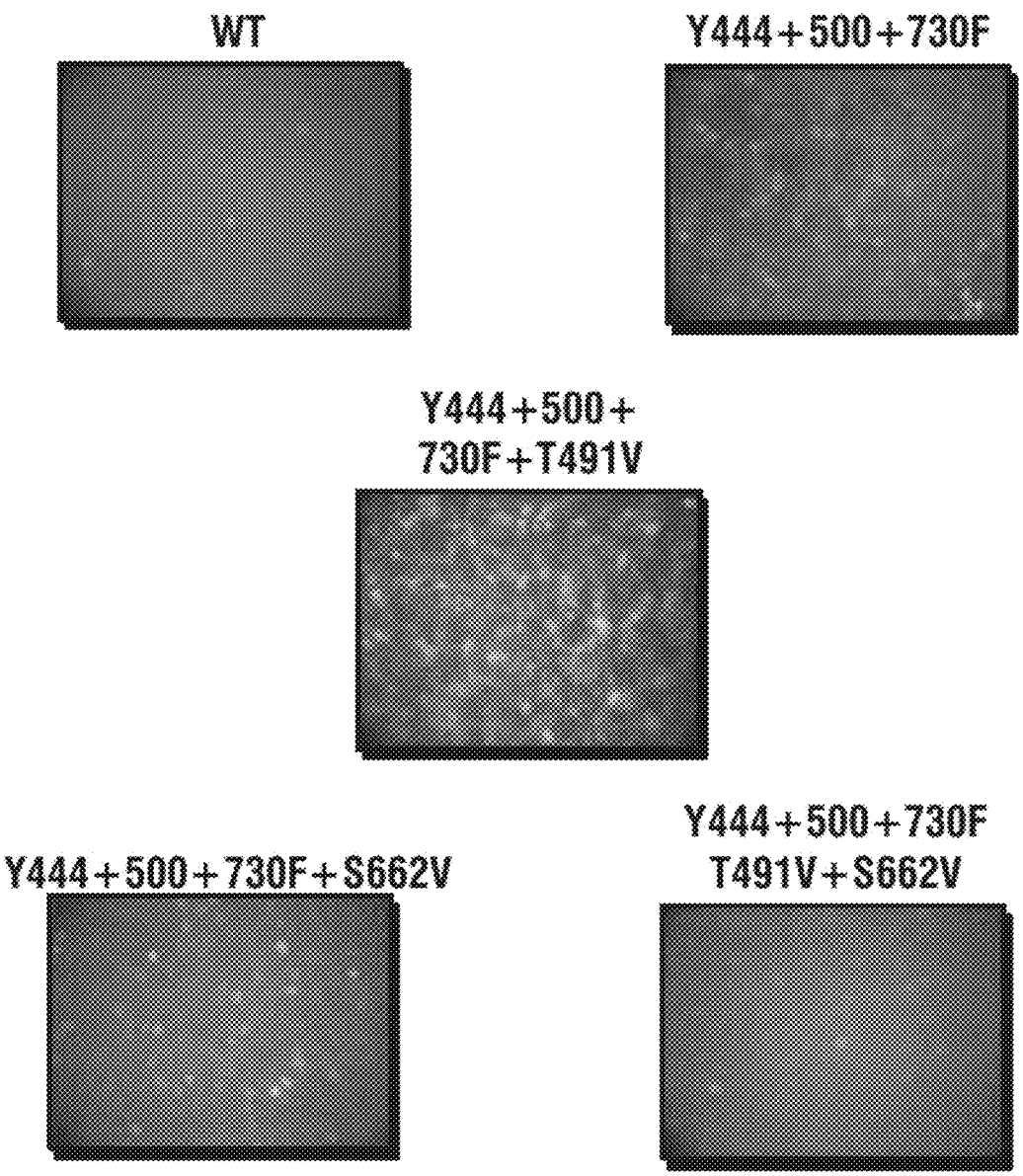
FIG. 28A and FIG. 28B demonstrate the evaluation of EGFP expression in H2.35 cell transduced with capsid optimized AAV2 vectors. The most efficient tyrosine, serine and threonine mutations were combined on single AAV2 capsid to produce several optimized AAV mutants. Efficiency of each vector was estimated on immortalized murine hepatocytes.
Figure 28B:
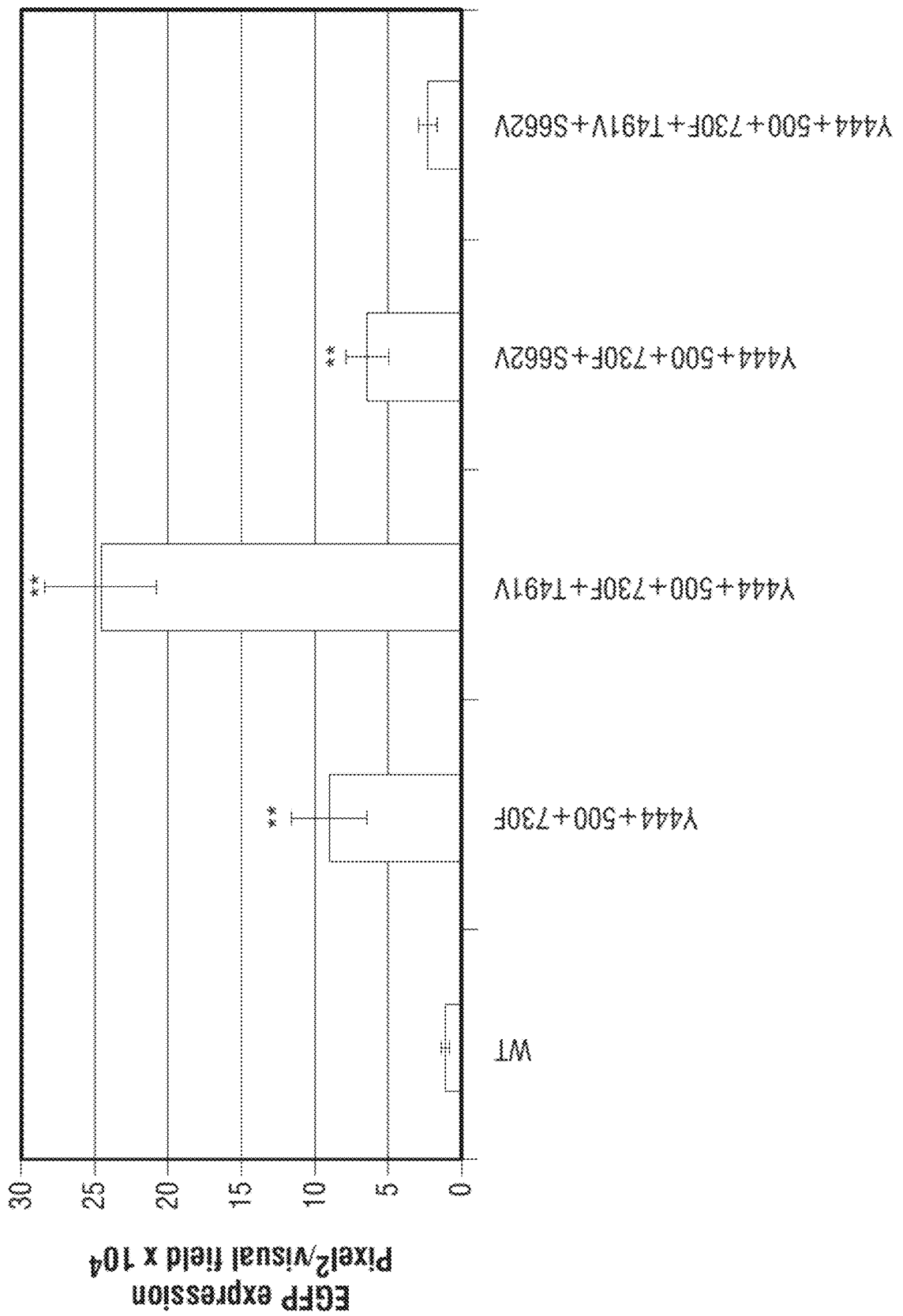

To that end, several multiple-mutants were generated as follows: two quadruple (Y444+500+730F+T491V; Y444+500+730F+S662V), and one quintuple (Y444+500+730F+T491V+S662V) mutant vectors. Comparison of the transduction efficiency of these mutants with the WT and the tyrosine triple-mutant AAV2 vectors in H2.35 cells showed that the expression level from the Y444+500+730F+T491V mutant was ~2-3-fold higher than for the tyrosine triple-mutant AAV2 vector, and ~24-fold higher than the WT AAV2 vector (FIG. 28A and FIG. 28B). Interestingly, combining the S662V mutation with the tyrosine triple-mutant vector, or with the tyrosine-threonine quadruple-mutant vector, negatively affected their transduction efficiency. Addition of several other threonine mutations, such as T550V and T659V, also did not augment the transduction efficiency of the Y444+500+730F+T491V quadruple-mutant AAV2 vector. Additional studies are warranted to gain a better understanding of the complex interactions among these surface-exposed Y, S, and T residues as well as their phosphorylation status.

Figure 29A:
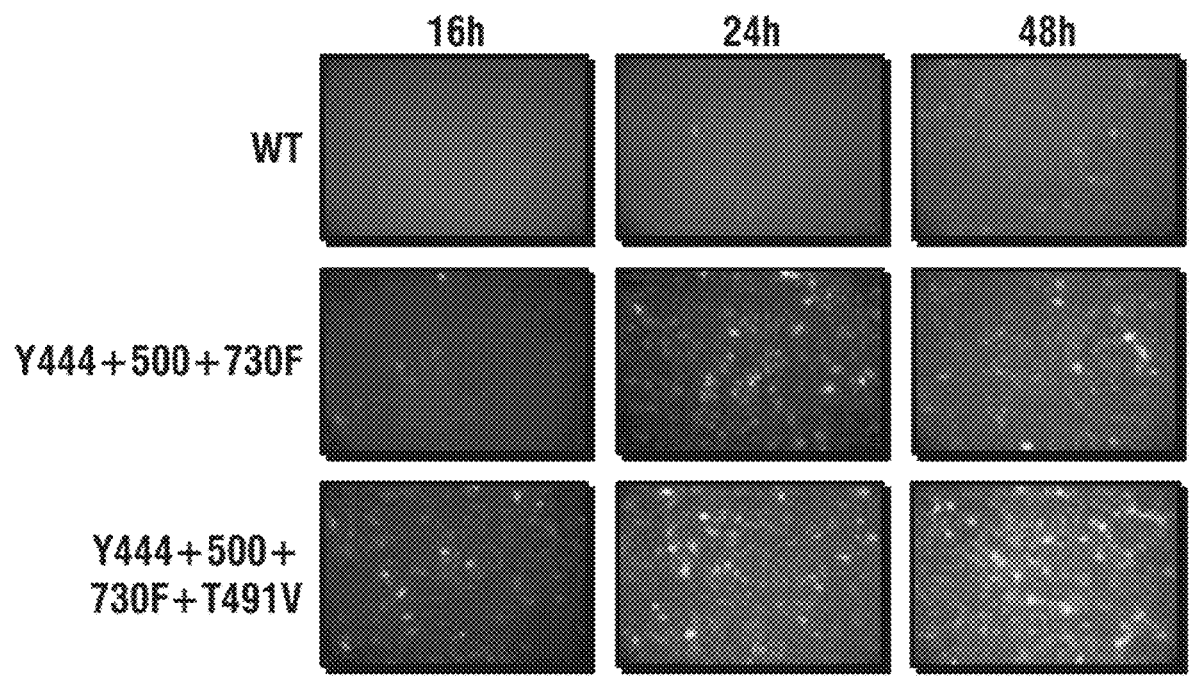
FIG. 29A and FIG. 29B illustrate the kinetics of EGFP expression in H2.35 cell mediated by capsid optimized AAV vectors.
Figure 29B:
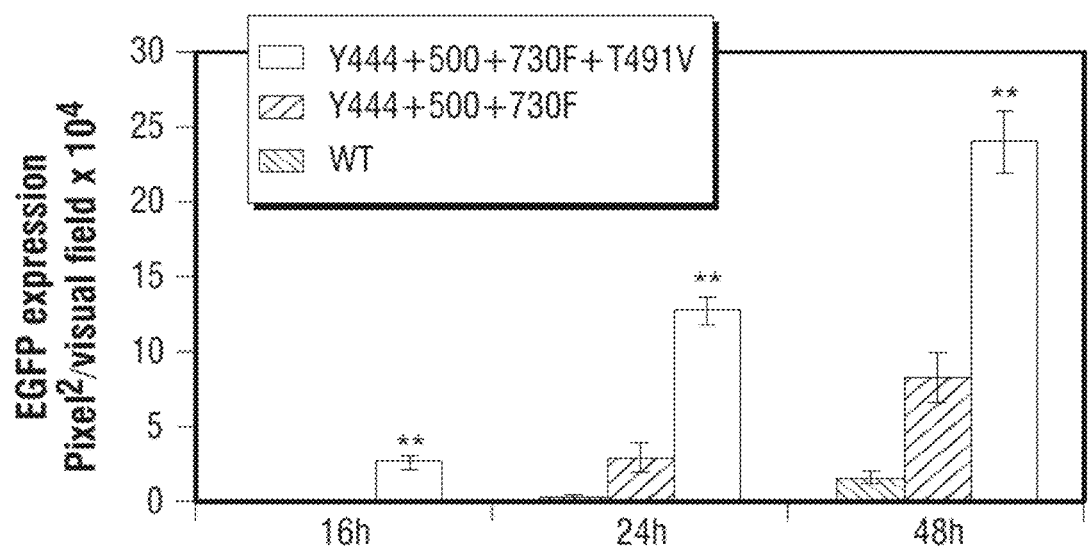
Figure 30A:
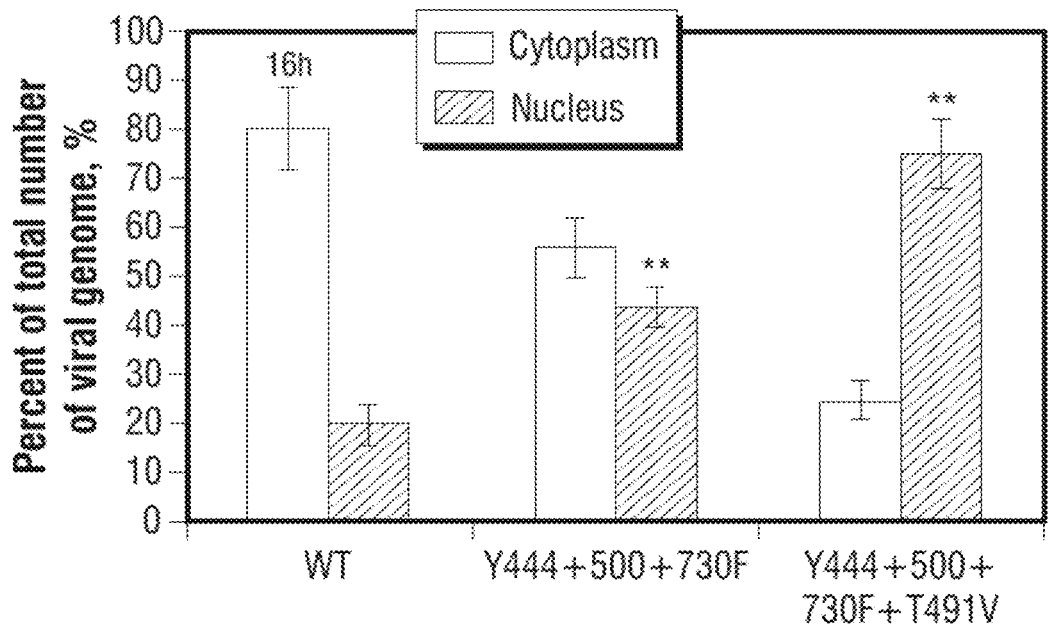
FIG. 30A and FIG. 30B show the analysis of intracellular trafficking of AAV multiple mutant vectors to the nucleus. Nuclear and cytoplasmic fraction of H2.35 cell infected with AAV2-WT, AAV2-Y444+500+730F and AAV2-Y444+500+730F+T491V mutant were separated and qPCR analysis was performed to evaluate vector genome distribution within cells at 16 hr (FIG. 30A) and 48 hr (FIG. 30B) post infection. ** P<0.001 vs. WT in nucleus was considered as significant.
Figure 30B:
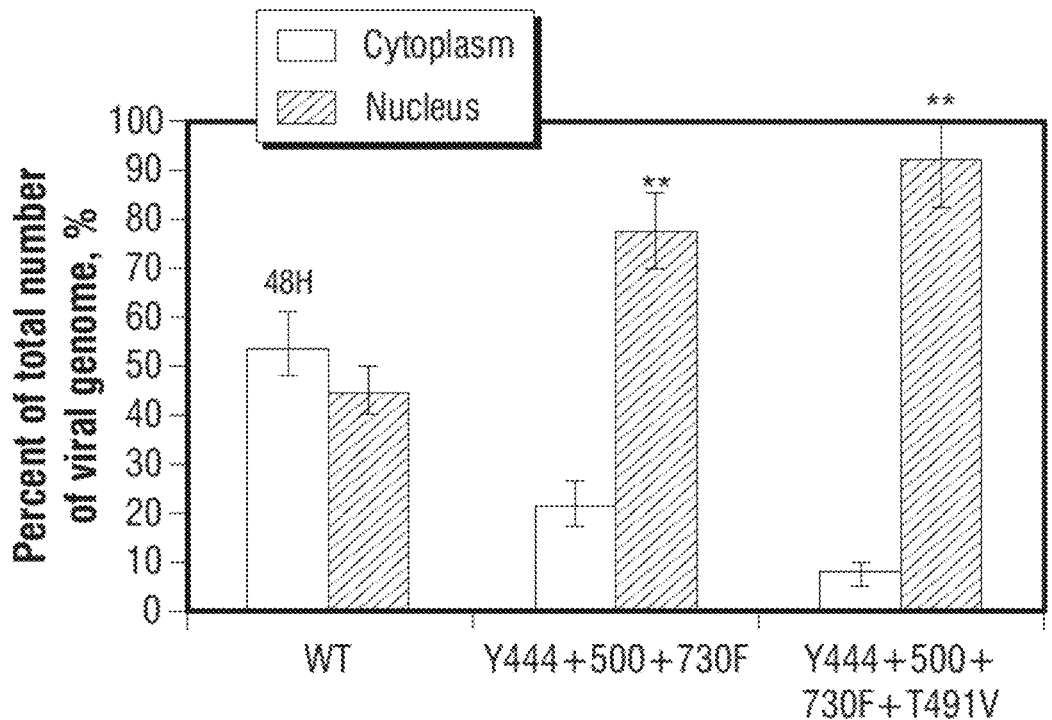

Multiple-Mutations Enhance Intracelluar Trafficking and Nuclear Translocation of AAV2 Vectors. Prevention of phosphorylation of surface-exposed tyrosine residues on the AAV2 capsid improved intracellular trafficking of tyrosine-mutant vectors and increases the number of the viral genomes translocated to the nucleus (Zhong et al., 2008; Zhong et al., 2008). In this example, the addition of the T491V mutant to the tyrosine triple-mutant vector was assigned for its ability to augment this transduction efficiency by further increasing nuclear transport of these vectors. To this end, the kinetics of transgene expression in H2.35 cells mediated by the Y444+500+730F+T491V quadruple-mutant were evaluated and compared to the Y444+500+730F triple-mutant and the WT AAV2 vectors. These results are shown in FIG. 29A and FIG. 29B. As can be seen, EGFP expression from the tyrosine-threonine quadruple-mutant vector was ~2-3 fold higher at each tested time point, and could be detected as early as 16 hr post-infection. These results suggested that the early-onset of transgene expression from the quadruple-mutant vectors could be due to more efficient nuclear transport of these vectors. To test this possibility experimentally, qPCR analysis was used to quantitate the vector genomes in cytoplasmic and nuclear fractions of H2.35 cells infected with the WT and the two mutant AAV2 vectors at different time points. The vector genome ratios in the two cellular fractions are shown in FIG. 30A and FIG. 30B. Whereas ~20% of the genomes from the WT AAV2 vectors, and ~45% of the genomes from the triple-mutant vectors were detected in the nuclear fraction 16 hr post-infection, more than 70% of the vector genomes from the quadruple-mutant were detected at the same time-point. Similarly, only ~45% of the genomes from the WT AAV2 vectors were detected in the nuclear fraction 48 hr post-infection, ~80% of the genomes from the triple-mutant vectors, and ~90% of the vector genomes from the quadruple-mutant were detected in the nuclear fraction at the same time-point. Thus, these data corroborated the hypothesis that combining the threonine (T491V) mutation with the tyrosine triple-mutant (Y444+500+730F) vector leads to a modest improvement in the nuclear translocation of these vectors, which correlated with a faster onset of gene expression and the observed improvement in the transduction efficiency.

Figure 31A:
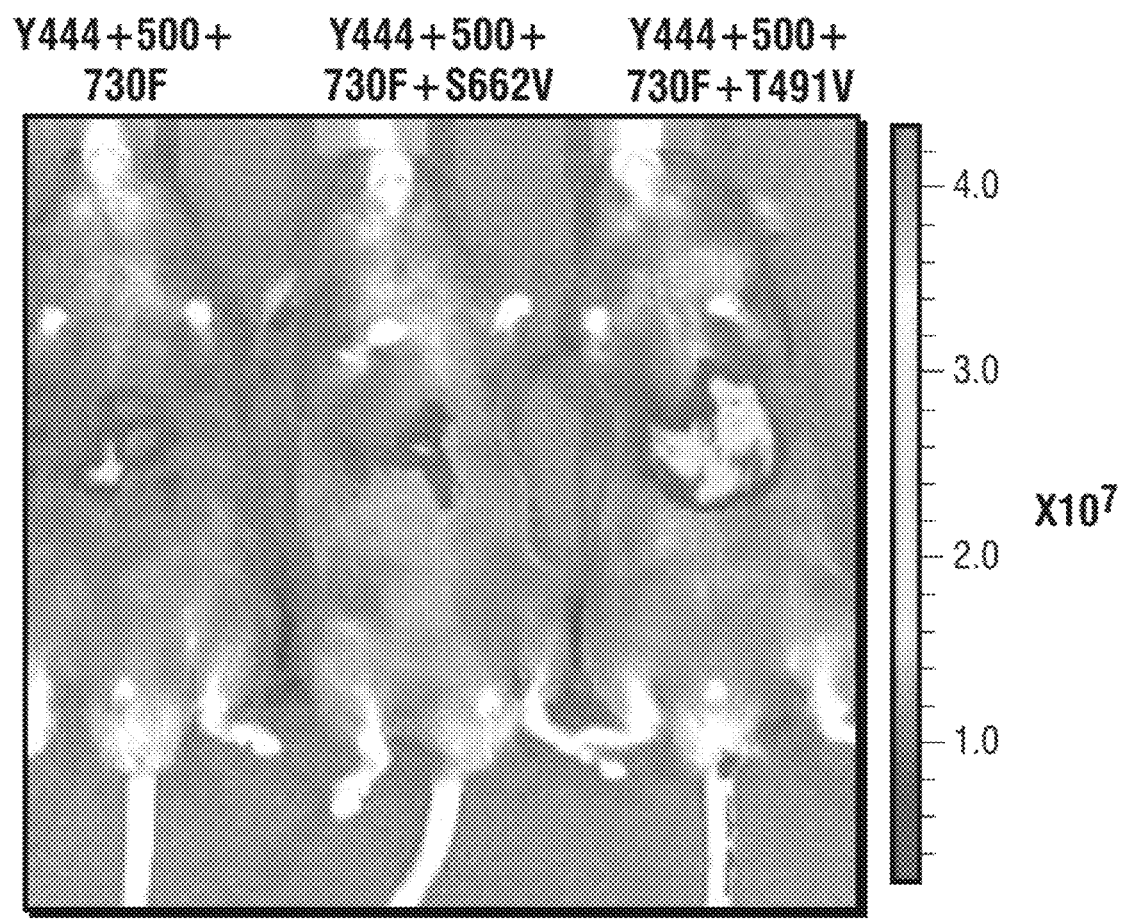
FIG. 31A and FIG. 31B show the in vivo imaging of luciferase gene expression following tail vein injection of multiple site-directed AAV2 capsid mutants. C57BL/6 mice were injected with $1\times10^{10}$ vg/animal of several most efficient mutant scAAV vectors carrying luciferase gene. Live images were taken to analyses difference in luciferase activity. The visual output represents the number of photons emitted/second/cm2 as a false color image where the maximum is red and the minimum is blue (FIG. 31A) and relative signal intensity (FIG. 31B) *P<0.005 was considered as significant.
Figure 31B:
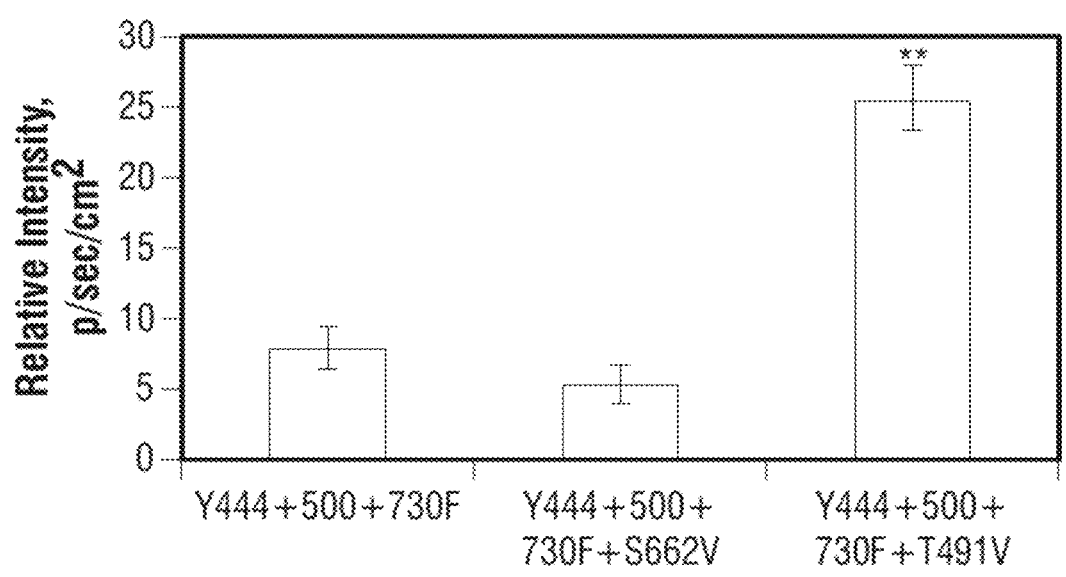

Optimized AAV2 Vectors are Highly Efficient in Transducing Murine Hepatocytes in Vivo. The transduction efficiency of the optimized AAV2 vectors was evaluated in a murine model in vivo. Each of multiple-mutant vectors was packaged with a single-stranded firefly luciferase (Fluc) AAV2 genome, and ~1×10$^{10}$ vgs of each vectors were injected intravenously into C57BL/6 mice (n=3 for each group). Levels of expression of Fluc gene, assessed two weeks post-injection by bioluminescence imaging, showed that expression from the Y444+500+730F+T491V quadruple-mutant vector was ~3-fold higher than that from the tyrosine triple-mutant vector. One representative animal from each group and the quantification of these data are presented in FIG. 31A and FIG. 31B. Consistent with the data obtained in vitro, the addition of S662V mutation had a negative effect on the transduction efficiency of both the tyrosine-triple-mutant and the tyrosine-threonine quadruple-mutant vectors. Exemplary single and multiple-mutation capsid proteins of the present invention include, but are not limited to, those illustrated in Table 5:

TABLE 5

Summary of Exemplary Mutations of Surface-Exposed Tyrosine (Y), Serine (S), and Threonine (T) Residues on the AAV2 Capsid

| Single Mutations | Double Mutations | Triple Mutations | Multiple Mutations |
|---|---|---|---|
| Y252F | Y252F + Y730F | Y444 + 500 + 730F | Y272 + 444 + 500 + 730F |
| Y272F | Y272F + Y730F | Y730F + S662V + T491V | Y272 + 444 + 500 + 730F |
| Y444F | Y444F + Y730F | S458 + 492 + 662V | Y272 + 444 + 500 + 730F |
| Y500F | Y500F + Y730F | T455 + 550 + 491V | 500 + 730F |
| Y700F | Y700F + Y730F | T550 + 659 + 491V | Y272 + 444 + 500 + 730F |
| Y704F | Y704F + Y730F | | 500 + 730F |
| Y730F | Y444F + T550F | | Y272 + 444 + 500 + 700 + 730F |
| S261V | S458V + S492V | | Y272 + 444 + 500 + 704 + 730F |
| S264V | S458V + S662V | | 704 + 730F |
| S267V | S492V + S662V | | Y252 + 272 + 444 + |
| S276V | T455 + T491V | | |

TABLE 5-continued

Summary of Exemplary Mutations of Surface-Exposed Tyrosine (Y), Serine (S), and Threonine (T) Residues on the AAV2 Capsid

| Single Mutations | Double Mutations | Triple Mutations | Multiple Mutations |
|---|---|---|---|
| S384V | T550 + T491V | | 500 + 704 + 730F |
| S458V | T659 + T491V | | Y272 + 444 + 500 + 730F |
| S468V | T671 + T491V | | 700 + 704 + 730F |
| S492V | Y730F + T491V | | Y252 + 272 + 444 + 500 + 700 + 704 + 730F |
| S498V | S662V + T491V | | |
| S578V | Y730F + S662V | | Y444 + 500 + 730F + T491V |
| S658V | | | 730F + T491V |
| S662V | | | Y444 + 500 + 730F + S458V |
| S662A | | | 730F + S458V |
| S662D | | | Y444 + 500 + 730F + S662V + T491V |
| S662F | | | Y444 + 500 + 730F + S662V + T491V |
| S662H | | | 730F + S662V + T491V |
| S662N | | | |
| S662L | | | Y444 + 500 + 730F + T550 + T491V |
| S662I | | | 730F + T550 + T491V |
| S668V | | | T491V |
| S707V | | | Y444 + 500 + 730F + T659 + T491V |
| S721V | | | 730F + T659 + T491V |
| T251V | | | T491V |
| T329V | | | |
| T330V | | | |
| T454V | | | |
| T455V | | | |
| T491V | | | |
| T503V | | | |
| T550V | | | |
| T592V | | | |
| T597V | | | |
| T581V | | | |
| T671V | | | |
| T659V | | | |
| T660V | | | |
| T701V | | | |
| T713V | | | |
| T716V | | | |

The first letter corresponds to the amino acid in the wild-type AAV2 capsid, the number is the VP3 amino acid position that was mutated, and the last letter is the mutant amino acid.

Discussion

Recombinant AAV-based vectors are attractive delivery vehicles for gene replacement therapy as a potential treatment for a variety of genetic disorders. Although AAV vectors have been used successfully in many animal models, and recently shown efficacy in several clinical trials, a number of steps in the life cycle of AAV continue to appear to limit the effectiveness of these vectors in gene therapy. Some of these steps include intracellular trafficking, nuclear transport, uncoating, and viral second-strand DNA synthesis (Ding et al., 2005; Harbison et al., 2005; Nonnenmacher and Weber, 2012).

The simple organization and natural plasticity of AAV structural and regulatory components provide a unique opportunity to manipulate the viral capsid and the genome to develop customized recombinant vectors with distinctive features. Significant progress has been made in the past decade to improve the specificity and the transduction efficiency of recombinant AAV vectors. For example, specific mutations in the viral inverted terminal repeat (ITR) sequences have led to development of self-complementary AAV (scAAV) vectors, which overcome the rate-limiting step of viral second-strand DNA synthesis, and dramatically increase transgene expression levels in various types of the cells and tissues (McCarty et al., 2003; Wang et al., 2003). Additional studies on capsid structure analyses, combined with a wealth of information emanating from mutagenesis studies on the capsid genes, have led to the identification of specific regions which play a critical role in vector encapsidation, tissue-tropism, and intracellular trafficking of these vectors (Lochire et al., 2006; Muzyczka and Warrington, 2005; Wu et al., 2006; Gao et al., 2003; Vandenberghe et al., 2009; Wu et al., 2006).

In the previous examples, it was shown that substitution of surface-exposed specific tyrosine (Y) and serine (S) residues on AAV2 capsids significantly increased the transduction efficiency of these vectors, both in vitro and in vivo, presumably by preventing phosphorylation, subsequent ubiquitination, and proteasome-mediated degradation. Since surface-exposed specific threonine (T) residues on AAV2 capsids would likewise be expected to undergo phosphorylation, in this example each of the 17 surface-exposed T residues were systematically mutagenized, and several single-mutant vectors were identified that could increase the transduction efficiency up to 4-fold. Combinations of multiple T mutations on a single capsid identified modifications that further augmented the transduction efficiency up to ~10-fold, compared with that of the WT AAV2 vector in HEK293 cells.

Two independent groups have previously reported mutations of specific T residues on AAV2 capsids. For example, Lochrie et al., 2006, targeted the T residues at positions 330, 454, 455, 491, 503, and 550 in a tour de force effort to identify surface regions that bind antibodies, and DiPrimio et al. (2008), targeted the T residue at position 659 in an effort to identify regions critical for capsid assembly and genome packaging. In both studies, the T residues were substituted with either alanine (A), serine (S), or lysine (K) residues, or by peptide substitution. However, no increase in the transduction efficiency of any of the mutant vectors was observed. In contrast, in the example, the surface-exposed T residues were substituted with valine residues. This further corroborates the recent observation for the critical role played by specific amino acid type in modulating the biological activity of AAV vectors (Aslanidi et al., 2012; Li et al., 2012).

When the most efficient threonine-mutation (T491V) was combined with a previously reported tyrosine triple-mutation (Y444+500+730F) (Markusic et al. 2010) to generate a Y-T quadruple-mutant (Y444+500+730F+T491V) vector, the transduction efficiency of this vector was ~2-3-fold higher than the tyrosine triple-mutant vector in murine hepatocytes, both in vitro and in vivo. However, combining the most efficient S-mutation (S662V) (Aslanidi et al., 2012) with the tyrosine triple-mutation negatively affected the transduction efficiency of the Y—S quadruple mutant (Y444+500+730F+S662V) vector as well as the Y—S-T pentuple-mutant (Y444+500+730F+S662V+T491V) vector. Although several other combinations showed greater transduction efficiency compared with the WT AAV2 vector, neither combination of similar (quadruple, pentuple or sextuple-tyrosine; and triple and quadruple-threonine mutants), nor combination of the best performing YST mutations reached the level of expression from the triple-tyrosine mutant vector. In view of the large number of combinations of mutations tested, only the mutations that significantly increased the transduction efficiency over the triple-tyrosine mutant vector were characterized in detail here.

Figure 32A:
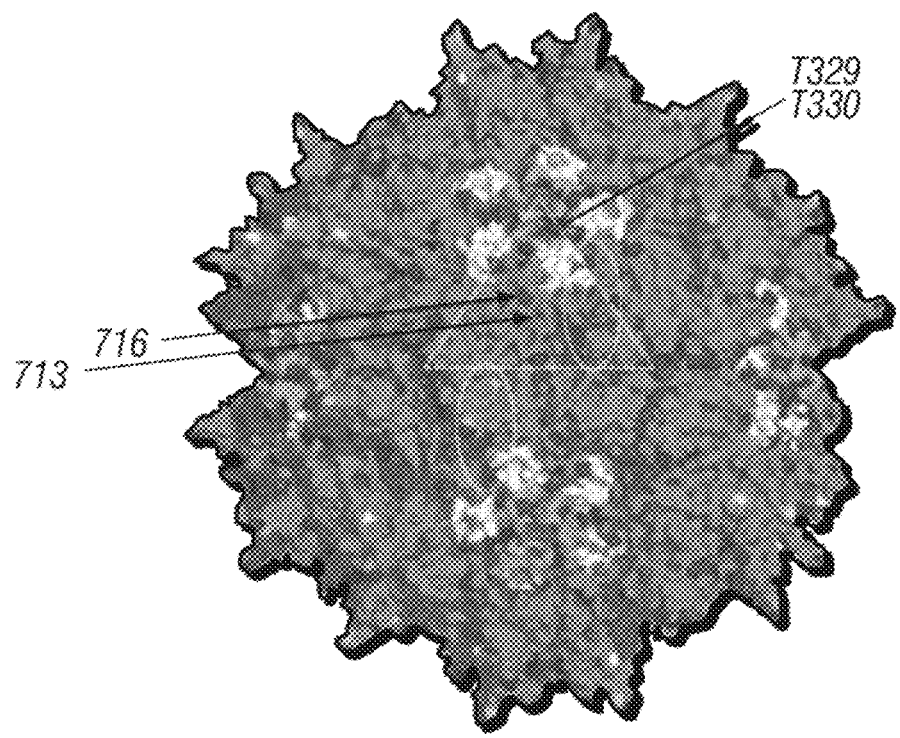
FIG. 32A and FIG. 32B illustrate the AAV2 capsid surface.
Figure 32B:
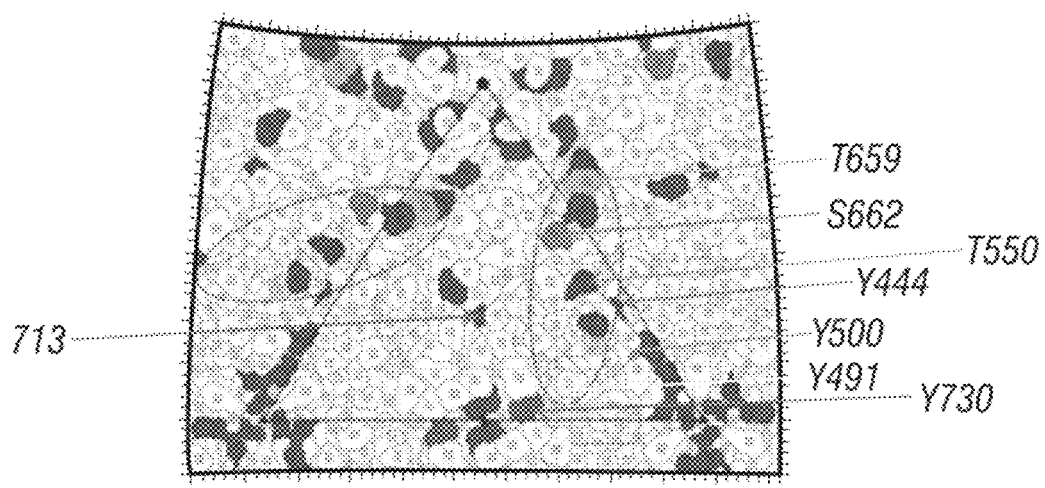

The 17 AAV2 surface-exposed threonine residues are scattered throughout the capsid. Four of the mutations (T329V, T330V, T713V, and T716V) resulted in significant defects in assembly and vector production, and they could not be further characterized. Residues 329 and 330 are located in the α-surface loop (DE loop) located between the RD and PE strands of the core β-barrel of the AAV2 VP3 structure (Xie et al., 2002). Five of these loops, from icosahedral five-fold symmetry related VP3s assembly a channel at this axis which connects the interior and exterior surfaces of the capsid (FIG. 32A). As was observed in a previous study (Bleker et al., 2006), titers for these mutants were significantly reduced consistent with a role for the channel in genome packaging. Residues 713 and 716 are located on the wall/raised capsid region between the depressions at and surrounding the icosahedral two- and five-fold axes, respectively (FIG. 32A and FIG. 32B). Their sidechains participate in polar interactions with symmetry related VP3 monomers and it is likely that mutation results in a defect in capsid assembly. A role in capsid assembly for residues located at the icosahedral two-fold axis is consistent with a recent report in which they observe that the AAV2 residues that mediated the interaction with the assembly-activating protein (AAP) were located at this capsid region (Naumer et al., 2012).

Residues T455, T491, T550, and T659, showing an increased transduction phenotype when mutated to valine or alanine, are located on the protrusions which surround the icosahedral three-fold axis (T455, T491, and T550) or on the HI loop (between PH and RI of the core β-barrel) (T659) which is lies on the depression surrounding the channel at the icosahedral five-fold axis of the AAV2 capsid. The residues on the protrusion, a prominent feature on the capsid assembled from two VP3 monomers, are located close to the top (455), side facing the two-fold depression (491), and side facing the depression surrounding the five-fold (550), respectively, of the protrusions. This AAV region contains the most variability in sequence and structure, and with the exception of residue 659, the other three threonine residues are located to define VP3 variable regions (VRs) (Govindasamy et al., 2006). Along with T659, these residues form a footprint on the capsid surface that extends over the top of the protrusion towards the depression surrounding the icosahedral five-fold axis (FIG. 32A and FIG. 32B). Their surface exposure is consistent with the potential to interact with host molecules, which could include kinases. Interestingly, this footprint is flanked by the residues in the triple-tyrosine mutant, Y444, Y500, and Y730, with T491 located proximal to tyrosine residue Y730 in a depiction of the capsid surface amino acids (FIG. 32B). This residue, which sits in the depression at the icosahedral axis of the capsid, showed the highest increase in transduction compared to WT AAV2 when of the seven surface-exposed tyrosines where mutated to phenylamine residues (Zhong et al. 2008). Significantly, the two-fold capsid region is observed to undergo pH-mediated structural transitions when the homologous AAV8 was examined at the conditions encountered during trafficking in the endocytic pathway (Nam et al., 2011). It is possible that the mutations of the AAV2 improve transduction efficiency through altered receptor binding mechanisms. Residues mediating AAV2 and AAV6 interaction with heparan sulfate receptors, R585 and R588, and K531 (structurally equivalent to E530 in AAV2), respectively, are close to this foot (FIG. 26B), and residues 491 and 500, in VRV, are located in one of two large regions on the surface of the AAV2 capsid that has been implicated in binding to the LamR receptor in AAV8 (Akache et al., 2006). Amino acids in VRV also play a role in the AAV9 capsid binding to its glycan receptor, galactose.

The decreased transduction efficiency phenotype of the mutants containing the S662V mutations is difficult to explain given the location of this residue within the footprint delineated by the residues which enhance transduction when mutated to eliminate potential phosphorylation (FIG. 32A and FIG. 32B). In addition, it has been shown that a mutation of this residue to valine improved transduction relative to WT AAV2 (Aslanidi et al., 2012). Residue S662, like T659, is located in the HI loop that extends over adjacent five-fold symmetry related VP3 monomers and likely plays a role in stabilizing the pentameric subunits. However, the serine side-chain is not engaged in any inter- or intra-subunit interactions, and while the HI loop has been reported to be a determinant of capsid assembly and genome packaging (DiPrimio et al., 2008), it tolerated single amino acid substitution (Aslanidi et al., 2012). Thus, its effect is likely due to the abrogation of a capsid interaction utilizing the footprint containing the triple-tyrosine mutant residues and T491. Significantly, the phenotypes for mutations in nearby amino acids that make up the HI loop, for example, amino acid residue 664, substituting either serine (mut45subSer14) or a FLAG epitope (mut45SubFLAG10), were non-infectious or not assembled into viral capsid (Wu et al., 2000). However, an HA insertion at the same position produced capsids that were partially defective, yet still bound heparin (Wu et al., 2000).

Whereas only ~45% of the vector genomes delivered by the WT AAV2 vectors were present in the nucleus at 48 h post infection, >90% of the vector genomes delivered by the Y-T quadruple-mutant vector were present at the same time point. This indicates improved trafficking kinetics for the mutant that would be consistent with reduced re-direction to the proteasome. The modest (~2-3-fold) increase in the transduction efficiency of these vectors compared to the tyrosine triple-mutant vectors is also consistent with the ~10% increase in nuclear vector genome delivery, i.e. ~90% compared to ~80%.

The various combinations of surface tyrosine, serine, and threonine modifications clearly showed that there is an optimal combination to achieve maximal augmentation. These studies also highlighted the requirement for specific residue types in AAV interactions during infection and for enhancing transduction. It is possible that the individual mutations, which did not show a significant increase in the transduction efficiency as single changes, can form superior vectors when combined in a single capsid.

TABLE 6

Comparison of Tyrosine Residues in AAV Serotypes
(Surface exposed residues are shown with an "*" following their amino acid position)

| AAV1 | AAV2 | AAV3 | AAV4 | AAV5 | AAV6 | AAV7 | AAV8 | AAV9 | AAV10 | AAV11 | AAV12 |
|---|---|---|---|---|---|---|---|---|---|---|---|
| *Y6* | *Y6* | *Y6* | *Y5* | *NA* | *Y6* | *Y6* | *Y6* | *Y6* | *Y6* | *Y6* | *Y6* |
| *Y50* | *Y50* | *Y50* | *Y49* | *Y49* | *Y50* | *Y50* | *Y50* | *Y50* | *Y50* | *Y50* | *Y50* |
| *Y52* | *Y52* | *Y52* | *Y51* | *Y51* | *Y52* | *Y52* | *Y52* | *Y52* | *Y52* | *Y52* | *Y52* |
| *Y79* | *Y79* | *Y79* | *Y78* | *Y78* | *Y79* | *Y79* | *Y79* | *Y79* | *Y79* | *Y79* | *Y79* |
| *Y90* | *Y90* | *Y90* | *Y89* | *Y89* | *Y90* | *Y90* | *Y90* | *Y90* | *Y90* | *Y90* | *Y90* |
| *Y93* | *Y93* | *Y93* | *Y92* | *Y92* | *Y93* | *Y93* | *Y93* | *Y93* | *Y93* | *Y93* | *Y93* |
| Y252* | Y252* | Y252* | Y246* | Y242* | Y252* | Y253* | Y253* | Y252* | Y253* | Y246* | Y255* |
| Y257 | Y257 | Y257 | Y251 | Y247 | Y257 | Y258 | Y258 | Y257 | Y258 | Y251 | Y260 |
| Y273* | Y272* | Y272* | Y263* | Y263* | Y273* | Y274* | Y275* | Y274* | Y275* | Y263* | Y272* |
| Y276 | Y275 | Y275 | NA | Y266 | Y276 | Y277 | Y278 | Y277 | Y278 | NA | NA |
| Y282 | Y281 | Y281 | Y272 | Y272 | Y282 | Y283 | Y284 | Y283 | Y284 | Y272 | Y281 |
| NA | NA | NA | NA | Y294 | NA | NA | NA | NA | NA | NA | NA |
| Y349 | Y348 | Y348 | Y339 | Y339 | Y349 | Y350 | Y351 | Y350 | Y351 | Y339 | Y348 |
| Y353 | Y352 | Y352 | Y343 | Y343 | Y353 | Y354 | Y355 | Y354 | Y355 | Y343 | Y352 |
| Y376 | Y375 | Y375 | Y366 | Y366 | Y376 | Y377 | Y378 | Y377 | Y378 | Y366 | Y375 |
| Y378 | Y377 | Y377 | Y368 | Y368 | Y378 | Y379 | Y380 | Y379 | Y380 | Y368 | Y377 |
| Y394 | Y393 | Y393 | Y387 | NA | Y394 | Y395 | Y396 | Y395 | Y396 | Y386 | Y395 |
| Y398 | Y397 | Y397 | Y391 | Y390 | Y398 | Y399 | Y400 | Y399 | Y400 | Y390 | Y399 |
| Y414 | Y413 | Y413 | Y407 | Y406 | Y414 | Y415 | Y416 | Y415 | Y416 | Y406 | Y415 |
| Y425 | Y424 | Y424 | Y418 | NA | Y425 | Y426 | Y427 | Y426 | Y427 | Y417 | Y426 |
| Y442* | Y441* | Y441* | Y435* | Y434* | Y442* | Y443* | Y444* | Y443* | Y444* | Y434* | Y443* |
| NA | NA | NA | NA | Y436 | NA | NA | NA | NA | NA | NA | NA |
| Y444* | Y443* | Y443* | NA | NA | Y444* | Y445* | Y446* | Y445* | Y446* | NA | NA |
| Y445* | Y444* | Y444* | NA | NA | Y445* | Y446* | Y447* | Y446* | Y447* | NA | NA |
| NA | NA | NA | NA | NA | NA | NA | NA | NA | NA | NA | Y465 |
| NA | NA | NA | NA | NA | NA | Y466 | NA | NA | NA | NA | NA |
| NA | NA | NA | NA | Y457 | NA | NA | NA | NA | NA | NA | NA |
| NA | NA | NA | NA | NA | NA | NA | NA | NA | NA | NA | Y475 |
| NA | NA | NA | NA | NA | NA | NA | NA | NA | NA | Y467 | Y476 |
| NA | NA | NA | NA | Y461 | NA | NA | NA | NA | NA | NA | NA |
| NA | NA | NA | NA | NA | NA | NA | NA | Y478 | NA | NA | NA |
| Y484 | Y483 | Y484 | NA | NA | Y484 | NA | Y486 | Y484 | Y486 | NA | NA |
| NA | NA | NA | Y491* | NA | NA | NA | NA | NA | NA | Y490* | Y499* |
| NA | Y500* | NA | NA | NA | NA | NA | NA | NA | NA | NA | NA |
| NA | NA | NA | Y504* | NA | NA | NA | NA | NA | NA | Y503* | Y512* |
| Y509 | Y508 | Y509 | NA | NA | Y509 | Y511 | Y511 | NA | Y511 | Y507 | NA |
| NA | NA | NA | NA | Y502 | NA | NA | NA | NA | NA | NA | NA |
| NA | NA | NA | NA | Y521* | NA | NA | NA | NA | NA | NA | NA |
| NA | NA | NA | NA | Y542* | NA | NA | Y557* | NA | Y557* | NA | NA |
| NA | NA | NA | NA | Y563* | NA | NA | NA | NA | NA | NA | NA |
| NA | Y576 | Y577 | NA | NA | NA | Y578 | Y579 | Y577 | Y579 | NA | NA |
| NA | NA | NA | NA | Y585* | NA | NA | NA | NA | NA | NA | NA |
| Y613* | Y612* | Y613* | Y611* | Y602* | Y613* | Y614* | Y615* | Y613* | Y615* | Y610* | Y619* |
| NA | NA | NA | Y612 | NA | NA | NA | NA | NA | NA | Y611 | Y620 |
| Y674* | Y673* | Y674* | Y672* | Y662* | Y674* | Y675* | Y676* | Y674* | Y676* | Y671* | Y680* |
| Y701* | Y700-S | Y701* | NA | Y689* | Y701* | Y702* | Y703* | Y701* | Y703* | NA | NA |
| Y705* | Y704* | Y705* | Y703* | Y693* | Y705* | NA | Y707* | Y705* | Y707* | Y702* | Y711* |
| NA | NA | NA | NA | NA | NA | NA | Y708 | Y706 | Y708 | NA | NA |

TABLE 6-continued Comparison of Tyrosine Residues in AAV Serotypes
(Surface exposed residues are shown with an "*" following their amino acid position)

| AAV1 | AAV2 | AAV3 | AAV4 | AAV5 | AAV6 | AAV7 | AAV8 | AAV9 | AAV10 | AAV11 | AAV12 |
|------|------|------|------|------|------|------|------|------|-------|-------|-------|
| Y721 | Y720 | Y721 | Y719 | Y709 | Y721 | Y722 | Y723 | Y721 | Y723 | Y717 | Y727 |
| Y731* | Y730* | Y731* | Y729* | Y719* | Y731* | Y732* | Y733* | Y731* | Y733* | Y728* | NA |

TABLE 7

Comparison of Lysine Residues in AAV Serotypes
(Surface exposed residues are shown with an "*" following their amino acid position)

| AAV1 | AAV2 | AAV3 | AAV4 | AAV5 | AAV6 | AAV7 | AAV8 | AAV9 | AAV10 | AAV11 | AAV12 |
|------|------|------|------|------|------|------|------|------|-------|-------|-------|
| NA | K24 | NA | NA | NA | NA | NA | NA | NA | NA | NA | NA |
| K26 | K26 | K26 | NA | NA | K26 | K26 | K26 | K26 | K26 | K26 | K26 |
| K31 | NA | NA | K30 | K30 | K31 | K31 | K31 | K31 | K31 | K31 | NA |
| K33 | K33 | K33 | K32 | K32 | K33 | K33 | K33 | K33 | K33 | K33 | K33 |
| K38 | NA | NA | NA | NA | K38 | K38 | K38 | NA | K38 | K38 | NA |
| NA | K39 | NA | NA | NA | NA | NA | NA | NA | NA | NA | NA |
| K51 | K51 | K51 | K50 | NA | K51 | K51 | K51 | K51 | K51 | K51 | K51 |
| K61 | K61 | K61 | K60 | NA | K61 | K61 | K61 | K61 | K61 | K61 | K61 |
| K77 | K77 | K77 | K76 | NA | K77 | K77 | K77 | K77 | K77 | K77 | K77 |
| NA | NA | NA | NA | NA | NA | NA | NA | NA | NA | NA | K81 |
| K84 | NA | K84 | K83 | NA | K84 | K84 | NA | K84 | K84 | K84 | NA |
| NA | K92 | K92 | K91 | NA | NA | NA | NA | K92 | NA | NA | K92 |
| NA | NA | NA | NA | K102 | NA | NA | NA | NA | NA | NA | NA |
| NA | K105 | NA | NA | NA | NA | NA | NA | K105 | NA | NA | NA |
| NA | NA | NA | NA | K115 | NA | NA | NA | NA | NA | NA | NA |
| K122 | K122 | K122 | K121 | K121 | K122 | K122 | K122 | K122 | K122 | K122 | K122 |
| K123 | K123 | K123 | K122 | K122 | K123 | K123 | K123 | K123 | K123 | K123 | K123 |
| K137 | K137 | K137 | NA | K136 | K137 | K137 | K137 | K137 | K137 | K137 | K137 |
| K142 | K142 | K142 | K141 | NA | K142 | K142 | K142 | K142 | K142 | K142 | K142 |
| K143 | K143 | K143 | K142 | K142 | K143 | K143 | K143 | K143 | K143 | K143 | K143 |
| NA | NA | NA | NA | NA | NA | NA | NA | NA | NA | NA | K148 |
| NA | NA | NA | NA | K150 | NA | NA | NA | NA | NA | NA | NA |
| NA | NA | NA | NA | K152 | NA | NA | NA | NA | NA | NA | NA |
| NA | NA | NA | NA | K153 | NA | NA | NA | NA | NA | NA | K160 |
| K161 | K161 | K161 | K160 | NA | K161 | K162 | K162 | K161 | K162 | K160 | K164 |
| NA | NA | NA | K161 | NA | NA | K163 | K163 | NA | K163 | K161 | K165 |
| NA | NA | NA | NA | NA | NA | NA | NA | NA | NA | NA | K166 |
| NA | NA | K164 | K163 | NA | NA | NA | NA | NA | NA | K163 | NA |
| NA | NA | NA | NA | K161 | NA | NA | NA | NA | NA | NA | K168 |
| K168 | NA | NA | K167 | NA | K168 | NA | NA | K168 | K169 | NA | NA |
| K169 | K169 | K169 | K168 | NA | K169 | K170 | K170 | K169 | K170 | K168 | NA |
| NA | NA | NA | K169 | NA | NA | NA | NA | NA | NA | NA | NA |
| NA | NA | NA | NA | K232 I | NA | NA | NA | NA | NA | NA | NA |
| **K258 *** | K258 | **K258 *** | K252 | NA | **K258 *** | **K259 *** | **K259 *** | **K258 *** | **K259 *** | NA | NA |
| NA | NA | NA | NA | K251 * | NA | NA | NA | NA | NA | NA | NA |
| K310 I | K309 | K309 I | K300 I | NA | K310 I | K311 I | K312 I | K311 I | K312 I | K300 I | K309 I |
| NA | NA | K310 I | NA | NA | NA | K312 I | NA | NA | NA | NA | NA |
| K315 I | K314 | K314 I | K305 I | K305 I | K315 I | K316 I | K317 I | K316 I | K317 I | K305 I | K314 I |
| K322 I | K321 | K321 I | K312 I | K312 I | K322 I | K323 I | K324 I | K323 I | K324 I | K312 I | K321 I |
| NA | NA | NA | NA | NA | NA | NA | **K333 *** | **K332 *** | **K333 *** | NA | NA |
| NA | NA | NA | NA | NA | NA | NA | NA | NA | NA | NA | K384 I |
| NA | NA | NA | NA | K394 I | NA | NA | NA | NA | NA | NA | NA |
| NA | NA | NA | K411 I | NA | NA | NA | NA | NA | NA | K410 I | K419 I |
| NA | NA | NA | NA | K425 I | NA | NA | NA | NA | NA | NA | NA |
| NA | NA | NA | NA | NA | NA | NA | **K449 *** | NA | NA | NA | NA |
| K459 I | NA | NA | NA | NA | K459 I | NA | NA | NA | NA | NA | NA |
| NA | NA | NA | NA | NA | NA | NA | **K462 *** | NA | NA | NA | NA |
| NA | NA | NA | K459 I | K451 I | NA | NA | NA | NA | NA | K458 I | K467 I |
| NA | NA | NA | K469 I | NA | NA | NA | NA | NA | NA | NA | NA |
| K476 I | NA | NA | K470 I | K462 I | K476 I | K478 I | K478 I | NA | K478 I | K469 I | K478 I |
| NA | NA | NA | K479 I | NA | NA | NA | NA | NA | NA | K478 I | K487 I |
| NA | NA | NA | NA | NA | NA | NA | NA | NA | NA | NA | K490I |
| **K491 *** | K490 | **K491 *** | **K485 *** | NA | **K491 *** | **K493 *** | NA | NA | NA | **K484 *** | **K490 *** |
| **K493 *** | NA | NA | NA | NA | **K493 *** | NA | NA | NA | NA | NA | NA |
| NA | NA | NA | **K492 *** | NA | NA | NA | NA | NA | NA | **K491 *** | **K493 *** |
| NA | NA | NA | **K503 *** | NA | NA | NA | NA | NA | NA | **K502 *** | **K511 *** |
| **K508 *** | K507 | **K508 *** | NA | NA | **K508 *** | **K510 *** | **K510 *** | NA | **K510 *** | NA | NA |
| **K528 *** | K527 | **K528 *** | NA | NA | **K528 *** | **K530 *** | **K530 *** | **K528 *** | **K530 *** | NA | NA |
| NA | NA | NA | NA | NA | **K531 *** | NA | NA | NA | NA | NA | NA |
| **K533 *** | K532 | **K533 *** | NA | NA | **K533 *** | NA | NA | NA | NA | NA | NA |
| NA | NA | NA | **K532 *** | NA | NA | NA | NA | NA | NA | NA | NA |
| **K545 *** | K544 | **K545 *** | NA | NA | **K545 *** | **K547 *** | **K547 *** | **K545 *** | **K547 *** | NA | NA |

TABLE 7-continued

Comparison of Lysine Residues in AAV Serotypes
(Surface exposed residues are shown with an "*" following their amino acid position)

| AAV1 | AAV2 | AAV3 | AAV4 | AAV5 | AAV6 | AAV7 | AAV8 | AAV9 | AAV10 | AAV11 | AAV12 |
|---|---|---|---|---|---|---|---|---|---|---|---|
| NA | NA | NA | K544 * | NA | NA | NA | NA | NA | NA | NA | NA |
| NA | K549 | NA | NA | NA | NA | NA | NA | NA | NA | NA | NA |
| NA | NA | NA | NA | NA | NA | K553 * | NA | NA | NA | NA | NA |
| NA | K556 | NA | NA | NA | NA | NA | NA | K557 * | NA | NA | NA |
| K567*- | NA | NA | NA | NA | K567 * | NA | K569 * | K567 * | K569 * | NA | NA |
| K621 I | K620 | K621 I | K619 I | K610 I | K621 I | K622 I | K623 I | K621 I | K623 I | K618 I | K627 I |
| K641 I | K640 | K641 I | K639 I | K630 I | K641 I | K642 I | K643 I | K641 I | K643 I | K638 I | K647 I |
| K650 I | K649 | K650 I | K648 I | K639 I | K650 I | K651 I | K652 I | K650 I | K652 I | K647 I | K656 I |
| NA | NA | NA | NA | NA | NA | NA | NA | K664 I | NA | NA | NA |
| K666 * | K665 | K666 * | NA | NA | K666 * | K667 * | K668 * | K666 * | K668 * | NA | NA |
| NA | NA | NA | NA | K676 I | NA | NA | NA | NA | NA | NA | NA |
| K689 I | K688 | K689 I | K687 I | K677 I | K689 I | K690 I | K691 I | K689 I | K691 I | K686 I | K695 I |
| K693 I | K692 | K693 I | K691 I | K681 I | K693 I | K694 I | K695 I | K693 I | K695 I | K690 I | K699 I |
| K707 * | K706 | K707 * | NA | NA | K707 * | K708 * | K709 * | K707 * | K709 * | NA | NA |
| NA | NA | NA | K718 I | NA | NA | NA | NA | NA | NA | K717 I | NA |

Residues in bold are surface-associated lysines = *
Resides that are located on the interior of the capsid = I
No homologous lysine at that position for that serotype = NA
Residues not visible in the crystal structure of AAVs are italicized; however, biochemical data suggests that these amino acids are located inside the AAV capsid until some point in the virus life cycle when they are then externalized.

Example 6—High-Efficiency Transduction of Primary Human HSCs and Erythroid Lineage-Restricted Expression by Capsid-Optimized AAV6-Serotype Vectors Hemoglobinopathies, such as β-thalassemia and sickle cell disease, are by far the most common monogenic diseases that afflict humans worldwide, with an incidence rate of 1:600. These diseases are also the ideal targets for the potential gene therapy, if high-efficiency transduction of HSCs, and erythroid lineage-restricted expression of the human β-globin gene can be achieved. Indeed, recombinant lentiviral vectors were recently shown to mediate β-globin gene transfer and transgene expression in an adult patient with severe β-thalassemia, which led to transfusion-independence. Unfortunately, however, the observed therapeutic benefit was also compromised by transcriptional activation of a cellular proto-oncogene, HMGA2 and clonal expansion of myeloid cells. Thus, it is important to develop alternatives to lentiviral vectors. Recombinant vectors based on a non-pathogenic human virus, the adeno-associated virus 2 (AAV2) have been developed and shown to be safe and effective in a number of recent clinical trials. Recombinant AAV2-globin vectors have been prepared previously, but the transduction efficiency of these vectors in primary human HSCs has not been evaluated.

More recently, up to 12 additional AAV serotype vectors have become available, and it has been documented that AAV6 is the most efficient serotype among AAV1 through AAV12 in transducing primary human CD34$^+$ cells. It has also been documented that site-directed mutagenesis of specific surface-exposed tyrosine (Y) residues on AAV serotype capsids leads to higher transduction efficiency both in vitro and in vivo in various cell types, and that Y705 and Y731 single-mutants are capable of transducing primary human CD34$^+$ cells more efficiently than their WT counterpart.

In the present studies, both mutations were combined to generate a tyrosine double-mutant (Y705+731F) self-complementary (sc) AAV6 vector to evaluate whether the transduction efficiency in primary human CD34$^+$ cells could be further augmented. In addition, the transcriptional potential of the following two erythroid cell-specific promoters were compared: (i) HS2-βp, and (ii) B19p6, both in vitro and in a murine xenograft model in vivo.

The transduction efficiency of the Y705+731F double-mutant scAAV6 vectors was significantly higher than that of the single-mutant or the WT scAAV6 vectors in CD34$^+$ cells in vitro. Transgene expression from the B19p6 was significantly higher than that from the HS2-βp, and could be further increased following erythroid differentiation. Expression from the B19p6 in the Y705+731F double-mutant scAAV6 vectors was also significantly higher than that from the HS2-βp in human CD34$^+$ cells in a murine xenograft model in vivo. Transgene expression was detectable up to 12 weeks post-transplantation in primary recipients, and up to 6 additional weeks in secondary transplanted animals. These data suggest that the Y705+731F scAAV6-B19p6-3β-globin vectors are well suited for the gene therapy of human hemoglobinopathies in general, and β-thalassemia and sickle cell disease in particular.

Materials and Methods

Cell Lines, Cells, and Cell Cultures. Human embryonic kidney 293 (HEK293) and erythroleukemia K562 cells were obtained from American Type Culture Collections (Manassas, Va.) and maintained in Dulbecco's-modified Eagle's medium (DMEM; Lonza, Inc.), or Iscove's modified Dulbecco's medium (IMDM; Irvine Scientific, Santa Ana, Calif., USA) supplemented with 10% fetal bovine serum (FBS; Sigma-Aldrich Co.), 100 mg/mL of penicillin and 100 U/mL of streptomycin (Invitrogen, Inc.). Human cord blood CD34$^+$ cells and CD36$^+$ cells were purchased from AllCells (AllCells Technologies, Emeryville, Calif.) and maintained in StemSpan™ Serum-Free Expansion Medium (SFEM) (StemCell Technologies, Vancouver, BC, Canada) with 10 ng/mL of recombinant human interleukin 6 (rhIL6) (Peprotech), 10 ng/mL of Interleukin 3 (rhIL3) (Peprotech, Rocky Hill, N.J.) and 10 ng/mL of recombinant human stem cell factor (rhSCF) (R&D Systems, Minneapolis, Minn., USA).

Plasmids. Plasmid pACGr2c6 and plasmid pscAAV2-CBAp-EGFP were gifts from Drs. R. Jude Samulski and Xiao Xiao, University of North Carolina at Chapel Hill, Chapel Hill, N.C. pscAAV2-HS2-βp-EGFP was constructed by replacing the CBAp in pscAAV2-CBAp-EGFP with the HS2-βp from pHPV37, obtained from Dr. Philippe LeBoulch, Harvard Medical School, Boston, Mass., USA Tyrosine double-mutant (DM) plasmid pAAV-Y705+731F was generated by using QuikChange® II Site-Directed Mutagenesis Kit (Stratagene, Santa Clara, Calif., USA). pscAAVCBAp-GLuc containing *Gaussia* luciferase (Gluc) reporter gene was used to generate plasmid pscAAV-B19p6-Gluc, in which the CBA promoter was replaced by the B19p6 promoter from plasmid pscAAV-B19p6-Fluc by digesting with MluI and AgeI restriction enzymes. Plasmid pscAAV-HS2-βp-Gluc was constructed using standard cloning methods. Briefly, the HS2-βp insert with MluI and AgeI sites was first cloned by polymerase chain reaction (PCR) from plasmid pscAAV-HS2-βp-globin using following primers-pair:

```
Bp-AgeI-F
(5'-GCGACCGGTGGTGTCTGTTTGAGGTTGCTA-3';
SEQ ID NO: 22)
and

HS2-MluI-R
(5'-CGACGCGTTCAGATCGATCTCTCCCCAGCAT-3';
SEQ ID NO: 23).
```

The PCR product was cloned as an insert in plasmid vector pscAAV-CBAp-GLuc following digestion with MluI and AgeI restriction enzymes and ligation.

Viral vector production. Viral vectors were packaged as described above. Briefly, HEK 293 cells were co-transfected with three plasmids using Polyethylenimine (PEI, linear, MW 25000, Polysciences, Inc., Warrington, Pa., USA), and medium was replaced 4 hrs posttransfection. Cells were harvested 72 hrs posttransfection, subjected to 3 rounds of freeze-thaw and digested with Benzonase (Invitrogen, Inc.). Vectors were purified by iodixanol (Sigma-Aldrich Co.) gradient ultra-centrifugation followed by ion exchange chromatography using HiTrap Q HP (GE Healthcare), washed with phosphate-buffered saline (PBS) and concentrated by centrifugation using centrifugal spin concentrators with 150 KDa molecular-weight cut-off (MWCO). Titers were determined by quantitative DNA slot blot using $^{32}$P-labeled specific DNA probes.

Induction of Erythroid Differentiation and Evaluation of Gluc Expression in vitro. Epo is commonly used for CD34$^+$ cells erythroid introduction. In this example, CD34$^+$ cells (15,000 cell/well, 3 well/group) were cultured in SFEM containing IL-3 (10 ng/mL), IL-6 (10 ng/mL), SCF (10 ng/mL) and with or without Epo (3 U/mL). CD34$^+$ and CD36$^+$ cells were cultured in SFEM with 10 ng/mL of rhIL6, rhIL3, and 10 ng/mL of rhSCF with or without 3 U/mL of recombinant human Epo for up to 15 days. Surface glycophorin A (GPA) expression were determined by flow cytometry using PE conjugated anti-GPA antibodies. K562 cells were seeded at a density of $1\times10^5$ cells/mL in 6-well plates and cultured for 4 days in the presence or absence of 3 U/mL of Epo or 0.6 mM sodium butyrate or 400 µM hydroxyurea (HU). Benzidine staining was used to determine hemoglobin synthesis. Briefly, 100 µL of 0.2% benzidine (Sigma-Aldrich Co.) staining buffer prepared in 0.5 M glacial acetic acid was added to 100 mL cells; and then 5 mL of 30% hydrogen peroxide ($H_2O_2$) was added to the mixture; after incubation at RT for 10 min, the proportion of benzidine positive cells was quantified using a hemocytometer under a light microscope.

For Epo-induction, equivalent numbers of K562 cells, CD34$^+$, and CD36$^+$ cells were cultured as described above, and at indicated time-points, were either mock-infected, or infected with scAAV6-Gluc vectors under the control of CBAp, HS2-βp, or B19p6 promoters, respectively, for 2 hrs. Gluc activity in the medium was examined at 18 hrs' post-infection using commercially available BioLux® *Gaussia* Luciferase Flex Assay Kits (New England Biolabs, Inc, Ipswich, Mass., USA) with an injector-equipped luminometer (BMG Labtech, FLUOstar Optima, Cary, N.C., USA).

Xenotransplantation. Equivalent numbers of human cord blood-derived CD34$^+$ cells were cultured in four round-bottom 15×75 mm Falcon tubes (BD Biosciences) and either mock-infected, or infected with $2\times10^4$ vgs/cell of WT-scAAV6-B19p6-Gluc, DM-scAAV6-HS2-βp-Gluc, or DM-scAAV6-B19p6-Gluc vectors for 2 hrs at 37° C. Tubes were gently shaken every 15 min during infection. Cells were then washed and resuspended at a cell density of $5\times10^6$/mL in DPBS prior to transplantation.

Five to 12-week-old NOD.CG-Prkdc$^{scid}$ Il2rgtm1Wjl/SzJ (NSG) female recipient mice were used in the present study since female mice have been reported to be more efficient recipient than male mice for engraftment of human HSCs. Mice were bred and kept in microisolator cages. Antibiotics were administrated by supplementing the drinking water with 0.2 mg/mL enrofloxacin (Bayer Healthcare, Shawnee Mission, Kans., USA) for 2 days before performing transplantation and 2 weeks post-transplantation to prevent infection. Mice were irradiated with a dose of 250 cGY from a Cesium-137 source at 4 hrs before injecting the mock- or AAV vector-transduced human cord blood-derived CD34$^+$ cells. Approximately $1\times10^6$ cells were injected into the lateral tail vein of each mouse.

Evaluation of Transgene Expression in Peripheral Blood. The method to evaluate Gluc activity was modified from the previously described protocols. Coelenterazine freebase, the Gluc substrate, was purchased from Nanolight Technology (Pinetop, Ariz., USA). To prepare the stock solution, one drop of concentrated HCl was added to 10 mL of methanol to make acidified methanol. The corresponding amount of acidified methanol (2 mL) was then added to coelenterazine (10 mg) in an amber vial to make 5 mg/mL (≈12 mM) substrate solution. Stock solution was aliquoted and stored at −80° C. For in vitro blood Gluc activity assay, the stock solution was freshly diluted to 100 mM in PBS supplemented with 5 mM NaCl (pH 7.2). Mice were restrained with the tail exposed. The lateral tail vein was punctured using a 1-mL insulin needle; five to 20 µL of blood was collected using 20-µL tips. Samples were collected in anti-coagulant tube in the presence of EDTA as an anticoagulant and placed on ice until all samples were collected. Blood samples were transferred to a 96-well plate, and the Gluc activity was measured using a plate luminometer (BMG Labtech, FLUOstar Optima, Cary, N.C., USA). Data were analyzed by plotting the relative light units (RLU) per second.

In vivo bioluminescence imaging. Mice were weighed to calculate the volume of substrate according to the dose of 4 mg/kg of body weight and anesthetized. The calculated volume of the 5 mg/mL of stock substrate solution was mixed with 100 µL of PBS and injected via retro-orbital route. In vivo bioluminescence images were acquired immediately over a period of 5 min using a Xenogen IVIS® Lumina II (Caliper Life Sciences) equipped with a cooled couple-charged device (CCD) camera (PerkinElmer Co., Alameda Calif.). Signal intensity was quantified using the camera control program, Living Image software version 4, and shown as photons/second/cm$^2$/steradian (p/s/cm$^2$/sr).

Cell sorting, lineage analyses, and transgene expression. Twelve-weeks post-transplantation of human CD34+ cells in primary recipient NSG mice, bone marrow cells were flushed from the bones of the hind limb with sterile PBS. Red blood cells were hemolyzed with ammonium chloride buffer. Cells were then labeled with fluorescein isothiocyanate (FITC) conjugated anti human CD45 and allophycocyanin (APC) conjugated anti mouse CD45 antibodies, and the percentage of human CD45-positive cells was calculated. For sorting of lineage specific cells, the bone marrow cells were labeled with FITC-conjugated anti human CD71 for erythroid, phycoerythrin (PE)-conjugated anti human CD19 for B cells, and APC-conjugated anti-human CD11b for monocytes and neutrophils. All antibodies were from BD Biosciences (San Jose, Calif.). Lineage-specific cells were sorted using BD Aria IIu Fluorescence-Activated Cell Sorter (BD Biosciences). For determining Gluc activity in the sorted cell populations, $\approx 4\times 10^4$ cells from each lineage were suspended in 100 mL PBS. Five mL of the cell mixtures were used for the in vitro Gluc activity assay as described above.

Figure 36C:
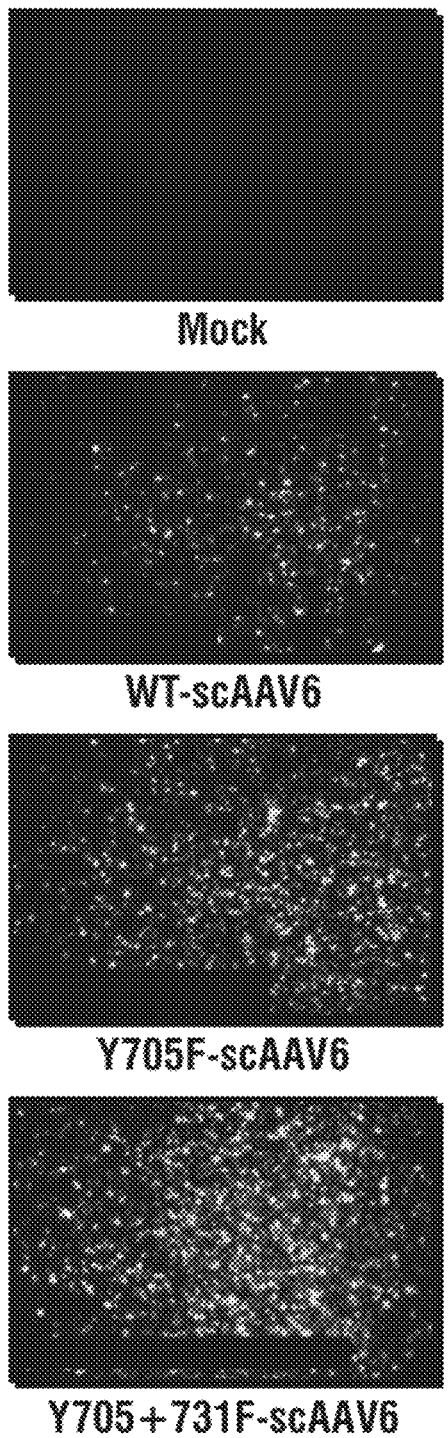
Figure 36D:
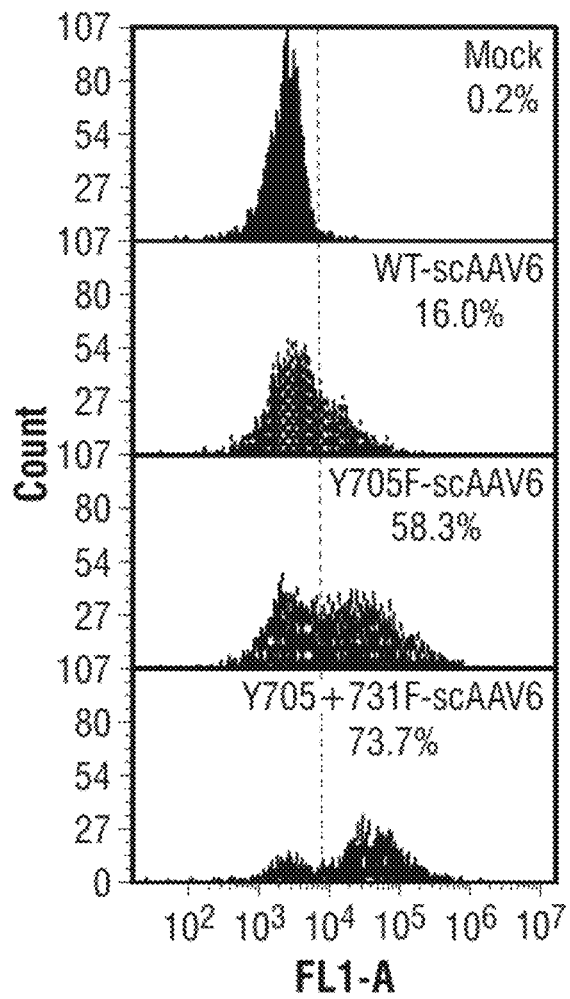
Figure 37C:
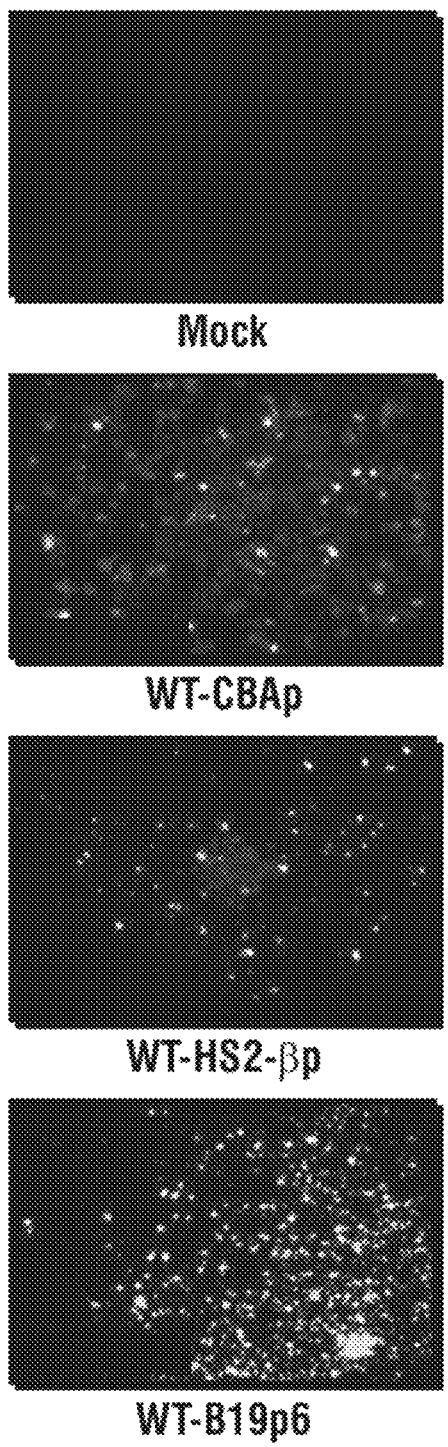
Figure 37D:
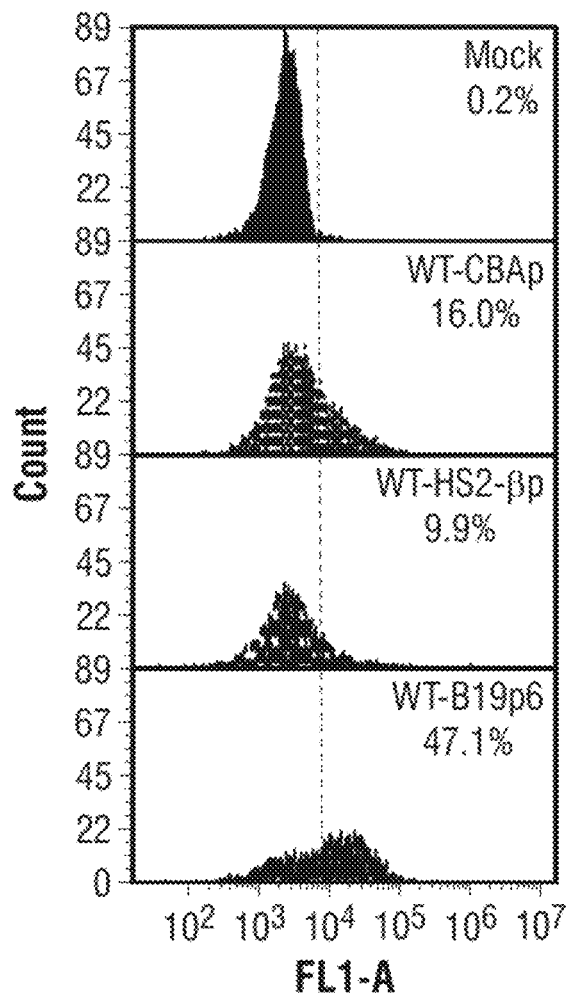

Secondary transplantation. Twelve-weeks post-primary transplantation, the whole bone marrow cells from a mouse transplanted with human CD34+ cells transduced with DM-scAAV6-B19p6-Gluc vectors were isolated as described above. Approximately $2\times 10^6$ bone marrow cells were transplanted into NSG mice (n=4) via retro-orbital injection following irradiation with 250 cGy. Mice were maintained on 0.2 mg/mL enrofloxacin in drinking water (Bayer Healthcare, Topeka, Kans., USA). Six-weeks' post-secondary transplantation, mice were subjected to whole-body bioluminescence imaging in vivo as described above.
Results Transduction Efficiency of Single- and Double-tyrosine Mutant scAAV6 Serotype Vectors in Human Hematopoietic Cells in vitro. AAV6 has been shown to be the most efficient serotype in transducing primary human HSCs, and that site-directed mutagenesis of specific surface-exposed tyrosine residues (Y705 and Y731) further increased the transduction efficiency of these vectors. Since the transduction efficiency of AAV2 and AAV3 serotype vectors could be further improved by combining the single tyrosine-mutations, the inventors and their colleagues evaluated the transduction efficiency of the Y705F+Y731F double-mutant (DM) scAAV6 vectors. Both human erythroleukemia K562 cells, and primary human CD34+ cells were either mock-infected, or infected with WT, or single (Y705F)-, or DM (Y705+731F) scAAV6 vectors. K562 cells were infected with $5\times 10^3$ vgs/cell, and human CD34+ cells were infected with $2\times 10^4$ vgs/cell. Transgene expression was determined by fluorescence microscopy and quantified by flow cytometry. These results are shown in FIG. 36A-FIG. 36D. As can be seen, the transduction efficiency of DM scAAV-CBAp-enhanced green fluorescent protein (EGFP) vectors was significantly higher than that of either WT or single-mutant scAAV6 vectors, both in K562 cells (FIG. 36A and FIG. 36B) and in CD34+ cells (FIG. 36C and FIG. 36D). The percentage of EGFP-positive cells increased from 24.0±4.0% to 46.0±6.1% in K562 cells, and from 16.0±2.0% to 73.7%±5.1% in CD34+ cells.

Transcriptional Potential of CBAp, HS2-βp, and B19p6 Promoters. With the ultimate objective of developing recombinant AAVs vectors for the potential gene therapy of human hemoglobinopathies, the inventors next evaluated the transcriptional potential of the following two erythroid-cell-specific promoters: HS2-βp, and the B19p6. The ubiquitous CBAp was used as an appropriate control. scAAV6 vectors containing the EGFP gene under the control of the three promoters were used to infect primary human CD34+ cells under identical conditions, and transgene expression was evaluated 72 hrs' post-infection. These results are shown in FIG. 37A, FIG. 37B, FIG. 37C, and FIG. 37D. In K562 cells (FIG. 37A and FIG. 37B), the EGFP expression level from DM-scAAV6-B19p6-EGFP vectors was $\approx$67.0±7.9%, which is significantly higher that from DM-scAAV6-CBAp-EGFP vectors ($\approx$40.0±1.0%), and from DM-scAAV6-HS2-βp-EGFP vectors ($\approx$26.1±2.9%). Similarly, in human CD34+ cells (FIG. 37C and FIG. 37D), whereas little transgene expression occurred in mock-infected cells, $\approx$16% of cells transduced with scAAV6-CBAp-EGFP vectors were EGFP-positive. Transgene expression from scAAV6-HS2-βp-EGFP occurred in $\approx$10% of cells, whereas $\approx$47% of cells transduced with scAAV6-B19p6-EGFP vectors were EGFP-positive.

Transgene expression from the CBAp, HS2-βp, and B19p6 promoters following erythroid differentiation in vitro. Since HS2-βp and B19p6 are erythroid-cell-specific promoters, the inventors examined whether transgene expression from these promoters could be further increased following erythroid differentiation of K562 cells. K562 cells were cultured for 4 days in the presence or absence of the 3 U/mL of erythropoietin (Epo), and equivalent numbers of cells were either mock-infected, or infected with $5\times 10^3$ vgs/cell of Y705+731F DM-scAAV6 vectors expressing the Gluc reporter gene under the control of the CBAp, HS2-βp, or the B19p6 promoters as described herein. Gluc activity was determined 18 hrs post-infection. As can be seen in FIG. 38A and FIG. 38B, transgene expression from B19p6 promoter in untreated K562 cells was significantly higher than that from CBAp and HS2-βp promoters (FIG. 38A). The extent of transgene expression from both HS2-βp and B19p6 increased up to 7-fold following Epo-induced differentiation, whereas no significant change was observed from the CBAp, with or without Epo-induced differentiation (FIG. 38B). Similar results were observed with butyrate- or HU-induced erythroid differentiation of K562 cells. However, since HU has been shown to increase the transduction efficiency of AAV vectors, and butyrate has been reported to be related to activation of p38 MAP kinase, which also affects AAV transduction, the observed increase in transgene expression may not solely be credited to erythroid differentiation.

Figure 39A:
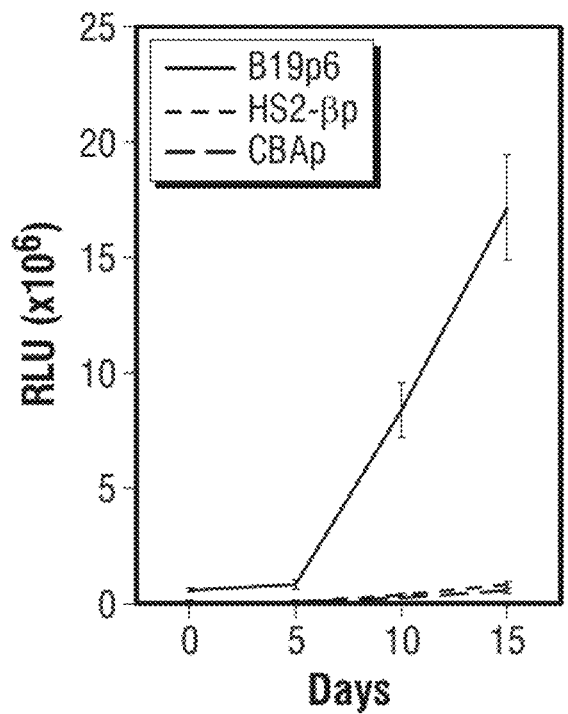
FIG. 39A, FIG. 39B, FIG. 39C, and FIG. 39D show the transcriptional potential of CBAp, HS2-βp and B19p6 promoters in primary human CD34$^+$ and CD36$^+$ human cells following erythroid differentiation. Approximately $1.5\times10^4$ CD34$^+$ cells, and $\approx 2\times10^4$ primary human CD36$^+$ erythroid progenitor cells were cultured with or without Epo (3 U/mL) for various indicated times, and infected with $1\times10^4$ vgs/cell scAAV6-Gluc vectors under identical conditions. Transgene expression levels were determined at 18 hrs' post-infection at each time-point. Gluc activity at various time-points was normalized to the group without Epo-induction, and the normalized absolute values are shown as average ±s.d. from triplicates for CD34$^+$ cells (FIG. 39A), and for CD36$^+$ cells (FIG. 39C). Fold changes in transgene expression following erythroid-differentiation were calculated by dividing the normalized Gluc activities by the initial activity on Day 0 (FIG. 39B and FIG. 39D)
Figure 39B:
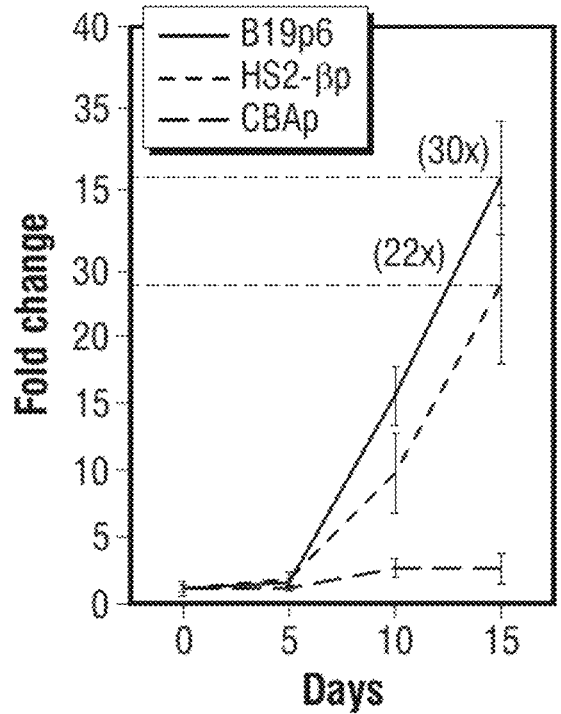
Figure 39C:
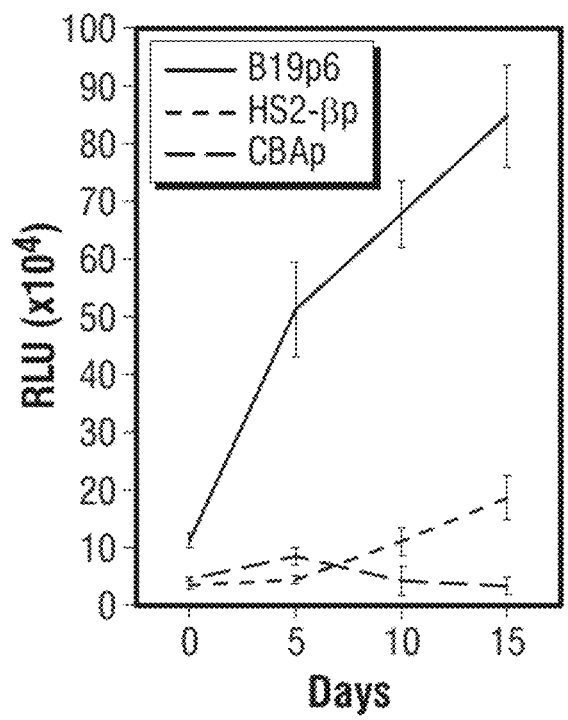
Figure 39D:
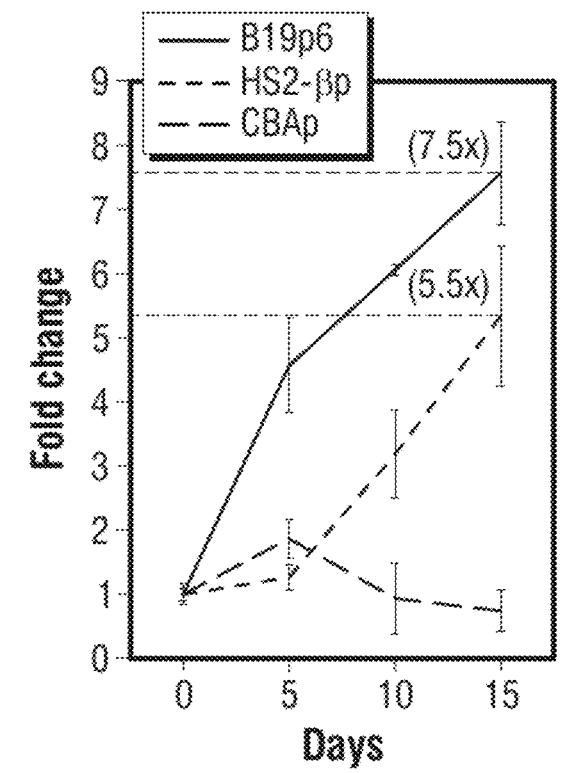

Epo is also commonly used to induce erythroid differentiation in CD34+ cells. In this example, CD34+ cells were cultured for various indicated days in the presence or absence of Epo, and equivalent numbers of cells were either mock-infected, or infected with $1\times 10^4$ vgs/cell of Y705+731F DM-scAAV6-Gluc vectors. Gluc activity was determined 18 hrs post-infection at each time-point. These results are shown in FIG. 39A-FIG. 39D. As is evident in FIG. 39A and FIG. 39B, transgene expression from both HS2-βp and B19p6 kept increasing until the end of the experiments, whereas expression from the CBAp remained unaffected, the extent of transgene expression from the HS2-βp and the B19p6 promoters increased up to 22-fold and 30-fold, respectively, 15 days post-erythroid differentiation. Similar results were obtained with primary human CD36+ erythroid progenitor cells (FIG. 39C and FIG. 39D). The extent of transgene expression from the HS2-βp and the B19p6 promoters increased up to 5.5-fold and 7.5-fold, respectively, 12 days post-erythroid differentiation.

Transgene Expression from the HS2-βp and B19p6 promoters in a xenograft murine model in vivo. Transgene expression from the HS2-βp and the B19p6 promoter was also evaluated in an immuno-deficient xenograft mouse model in vivo. Female non-obese diabetic severe combined immune-deficient (SCID), gamma (NSG) mice have been reported to be a good xenotransplantation model for assaying human cell engraftment. In this example, ≈1×10$^6$ primary human CD34$^+$ cells were either mock-infected, or infected by WT or Y705+731F DM-scAAV6 vectors expressing Gluc under the control of HS2-βp or the B19p6 promoters, respectively.

Figure 40A:
FIG. 40A and FIG. 40B show the bioluminescence imaging of mice transplanted with human CD34$^+$ cell in vivo. NSG mice transplanted with mock-infected, or various indicated scAAV6 vector-infected primary human CD34$^+$ cells was acquired by a Xenogen IVIS® Imaging System 6-weeks post-transplantation. Images of representative animals from each group are shown (FIG. 40A). The luminescence signal intensity was quantified as photons/second/cm$^2$/steradian (p/s/cm$^2$/sr) using the Living Image® software (FIG. 40B)
Figure 40B:
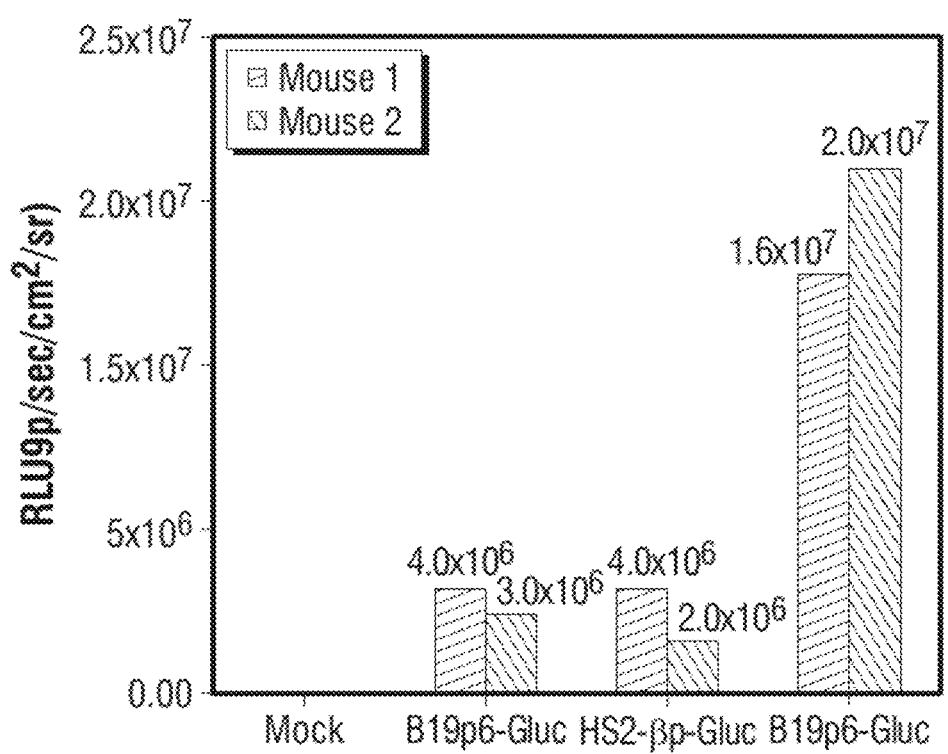

Whole-body bioluminescence images (FIG. 40A), acquired as detailed herein at 6 weeks post-implantation, corroborated that whereas no transgene expression occurred in mice transplanted with mock-infected human CD34$^+$ cells, expression from the B19p6 promoter in Y705+731F DMscAAV6 vectors was up to 5-fold higher than that from the B19p6 promoter in WT scAAV6 vectors, or from the HS2-βp promoter in Y705+731F DM-scAAV6 vectors (FIG. 40B).

Figure 41A:
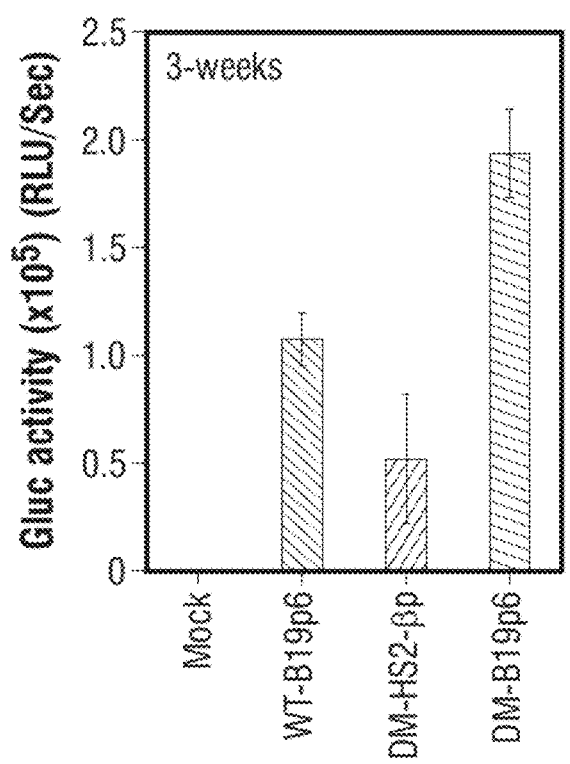
FIG. 41A and FIG. 41B show the relative levels of transgene expression from HS2-βp and B19p6 promoters in primary human CD34$^+$ cells following xenotransplantation in NSG mice. Approximately $1\times10^6$ primary human CD34$^+$ cells were either mock-infected, or infected with $2\times10^4$ vgs/cell of WT-scAAV6-B19p6-Gluc, Y705+731F DM-scAAV6-HS2-βbp-Gluc, or Y705+731F DM-scAAV6-B19p6-Gluc vectors under identical conditions, and engrafted into NSG mice as described in the following examples. Gluc activity was measured 3-weeks' (FIG. 41A) and 12-weeks' (FIG. 41B) postengraftment in peripheral blood using a luminometer. Total relative light units (RLU) per second were calculated, and results are presented as mean±s.d., with P<0.001 as calculated by Student's t-test.
Figure 41B:
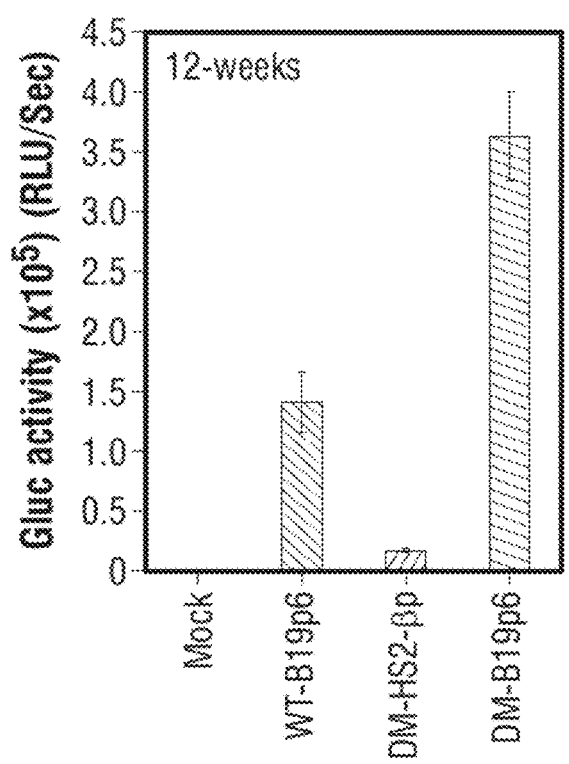

Since Gluc is secreted and it has very high tissue absorption, human CD34$^+$ cell engraftment in NSG mice and transgene expression levels were monitored in vivo both by Gluc activity in peripheral blood (3 weeks and 12 weeks post-transplantation). As seen in FIG. 41A, Gluc expression from the B19p6 promoter in the WT scAAV6 vectors was >2-fold higher than that from the HS2-βp promoter in the Y705+731F double-mutant scAAV6 vectors, and expression from the B19p6 promoter in the Y705+731F double-mutant scAAV6 vectors was ≈4-fold higher than that from the HS2-βp promoter in Y705+731F double-mutant scAAV6 vectors in peripheral blood in NSG mice 3 weeks post-transplantation (FIG. 41A). The extent of transgene expression was further increased from the B19p6 promoter 12 weeks post-transplantation (FIG. 41B).

Figure 42:
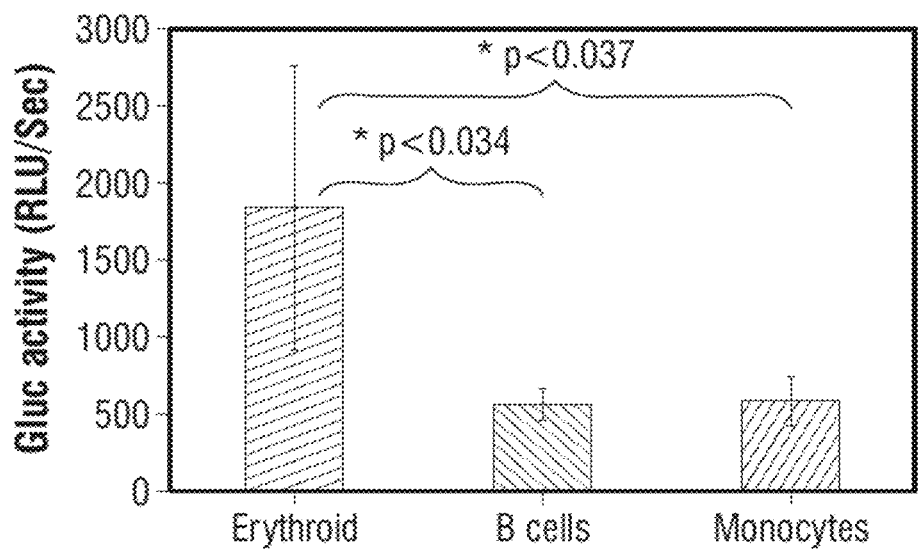
FIG. 42 shows the transgene expression in various human hematopoietic lineages 12-weeks post-transplantation of human CD34$^+$ cells in primary recipient NSG mice. Bone marrow cells were harvested, and human lineage-specific cells were sorted and Gluc activity in the sorted cell populations, was determined as described above. *p<0.034 (erythroid vs. B cells) and *p<0.037 (erythroid vs. monocytes)

To evaluate whether the observed transgene expression from the B19p6 promoter was restricted to human erythroid progenitor cells, whole bone marrow cells were harvested from primary recipient mice 12 weeks post-transplantation. Anti-human antibodies were used to sort for erythroid, B cells, and monocytes using lineage-specific antibodies as described. Gluc activity in the sorted cell populations was determined as described above. These results, shown in FIG. 42, suggest that transgene expression from the B19p6 promoter is largely restricted to human erythroid progenitor cells.

Figure 43:
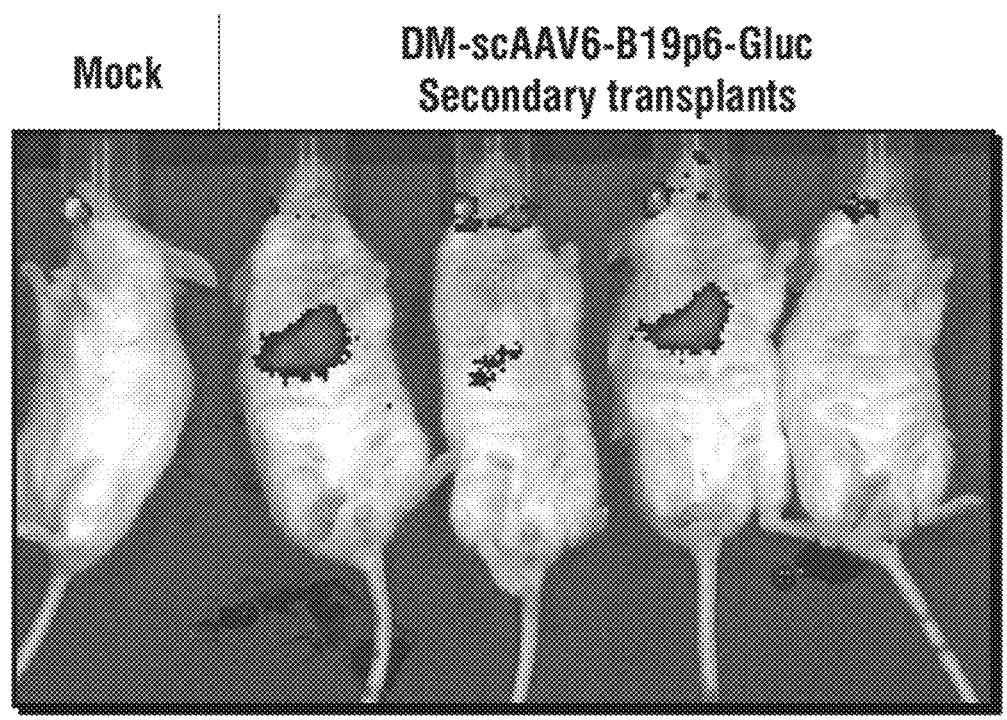
FIG. 43 shows the bioluminescence imaging of mice following secondary transplantation. Whole bone marrow cells from NSG mice transplanted with mock-infected, or DM scAAV6-B19p6-Gluc vector-infected primary human CD34$^+$ cells were harvested 12-weeks post-primary transplantation, and transplanted into secondary recipient mice. Six-weeks post secondary transplantation, mice were subjected to whole-body bioluminescence imaging in vivo as described above.

To further evaluate whether long-term repopulating human stem cells were transduced, whole bone marrow cells from a mouse transplanted with human CD34$^+$ cells transduced with DM-scAAV6-B19p6-Gluc vectors were isolated 12-weeks post-transplantation, and transplanted into secondary recipient mice (n=4). Whole-body bioluminescence imaging in vivo was performed 6-weeks post-secondary transplantation as described above. As can be seen in FIG. 43, transgene expression was observed in each animal, albeit at low levels, due to <1% engraftment of human cells. These results, nonetheless, document that DM scAAV6 vectors are capable of transducing long-term repopulating human stem cells.

Discussion

An ideal gene therapy vector for the potential gene therapy of βthalassemia and sickle cell disease would be one with which high-efficiency transduction of primitive human HSCs could be achieved, and following erythroid differentiation, robust levels of expression of the transduced human b-globin gene could be obtained. The development of lentiviral vectors by a number of investigators has indeed achieved these objectives, but their long-term safety as gene therapy vehicles remains an open question. The development of first-generation recombinant AAV2 vectors for the potential gene therapy of βthalassemia and sickle cell disease have been described elsewhere, but in retrospect, it has become clear that the use of the WT AAV2 capsid, and the single-stranded nature of the vector genome, were major obstacles to achieving therapeutic levels of the human β-globin gene. In addition, the use of murine models of these diseases was not predictive of the potential efficacy of a number of alternative serotypes of AAV vectors.

Based on more recent studies, in which AAV6 was identified to be the most efficient serotype for transducing human HSCs, and the observation that B19p6 is more robust than HS2-βp for mediating erythroid lineage-restricted expression, it was reasoned that combining these features might lead to the development of an ideal vector for the potential gene therapy of β-thalassemia and sickle cell disease, especially since the safety and efficacy of AAV vectors have now been established unequivocally in a number of Phase I/II clinical trials in humans. Indeed, the Y705+731F double-mutant scAAV6 vectors containing the B19p6, described here, were determined to be the most efficient in transducing primary human CD34$^+$ cells, and mediating erythroid lineage-restricted transgene expression, both in vitro and in vivo. It is also possible that the transduction efficiency of these vectors can be augmented further, based on our recent observations that site-directed mutagenesis of specific surface-exposed serine and threonine residues improves the transduction efficiency of AAV2 serotype vectors [35], and most of these residues are highly conserved in all AAV serotypes.

The basic underlying molecular mechanism of increased transduction efficiency of the Y705+731F double-mutant scAAV6 vectors in human CD34$^+$ cells is not readily apparent. Based on recent studies with tyrosine-mutant AAV2 and AAV3 serotype vectors, it appears that improved intracellular trafficking and/or nuclear transport lead to the observed effect. However, the alternative hypothesis that a more efficient cellular receptor-mediated viral vector entry also play a role, cannot be ruled out since the extent of transgene expression from the B19p6 promoter in human CD36$^+$ erythroid progenitor cells was –20-fold lower than the more primitive CD34$^+$ HSCs.

In this example, pre-treatment of CD34$^+$ cells with EGF had no effect on the transduction efficacy of AAV6 vectors, and K562 cells, which are known to lack expression of EGFR, could be efficiently transduced by AAV6 vectors, which were inhibited by FBS. Although erythroid lineage-restricted transgene expression from the B19p6 promoter in primary human HSCs in vitro has previously been reported, those studies were carried out with the first-generation, single-stranded AAV2 serotype vectors, which were clearly sub-optimal. scAAV1 and scAAV7 serotype vectors were subsequently used, and the erythroid cell-specificity of the B19p6 promoter in vivo was corroborated, those studies were carried out in murine HSCs, which were clearly not predictive for human HSCs. In this example, sustained transgene expression was observed in human HSCs, both in primary as well as in secondary transplant recipient mice.

However, because of less than 1% engraftment of human cells in secondary transplant recipients, it was not possible to document stable integration of the AAV proviral genomes. In this context, it is important to emphasize that the general conclusion that AAV genomes do not integrate, has largely been derived from previously published studies, all of which were carried out with post-mitotic cells and tissues, such as liver, muscle, brain, and retina, in which the AAV genomes remain episomal, although integration in liver has been reported by several investigators. In published studies with primary murine HSCs, stable integration of the AAV proviral genomes has been documented in both primary as well as secondary transplant recipient mice, and in a recently-published collaborative study, long-term transduction and multi-lineage engraftment has been reported of human HSCs in a mouse xenograft model.

Example 7—Optimizing Transduction Efficiency of Capsid-Modified AAV6 Serotype Vectors in Primary Human Hematopoietic Stem Cells Although recombinant adeno-associated virus serotype 2 (AAV2) vectors have gained attention because of their safety and efficacy in numerous phase I/II clinical trials, their transduction efficiency in hematopoietic stem cells (HSCs) has been reported to be low. Only a few additional AAV serotype vectors have been evaluated, and comparative analyses of their transduction efficiency in HSCs from different species have not been performed.

Transplantation of patient-derived, genetically modified autologous hematopoietic stem cells (HSCs) is the most promising alternative to date to allogeneic transplantation potentially to cure certain genetic diseases, such as β-thalassemia and sickle cell disease. In a more recent clinical trial, a recombinant lentiviral vector-mediated β-globin gene transfer in an adult patient with severe β-thalassemia led to transfusion independence. However, the observed therapeutic benefit was also accompanied by transcriptional activation of a cellular proto-oncogene, HMGA2, after lentiviral vector integration, leading to clonal expansion of myeloid cells. Alternatives to lentiviral vectors are needed. The safety and clinical efficacy of recombinant vectors based on a non-pathogenic human virus, adeno-associated virus 2 (AAV2), have attracted attention. However, there is much controversy with reference to the transduction efficiency of AAV2 vectors in human HSCs. For example, it has been previously reported that AAV2 vectors efficiently transduce human CD34 cells at relatively low multiplicities of infection, whereas some investigators have reported that successful transduction of human CD34 cells by AAV2 vectors requires exceedingly high ($>10^6$) multiplicities of infection. One group claimed that the alleged transduction of human CD34 cells by AAV2 vectors is due to contaminants.

In recent years, numerous additional AAV serotype vectors have become available, but only a few of these vectors have been evaluated for their ability to transduce human HSCs. It was reported that AAV3 vectors did not show any advantage over AAV2 vectors, and that AAV2 vectors transduce human cord blood CD34 cells more efficiently than AAV3 and AAV5 vectors. It was also previously documented that AAV6 was the most efficient serotype among AAV1 through AAV6 for human CD34 cells. However, all previous studies have been limited to in vitro conditions only. It was previously reported that AAV1 vectors mediate the highest levels of transgene expression among AAV1, AAV2, AAV4, AAV5, AAV7, AAV8 and AAV10 serotypes in murine HSCs in vivo. It has been documented that site-directed mutagenesis of surface-exposed tyrosine residues on AAV serotype capsids leads to higher transduction efficiency both in vitro and in vivo in various cell types.

In this example, the transduction efficiency of the 10 available AAV serotype vectors was systematically evaluated in primary HSCs from mice, cynomolgus monkeys and humans. It was shown that:

(i) AAV1 vectors transduced primary murine HSCs most efficiently;

(ii) none of the 10 AAV serotype vectors transduced cynomolgus monkey HSCs well in vitro;

(iii) AAV6 vectors were the most efficient in transducing primary human HSCs both in vitro and in a mouse xenograft model in vivo; and (iv) the transduction efficiency of AAV6 vectors was augmented further following site-directed mutagenesis of specific surface-exposed tyrosine residues both in vitro and in vivo. These results indicated that the optimized AAV6 vectors of the present invention are safe and effective alternatives to lentiviral vectors in HSC-based gene therapy in humans.

Methods

Plasmids. All AAV serotype vectors are encapsidated using the AAV2 inverted terminal repeats and rep sequences, and these plasmids are designated as pATGrep/cap or pACGrep/cap, in which ATG and ACG denote the start codon for Rep78/68 proteins. It was previously reported that mutation of the start codon of rep78/68 from ATG to ACG could up-regulate AAV packaging efficiency. pACG2/6 was constructed by replacing the fragment between XbaI and NcoI in pATG2/6 by the fragment between XbaI and NcoI in pACG2/2. pACG2/1-pACG2/6 were obtained from Dr. R. Jude Samulski, University of North Carolina, and pACG2/7 pACG2/10 were obtained from Dr. James M. Wilson, University of Pennsylvania). Y to F capsid mutants were generated with pACG2/6 using QuikChange II Site-Directed Mutagenesis Kit (Stratagene, La Jolla, Calif., USA). Polymerase chain reaction (PCR) was performed according to the manufacturer's instructions. All mutants were sequence-screened before use.

AAV vector production. Viral vectors were packaged using the protocol described above. Briefly, HEK 293 cells were cotransfected with three plasmids in the presence of polyethyleneimine (PEI, linear, molecular weight 25,000 Da; Polysciences, Inc.), and medium was replaced 4 hrs after transfection. Cells were harvested at 72 hrs after transfection, subjected to three rounds of freeze-thaw, digested with benzonase (Invitrogen, Inc.) and purified by iodixanol (Sigma-Aldrich Co.) gradient ultra-centrifugation followed by ion exchange chromatography using HiTrap SP HP for AAV2 and HiTrap Q HP for all other serotypes (GE Healthcare) or purified through two rounds of cesium chloride gradient centrifugation. Titers were determined by quantitative DNA slot blot using $^{32}$P-labeled specific DNA probes as previously described or titered using a Taqman quantitative PCR assay.

Mice. Four-month-old male C57BL/6 mice were purchased from the Jackson Laboratory (Bar Harbor, Me., USA), and maintained in a suitable animal care facility. For xenotransplantation, 6- to 8-week-old male NOD.CB17-Prkdc$^{scid}$/NcrCrl (NOD/SCID) mice were maintained in a specific pathogen-free facility. All experimental protocols involving animals were approved Institutional Animal Care and Use Committee guidelines.

Cell isolation and culture. Human embryonic kidney 293 (HEK293) and human erythroleukemia K562 cells were obtained from the American Type Culture Collection, and maintained in Dulbecco's modified Eagle's medium (DMEM; Lonza, Inc.), or Iscove's modified Dulbecco's medium (IMDM; Irvine Scientific, Santa Ana, Calif., USA) supplemented with 10% fetal bovine serum (FBS; Sigma- Aldrich Co.), 100 µg/mL penicillin and 100 U/mL streptomycin (Invitrogen, Inc.) at 37° C.

Human bone marrow CD34+ and umbilical cord blood CD34+ cells either was purchased from All-Cells (Berkeley, Calif., USA), or were obtained under an institutional review board-approved protocol, and maintained in either StemSpan SFEM medium (STEMCELL Technologies, Inc, Vancouver, BC, CANADA) or IMDM with 10 ng/mL rhIL6 (PeproTech), 10 ng/mL rhIL3 (PeproTech, Rocky Hill, N.J., USA) and 1 ng/mL rhSCF (R&D Systems, Minneapolis, Minn., USA). CD34+ cell purity was determined by flow cytometry and was >90%. Mouse HSCs, which were positive for Sca-1 and c-kit and negative for lineage markers (c-kit+, Sca-1+, lin−), were isolated from 4-month-old male C57BL/6 mice as previously reported with slight modification. Briefly, femurs and tibias were obtained from C57BL/6 mice, and bone marrow cells were flushed from the bones with phosphate-buffered saline (PBS). The lineage-negative cells were isolated by immunomagnetic separation using Lineage Cell Detection Cocktail (Miltenyi Biotec, Inc, Auburn, Calif., USA). APC-conjugated CD117 (c-kit) antibody and Alexa Fluor 700 conjugated Sca-1 antibody (Miltenyi Biotec Inc) were used during fluorescence-activated cell sorting (FACS). Mouse c-kit+, Sca-1+ and lin− cells were maintained and infected in IMDM in the presence of 10 ng/mL of mIL6, 10 ng/mL of mIL3 and 1 ng/mL of mSCF. Cynomolgus monkey (*Macaca fascicularis*) CD34+ cells were isolated from bone marrow from four monkeys according to established immunoselection protocols and cryopreserved using a controlled rate cryopreservation protocol in aliquots before use. Cells were recovered and maintained in IMDM in the presence of 10% FBS, 10 ng/mL rhIL6, 10 ng/mL rhIL3 and 1 ng/mL rhSCF for 4 hrs before infection.

Visualization of AAV vectors localization using confocal microscopy. The method used to label AAV vectors with cyanine 3 (Cy3; Amersham Life Sciences, Pittsburgh, Pa., USA) was modified from a previously published protocol. Briefly, purified vectors were concentrated with Microcon YM-100 Centrifugal Filter unit (Millipore, Billerica, Mass., USA), and the dye in sodium carbonate solution (pH 9.3, final concentration 0.1 mol/L) was added. After incubating for 1.5 h at room temperature with gentle shaking, the vector-dye mixture was dialyzed with 20K MWCO Slide-A-Lyzer® Dialysis Cassettes (ThermoFisher) in PBS overnight to remove the unconjugated dye. Vectors were collected and titered before use. Because cord blood CD34+ cells are suspension cells, to minimize the loss of cells during the procedure, poly-L-lysine (Sigma-Aldrich Co.) was used to coat the acid-washed coverslips and slides to provide stable adhesion. Cells were seeded in poly-L-lysine treated coverslips in 24-well plates the day before infection and then infected at $2 \times 10^4$ vector genomes (vgs)/cell for the indicated time length. The medium was removed, and cells were washed with PBS and fixed with 4% paraformaldehyde (USB Corp, Cleveland, Ohio, USA) for 8 min at room temperature. Coverslips with cells attached were transferred to slides and mounted with ProLong Gold antifade reagent with DAPI (Invitrogen, Inc.). Images were acquired by confocal microscopy (Leica TCS SP5; Leica Microsystems GmbH, Wetzlar, Germany) using oil immersed ×63 objective lens.

Ex vivo transduction of HSCs. Frozen human cord blood CD34+ cells were recovered and seeded in 96-well or 12-well plates (BD Biosciences) with either StemSpan SFEM or complete IMDM containing 10 ng/mL rhIL6, 10 ng/mL rhIL3 and 1 ng/mL rhSCF for 2 hrs before infection to allow the cells to recover. Human CD34+ cells were infected in the same medium unless otherwise specified. Different transduction conditions were compared in some experiments. To evaluate the effect of FBS, equivalent numbers of CD34+ cells from same lots were transduced either in the absence of or in the presence of 10% FBS in IMDM. To determine the influence of the duration of infection, cells were infected either for 2 hrs or for 16 hrs. To examine the impact of different combinations of cytokines, equivalent numbers of CD34+ cells were transduced either under condition 1, IMDM containing 10 ng/mL rhFlt3, 10 ng/mL rhTPO and 1 ng/mL rhSCF, or condition 2, IMDM containing 10 ng/mL rhIL6, 10 ng/mL rhIL3 and 1 ng/mL rhSCF. Cynomolgus monkey CD34+ cells were infected in the presence of 10 ng/mL rhIL6, 10 ng/mL rhIL3 and 1 ng/mL rhSCF. Mouse stem cells were infected in the presence of 10 ng/mL mIL6, 10 ng/mL mIL3 and 1 ng/mL mSCF. Cells were infected at various viral particles-to-cell ratios at 37° C. for 2 hrs or 16 hrs. Mock-infected or infected cells were infused into recipient mice immediately after infection, or examined for transgene expression by fluorescence microscopy or by flow cytometry (Accuri C6; BD Biosciences) 48-72 hrs after infection.

Xenotransplantation. All experiments were performed under protocols approved by the City of Hope Institutional Animal Care and Use Committee. Transplantations were performed as previously described. Briefly, 6- to 8-week-old male NOD.CB17-Prkdc$^{scid}$/NCrCrl (NOD/SCID) mice (Charles River, Wilmington, Mass., USA) were maintained in a specific pathogen-free facility at the Animal Resources Center, City of Hope Medical Center, and placed on sulfamethoxazole and trimethoprim oral pediatric antibiotic (Hi-Tech Pharmacal Co, Inc, Amityville, N.Y., USA) (10 mL/500 mL $H_2O$) for at least 48 hrs before transplant. Mice were sub-lethally irradiated with 350 cGy from a $^{137}Cs$ source and allowed to recover for a minimum of 4 hrs before transplantation. Approximately $10^6$ CD34+ cells were infused in the tail vein in a volume of 200 µL. Femoral marrow and the spleen were harvested for analysis from each mouse at 16-22 weeks after transplantation. Each group consisted of three to 10 mice.

In vivo imaging. Luciferase expression in xeno-transplanted mice was measured by serial bi-weekly bioluminescent imaging using a Xenogen In Vivo Imaging System (Caliper Life Sciences, Inc.) starting 4 weeks after transplantation as described previously. Briefly, mice were anesthetized with oxygen containing 4% isoflurane (Phoenix Pharmaceuticals, St. Joseph, Mo., USA) for induction and 2.5% for maintenance. Luciferin (Caliper Life Sciences, Inc) was injected intraperitoneally at a dose of 0.15 mg/g of mouse weight. Photons were accumulated over a 5-min exposure from the ventral aspect 10 min after injection. Living Image 3.0 software (Caliper Life Sciences, Inc.) was used to calculate light emission.

Flow cytometry analysis. In vitro expression was analyzed 22 hrs after rAAV transduction. Cells were washed with PBS containing 5% fetal calf serum, 0.1% sodium azide (Mediatech, Manassas, Va., USA) solution before analysis using a Cyan ADP Flow Cytometer (Dako, Glostrup, Denmark). Engraftment of human cells in bone marrow and spleen of xenografted mice was analyzed as described previously. Lineage distribution was assessed in bone marrow and spleen cell suspensions after staining with human specific FITC-conjugated anti-CD45 (Becton Dickinson, Mountain View, Calif., USA).

rAAV frequency detection. The rAAV genome frequencies were detected in marrow cells of transplant recipients by quantitative real-time PCR with vector-specific primers and probes using a 7900HT Sequence Detection System (Applied Biosystems, Foster City, Calif., USA). The single-copy human gene ApoB served to quantitate human cell equivalents and as a template integrity control.

Results and Discussion

Figure 44A:
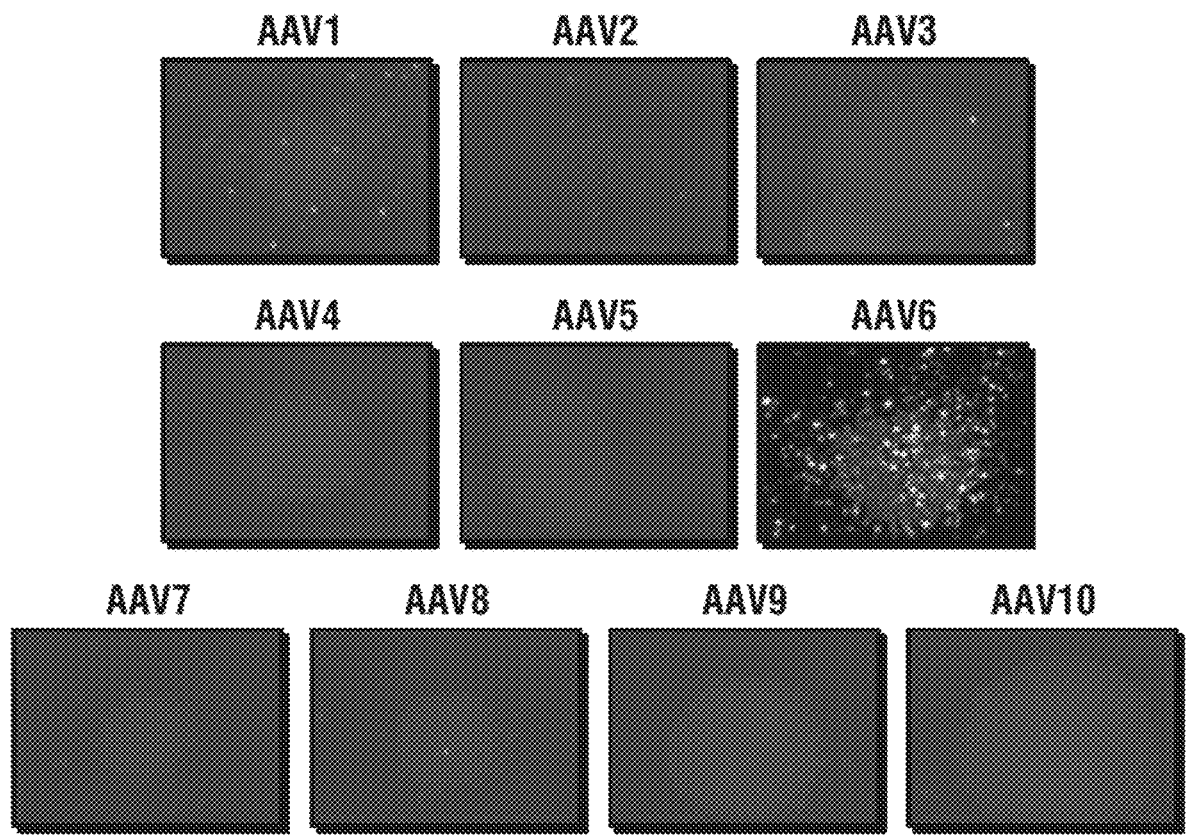
FIG. 44A and FIG. 44B show comparative analyses of the transduction efficiencies of scAAV1 through AAV10 serotype vectors in primary human CD34$^b$ cells. Equivalent numbers of cells from a single donor were infected with scAAV serotype vectors at $2\times10^4$ vgs/cell under identical culture conditions in IMDM containing 10% FBS, 10 ng/mL of hIL6, 10 ng/mL of hIL3 and 1 ng/mL of rhSCF for 16 hrs. Transgene expression was evaluated 48 hrs after transduction by fluorescence microscopy (FIG. 44A), and the data were quantitated by flow cytometry (FIG. 44B)
Figure 44B:
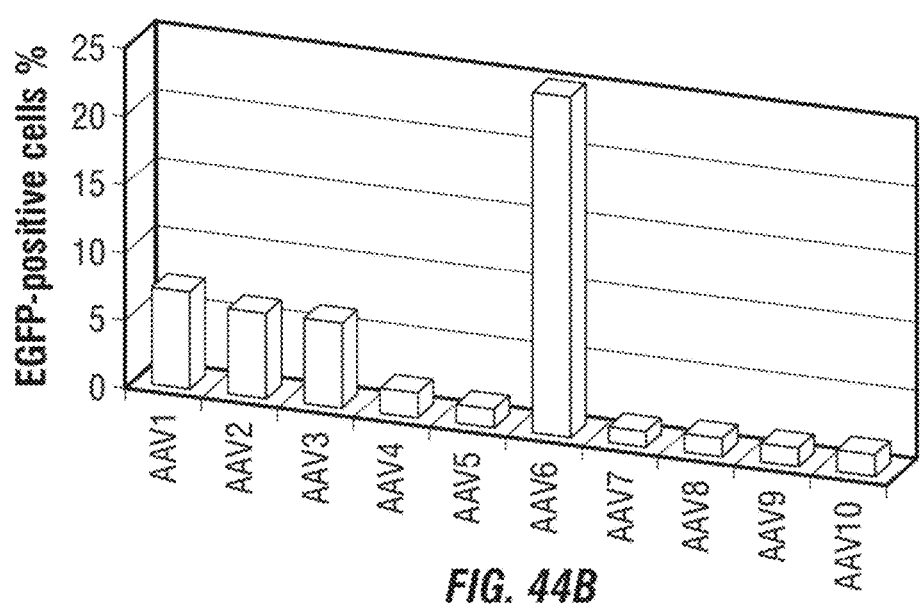

Transduction efficiency of different AAV serotype vectors in murine, monkey and human HSCs in vitro. It has been previously reported that the transduction efficiency of conventional single-stranded AAV vectors in murine and human HSCs is negatively affected owing to the rate-limiting step of viral second-strand DNA synthesis. In this example, the transduction efficiency of the 10 serotypes was evaluated using self-complementary (sc) AAV vectors containing the enhanced green fluorescent protein (EGFP) reporter gene driven by the chicken β-actin promoter (CBAp). Primary murine Sca-1$^+$, c-kit$^+$, lin$^-$ cells (>80% purity, >95% viability) from C57BL/6 mice, CD34$^+$ cells from blood of cynomolgus monkeys (approximately 90% purity, approximately 90% viability) and CD34$^+$ cells from human umbilical cord blood or bone marrow (approximately 94% purity, approximately 98% viability) were either mock-transduced or transduced with scAAV-CBAp-EGFP serotype vectors. Transgene expression was analyzed 48-72 hrs after infection by fluorescence microscopy and FACScan analyses. The results from a representative experiment with human CD34$^+$ cells are shown in FIG. 44A and FIG. 44B. Although the transduction efficiency was low, AAV1 serotype vectors were the most efficient in mediating transgene expression in murine HSCs. AAV6 differs from AAV1 in only six amino acids, but AAV6 vectors failed to transduce murine HSCs in vitro.

Similarly, AAV2 vectors transduced CD34 cells from cynomolgus monkeys at low levels comparable to levels reported for rhesus monkeys, and tyrosine mutations did not significantly enhance the transduction efficiency of scAAV6 vectors in these cells. Of the 10 serotypes evaluated, AAV6 vectors transduced human CD34 cells most efficiently. The lack of enhanced functional transgene expression in mouse or cynomolgus monkey HSCs, compared with human CD34 cells, suggests species-specific differences. Because differences in the transduction efficiency of scAAV6 vectors with different donor cells were evident, all subsequent studies were carried out with scAAV6 serotype vectors and human CD34$^+$ cells as follows.

Figure 45A:
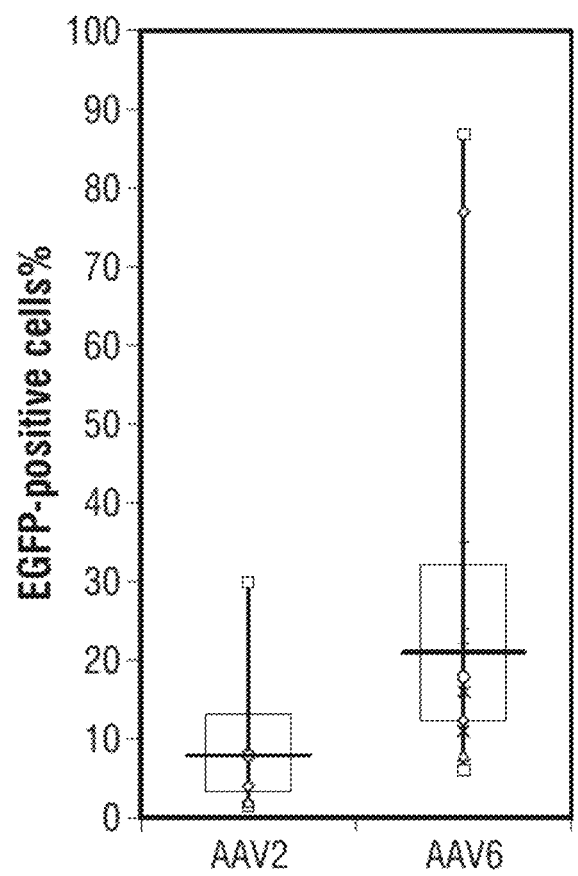
FIG. 45A, FIG. 45B, and FIG. 45C show the comparative analyses of the transduction efficiencies of scAAV2 and AAV6 serotype vectors in primary human CD34 cells from multiple donors.
Figure 45B:
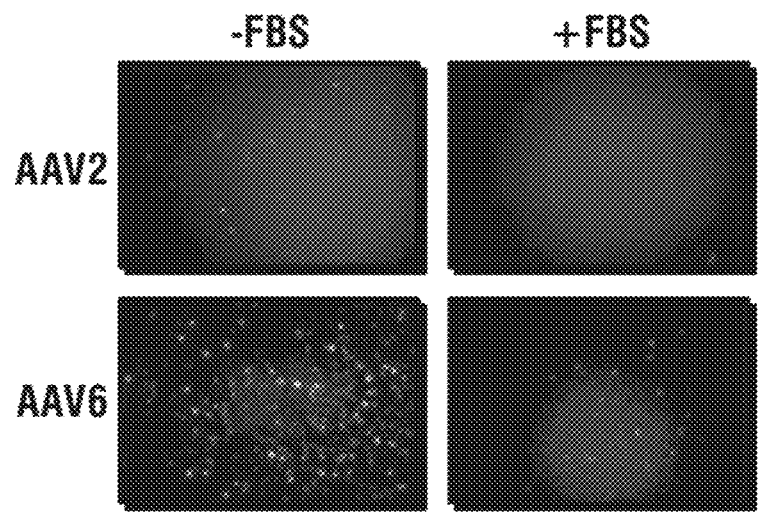
Figure 45C:
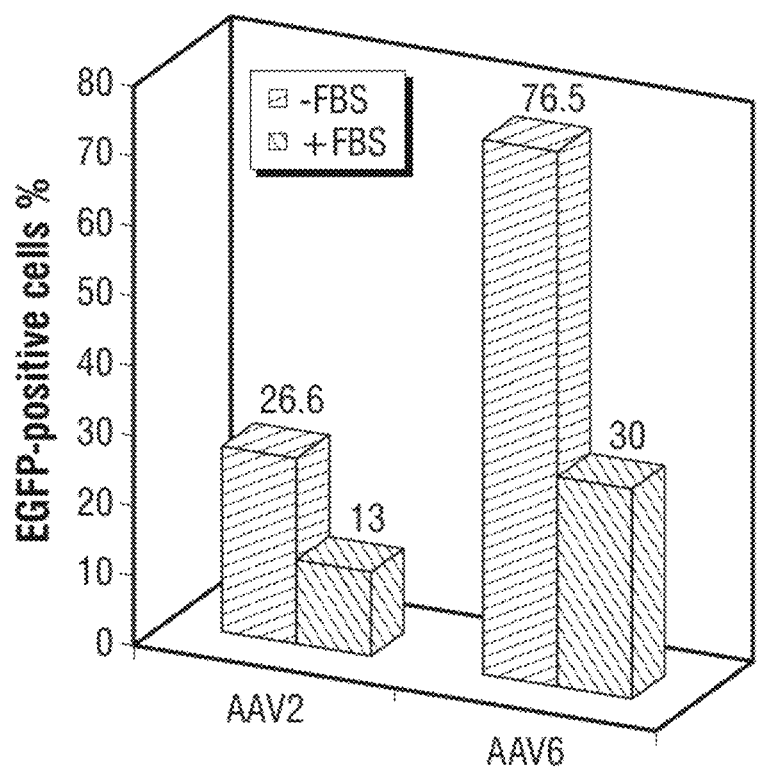
Figure 46A:
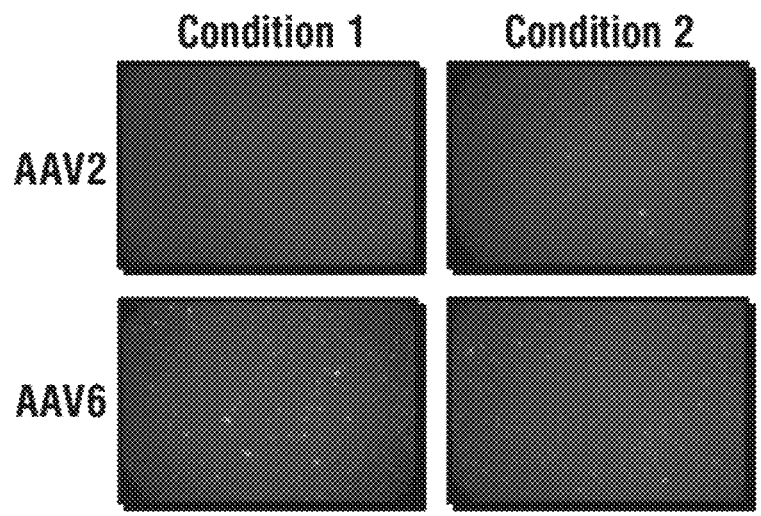
FIG. 46A, FIG. 46B, and FIG. 46C show the transduction efficiencies of scAAV2 and AAV6 serotype vectors in primary human CD34$^b$ cells under different culture conditions.
Figure 46B:
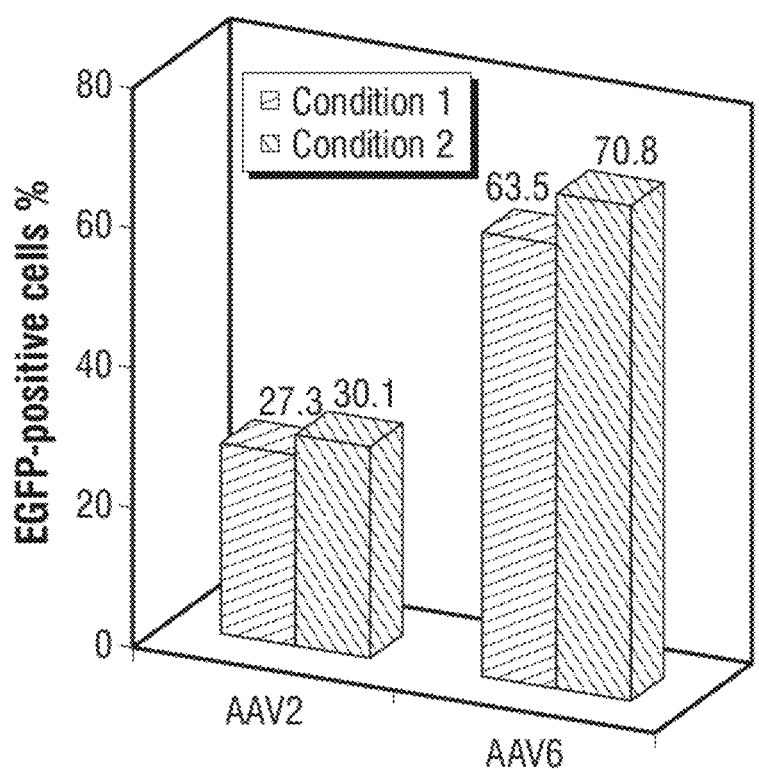
Figure 46C:
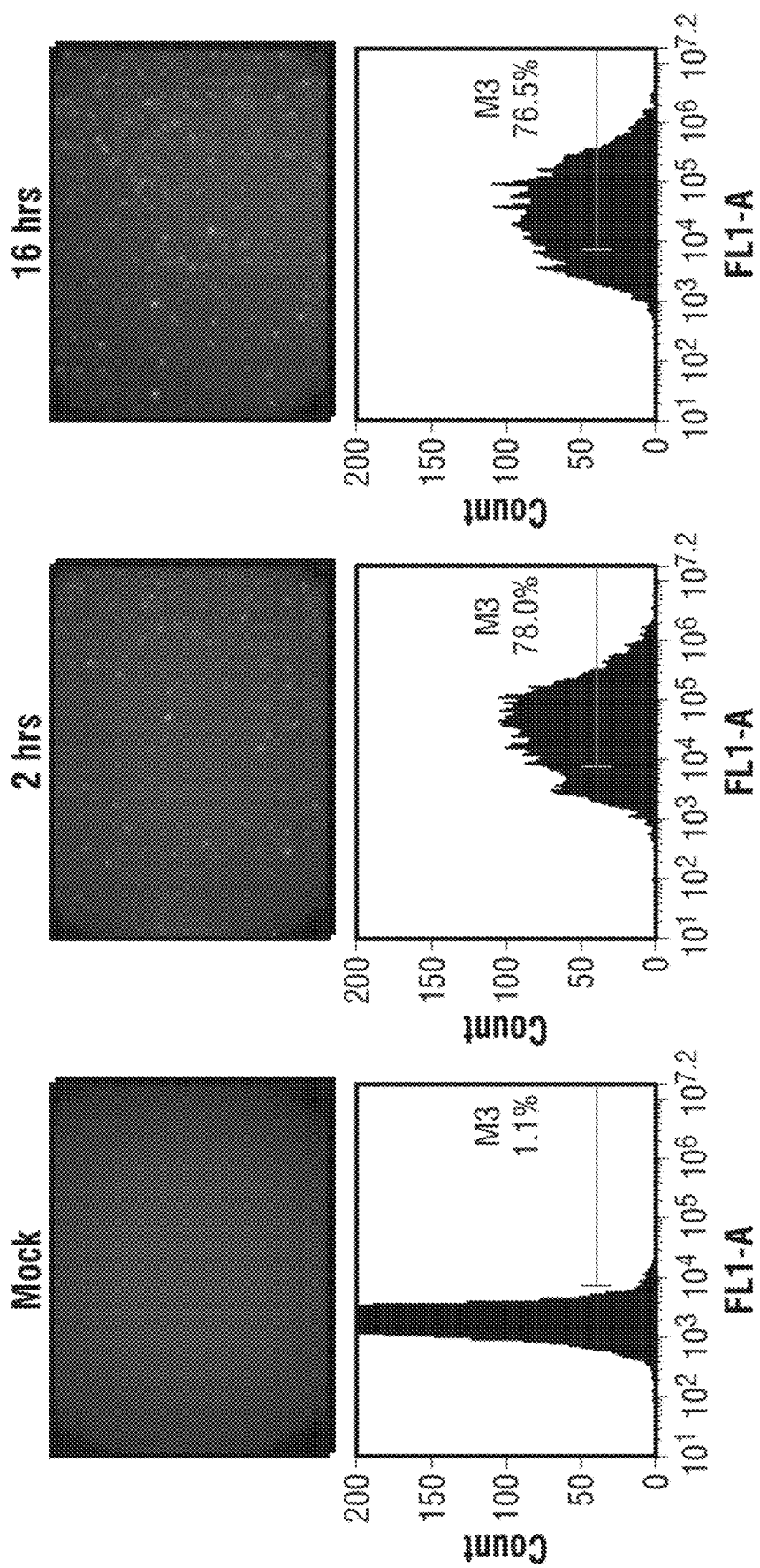

Transduction efficiency of scAAV6 vectors in human CD34$^+$ cells: Effects of donor variation and culture conditions in vitro. A significant donor variation in the transduction efficiency of ssAAV2 vectors in primary human bone marrow-derived CD34$^+$ cells has been previously reported. During the course of this study, a similar donor variation was observed in the transduction efficiency of scAAV6 in human cord blood-derived CD34$^+$ cells. These results are shown in FIG. 45A. Although the transgene expression mediated by scAAV2 vectors ranged from 2-30%, the percentage of EGFP-positive cells transduced by scAAV6 vectors ranged from 6-87% of cells from several different donors (n=11). No significant variation in the transduction efficiency was observed in K562 cells using the same viral vector stocks, and when CD34 cells from pooled cord blood from 10-15 donors were used, there was less variation than observed in CD34$^+$ from a single donor. The results of transduction experiments performed under numerous conditions are shown in FIG. 45B, FIG. 45C and FIG. 46A-FIG. 46D. Although it is possible the observed variation is due to factors such as the use of cryopreserved versus freshly isolated cells and the purity of the different CD34$^+$ cell populations, these data suggest that similar to AAV2 vectors, the wide range of transduction efficiencies of AAV6 vectors is due to differential levels of expression of the putative receptor/co-receptor on these cells.

Figure 47A:
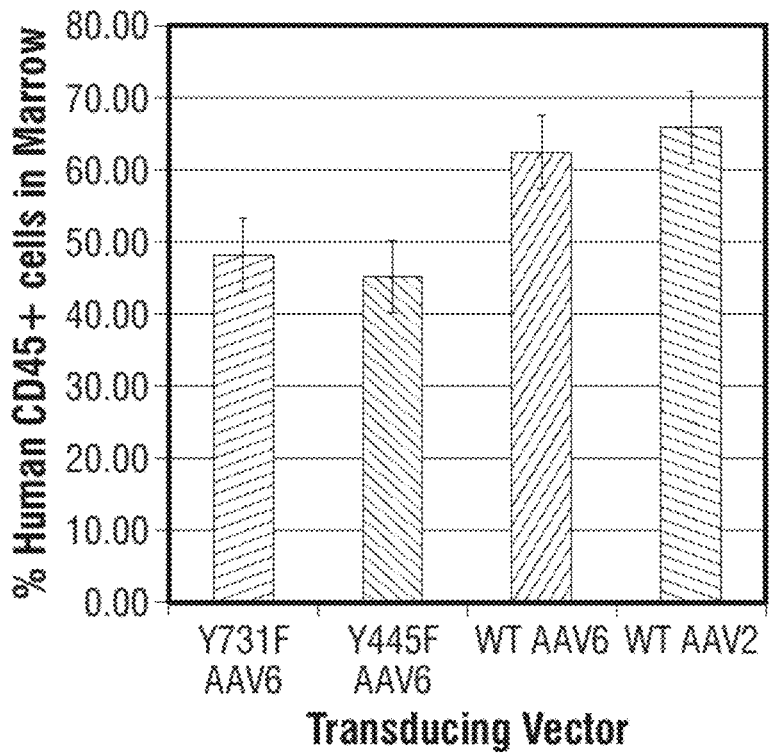
FIG. 47A and FIG. 47B show the engraftment of human cells in the marrow (FIG. 47A) and spleen (FIG. 47B) of NOD/SCID mice. Mononuclear cells from the marrow and spleen of transplant recipients were analyzed for human CD45 expression at the time of harvest 16-22 weeks after transplantation. The presence of human CD45$^b$ cells indicates human cell engraftment.
Figure 47B:
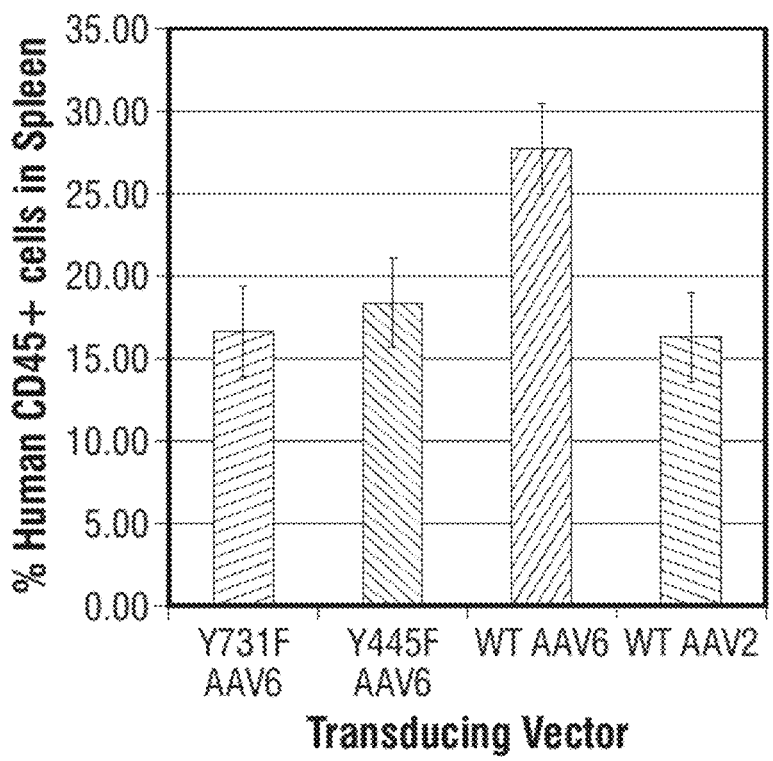

Although epidermal growth factor receptor (EGFR) was identified recently to be the cellular receptor for AAV6, in this study, pre-treatment of CD34$^+$ cells with epidermal growth factor had no effect on the transduction efficiency of AAV6 vectors, and K562 cells, which are known to lack expression of EGFR, could be efficiently transduced by AAV6 vectors (data not shown). More recently, Denard et al. reported that galectin-3-binding protein in human sera agglutinates AAV6 vectors, which results in decreased transduction efficiency of these vectors. Significant inhibition in AAV6 vector-mediated transgene expression was observed in the presence of serum (FIG. 47B and FIG. 47C). The identity of the putative receptor for AAV6 vectors in human CD34$^+$ cells remains elusive, and additional studies are warranted. In related studies, treating K562 cells with Proteinase K (Sigma-Aldrich Co.) was shown to dramatically decrease AAV6 vector-mediated transduction, but no significant change was observed after treatment with phospholipase A2. The implication is that AAV6 uses a protein rather than a lipid on K562 cells for binding and entry into these cells. In addition, because AAV6 is known to have evolved from recombination between AAV1 and AAV2, and because AAV2 uses heparan sulfateproteoglycan (HSPG) as the primary cellular receptor, the level of HSPG expression on K562 cells surface was examined by FACS. Although abundant expression of HSPG on K562 cells was observed, AAV6 infection could not be inhibited by heparin, suggesting either AAV6 does not use HSPG as a receptor, or HSPG is not the only receptor for AAV6. The effect of inhibitors of O-linked and N-linked glycosylation was also evaluated on the transduction efficiency of AAV6 vectors in K562 cells. Although the O-glycan inhibitors did not significantly reduce the transduction efficiency, the treatment of cells with tunicamycin (Sigma-Aldrich Co.) for 24 hrs, which blocks the synthesis of all N-linked glycoproteins on the cell surface, markedly reduced the transduction efficiency.

Efficient entry of scAAV6 vectors in human CD34$^+$ cells. To examine whether the ability to enter human CD34$^+$ cells was the primary reason for the observed efficient transduction of these cells by AAV6 serotype vectors, scAAV1, scAAV2, scAAV3, scAAV6 and scAAV9 serotype vectors were labeled with the fluorescent dye, Cy3, and incubated with CD34$^+$ cells as described previously. Typical images at 0.5 mm were captured, and Cy3-positive cells were enumerated under a confocal microscope from 100 cells. In AAV1 and AAV9 vector groups, <10% of Cy3-positive cells were observed, and the percentages of Cy3-positive cells ranged from 8-12% in AAV2 and AAV3 vector groups. Approximately 60% of CD34$^+$ cells transduced with AAV6 vectors were Cy3-positive. These data suggest that AAV6 vectors enter human CD34$^+$ cells significantly more efficiently than other AAV serotypes. Most of the Cy3-labeled AAV6 vectors accumulated in the perinuclear region 2 hrs after infection, and a fraction entered the nucleus by 24 hrs, consistent with findings with AAV2 serotype vectors. Inefficient translocation of AAV6 vectors into nuclei might be an additional rate-limiting step for optimal transduction of HSCs by these vectors. In some cells, the signal from Cy3 was observed in the nuclei. Because Cy3 was conjugated with the capsid, the appearance of Cy3 in the nuclei implies that the failure of a fraction of the vectors to undergo uncoating might be an additional rate-limiting step for transgene expression in HSCs mediated by AAV6 vectors.

Enhanced transduction by tyrosine-mutant AAV6 vectors in human CD34$^+$ cells in vitro. Mutations of the seven surface-exposed tyrosine residues in AAV2 capsids facilitate viral nuclear transport by limiting proteasome-mediated degradation, leading to high-efficiency transduction. Because six of seven of these tyrosine residues are highly conserved in AAV6, point mutations were generated in each of the six tyrosine residues (Y252F, Y273F, Y445F, Y701F, Y705F, Y731F) using specific primer pairs. scAAV6-CBAp-EGFP vectors containing the wild-type (WT) and each one of the six tyrosine-mutant vectors were evaluated for their transduction potential in primary human CD34$^+$ cells at $5 \times 10^3$ vgs/cell. The transduction efficiency of two of the tyrosine-mutant vectors (705F>Y731F) was significantly higher compared with the WT scAAV6 vectors.

The transduction efficiency of WT and tyrosine-mutant ssAAV6 vectors was evaluated using a different reporter gene, mCherry. WT and two tyrosine-mutant ssAAV6-CBAp-mCherry vectors (Y445F and Y731F) were used to transduce human CD34$^+$ cells at either $2 \times 10^4$ vgs/cell or $5 \times 10^4$ vgs/cell, and transgene expression was evaluated at 46 hrs after transduction. The WT ssAAV6 and AAV2 vectors were inefficient in mediating transgene expression; however, the transduction efficiency of two of the tyrosine-mutant vectors was shown to range from 24-58%.

Enhanced in vivo transduction mediated by tyrosine-mutant ssAAV6 vectors in immune-deficient mice xeno-transplanted with human CD34$^+$ cells. The ability of WT and two tyrosine-mutant ssAAV6 vectors to transduce long-term in vivo engrafting human cord blood stem cells was evaluated in a humanized NOD-SCID xenograft mouse model. The vectors encoded the firefly luciferase (Luc) gene under the control of the CBAp in a single-stranded AAV2 genome. Cord blood CD34$^+$ cells transduced with WT and mutant AAV6 vectors all supported long-term engraftment and hematopoiesis. In vivo transgene expression measured by real-time bioluminescent imaging revealed that CD34$^+$ cells transduced with Y731F-ssAAV6 vectors supported the highest level of long-term in vivo transduction, up to 22 weeks, the end of the experiment. Y445F-ssAAV6 vectors appeared to be less efficient in supporting in vivo transduction than the WT ssAAV6 vectors. Comparison with the standard ssAAV2 vectors revealed that both WT and mutant ssAAV6 vectors were more efficient in supporting long-term in vivo transduction.

Analysis of the CD45$^+$ human cell populations in the marrow of xeno-transplanted mice at the time of harvest at 18-22 weeks after transplantation revealed that 45-63% of cells were of human origin indicating successful long-term engraftment and a lack of toxicity of AAV transduction. In addition, 16-28% of spleen cells were found to be of human origin, consistent with trafficking or seeding (or both) of the input human CD34$^+$ cells and their progeny.

To estimate the long-term persistence of vector genomes in the marrow, the frequency of the ssAAV-Luc genome relative to a single-copy cellular gene ApoB in high-molecular-weight marrow DNA was evaluated using a quantitative Taqman real-time PCR assay at the time of harvest of xeno-transplant recipients. The average frequency of Y731F-AAV6 and Y445F-AAV6 vectors was found to be higher than the frequency of WT AAV6 vectors. These results collectively indicated that human CD34$^+$ cells transduced with WT AAV6 and Y-F mutant AAV6 vectors were capable of supporting long-term engraftment and hematopoiesis in vivo with no associated toxicity. The relative persistence of rAAV genomes in the marrow of transplant recipients at 16-22 weeks after transplantation indicate that these vectors are capable of mediating stable transduction of long-term in vivo engrafting stem cells.

Site-directed mutagenesis of specific surface-exposed serine and threonine residues on AAV2 capsid increases the transduction efficiency of these vectors. In conclusion, these results have identified that of the 10 AAV serotype vectors currently available, AAV6 is the most efficient in transducing primary human HSCs, both in vitro and in a murine xenograft model in vivo. Additional capsid modifications (to even further increase the transduction efficiency) have significant implication in the adaptation of these vectors for use in human gene therapy of diseases involving the hematopoietic system.

Example 8—Reprogramming Adipose Tissue-Derived Mesenchymal Stem Cells into Pluripotent Stem Cells by a Mutant Adeno-Associated Viral Vector Stem cells and induced pluripotent stem (iPS) cells hold great promise for regenerative medicine or cell-based therapy. Personalized or disease-specific iPS cells can be used for pathogenesis studies, drug screening, and gene corrections (Stadtfeld and Hochedlinger, 2010). Mouse and human iPS cells have been established by transient overexpression of certain transcription factors (i.e., Oct4, Sox2, Klf4, and c-Myc), using various gene delivery vectors, including retrovirus, lentivirus, adenovirus, adeno-associated virus, Sendai virus, plasmid, and nonviral minicircle (Takahashi and Yamanaka, 2006; Takahashi et al., 2007; Okita et al., 2008; Fusaki et al., 2009; Sommer et al., 2009; Zhou and Freed, 2009; Jia et al., 2010; Weltner et al., 2012b). Non-DNA-based methods have also been developed to increase the safety of iPS cells for clinical application, but these have shown lower reprogramming efficiency (Zhou et al., 2009; Cho et al., 2010; Warren et al., 2010). One of the potential problems with the DNA-based reprogramming method is the use of oncogenic transcription factor, c-Myc, to generate iPS cells. Studies have shown that tumor-associated death occurred in chimeras derived from iPS cells with c-Myc, and that mice derived from iPS cells that have not been transduced with c-Myc showed a significantly reduced incidence of tumorigenicity (Nakagawa et al., 2008), suggesting the reactivation of the c-myc transgene may result in tumor formation (Okita et al., 2007). These findings raise serious concern about the safety of iPS cells in clinical applications. Therefore, to make iPS cells safer for cell therapy, the elimination of c-Myc in cell reprogramming is highly recommended.

Adeno-associated virus (AAV) is a nonpathogenic parvovirus that has never been associated with any human diseases (Daya and Berns, 2008). Recombinant AAV (rAAV) vectors have been used extensively in gene therapy as a gene delivery tool and have been proven to be safe (Grieger and Samulski, 2012). Compared with other virus-based delivery methods, such as retrovirus, lentivirus, and adenovirus, rAAV carries no viral gene and has less immunogenicity toward transduced cells and human subjects (Daya and Berns, 2008). Studies on cell reprogramming kinetics demonstrate that transgene expression should be maintained for at least 12 days to obtain fully reprogrammed iPS cells (Brambrink et al., 2008). Previous studies showed that rAAV-mediated transgene expression could be sustained for several weeks in nondividing cells (Song et al., 1998, 2001a). In addition, triple tyrosine mutant AAV2 vectors (Y444+500+730F) showed high infection efficiency toward primary murine bone marrow-derived mesenchymal stem cells (BM-MSCs) and fibroblasts (Li et al., 2010). These features make the tyrosine mutant rAAV vector a good candidate to generate safer iPS cells.

Various cell types, including skin fibroblasts, keratinocytes, neural stem cells, CD34+ cord blood cells, bone marrow mononuclear cells (BM-MNCs), and adipose tissue-derived mesenchymal stem cells (AT-MSCs), have been tested and evaluated for cell reprogramming (Takahashi and Yamanaka, 2006; Kim et al., 2009; Sun et al., 2009; Aasen and Belmonte, 2010; Kunisato et al., 2010; Takenaka et al., 2010). Compared with other cell types, AT-MSCs have been shown to be compatible with embryonic stem (ES) cell culture medium and used as feeder layers for ES cell growth. In addition, obtaining AT-MSCs is relatively less invasive and easy. Further, AT-MSCs, compared with IMR90 fibroblasts, showed an approximately 20-fold increase in reprogramming efficiency using four reprogramming factors (Sun et al., 2009). These observations indicate that AT-MSCs may be a suitable starting cell type in developing novel cellular reprogramming methods. Taken together, the aim of the present study was to test the feasibility of using triple tyrosine mutant AAV2 vectors (Y444F+Y500F+Y730F), designated AAV2.3 m, to generate iPS cells from mouse adipose tissue-derived mesenchymal stem cells in the absence of c-Myc.

Materials and Methods

Construction of pTR-AAV-CMV-mKOS vector. An rAAV vector has been designed that can polycistronically express three mouse transcription factors (Klf4, Oct4, and Sox2), using the cytomegalovirus (CMV) promoter. The fragment, consisting of c-Myc-F2A-Klf4-T2A-Oct4-E2A-Sox2 (MKOS), was removed from plasmid pCAG2LMKOSimO (Addgene, Cambridge, Mass.) by restriction enzyme digestion, using BsaBI. Then, this MKOS fragment was digested with DraI and XbaI, and directly cloned into the HincII- and XbaIdigested pTR-CMV-AAT vector backbone. The resulting vector (pTR-CMV-c-Myc-F2A-Klf4-T2A-Oct4-E2A-Sox2) was further digested with XbaI and BstBI to remove the c-Myc coding sequences, followed by a fill-in reaction with Klenow fragment to generate the plasmid pTR-AAV-CMV-Klf4-T2AOct4-E2A-Sox2 (pAAV-CMV-mKOS). In this vector, the reprogramming cassette is flanked by inverted terminal repeat (ITR) sites and therefore can be packaged into the rAAV vector. To generate iPS cells from AT-MSCs, the vector was packaged into a triple tyrosine mutant AAV2 capsid (Y730+500+444F) and designated it rAAV2.3 m-CMVmKOS.

Mouse AT-MSC isolation and feeder cell preparation. For a primary culture of AT-MSCs, a stromal vascular fraction (SVF) was freshly isolated from white adipose tissue of a human PiZ-hAAT transgenic mouse and a C57BL/6 mouse (6-8 weeks old). Adipose tissue was first enzymatically digested with 0.075% type I collagenase (Sigma-Aldrich Co.) in phosphate-buffered saline (PBS) for 1 hr at 37° C. with gentle agitation. The collagenase was then inactivated with an equal volume of Dulbecco's modified Eagle's medium (DMEM) supplemented with 10% fetal bovine serum (FBS), and the suspension was centrifuged at 1000×g for 5 min at room temperature. The resulting cell pellet was resuspended in 160 mM $NH_4Cl$, incubated at room temperature for 2 min to eliminate contaminating red blood cells, and filtered through a 100-μm nylon mesh strainer to remove debris. The resulting AT-MSC-containing cell pellet was collected by centrifugation as described previously, resuspended in DMEM-10% FBS medium, and plated on plastic tissue culture dishes. Adherent cells were cultured in DMEM-10% FBS medium supplemented with basic fibroblast growth factor (bFGF, 5 ng/mL) under hypoxic conditions (5% $O_2$ and 5% $CO_2$) for expansion (Yoshida et al., 2009). For SNL76/7 feeder cells: SNL76/7 cells purchased from the American Type Culture Collection (ATCC, Manassas, Va., USA) were maintained in DMEM supplemented with 10% FBS and 1% penicillin-streptomycin. To prepare the feeder layer, mitomycin C (10 μg/mL; Sigma-Aldrich Co.) was added to the SNL76/7 cell culture medium, followed by incubation for 2 hr. These cells were then washed twice with PBS and replated onto a 6-well plate at a cell density of $2 \times 10^5$ cells per well. It is recommended that mitomycin C-treated SNL76/7 feeder cells be used within 1 week.

Flow cytometric analysis. Fluorescence-activated cell-sorting (FACS) analysis of mouse AT-MSCs (passage 3) was carried out with either a BD LSRII analyzer (BD Biosciences, San Jose, Calif.) or an Accuri C6 flow cytometer (BD Biosciences). Antibodies used in this study were fluorescein isothiocyanate (FITC)-conjugated anti-CD90, -CD105, -CD31, and -CD45. All were purchased from eBiosciences (San Diego, Calif., USA). Dead cells stained with propidium iodide (PI) were excluded from the analysis.

Generation of iPS cells, using AT-MSCs. On the day before rAAV infection, AT-MSCs at an early passage (<passage 3) were seeded on a 6-well plate at a density of $6 \times 10^4$ cells per well. The next day, AT-MSCs in serum-free medium were infected with rAAV2.3 m-CMV-mKOS (multiplicity of infection [MOI], $10^6$). Six days after rAAV infection, the medium (DMEM containing 10% FBS) was replaced with ES cell specialized culture medium supplemented with 10% KnockOut serum replacement (KnockOut SR®; Invitrogen, Inc.), 1% FCS, 1% penicillin-streptomycin, 1% L-glutamine, 0.01% monothioglycerol (Sigma-Aldrich Co.), leukemia inhibitory factor (LIF, 1000 U/mL), and vitamin C (50 μg/mL) (Esteban et al., 2010). This was then incubated under hypoxic conditions as previously described (Yoshida et al., 2009). Three to 5 weeks after the induction, ES cell-like colonies were handpicked and placed on feeder cells for expansion.

Immunocytochemistry and alkaline phosphatase staining. HEK293 cells grown on 24-well plates were fixed with 4% paraformaldehyde in PBS for 15 min at room temperature. After washing with PBS, the cells were treated for 10 min with PBS containing 0.1% Triton X-100, followed by 1 hr of incubation with 1% bovine serum albumin (BSA) for blocking. The primary antibodies used were anti-Oct4 (diluted 1:400, C-10), anti-Sox2 (diluted 1:400, Y-17), anti-Klf4 (diluted 1:400, H-180), and anti-SSEA (stage-specific embryonic antigen)-1 (diluted 1:400, 480). All were purchased from Santa Cruz Biotechnology (Santa Cruz, Calif., USA). The secondary antibodies used were rhodamine-conjugated goat anti-mouse IgG (diluted 1:400; Millipore, Billerica, Mass.), rhodamine conjugated goat anti-mouse IgM (diluted 1:400; Millipore), FITC-conjugated donkey anti-rabbit IgG (diluted 1:400; Santa Cruz Biotechnology), and FITC-conjugated donkey anti-goat IgG (diluted 1:400; Santa Cruz Biotechnology). The nuclei were stained with 4',6-diamidino-2-phenylindole (DAPI; Sigma-Aldrich Co.). Alkaline phosphatase staining was performed with an alkaline phosphatase staining kit (Stemgent, Cambridge, Mass.) in accordance with the manufacturer's instructions. In addition, primary antibodies used for teratoma immunostaining were as follows: anti-α-fetoprotein (AFP; Abcam, Cambridge, Mass.), a-smooth muscle actin (SMA; Abcam), and b3-tubulin (Santa Cruz Biotechnology). Staining with Stain-Alive SSEA-1 antibody (Stemgent) was performed according to the manufacturer's instructions.

Western blotting. Western blotting was performed as previously described (Takahashi et al., 2007). Primary antibodies used were antiOct4 (diluted 1:500), anti-Sox2 (diluted 1:500), and anti-Klf4 (diluted 1:500). All were purchased from Santa Cruz Biotechnology. Secondary antibodies used in this study were horseradish peroxidase (HRP)-conjugated anti-mouse IgG (diluted 1:500) and HRP-conjugated anti-rabbit (diluted 1:500) (GE Healthcare), and HRP-conjugated anti-goat IgG (diluted 1:500; Santa Cruz Biotechnology).

Southern blotting. Total cellular DNA was purified from rAAV-iPS cells, using a DNeasy blood and tissue kit (Qiagen, Inc., Chatsworth, Calif., USA) and then subjected to Southern blotting analysis as described (Song et al., 2001a). Briefly, 25 µg of total cellular DNA was digested with or without XmnI (a single cutter of the AAV vector). DNA fragments were separated by electrophoresis on a 0.8% agarose gel. Southern blot hybridization, using a $^{32}$P-labeled DNA probe (CMV promoter, 599 bp), was performed at 60° C.

PCR and RT-PCR. Total DNA was purified with a Qiagen DNeasy® blood and tissue kit according to the manufacturer's instructions. The vector-specific primers used in PCR to detect rAAV DNA were CMV-F (5'-CGTGTACGGTGG-GAGGTCTATATAA-3'; SEQ ID NO:24) and CMV-R (5'-GGATCGGTCCCGGTGTCT-3'; SEQ ID NO:25). For the quantification of rAAV vector DNA in rAAV-iPSC clones, quantitative real-time PCR (qPCR) was performed with vector-specific primers and a probe for CMV promoter sequences:

```
forward primer,
                                    (SEQ ID NO: 26)
5'-CGTGTACGGTGGGAGGTCTATATAA-3';;

reverse primer,
                                    (SEQ ID NO: 27)
5'-GGATCGGTCCCGGTGTCT-3';;
and probe,
                                    (SQ ID NO: 28)
5'-6FAM-ACGCCATCCACGCTGTTTTGACCT-TAMRA-3'
```

(Keeler et al., 2012). In RT-PCR analysis, total RNA was purified with TRIzol® reagent (Invitrogen, Inc.). Total RNA (2 µg) was used for the reverse transcription reaction using Qiagen Omniscript reverse transcriptase and oligo(dT) primers, according to the manufacturer's instructions. Real-time PCR was performed with SYBR green qPCR supermix (Invitrogen, Inc.) and was analyzed with the DNA Engine Opticon® 2 system (Bio-Rad, Hercules, Calif., USA).

The primers used to detect endogenous reprogramming gene expression in real-time PCR were as follows:

```
Endo Oct4-F
(5'-CCAACGAGAAGAGTATGAGGC-3';  SEQ ID NO: 29)

Endo Oct4-R
(5'-GT GCTTTTAATCCCTCCTCAG-3';  SEQ ID NO: 30)

Endo Sox2-F
(5'-TCTGTGGTCAAGTCCGAGGC-3';  SEQ ID NO: 31)

Endo-Sox2-R
(5'-TTCTCCAGTTCGCAGTCCAG-3';  SEQ ID NO: 32)

Endo-Klf4-F
(5'-GGCGAGAAACCTTACCACTGT-3';  SEQ ID NO: 33)

Endo-Klf4-R
(5'-TACTGAACTCTCTCTCCTGGCA-3';  SEQ ID NO: 34)

Endo-c-Myc-F
(5'-TCAAGCAGACGAGCACAAGC-3';  SEQ ID NO: 35)

Endo-c-Myc-R
(5'-TACAGTCCCAAAGCCCCAG C-3';  SEQ ID NO: 36)

Endo-GAPDH-F
(5'-AGGTCGGTGTGAACGGATTTG-3';  SEQ ID NO: 37);
and

Endo-GAPDH-R
(5'-TGTAGACCATGTAGTTGAGGTCA-3';  SEQ ID NO: 38).
```

The primers used to detect vector-specific gene expression in RT-PCR were as follows:

```
K2AO-F
(5'-ACACCTGCGAACTCACACAG-3';  SEQ ID NO: 39),

K2AO-R
(5'-AGTTGCTTTCCACTCGTGCT-3';  SEQ ID NO: 40).

GAPDH-F
(5'-ACCCAGAAGACTGTGGATGG-3';  SEQ ID NO: 41),
and

GAPDH-R
(5'-CCCTGTTGCTGTAGCCGTAT-3';  SEQ ID NO: 42).
```

Teratoma formation and examination. Approximately $9 \times 10^6$ rAAV2.3 m-iPS cells were resuspended in DMEM containing 10% FBS and injected subcutaneously into C57BL/6 mice. Three weeks after injection, teratomas were dissected and fixed with 4% paraformaldehyde in PBS. Paraffin-embedded tissue was sliced and stained with hematoxylin and eosin (H&E).

In vitro differentiation. To generate embryoid bodies (EBs), rAAV2.3 m-iPS cells were harvested by treatment with trypsin. The cells were transferred onto a Petri dish for growing bacteria and cultured in ES cell culture medium without LIF. After 5 days as a floating culture, EBs were collected and transferred to a gelatin-coated cell culture plate and cultured in the same medium for another 9 days.

Results

Isolation and characterization of adipose tissue-derived mesenchymal stem cells. Before reprogramming, a detailed characterization of AT-MSCs was performed. The stromal vascular fraction (SVF) was isolated from white adipose tissue of both mutant human al-antitrypsin (PiZ-hAAT) transgenic mice and C57BL/6J mice. The initially adherent cells grew into spindle-shaped cells that developed into visible colonies 1 week after plating on cell culture plates. The cells began to proliferate rapidly under hypoxic conditions (5% $O_2$). After the third passage, lineage-specific cell surface markers were examined by FACS. Among the suggested markers, proliferating mesenchymal stem cells exhibited CD90 (71.4%) and CD105 (70.7%), whereas they were negative for hematopoietic lineage markers, such as CD45 (<95%), or endothelial cell markers, such as CD31 (<95%). In comparison with mouse embryonic fibroblasts (MEFs), the most common starting cell type used in cell reprogramming, it was shown that AT-MSCs have alkaline phosphatase activity and that AT-MSCs expressed a low level of c-Myc and pluripotency-related genes, including Oct4, Sox2, and Klf4. Consistent with previous findings (Zhu et al., 2008), these observations suggested that AT-MSCs have a potential advantage as a starting cell type for generating iPS cells.

Generation and evaluation of rAAV vectors expressing Klf4, Oct4, and Sox2. Previous studies suggested that generating iPS cells requires reprogramming genes expressed for at least 12 days (Brambrink et al., 2008). To test whether transgene expression kinetics from the rAAV vector met this requirement, a secretory protein (human α1-antitrypsin, hAAT) was used as a reporter and showed that rAAV vector-mediated transgene expression was sustained for up to 3 weeks (testing period) in non-dividing cells and declined to a nearly undetectable level in dividing cells after 8 days. These kinetics profiles suggested that the rAAV vector has the potential to generate iPS cells. To efficiently deliver reprogramming factors and avoid the potential problems of introducing multiple vectors into the same cell, a single rAAV vector, pAAVCMV-mKOS, was generated, which polycistronically expresses mouse Klf4, Oct4, and Sox2. In this vector, the CMV promoter drives the reprogramming cassette Klf4-T2A-Oct4-E2A-Sox2, which was originally derived from pCAG2LMKOSimO (Kaji et al., 2009). Plasmid transfection of this vector showed that ES cell-specific proteins were highly expressed in HEK293 cells, indicating that the transgenes correctly expressed those specific proteins. To select an efficient rAAV serotype for the transduction of AT-MSCs, ATMSCs were transfected with several different rAAV vectors expressing green fluorescent protein (GFP), including rAAV1, 2, 5, and 7 and tyrosine mutant rAAV (rAAV2.3 m and −2.6 m). Results from these experiments showed that the tyrosine mutant AAV vectors mediated much higher transduction efficiency than did wild-type AAV vectors. Consistent with observations from previous studies (Blin et al., 2010; Li et al., 2010), this finding indicated that tyrosine mutant AAV vectors have an advantage for gene delivery to AT-MSCs. Quantitative analysis by FACS also showed that rAAV2.3 m infected AT-MSCs efficiently and that transgene expression in AT-MSCs was sustained for up to 3 weeks. Based on previous results, the reprogramming vector was packaged into rAAV2.3 m (rAAV2.3 m-CMV-mKOS) to generate iPS cells from AT-MSCs.

Generation of induced pluripotent stem cells from adipose tissue-derived mesenchymal stem cells. Freshly isolated AT-MSCs from C57BL/6 mice and PiZ-hAAT transgenic mice were infected with rAAV2.3 m-CMV-mKOS. Six days after the infection the culture medium (DMEM containing 10% FBS) was replaced with ES cell culture medium containing leukemia inhibitory factor (LIF). Cell reprogramming was monitored by staining with StainAlive® SSEA-1 antibody. Four weeks later, distinct types of colonies were observed that were flat and resembled mouse ES colonies. On day 30, mouse ES cell-like colonies and disassociated cell colonies were picked up by enzymatic digestion for further examination. These ES-like cells were plated on mitotically arrested SNL feeder cells with ES cell medium containing LIF and it was observed that they formed tightly packed and flat colonies. The appearance of these cells was similar to that of mouse ES cells, characterized by large nuclei and scant cytoplasm. These cells showed feeder dependency at early passages, but can maintain an undifferentiated state on gelatin-coated tissue culture plates at later passages and are able to proliferate for at least 80 passages. Furthermore, they expressed ES cell-specific proteins, including Oct4 and Sox2, and specific surface antigens, such as stage-specific embryonic antigen SSEA-1.

In these studies, feeder cells were used as a negative control to show the specificity of antibodies used. Because these cell clones were similar in appearance and markers compared with ES cells, they were named rAAV2.3 m-derived iPS (rAAV2.3 m-iPS) cells. To this end, the estimated iPS generation efficiency was 1-22 colonies for $6 \times 10^4$ cells as initial cell number (0.0016-0.036%).

Detection of rAAV DNA in rAAV2.3 m-derived iPS cells. To test whether rAAV vector DNA persists in rAAV derived iPS cells, total cellular DNA isolated from representative clones was subjected to Southern blotting analysis, using a $^{32}P$-labeled CMV probe. When total cellular DNA was treated with no restriction enzyme, only a high molecular weight (HMW) band, but no low molecular weight (LMW) band, was detected, indicating that rAAV vector DNA was integrated into the cellular genome. When total cellular DNA was treated with XmnI (a single cutter of the vector), the HMW band completely disappeared and two or three bands were detected. Because the sizes of the bands (8.5, 5.5, and 3.8 kb) were greater than that of the predicted vector fragment (3.5 kb) and did not match the predicted size of the head-to-tail (H-T, 4.7-kb) junction and head-to-head junction (H—H, 7.0-kb), these signals indicated that rAAV vector DNA integrated into two or three sites in the cellular genome.

To confirm rAAV DNA integration, PCRbased analysis was performed. Vector-specific PCR analysis showed that rAAV DNA was detectable in rAAV2.3 m-iPS cells. Quantitative genomic PCR (qPCR), using vector DNA-specific primers and probe, showed that vector DNA was detectable in all rAAV-iPSC clones at various passages. To eliminate the possibility of episomal DNA contamination, two clones were passaged to 14 and 18 passages. Quantitative PCR analysis again showed that rAAV vector DNA was detectable in all passages and clones. Because culture of rAAViPSCs at early passages requires feeder cells, those feeder cell DNAs were co-isolated with the genomic DNA of rAAViPSCs, resulting in an underestimate of the copy numbers of rAAV vector DNA per rAAV-iPSC. To avoid this limitation, an iPSC clone was passaged to 20 passages, and 5 subclones were isolated. These cells were cultured without feeder cells. All the subclones contained one or two copies of rAAV vector DNA per cell. Collectively, results from both Southern blot and PCR analysis showed that rAAV viral DNA was integrated into the cellular genome in all the rAAV-iPSCs.

Characterization of rAAV2.3 m-iPS cells. To test whether rAAV DNA was actively expressing the transgenes, vector mRNA-specific RT-PCR analysis was performed. Results from these experiments showed that transgene expression in rAAV-iPSCs was silenced. Real-time PCR analysis showed that rAAV2.3 m-iPS cells maintained under feeder-free conditions expressed endogenous Oct4, Sox2, c-Myc, and Klf4. To test the pluripotency of these rAAV2.3 m-iPS cells in vivo, xrAAV2.3 m-iPS cells (rAAV2.3 m-iPS clones 01 and 02) were transplanted into C57BL/6 mice. Three weeks after injection, teratoma formation was observed with comparable efficiency to mouse J1ES cells as control. Histological examinations showed that the teratoma contained various tissues, including neural epithelium, gutlike epithelium, bonelike cells, and muscle-like cells. By immunostaining cells expressing α-fetoprotein (AFP; endoderm marker), αsmooth muscle actin (SMA; mesoderm marker), and β3-tubulin (ectoderm marker) in the teratoma were observed. In addition, the capability of these cells was evaluated for in vitro differentiation. After 5 days of freefloating culture, rAAV2.3 m-iPS cells began to aggregate and formed spherical clusters, so-called embryonic bodies (EBs). The EBs were then cultured on gelatin-coated plate in ES culture medium without LIF. After 2 weeks' culture, immunostaining was performed, and cells positive for α-fetoprotein, α-smooth muscle actin, and β-tubulin were detected. These results indicate that rAAV2.3 m-iPS cells are pluripotent and can be further differentiated into various tissues in vitro and in vivo.

Discussion

Recombinant adeno-associated virus (rAAV) has been widely used in preclinical and clinical studies and has been proven to be an effective and safe vector for the delivery of therapeutic genes to treat inherited disorders, such as Leber's congenital amaurosis (LCA) (Maguire et al., 2008; Simonelli et al., 2010), hemophilia B (Manno et al., 2006; Nathwani et al., 2011), and $α_1$-antitrypsin (AAT) deficiency (Flotte et al., 2011). There is no evidence showing that wild-type or recombinant AAV is associated with any human disease. One study reported that AAV2.3 m shows relatively high infection efficiency toward murine bone marrow-derived mesenchymal stem cells and fibroblasts (Li et al., 2010), which makes AAV2.3 m a unique candidate vector for generating iPS cells. In this example, mouse iPS cells were successfully generated, using a single polycistronical AAV2.3 m vector expressing three transcription factors: mouse Klf4, Oct4, and Sox2. The generated rAAV2.3 m-iPS cells expressed endogenous ES cell-specific proteins (such as Oct4, Sox2, and SSEA-1), formed teratomas in recipient mice, proliferated to at least 80 passages, and could be maintained under feeder-free (gelatin coating) culture conditions at later passages. More importantly, it was shown that delivery of only three transcription factors is sufficient for AAV2.3 m-mediated reprogramming and that transgene expression in rAAV2.3 m-iPS cells is silenced. Considering that c-myc is an oncogene, generating iPS cells in the absence of c-Myc may be a great advantage in improving the safety of rAAV-derived iPS cells.

Studies have suggested that cell types that express high endogenous levels of particular transcription factors may have an advantage for cell reprogramming (Eminli et al., 2008). The gene expression profiles of isolated AT-MSCs were examined by RT-PCR assay. Consistent with previous studies (Zhu et al., 2008), it was found that isolated ATMSCs expressed endogenous Oct4, Sox2, Klf4, and c-Myc. This endogenous gene expression profile in isolated AT-MSCs may play an important role in promoting the generation of iPS cells by three transcription factors. In addition to endogenous expression of reprogramming genes, AT-MSCs have several additional advantages for generating iPS cells. For example, isolation, characterization, and handling of ATMSCs in vitro are relatively simple; it has been shown that ATMSCs tolerate ES cell culture medium. Collectively, these observations suggest that AT-MSCs are excellent cell sources for generating iPS cells (Sun et al., 2009; Aoki et al., 2010). It should be noted that in some experiments cell apoptosis was observed when older passages of AT-MSCs were used, probably due to incomplete epigenetic changes, which may lead to programmed cell death during the cellular reprogramming processes. This observation also highlights that the quality of isolated AT-MSCs is critical in rAAV2.3 m-mediated cellular reprogramming.

Generating iPS cells without c-Myc has not been reported in studies using other vectors, including adenovirus (Zhou and Freed, 2009), adeno-associated virus (Weltner et al., 2012b), a plasmid-based method (Okita et al., 2008), and nonviral minicircle DNA vectors (Jia et al., 2010). In this example, delivery of three reprogramming factors in the absence of c-Myc by rAAV2.3 m vector was shown to generate iPS cells. One of the reasons for this success is the use of AT-MSCs as the starting cells. The low-level expression of Oct4, Sox2, Klf4, and c-Myc in mouse AT-MSCs likely enhanced the cellular reprogramming processes, and thus exogenous genes, such as c-myc, could be eliminated.

Further improvement of reprogramming efficiency, such as by incubation with certain small molecules, may lower the required vector dose (or MOI) and thus increase the opportunity to derive rAAV-free iPS cells. Several studies have demonstrated that certain small molecules or drugs can enhance iPS induction efficiency (Li et al., 2009; Chen et al., 2010; Mali et al., 2010; Yang et al., 2011). These small molecules may participate in epigenetic processes, thereby overcoming epigenetic barriers during cellular reprogramming.

However, most of them are tested and evaluated in the context of fibroblast-based cellular reprogramming, and little is known about whether AT-MSCs tolerate these treatments or how well rAAV-transduced AT-MSCs react to small molecules during cellular reprogramming processes. It is therefore of great interest to investigate the interplay between these genetic factors and small molecules in rAAV2.3 m-mediated cellular reprogramming. A better understanding of the mechanism underlying the rAAV-mediated cellular reprogramming process might help us identify participating factors in order to improve reprogramming efficiency.

Analysis of DNA isolated from five subclones showed that the viral copy number per cell ranged from 1.25 to 1.95. Consistent with previous observations described by Weltner and colleagues, who used four rAAV2 vectors to infect murine fibroblasts by multiple infections (Weltner et al., 2012b), results from Southern blotting and PCR-based analyses indicated that rAAV DNA integrated into the cellular genome of iPS cells. Together, these observations suggest a new paradigm concerning the molecular fate of rAAV genomes in host cells. In nondividing cells, rAAV DNA persists in host cells as episomal forms (linear or circular), which have been well documented and accepted (Duan et al., 1998; Song et al., 2001b; Schnepp et al., 2003). However, in dividing cells, rAAV DNA may have two fates: (1) it can be diluted or lost as the host cell divides, which has been reported (Nakai et al., 2001; Song et al., 2004); or (2) rAAV DNA can also integrate into the cellular genome as the host cell divides. Although the proportions of rAAV DNA for each direction require complex detailed quantification, the data demonstrated that both events exist in dividing host cells. Recombinant AAV DNA integration has been reported under the selection conditions described (Nakai et al., 1999). However, rAAV DNA integration in every iPS clone has not been observed until more recently (Weltner et al., 2012a). Weltner and colleagues used four rAAV2 vectors (each expressing one programming factor) and fibroblasts, whereas this study used one rAAV2.3 vector expressing three factors and AT-MSCs. The consistent observations from these two different studies suggest that rAAV integration in generating iPS cells is not vector or cell type dependent. It is possible that during the rAAV mediated reprogramming process the rAAV-integrated cells gain prolonged transgene (reprogramming factors) expression and have the growth advantage over the cell clones that do not have the integrated transgene. Although different methods were used, results from this study, as well as those of others, raise important questions, including what critical factors attribute to the integration, the effects of the integration, and how to control or avoid the integrations. Although answering these questions requires further investigations, it is clear that generating iPS cells does not require vector DNA integration (Fusaki et al., 2009; Zhou and Freed, 2009) and that rAAV DNA integration is controllable (McCarty et al., 2004; Song et al., 2004; Zhang et al., 2007). In addition, carrying no viral or bacterial gene in rAAV vector can be considered an advantage for generating iPS cells.

Many studies have shown that rAAV can mediate long-term transgene expression in vitro and in vivo (Song et al., 2001a; Daya and Berns, 2008). Surprisingly, it was found that reprogramming gene expression was silenced in rAAV2.3 miPS cells. It has been shown that the retroviral transgene is silenced in retrovirus-mediated cell reprogramming (Okita et al., 2007), and that the timing of retroviral silencing correlates with the quality of induced pluripotent stem cell lines (Okada and Yoneda, 2011). Such retroviral transgene silencing may result from the activation of potent repressor factors or the reduction of certain activating factors after directly reprogramming somatic cells to pluripotent states (Hotta and Ellis, 2008). In addition, CMV promoter activity has been shown to be progressively silenced in pluripotent stem cells (Xia et al., 2007; Meilinger et al., 2009). In rAAV2.3 m-mediated cell reprogramming, whether transgene silencing resulted from the activation of certain endogenous potent repressor or from the reduction of CMV promoter activity in rAAV-iPS cells remains elusive.

In summary, this example demonstrates that triple tyrosine mutant AAV2 vectors can reprogram mouse adipose tissue-derived mesenchymal stem cells into the pluripotent state in the absence of c-Myc. The transgene expression was silenced after reprogramming, although rAAV DNA was detectable in iPS cells. Considering the well-known safety features of rAAV vectors, this rAAV2.3 m-mediated cell reprogramming method may provide a novel path for enhancing the application of iPS cells. Further studies are recommended to derive rAAV-free iPS cell clones.

Example 9—Rationally Designed Capsid and Transgene Cassette of AAV6 Vectors for Dendritic Cell-Based Cancer Immunotherapy Dendritic cell (DC)-based immunotherapy has recently demonstrated a great potential for clinical applications; however, additional progress in the methods of tumor-specific antigen delivery to DCs is necessary for the further development of antitumor vaccines. To this end, a capsid-optimized adeno-associated virus serotype 6 (AAV6-T492V+S663V) vector was developed by site-directed mutagenesis of surface-exposed serine (S) and threonine (T) residues, which have a critical role in intracellular trafficking of AAV vectors. This double-mutant AAV6 vector had 5-fold greater transduction efficiency in monocyte-derived DCs (moDCs) compared with wild-type (WT)-AAV6 vectors. The increase in the transduction efficiency correlated with the improved nuclear translocation of AAV6-T492V+S663V over that of the WT-AAV6 vector. Additional studies of the CD11c promoter identified critical regulatory elements that fit into the AAV expression cassette and drive EGFP expression in moDCs. Development of a chimeric promoter (chmCD11c) that contains functional modules of CD11c and a Simian virus (SV40) enhancer element dramatically increased the EGFP expression in moDCs. MoDCs transduced by the capsid-optimized AAV6 vector carrying human prostate-specific antigen (hPSA) driven by CBA (AAV6-T492V+S663V-CBA-hPSA) or chmCd11c (AAV6-T492V+S663V-chmCD11c-hPSA) generated specific T-cell clone proliferation and superior cytotoxic T lymphocytes (CTLs) with higher killing capability against human prostate adenocarcinoma cells, LNCaP, compared with WT-AAV6 induced CTLs. This example demonstrates that optimization of capsid and promoter components of AAV vectors are a useful tool in efficiently targeting of moDCs and an important tool for cancer immunotherapy.

Recent progress in cancer immunology has highlighted the potential utility of immunotherapy for clinical applications. Since dendritic cells (DCs) are potent regulators of the immune system, much research is being done to understand how DCs can be used to induce and redirect anti-tumor immunity. Although tremendous progress has been made in the past decade for ex vivo DC-based immunotherapy, reliable methods for in vivo tumor-specific antigen delivery have not yet been developed. Among a variety of viral vectors widely used for cell modifications, adeno-associated virus (AAV), a non-pathogenic human parvovirus, has gained attention as a safe vector, and is currently in use in a number of gene therapy clinical trials for the treatment of several diseases, including hemophilia B, Parkinson's disease, muscular dystrophy, and ocular diseases.

However, in previous studies, it became clear that naturally-occurring serotypes of AAV vectors were not optimal for transduction of a number of cell types, and their efficacy can be significantly enhanced by modifying the surface-exposed amino acids on their capsid, such as tyrosine, serine or threonine. These surface-exposed residues can be phosphorylated by cellular kinases such as epidermal growth factor receptor protein tyrosine kinase and mitogenactivated protein kinase, both of which negatively regulate the efficiency of AAV-mediated gene transfer by targeting the vectors for proteasome-mediated degradation. These studies resulted in the development of next generation recombinant AAV vectors containing one or several point mutations on the capsid that transduce various cell types and tissues more efficiently compared with wild-type (WT) AAV vectors.

Although ex vivo DC-based vaccine approaches continue to be proving grounds for cancer immunotherapy, fundamental limits including poor accessibility, high-cost and minimal standardization are impeding the development of methods for in vivo DC targeting. Even though AAV is widely used as a potent in vivo delivery vehicle, vector promiscuity remains a major obstacle for specific targeting of particular cell types. Nevertheless, cell-restricted gene expression can be achieved by selection of specific promoter elements. The relatively small packaging capacity of AAV vectors, B2.4 kb for self-complementary AAV used throughout these studies, required the use of a sufficiently short promoter with a size much smaller than typically present in the human genome. [21] However, unique transcription factor (TF) binding sites (TFBSs), which control tissue-specific gene expression, can be identified within the promoter's functional modules. Thus, it is possible to develop a short chimeric promoter necessary to fit into the viral expression cassette without sacrificing specificity.

In this example, the natural flexibility of AAV's structural and regulatory components was exploited to optimize the capsid of AAV6 and to develop a chimeric promoter derived from the CD11c co-stimulatory molecule and documented the following: (i) site-directed mutagenesis of the critical surface-exposed serine (S663) and threonine (T492) residues on the AAV6 capsid to valine (V) leads to increased transduction efficiency of monocyte-derived DCs (moDCs) by mutant vectors compared with the WT-AAV6 vector; (ii)

combination of functionally sufficient regions of the CD11c promoter and Simian virus (SV40) enhancer element efficiently drive enhanced green fluorescent protein (EGFP) expression in moDCs transduced by AAV6 vectors; (iii) transduction of moDCs with capsid-optimized AAV6 vectors encoding human prostate-specific antigen (hPSA) driven by chmCD11c generates specific cytotoxic T lymphocytes (CTLs) with high killing activity against the human prostate adenocarcinoma cell line LNCaP.

Materials and Methods

Cells and antibodies. Leukapheresis-derived peripheral blood mononuclear cells (AllCells, Alameda, Calif., USA) were purified on Ficoll-Paque (GE Healthcare). Semi-adherent cell fractions were incubated in serum-free X-VIVO medium (Lonza, Inc.) with supplements of recombinant human rIL-4 (50 μg mL$^{-1}$) and rGM-CSF (100 μg mL$^{-1}$) (Peprotech, Rocky Hill, N.J., USA). Cell maturation was initiated with a cytokine mixture including 10 ng mL$^{-1}$ TNF-cL, 10 ng mL$^{-1}$ IL-1, 10 ng mL$^{-1}$ IL-6 and 1 mg mL$^{-1}$ PGE2 (Peprotech) for 48 hrs. Phenotypical changes of mature DCs were characterized by FACS analysis on co-stimulatory molecules expression levels (CD80, RPE, murine IgG1; CD83, RPE, murine IgG1; CD86, FITC, murine IgG1; Invitrogen, Inc.). Human prostate adenocarcinoma cell lines LNCaP (American Type Culture Collection) were maintained as monolayer cultures in DMEM (Invitrogen, Inc.) supplemented with 10% FBS (Sigma-Aldrich Co.) and antibiotics (Lonza, Inc.).

Site-directed mutagenesis. A two-stage PCR was performed with plasmids pACGr2c2 and pACGr2c6 using Turbo Pfu Polymerase (Stratagene, Santa Clara, Calif., USA). Briefly, in stage one, two PCR extension reactions were performed in separate tubes for the forward and reverse PCR primer for three cycles. In stage two, the two reactions were mixed and a PCR was performed for an additional 15 cycles, followed by DpnI digestion for 1 hr. Primers were designed to introduce changes from serine (TCA) or threonine (AGC) to valine (GTA or GTC) for each of the residues mutated.

Cloning of CD11c promoter. Human peripheral blood mononuclear cells were used to isolate genomic DNA with the PureLink gDNA mini kit (Invitrogen, Inc.). The integrity of genomic DNA was assessed by agarose gel electrophoresis before used as the template for subsequent PCRs. RedTaq genomic DNA Polymerase (Sigma-Aldrich Co.) was used for amplification of fragments of the CD11c promoter region with a length of ≈700 bp for each. Fragments were cloned into scAAV-CBA-EGFP plasmid by substitution of CBA promoter to drive EGFP expression Production of recombinant AAV vectors. Recombinant AAV vectors were generated as described previously by triple transfection of HEK293 cells using Polyethylenimine (linear, MW 25000; Polysciences, Inc.). Cells were harvested 72 hrs post transfection, and vectors were purified by iodixanol (Sigma-Aldrich Co.) gradient centrifugation followed by ion exchange column chromatography (HiTrap Sp Hp 5 mL; GE Healthcare). Virus was then concentrated into lactated Ringer's using centrifugal spin concentrators (Apollo, 150-KDa cutoff, 20-mL capacity, Orbital Biosciences). Titers of the vectors were determined by qPCR with the following primer pair, specific for the bovine growth hormone polyA region in the viral cassette: forward 5'-TAGTTGCCAGCCATCTGTTG-3'; (SEQ ID NO:43); reverse 5'-GCGATGCAATTTCCTCATTT-3' (SEQ ID NO:44) and SYBR Green® PCR Master Mix (Invitrogen, Inc.).

In vitro transduction assays. moDCs were transduced with AAV vectors with 2000 vgs per cell and incubated for 48 hrs. Transgene expression was assessed as the total area of green fluorescence (pixel$^2$) per visual field (mean±s.d.) by the ImageJ software. Images were obtained by fluorescent microscope Leica CTR4000 (Wetzlar, Germany) with 20×objective. Analysis of variance was used to compare test results and the control, which were determined to be statistically significant.

Analysis of vector genome distribution in cytoplasm and nuclear fractions. Approximately 2×10$^6$ DCs were infected by various AAV vectors with multiplicity of infection (MOI) 10000 vgs per cell. Cells were collected at different time points, treated with trypsin to remove adsorbed viral particles and then washed extensively with phosphate buffer saline. Nuclear and cytoplasmic fractions were separated with the Nuclear and Cytoplasmic Extraction Reagents kit (Thermo Scientific) according to the manufacturer's instructions. Viral genomes were extracted by Proteinase K digestion followed by phenol/chloroform purification and DNA precipitation by EtOH. Viral DNA was detected by qPCR analysis with the bovine growth hormone-specific primers as described above. The difference in amount of viral genome between cytoplasmic and nuclear fractions was determined by the following rule: $C_T$ values for each sample from cells treated with virus were normalized to the corresponding $C_T$ from mock-treated cells ($\Delta C_T$). For each pair wise set of samples, the fold change in packaged genome presence was calculated as fold change=$2^{-(\Delta C_T\text{-}cytoplasm - \Delta C_T\text{-}nucleus)}$. Data from three independent experiments were presented as a percentage of the total amount of viral genome in the nuclear and cytoplasmic fractions or as a ratio between two samples infected with different vectors.

Western blot analysis. Western blot analysis was performed as described previously.[15] Cells were lysed in buffer (50 mM Tris-HCl, pH 7.5, 120 mM NaCl, 1% Nonidet P-40, 10% glycerol, 10 mM Na$_4$P$_2$O$_7$, 1 mM phenylmethylsulfonyl fluoride, 1 mM EDTA and 1 mM EGTA) with protease inhibitors mixture (Set 2; Calbiochem, Darmstadt, GERMANY). Samples were normalized by protein concentration and separated on 12% polyacrylamide/SDS gels, followed by transfer onto a nitrocellulose membrane. Primary antibodies, anti-hPSA or anti-β-actin (rabbit mAb 1:1000; Cell Signaling, Inc.), followed by secondary horseradish peroxidase-linked antibodies (1:1000; Cell Signaling, Inc.) were used to visualize the difference in protein expression.

Specific CTL generation and cytotoxicity assay. CTL generation was performed as described previously. moDCs were generated as described herein. Immature DCs were infected with AAV vectors encoding hPSA (Origene, Rockville, Md., USA) or EGFP (nonspecific control) driven by CBA or chimeric CD11c promoters. Cells underwent maturation as described above. After 48 hrs, mature DCs were mixed with non-adherent peripheral blood mononuclear cells from a donor at a ratio of 20:1. CTLs were cultured in X-VIVO medium containing recombinant human IL-2 (20 ng mL$^{-1}$) and IL-7 (20 ng mL$^{-1}$) at 20×10$^6$ cells in 25 cm$^2$ flasks with ⅓ of medium replaced and fresh cytokines added every 2 days. After 7 days post priming, the cells were harvested and used for killing assays against human prostate adenocarcinoma cells line, LNCaP. A killing curve was generated and specific cell lysis was determined by FACS analysis of live/dead cell ratios. Briefly, pre-stained with 3,3-dioctadecyloxacarbocyanine (DiOC18(3)), a green fluorescent membrane stain, 1×10⁵ target LNCaP cells were co-cultured overnight with different ratios of CTLs (80:1, 50:1, 20:1, 10:1, 5:1). Membrane-permeable nucleic acid counterstain, propidium iodide, was added to label the cells with compromised plasma membranes. Percentages of killed, double stain-positive cells, were used to evaluate efficiency of CTLs.

Statistical analysis. Results are presented as mean±s.d. Differences between groups were identified using a grouped-unpaired two-tailed distribution of Student's t-test. P-values <0.05 were considered as statistically significant.

Results

Figure 48A:
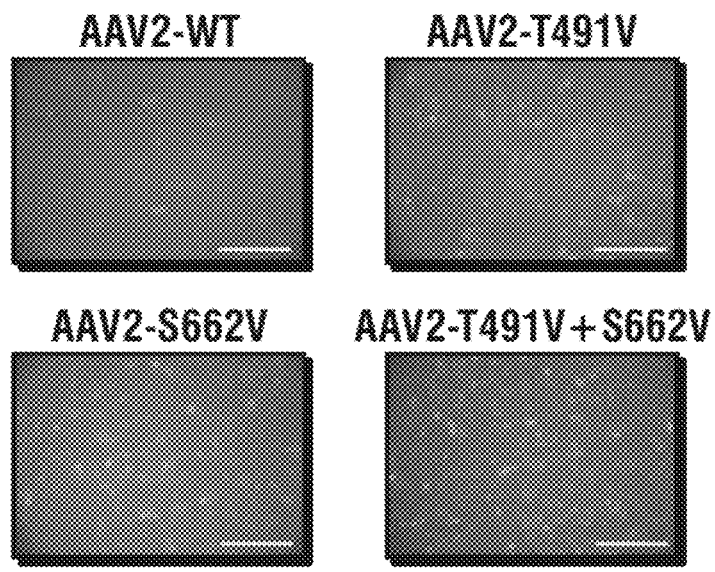
FIG. 48A, FIG. 48B, FIG. 48C, and FIG. 48D show the analysis of EGFP expression driven by CBA promoter after transduction of moDCs with individual site-directed scAAV2 and scAAV6 capsid mutants.
Figure 48B:
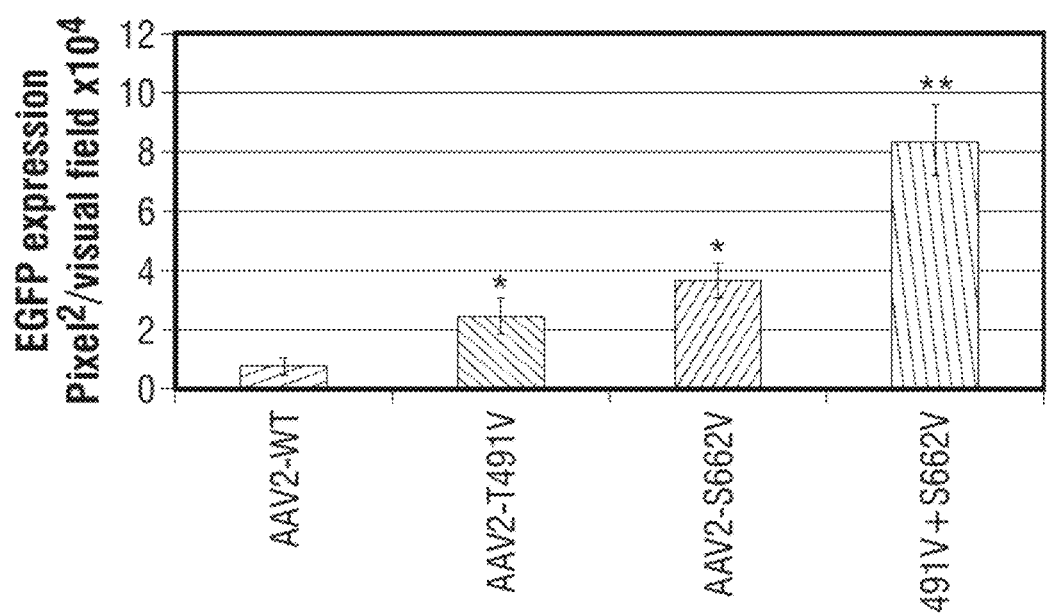
Figure 48C:
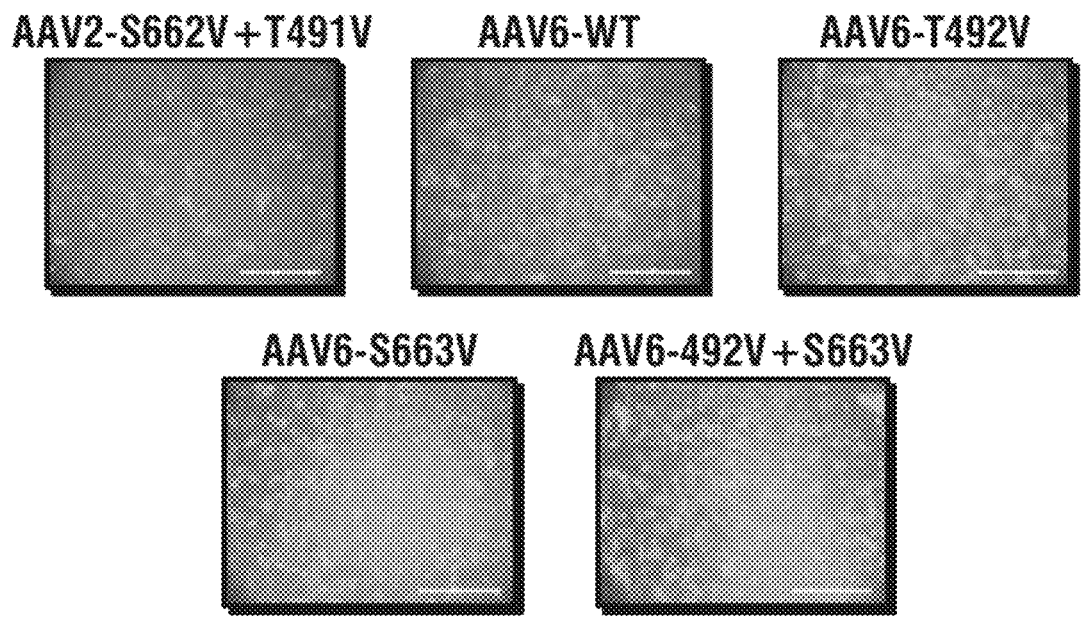
Figure 48D:
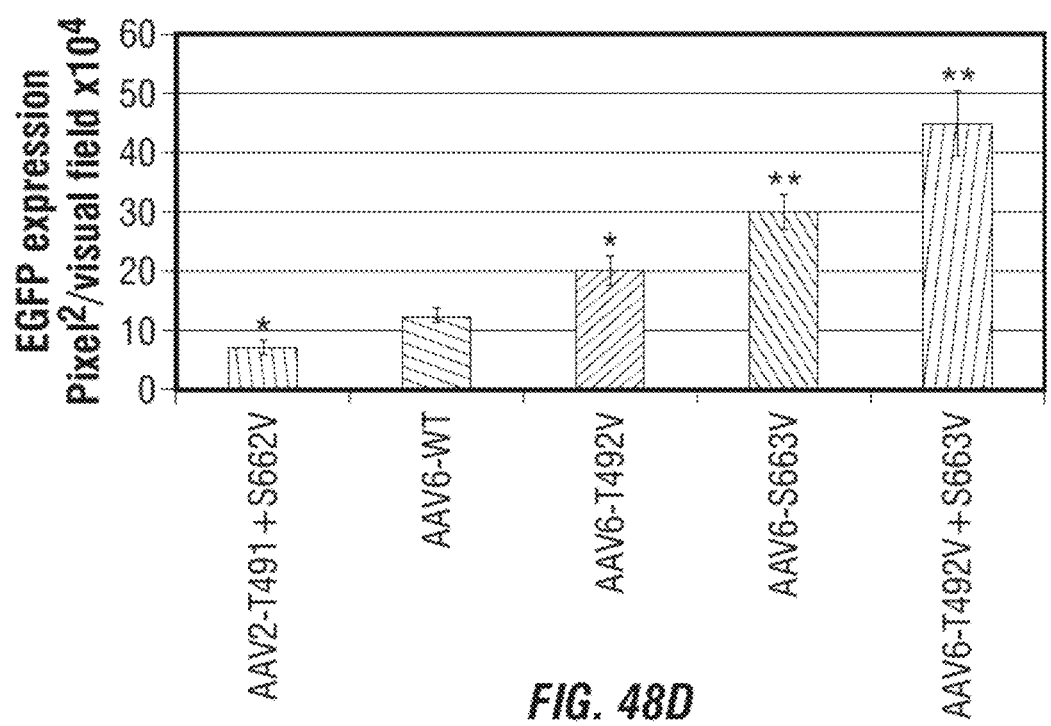

Site-directed mutagenesis of surface-exposed serine (S) and threonine (T) residues on AAV2 and AAV6 capsid improves vector-mediated transgene expression. Recent studies of the AAV2 crystal structure combined with the data from various mutagenesis experiments on the capsid genes have outlined the role of several specific residues involved in interaction of these vectors with cellular components during infection. Genetic modification of these regions can increase the efficiency of transduction of different tissues and cells by AAV vectors, most likely by preventing phosphorylation of serine (S) and threonine (T) residues, and subsequent degradation of vectors by the host proteasome machinery. These studies have led to the development of several AAV2 vectors, such as AAV2-S662V, AAV2-T491V and AAV2-T491+S662V, which can increase the transduction efficiency of moDCs by B6-, 4- and 8-fold, respectively. However, the transduction efficiency of the most efficient AAV2 mutant vector was ≈2-fold lower than that of WT-AAV6 vectors. It was hypothesized that a similar optimization strategy described above for AAV2 could be applied to the AAV6 serotype since it contains 17 surface-exposed serine (264, 268, 277, 385, 453, 455, 467, 472, 499, 547, 551, 587, 588, 663, 669, 703 and 708), and 18 threonine (246, 251, 265, 326, 331, 332, 492, 494, 502, 504, 553, 589, 593, 665, 672, 702, 714 and 722) residues. Priority was given to the positions that are conserved among various serotypes, and showed better performance in AAV2 studies, such as S663 and T492. Indeed, site-directed mutagenesis of these positions led to an increase in transduction efficiency of both mutant AAV6 vectors in moDCs by ≈2- to 3-fold (FIG. 48C and FIG. 48D). Combinations of these mutations on a single AAV6 capsid further increased the transduction by ≈2-fold compared with single mutant vectors, and ≈5-fold compared with WT-AAV6 vectors (FIG. 48C and FIG. 48D). Consistent with previously published data, high efficiency transduction of capsid-optimized AAV6 vectors did not induce phenotypical changes in immature moDCs.

Figure 49D:
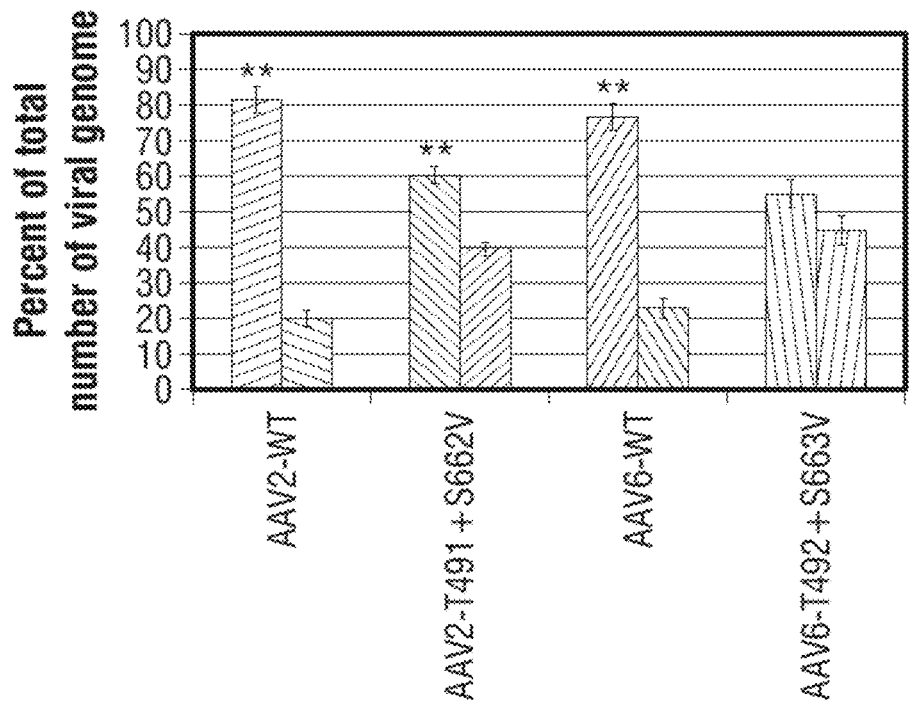
Figure 49E:
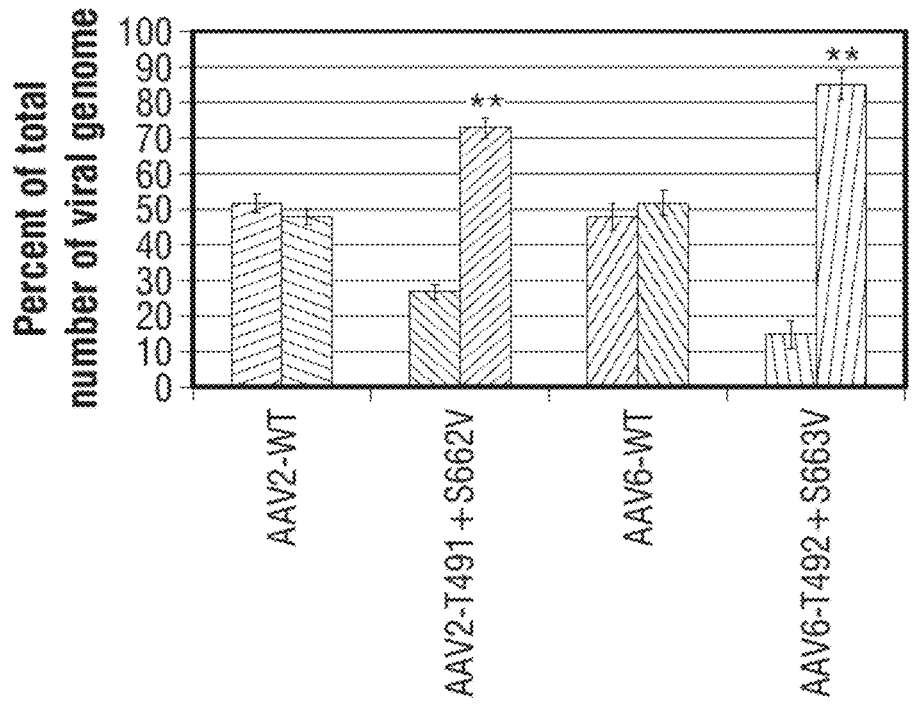

Optimization of the capsid enhances intracellular trafficking and nuclear translocation of AAV6 vectors. Development of a small, efficient chimeric CD11c promoter for AAV-based gene delivery to DCs augmented AAV particle entry into cells. Data obtained from qPCR analysis on a cytoplasmic fraction of moDC 2 hrs post infection implied that neither single nor double mutations on AAV2 or AAV6 capsid increased the viral entry (FIG. 49A and FIG. 49B). However, WTAAV6 and AAV6-T492V+S663V entered moDCs B3-fold more efficiently than WT-AAV2 and AAV2-T491V+S662V vectors (FIG. 49C). This result roughly correlates with the difference in transduction efficiency of these AAV serotypes in moDCs. Analysis of viral genome distribution in the cytoplasm and the nucleus at different time points revealed that AAV2-T491V+S662V and AAV6-T492V+S663V translocate to the nucleus more efficiently than the corresponding WT-AAV vectors. Thus, ≈20-25% of the genomes from the WT vectors were detected in the nuclear fraction 16 h post infection compared with 40-45% of the capsid-optimized vector genomes detected at the same time point (FIG. 49D). Similarly, ≈50% of the genomes from the WT vectors were detected in the nuclear fraction 48 hrs post infection, ≈75% of the genomes from the double-mutant AAV2 vectors, and ≈85% of the vector genomes from the double-mutant AAV6 vectors were detected in the nuclear fraction at the same time point (FIG. 49E). This result suggests that another mechanism might be involved in the difference of nuclear trafficking of AAV6 over AAV2 vectors.

Figure 50A:
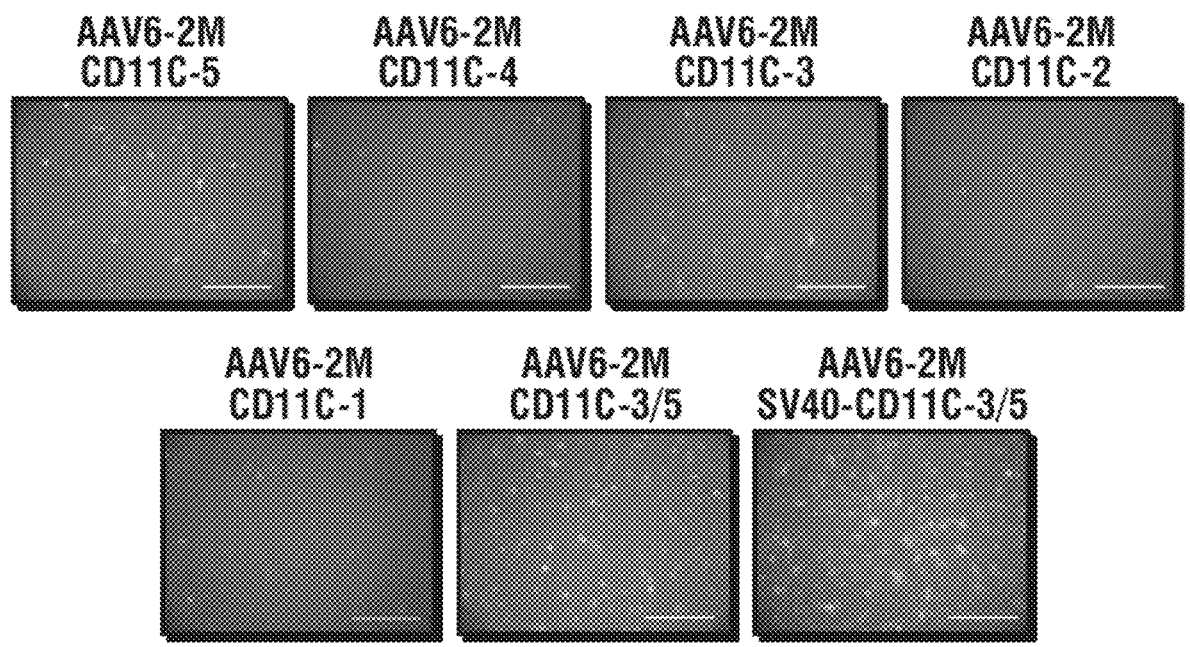
FIG. 50A and FIG. 50B show the analysis of EGFP expression driven by short promoter regions after transduction of cells with individual site-directed AAV6-2M.
Figure 50B:
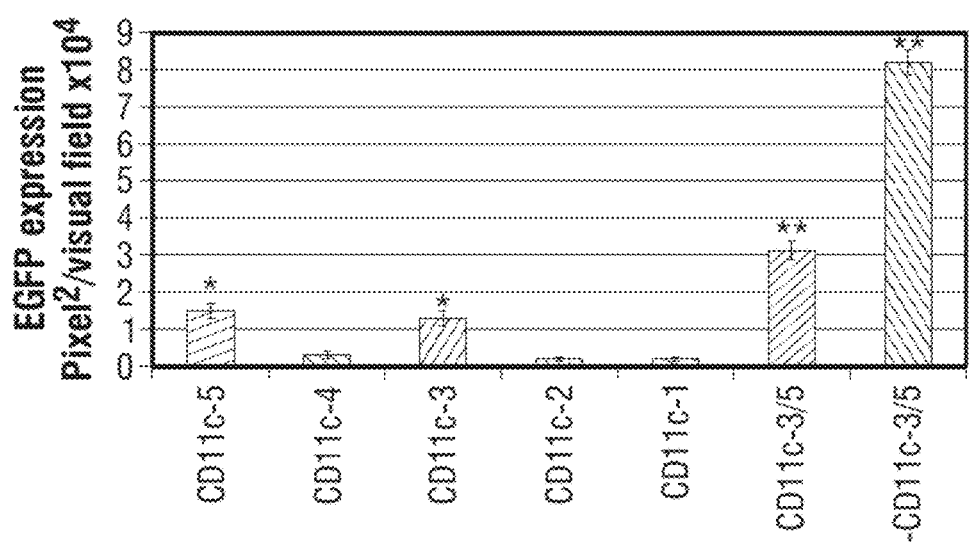

The length of the promoter region that drives CD11c expression, the common co-stimulatory molecule within DC subsets, is too big to fit into the relatively small size of the AAV vector. Therefore, five different regions with lengths ≈700 bp were amplified from the full-length CD11c promoter and cloned into an AAV vector expression cassette. To investigate the basis of promoter function, each construct was packaged into capsid-optimized AAV6-T492V+S663V vectors described above and evaluated for the ability to express EGFP in moDCs. Results showed that two short promoter regions, CD11c-3 and CD11c-5, could efficiently drive EGFP expression (FIG. 50A and FIG. 50B). However, three other promoter parts, CD11c-1, CD11c-2 and CD11c4, were not able to express EGFP. These data suggest that regulatory elements that affect specificity and the level of gene expression are not evenly distributed throughout the whole promoter and some particular regions can be further studied to replace the entire CD11c promoter. Next, freely available software was used to identify possible putative binding sites for DC-specific TFs, which are the likely cause of functional activity of a particular part of the CD11c promoter. The top TFs predicted for each of the five regions of the CD11c promoter were selected based on their scores, which essentially reflect binding affinity of TFs to particular DNA sequences. The maps of each part were then created to show the relative positions of the TFs. Next, a chimeric CD11c (chmCD11c) promoter was developed by combining functional modules of CD11c-3 (235 bp) and CD11c-5 (486 bp) predicted via computational analysis (FIG. 51A-FIG. 51C) and the commonly used Simian virus (SV40) enhancer element (235 bp). These data indicated that these two new promoters, CD11c-3/5 and SV40-CD11c-3/5 (chmCD11c), can increase the EGFP expression by 3- to 5-fold correspondingly compared with CD11c-3 and CD11c-5 alone when packaged into double-mutant AAV6 vectors (FIG. 51A and FIG. 51B). The specificity of these vectors for DC cells was demonstrated by their lack of expression in HEK293 and HeLa cells. It is also interesting to note that freshly isolated monocytes transduced with capsid-optimized AAV can express EGFP driven by the CBA promoter while differentiating into immature DCs. However, gene expression under the chmCD11 promoter is 'turned on' only after DCs undergo maturation with supplementary cytokines.

Generation of hPSA CTLs by moDCs transduced by optimized AAV6 vectors. Since capsid-optimized AAV6 vectors containing the chmCD11c promoter can mediate efficient gene expression in moDCs, the ability of moDCs transduced with these vectors was examined for their ability to stimulate CTLs for specific killing of target cells. Given that PSA, also known as kallikrein-3 (KLK3), is commonly used as a target for immunotherapy, it was cloned into an expression cassette under the control of the CBA or chmCD11c promoters and packaged into the best performing AAV6 capsid mutant and AAV6 WT. First, PSA protein expression was evaluated in moDCs transduced with the vectors described above. These data indicated that chmCD11c (SV40-CD11c-3/5) and CBA promoter can drive hPSA gene expression and this expression can be augmented by capsid optimization (FIG. 50A-FIG. 50B). Next, CTLs were stimulated once with moDC/hPSA delivered by vectors as described. Cytotoxic T-cell assay using human prostate adenocarcinoma cell line, LNCaP, as a target cell type was performed. Results of these experiments suggest that moDCs transduced with AAV/PSA can effectively stimulate specific T-cell clone proliferation and killing activity compared with moDCs expressing EGFP. The killing activity of CTLs roughly correlated with PSA expression in moDCs transduced by different AAV6 vectors. Although the activity of the CTLs stimulated in vitro with the chmCD11c promoter encapsulated in the capsid-optimized vector was lower than that generated by the CBA promoter, this cell-specific promoter has the advantage of being specific for direct in vivo DC transduction.

Discussion

DCs have an essential role in initiation and regulation of antigen-specific immune response. Anti-tumor vaccines based on genetically modified moDCs have proven to be an attractive therapeutic tool in a number of clinical trials. However, lack of reliable strategies of tumor-associated antigen loading to DCs can explain, at least in part, the limited efficacy of ex vivo vaccine approaches. Not least important, an adequate method for the direct activation of the host immune system, and initiation of protective anti-cancer immunity has not yet been developed.[3]

AAV vector-based antigen delivery has successfully been utilized for human DCs and as a vaccination strategy in several cancer models. However, recent data suggest that genetic modification of the AAV capsid and expression cassette can dramatically improve the vector's effectiveness by changing the affinity for cellular receptors, therefore accelerating intracellular trafficking and overcoming the rate-limiting step of viral second-strand DNA synthesis. Previously published data on the mutagenesis of surface-exposed serine (S) residues on AAV2 capsid underlined the importance of these residues for vector-mediated gene transfer to moDCs. In more recently-published data, nearly one hundred single tyrosine (Y), serine (S) and threonine (T) and multiple AAV2 capsid mutants were analyzed, and several combinations were discovered with improved infectivity compared with WT-AAV2 vectors in a number of cell types. Previous work on improvement of infectivity of AAV vectors was done on serotype 2 capsid since these vectors were the most extensively studied and used for several clinical trials. However, AAV6 was shown to perform better on moDCs in recent studies. Considering the similarity of capsid structure between AAV2 and AAV6 serotypes, the inventors hypothesized that mutations of the conserved serine and threonine residues could lead to improvement of transduction efficiency of these vectors. Several attempts to improve AAV6 vectors were done previously and these studies were focused on mutagenesis achieved for CD34+ cells. These same vectors were not able to efficiently transduce moDCs. This can be explained, to some extent, by recent findings that infectivity of each capsid-modified AAV vector is roughly correlated with the profile and activity of cellular kinases for given cell types. In fact, site-directed mutagenesis of T492 and S663 on AAV6 capsid to valine (V) improved transduction efficiency of these vectors in moDCs. Combination of both mutations on a single capsid led to further augmentation of transduction by ≈5-fold compared with WT-AAV6 vectors. This significant improvement in infectivity of capsid-optimized over WT-AAV6 vectors was associated with advanced nuclear translocation and not facilitated viral entry into cells which was confirmed by qPCR analysis. These data indicate that ≈85% of viral genomes of mutant vectors accumulated in the nucleus 24 hrs post infection compared with ≈50% of WT-AAV6 vectors at the same time point of tyrosine residues.

Another important advantage of the employment of such capsid modified AAV6 vectors for vaccination studies is that efficient nuclear translocation in DCs will provide less material for potential presentation, and might prevent induction of immunocompetition in immune responses against vector-derived and antigen-derived epitopes. The current and recent studies highlight the requirement for specific residue types and certain conserved positions on the AAV capsid for improvement of infection. However, it is possible that other optimal combinations could be discovered by combining mutations on a single AAV6 capsid, which were not included in the present studies to achieve maximal augmentation in transduction efficiency.

On the other hand, the use of specific promoters represents an important approach for immunization to limit gene expression to target cells and address safety concerns associated with viral vector-based vaccines. Though self-complementary AAV (scAAV) vectors bypass the requirement for viral second-strand DNA synthesis and significantly improve gene expression in a number of cells including DCs, the packaging capacity of these vectors (≈2.4 kb) is significantly smaller than that of conventional single-stranded (ssAAV) vectors (≈5 kb). A common AAV expressing cassette includes the promoter, the gene of interest and the polyA signal which limits the size of each functional element. DC-specific promoters, such as CD11c, which restrict expression of the respective genes to immature and mature antigen-presenting cells, are much larger in size. To this end, the inventors and their collaborators first identified short DNA elements of CD11c promoter that activated EGFP expression in the context of this AAV vector expression cassette. Computational analysis was then used to predict possible TFBSs involved in promoter activity and categorized these factors into three groups.

The first group includes binding motifs for TFBSs, which are shown to be associated with DC development and maturation such as PU1, Ikaros, Ap1, Sp1, IRF-2 and IRF-8.42, 45, 46 The second group contains TFs widely involved in many cells including DC development and differentiation such as PPAR-cL and PPAR-'y, STAT3 and E2A, or pro-inflammatory cytokine regulation such as NF-kB and STAT5. The third group lists TFs such as Topors-1, RFX, Pax5 and HMGIY involved in transcriptional regulation in many cell types, which attracted attention because computational analysis revealed the corresponding binding sites on both parts of the CD11c promoter that showed functional activity.

Finally, the DNA sequences enriched with these TFBSs were combined together with an SV40 enhancer element to build a chimeric promoter (SV40-CD11c-3/5) with cumulative activity in moDCs. The present example outlined the possibility of development of rationally designed chimeric promoters, which can drive high levels of expression without sacrificing specificity in DCs. However, these studies were limited to DCs derived from monocytes that undergo phenotypical changes through stimulation by a particular cytokine mixture.

Although CD11c is a common marker within DC subsets, it is possible that other parts of the full-length promoter may be responsible for promoter activity due to a difference in transcriptional network activated during development of these DC lineages. Moreover, since in vitro DC maturation can be promoted by different stimuli, such as LPS, CD40L/TNF-cL or cytokine mixture, which activate only partially overlapping signaling cascades, it is possible to intentionally select some parts of the promoter over others for the maturation cocktail of choice.

Considering the relatively short period between the initiation of maturation and cytopathic changes in DCs, rapid expression of antigen is critical to provide appropriate signals for T-cell activation. Thus, the inventors evaluated whether increased transduction efficiency of moDCs by mutant AAV6 vectors is associated with better antigen presentation and consequent priming of T cells. These results suggest that modifications of S663V and T492V on the AAV6 capsid are indeed beneficial in terms of producing more effective vectors for gene delivery to DCs, and generating robust antigen-specific CTLs. Antigen expression in DCs driven by the short chmCD11c (SV40-CD11c-3/5) promoter, as well as the killing ability of the corresponding CTLs, was lower than generated by the CBA promoter in the same AAV capsid, though overall the activity of these CTLs was superior. In summary, these results provide proof of the efficacy and safety of a combination of capsid-modified and promoter-optimized AAV vectors for use in DC-based anti-cancer vaccine development.

REFERENCES

The following references, to the extent that they provide exemplary procedural or other details supplementary to those set forth herein, are specifically incorporated herein by reference:

Aasen, T, and Belmonte, J C, "Isolation and cultivation of human keratinocytes from skin or plucked hair for the generation of induced pluripotent stem cells," *Nat. Protocol.*, 5:371-382 (2010).

Abella, J V et al., "Met/hepatocyte growth factor receptor ubiquitination suppresses transformation and is required for Hrs phosphorylation," *Molec. Cell. Biol.*, 25:9632-9645 (2005).

Akache, B et al., "The 37/67-kilodalton laminin receptor is a receptor for adeno-associated virus serotypes 8, 2, 3, and 9," *J. Virol.*, 80:9831-9836 (2006).

Aldrich, W A et al., "Enhanced transduction of mouse bone marrow-derived dendritic cells by repetitive infection with self-complementary adeno-associated virus 6 combined with immunostimulatory ligands," *Gene Ther.*, 13(1):29-39 (2006).

Alexander, I E et al., "Transfer of contaminants in adeno-associated virus vector stocks can mimic transduction and lead to artifactual results," *Hum. Gene Ther.*, 8:1911-1920 (1997).

Allen, H et al., "Expression of epidermal-growth-factor receptor in the K562 cell line by transfection," *Biochem. J.*, 271:785-790 (1990).

Andreakos, E et al., "Activation of NF-κB by the intracellular expression of NF-κB-inducing kinase acts as a powerful vaccine adjuvant," *Proc. Nat'l. Acad. Sci. USA*, 103(39):14459-14464 (2006).

Aoki, T et al., "Generation of induced pluripotent stem cells from human adipose-derived stem cells without c-MYC," *Tissue Eng. Part A*, 16:2197-2206 (2010).

Aslanidi, G V et al., "Optimization of the capsid of recombinant adeno-associated virus 2 (AAV2) vectors: the final threshold?" *PLoS One*, 8:e59142 (2013).

Aslanidi, G V et al., "An inducible system for highly efficient production of recombinant adeno-associated virus (rAAV) vectors in insect Sf9 cells," *Proc. Nat'l. Acad. Sci. USA*, 106(13):5059-5064 (2009).

Aslanidi, G V et al., "Ectopic expression of wnt10b decreases adiposity and improves glucose homeostasis in obese rats," *Am. J. Physiol. Endocrinol. Metab.*, 293(3): E726-E736 (2007).

Aslanidi, G V et al., "High-efficiency transduction of human monocyte-derived dendritic cells by capsid-modified recombinant AAV2 vectors," *Vaccine*, 30:3908-3917 (2012).

Asokan, A et al., "The AAV vector toolkit: poised at the clinical crossroads," *Mol. Ther.*, 20:699-708 (2012).

Bainbridge, J W et al., "Effect of gene therapy on visual function in Leber's congenital amaurosis," *N. Engl. J. Med.*, 358(21):2231-2239 (2008).

Banchereau, J and Steinman, R M, "Dendritic cells and the control of immunity," *Nature*, 392(6673):245-252 (1998).

Beatty, G L and Vonderheide, R H, "Telomerase as a universal tumor antigen for cancer vaccines," *Exp. Rev. Vaccines*, 7(7):881-887 (2008).

Bleker, S et al., "Impact of capsid conformation and Rep-capsid interactions on adeno-associated virus type 2 genome packaging," *J. Virol.*, 80:810-820 (2006).

Blin, G et al., "A purified population of multipotent cardiovascular progenitors derived from primate pluripotent stem cells engrafts in postmyocardial infarcted nonhuman primates," *J. Clin. Invest.*, 120:1125-1139 (2010).

Boisleve, F et al., "Implication of the MAPK pathways in the maturation of human dendritic cells induced by nickel and TNF-α," *Toxicology*, 206(2):233-244 (2005).

Boutin, S et al., "Prevalence of serum IgG and neutralizing factors against adeno-associated virus (AAV) types 1, 2, 5, 6, 8, and 9 in the healthy population: implications for gene therapy using AAV vectors," *Hum. Gene Ther.*, 21:704-712 (2010).

Brambrink, T et al., "Sequential expression of pluripotency markers during direct reprogramming of mouse somatic cells," *Cell Stem Cell*, 2:151-159 (2008).

Brantly, M L et al., "Sustained transgene expression despite T lymphocyte responses in a clinical trial of rAAV1-AAT gene therapy," *Proc. Nat'l. Acad. Sci. USA*, 106(38): 16363-16368 (2009).

Brown, B D and Lillicrap, D, "Dangerous liaisons: the role of 'danger' signals in the immune response to gene therapy," *Blood*, 100(4):1133-1140 (2002).

Cao, O et al., "Induction and role of regulatory CD4+CD25+ T cells in tolerance to the transgene product following hepatic in vivo gene transfer," *Blood*, 110(4):1132-1140 (2007).

Carrillo-Tripp, M et al., "VIPERdb2: An enhanced and web API enabled relational database for Structural Virology," *Nucl. Acids Res.*, 37:D436-442 (2009).

Castanier, C et al., "Mitochondrial dynamics regulate the RIG-I-like receptor antiviral pathway," *EMBO Rep.*, 11(2):133-138 (2010).

Cavazzana-Calvo M et al., "Transfusion independence and HMGA2 activation after gene therapy of human β-thalassaemia," *Nature*, 467:318-322 (2010).

Cearley, C N and Wolfe, J H, "A single injection of an adenoassociated virus vector into nuclei with divergent connections results in widespread vector distribution in the brain and global correction of a neurogenetic disease," *J. Neurosci.*, 27:9928-9940 (2007).

Chapuis, F et al., "Differentiation of human dendritic cells from monocytes in vitro," *Eur. J. Immunol.*, 27(2):431-441 (1997).

Chatterjee, S et al., "Transduction of primitive human marrow and cord blood-derived hematopoietic progenitor cells with adeno-associated virus vectors," *Blood*, 93:1882-1894 (1999).

Chen, T T et al., "E-cadherin-mediated cell-cell contact is critical for induced pluripotent stem cell generation," *Stem Cells*, 28:1315-1325 (2010).

Chen, T T et al., "Establishment and characterization of a cancer cell line derived from an aggressive childhood liver tumor," *Ped. Blood Cancer*, 53:1040-1047 (2009).

Cheng, B et al., "Development of optimized AAV3 serotype vectors: mechanism of high-efficiency transduction of human liver cancer cells," *Gene Ther.*, 19(4):375-384 (2011).

Chiorini, J A et al., "Cloning and characterization of adeno-associated virus type 5," *J. Virol.*, 73:1309-1319 (1999).

Chiorini, J A et al., "Cloning of adeno-associated virus type 4 (AAV4) and generation of recombinant AAV4 particles," *J. Virol.*, 71:6823-6833 (1997).

Cho, H J et al., "Induction of pluripotent stem cells from adult somatic cells by protein-based reprogramming without genetic manipulation," *Blood*, 116:386-395 (2010).

Cideciyan, A V et al., "Human gene therapy for RPE65 isomerase deficiency activates the retinoid cycle of vision but with slow rod kinetics," *Proc. Nat'l. Acad. Sci. USA*, 105(39):15112-15117 (2008).

Cohn, E F et al., "Efficient induction of immune tolerance to coagulation factor IX following direct intramuscular gene transfer," *J. Thromb. Haemost.*, 5(6):1227-1236 (2007).

Cuzzocrea, S et al., "Pyrrolidine dithiocarbamate attenuates the development of acute and chronic inflammation," *Br. J. Pharmacol.*, 135(2):496-510 (2002).

Dai, Y and Siemann, D W, "BMS-777607, a small-molecule Met kinase inhibitor, suppresses hepatocyte growth factor-stimulated prostate cancer metastatic phenotype in vitro," *Molec. Cancer Therapeut.*, 9:1554-1561 (2010).

Dalkara, D et al., "Enhanced gene delivery to the neonatal retina through systemic administration of tyrosine-mutated AAV9," *Gene Ther.*, 19:176-181 (2012).

Daya, S, and Berns, K I, "Gene therapy using adeno-associated virus vectors," *Clin. Microbiol. Rev.*, 21(4):583-593 (2008).

Dean, J et al., "Role of cyclic AMP-dependent kinase response element-binding protein in recombinant adeno-associated virus-mediated transduction of heart muscle cells," *Hum. Gene Ther.*, 20(9):1005-1012 (2009).

Dejardin, E, "The alternative NF-kappaB pathway from biochemistry to biology: pitfalls and promises for future drug development," *Biochem. Pharmacol.*, 72(9):1161-1179 (2006).

den Brok, M H et al., "Dendritic Cells: Tools and Targets for Antitumor Vaccination," *Exp. Rev. Vaccines*, 4(5):699-710 (2005).

Denard, J et al., "Human galectin 3 binding protein interacts with recombinant adeno-associated virus type 6," *J. Virol.*, 86:6620-6631 (2012).

Ding, W et al., "Intracellular trafficking of adeno-associated viral vectors," *Gene Ther.*, 12:873-880 (2005).

DiPaolo, N C et al., "Virus binding to a plasma membrane receptor triggers interleukin-1 alpha-mediated proinflammatory macrophage response in vivo," *Immunity*, 31(1):110-121 (2009).

DiPrimio, N et al., "Surface loop dynamics in adeno-associated virus capsid assembly," *J. Virol.*, 82(11):5178-5189 (2008).

Dobrzynski, E et al., "Induction of antigen-specific CD4+ T-cell anergy and deletion by in vivo viral gene transfer," *Blood*, 104(4):969-977 (2004).

Donsante, A et al., "AAV vector integration sites in mouse hepatocellular carcinoma," *Science*, 317:477 (2007).

Douar, A M et al., "Intracellular trafficking of adeno-associated virus vectors: routing to the late endosomal compartment and proteasome degradation," *J. Virol.*, 75:1824-1833 (2001).

Duan, D et al., "Circular intermediates of recombinant adeno-associated virus have defined structural characteristics responsible for long-term episomal persistence in muscle tissue," *J. Virol.*, 72:8568-8577 (1998).

Duan, D et al., "Endosomal processing limits gene transfer to polarized airway epithelia by adeno-associated virus," *J. Clin. Invest.*, 105:1573-1587 (2000).

Edelmann, S L et al., "Comparative promoter analysis in vivo: identification of a dendritic cell-specific promoter module," *Blood*, 118:40-49 (2011).

Eisold, S et al., "Induction of an anti-tumoral immune response by wild-type adeno-associated virus type 2 in an in vivo model of pancreatic carcinoma," *Pancreas*, 35(1):63-72 (2007).

Eminli, S et al., "Reprogramming of neural progenitor cells into induced pluripotent stem cells in the absence of exogenous Sox2 expression," *Stem Cells*, 26:2467-2474 (2008).

Emsley, P, and Cowtan K, "Coot: model-building tools for molecular graphics," *Acta Crystallogr. D. Biol. Crystallogr.*, 60:2126-2132 (2004).

Esteban, M A et al., "Vitamin C enhances the generation of mouse and human induced pluripotent stem cells," *Cell Stem Cell*, 6:71-79 (2010).

Ferrari, F K et al., "Second-strand synthesis is a rate-limiting step for efficient transduction by recombinant adeno-associated virus vectors," *J. Virol.*, 70:3227-3234 (1996).

Figdor, C G et al., "Dendritic cell immunotherapy: mapping the way," *Nat. Med.*, 10(5):475-480 (2004).

Finn, J D et al., "Proteasome inhibitors decrease AAV2 capsid derived peptide epitope presentation on MHC class I following transduction," *Mol. Ther.*, 18(1):135-142 (2010).

Fisher, K J et al., "Transduction with recombinant adeno-associated virus for gene therapy is limited by leading-strand synthesis," *J. Virol.*, 70:520-532 (1996).

Fisher-Adams, G et al., "Integration of adeno-associated virus vectors in CD34+ human hematopoietic progenitor cells after transduction," *Blood*, 88:492-504 (1996).

Flotte, T R et al., "Phase 2 clinical trial of a recombinant adeno-associated viral vector expressing alpha1-antitrypsin: interim results," *Hum. Gene Ther.*, 22:1239-1247 (2012).

Fusaki, N et al., "Efficient induction of transgene-free human pluripotent stem cells using a vector based on Sendai virus, an RNA virus that does not integrate into the host genome," *Proc. Jpn. Acad. Ser. B Phys. Biol. Sci.*, 85:348-362 (2009).

Gao, G P et al., "Adeno-associated viruses undergo substantial evolution in primates during natural infections," *Proc. Nat'l. Acad. Sci. USA*, 100(10):6081-6086 (2003).

Gao, G P et al., "Clades of adeno-associated viruses are widely disseminated in human yissues," *J. Virol.*, 78:6381-6388 (2004).

Gao, G P et al., "Novel adeno-associated viruses from Rhesus monkeys as vectors for human gene therapy," *Proc. Nat'l. Acad. Sci. USA*, 99:11854-11859 (2002).

Gilmore, T D, "Introduction to NF-κB: players, pathways, perspectives," *Oncogene*, 25(51):6680-6684 (2006).

Girod, A et al., "Genetic capsid modifications allow efficient re-targeting of adeno-associated virus type 2," *Nature Med.*, 5(12):1438 (1999).

Glushakova, L G et al., "AAV3-mediated transfer and expression of the pyruvate dehydrogenase E1 alpha subunit gene causes metabolic remodeling and apoptosis of human liver cancer cells," *Molec. Genet. Metabol.*, 98:289-299 (2009).

Goodman, S et al., "Recombinant adeno-associated virus-mediated gene transfer into hematopoietic progenitor cells," *Blood*, 84:1492-1500 (1994).

Gotoh, A, and Ohyashiki, K, "Role of bortezomib in the treatment of multiple myeloma," *Nippon Rinsho*, 65(12):2309-2314 (2007).

Gourzi, P et al., "Viral induction of AID is independent of the interferon and the Toll-like receptor signaling pathways but requires NF-κB," *J. Exp. Med.*, 204(2):259-265 (2007).

Govindasamy, L et al., "Structurally mapping the diverse phenotype of adeno-associated virus serotype 4," *J. Virol.*, 80:11556-11570 (2006).

Gray, S J et al., "Directed evolution of a novel adeno-associated virus (AAV) vector that crosses the seizure-compromised blood-brain barrier (BBB)," *Mol. Ther.*, 18(3):570-578 (2010).

Grieger, J C, and Samulski, R J, "Adeno-associated virus vectorology, manufacturing, and clinical applications," *Methods Enzymol.*, 507:229-254 (2002).

Guo, F et al., "Lack of nuclear factor-κB2/p100 causes a RelB-dependent block in early B lymphopoiesis," *Blood*, 112(3):551-559 (2008).

Habib, A A et al., "The epidermal growth factor receptor engages receptor interacting protein and nuclear factor-kappa B (NF-κB)-inducing kinase to activate NF-κB. Identification of a novel receptor-tyrosine kinase signalosome," *J. Biol. Chem.*, 276(12):8865-8874 (2001).

Han, Z et al., "Stable integration of recombinant adeno-associated virus vector genomes after transduction of murine hematopoietic stem cells," *Hum. Gene Ther.*, 19:267-278 (2008).

Handa, A et al., "Adeno-associated virus (AAV)-3-based vectors transduce haematopoietic cells not susceptible to transduction with AAV-2-based vectors," *J. Gen. Virol.*, 81 (Pt 8):2077-2084 (2000).

Hansen, J et al., "Adeno-associated virus type 2-mediated gene transfer: altered endocytic processing enhances transduction efficiency in murine fibroblasts," *J. Virol.*, 75:4080-4090 (2001).

Hansen, J et al., "Impaired intracellular trafficking of adeno-associated virus Type 2 vectors limits efficient transduction of murine fibroblasts," *J. Virol.*, 74:992-996 (2000).

Harbison, C E et al., "The parvovirus capsid odyssey: from the cell surface to the nucleus," *Trends Microbiol.*, 16:208-214 (2008).

Harley, C B, "Telomerase and cancer therapeutics," *Nat. Rev. Cancer*, 8(3):167-179 (2008).

Hauswirth, W W et al., "Treatment of leber congenital amaurosis due to RPE65 mutations by ocular subretinal injection of adeno-associated virus gene vector: short-term results of a phase I trial," *Hum. Gene Ther.*, 19:979-990 (2008).

Hayden, M S, and Ghosh, S, "Signaling to NF-kB," *Genes Develop.*, 18(18):2195-2224 (2004).

Heiser, A et al., "Autologous dendritic cells transfected with prostate-specific antigen RNA stimulate CTL responses against metastatic prostate tumors," *J. Clin. Invest.*, 109(3):409-417 (2002).

High, K A, and Aubourg, P, "rAAV human trial experience," *Methods Mol. Biol.*, 807:429-457 (2011).

Hiscott, J et al., "Convergence of the NF-κB and interferon signaling pathways in the regulation of antiviral defense and apoptosis," *Ann. N.Y. Acad. Sci.*, 1010:237-248 (2003).

Hiscott, J et al., "Manipulation of the nuclear factor-kappaB pathway and the innate immune response by viruses," *Oncogene*, 25(51):6844-6867 (2006).

Hoos, A et al., "A methodological framework to enhance the clinical success of cancer immunotherapy," *Nat. Biotechnol.*, 29:867-870 (2011).

Hotta, A, and Ellis, J, "Retroviral vector silencing during iPS cell induction: An epigenetic beacon that signals distinct pluripotent states," *J. Cell Biochem.*, 105:940-948 (2008).

Humbert, J M and Halary, F, "Viral and non-viral methods to genetically modify dendritic cells," *Curr. Gene Ther.*, 12:127-136 (2012).

Imren, S et al., "High-level beta-globin expression and preferred intragenic integration after lentiviral transduction of human cord blood stem cells," *J. Clin. Invest.*, 114:953-962 (2004).

Imren, S et al., "Permanent and panerythroid correction of murine beta thalassemia by multiple lentiviral integration in hematopoietic stem cells," *Proc. Nat'l. Acad. Sci. USA*, 99:14380-14385 (2002).

Jayandharan, G R et al., "Activation of the NF-kB pathway by adeno-associated virus (AAV) vectors and its implications in immune response and gene therapy," *Proc. Nat'l. Acad. Sci. USA*, 108(9):3743-3748 (2011).

Jia, F et al., "A nonviral minicircle vector for deriving human iPS cells," *Nat. Methods*, 7:197-199 (2002).

Jiang, H et al., "Effects of transient immunosuppression on adenoassociated, virus-mediated, liver-directed gene transfer in rhesus macaques and implications for human gene therapy," *Blood*, 108(10):3321-3328 (2006).

Kaji, K et al., "Virus-free induction of pluripotency and subsequent excision of reprogramming factors," *Nature*, 458:771-775 (2009).

Kashiwakura, Y et al., "Hepatocyte growth factor receptor is a coreceptor for adeno-associated virus type 2 infection," *J. Virol.*, 79:609-614 (2005).

Kauss, M A et al., "Enhanced long-term transduction and multilineage engraftment of human hematopoietic stem cells transduced with tyrosine-modified recombinant adenoassociated virus serotype 2," *Hum. Gene Ther.*, 21:1129-1136 (2010).

Keeler, A M et al., "Long-term correction of very long-chain acyl-CoA dehydrogenase deficiency in mice using AAV9 gene therapy," *Mol. Ther.*, 20:1131-1138 (2012).

Keen-Rhinehart, E et al., "AAV-mediated leptin receptor installation improves energy balance and the reproductive status of obese female Koletsky rats," *Peptides*, 26(12):2567-2578 (2005).

Kim, J B et al., "Generation of induced pluripotent stem cells from neural stem cells," *Nat. Protocol.*, 4:1464-1470 (2009).

Kohlbrenner, E et al., "Successful production of pseudotyped rAAV vectors using a modified baculovirus expression system," *Mol. Ther.*, 12:1217-1225 (2005).

Kota, J et al., "Therapeutic microRNA delivery suppresses tumorigenesis in a murine liver cancer model," *Cell*, 137:1005-1017 (2009).

Kube, D M, and Srivastava, A, "Quantitative DNA slot blot analysis: inhibition of DNA binding to membranes by magnesium ions," *Nucl. Acids Res.*, 25(16):3375-3376 (1997).

Kumar, N et al., "NF-κB signaling differentially regulates influenza virus RNA synthesis," *J. Virol.*, 82(20):9880-9889 (2008).

Kunisato, A et al., "Generation of induced pluripotent stem cells by efficient reprogramming of adult bone marrow cells," *Stem Cells Dev.*, 19:229-238 (2010).

Kurpad, C et al., "Adeno-associated virus 2-mediated transduction and erythroid lineage-restricted expression from parvovirus B19p6 promoter in primary human hematopoietic progenitor cells," *J. Hematother. Stem Cell Res.*, 8:585-592 (1999).

Lee, C C et al., "Effect of age on the frequency, cell cycle, and lineage maturation of rhesus monkey (*Macaca mulatta*) CD34+ and hematopoietic progenitor cells," *Pediatr. Res.*, 2005; 58:315-322.

Levasseur, D N et al., "Correction of a mouse model of sickle cell disease: lentiviral/antisickling beta-globin gene transduction of unmobilized, purified hematopoietic stem cells," *Blood*, 102:4312-4319 (2003).

Levy, H C et al., "Heparin binding induces conformational changes in adeno-associated virus serotype 2," *J. Struct. Biol.*, 165(3):146-156 (2009).

Li, C et al., "Cellular immune response to cryptic epitopes during therapeutic gene transfer," *Proc. Nat'l. Acad. Sci. USA*, 106(26):10770-10774 (2009).

Li, C et al., "Single amino acid modification of adeno-associated virus capsid changes transduction and humoral immune profiles," *J. Virol.*, 86:7752-7759 (2012).

Li, H et al., "Assessing the potential for AAV vector genotoxicity in a murine model," *Blood*, 117:3311-3319 (2011).

Li, M et al., "High-efficiency transduction of fibroblasts and mesenchymal stem cells by tyrosine-mutant AAV2 vectors for their potential use in cellular therapy," *Hum. Gene Ther.* 21:1527-1543 (2010).

Li, Q, and Verma, I M, "NF-κB regulation in the immune system," *Nat. Rev. Immunol.*, 2(10):725-734 (2002).

Li, W et al., "Generation of human-induced pluripotent stem cells in the absence of exogenous Sox2," *Stem Cells*, 27:2992-3000 (2009).

Lich, J D et al., "Monarch-1 suppresses non-canonical NF-kappaB activation and p52-dependent chemokine expression in monocytes," *J. Immunol.*, 178(3):1256-1260 (2007).

Lind, E F et al., "Dendritic cells require the NF-κB2 pathway for cross-presentation of soluble antigens," *J. Immunol.*, 181(1):354-363 (2008).

Ling, C et al., "Human Hepatocyte Growth Factor Receptor is a Cellular Co-Receptor for AAV3," *Hum. Gene Ther.*, 21:1741-1747 (2010).

Ling, C Q et al., "Inhibitory effect of recombinant adeno-virus carrying melittin gene on hepatocellular carcinoma," *Ann. Oncol.*, 16:109-115 (2005).

Liu, M A, "Immunologic basis of vaccine vectors," *Immunity*, 33(4):504-515 (2010).

Liu, S et al., "Melittin prevents liver cancer cell metastasis through inhibition of the Rac1-dependent pathway," *Hepatology (Baltimore, Md. )*, 47:1964-1973 (2008).

Liu, X et al., "Targeting the c-MET Signaling Pathway for Cancer Therapy," *Exp. Opin. Invest. Drugs*, 17:997-1011 (2008).

Liu, Y L et al., "Optimized production of high-titer recombinant adeno-associated virus in roller bottles," *Biotechniques*, 34(1):184-189 (2003).

Lizundia, R et al., "Host species-specific usage of the TLR4-LPS receptor complex," *Innate Immun.*, 14(4):223-231 (2008).

Lochrie, M A et al., "Mutations on the external surfaces of adeno-associated virus type 2 capsids that affect transduction and neutralization," *J. Virol.*, 80(2):821-834 (2006).

LoDuca, P A et al., "Hepatic gene transfer as a means of tolerance induction to transgene products," *Curr. Gene Ther.*, 9(2):104-114 (2009).

Loiarro, M et al., "Peptide-mediated interference of TIR domain dimerization in MyD88 inhibits interleukin-1-dependent activation of NF-κB," *J. Biol. Chem.*, 280(16): 15809-15814 (2005).

Ma, H et al., "Oral adeno-associated virus-sTRAIL gene therapy suppresses human hepatocellular carcinoma growth in mice," *Hepatology (Baltimore, Md.)*, 42:1355-1363 (2005).

Madsen, D et al., "AAV-2 induces cell mediated immune responses directed against multiple epitopes of the capsid protein VP1," *J. Gen. Virol.*, 90(11):2622-2633 (2009).

Maguire, A M et al., "Safety and efficacy of gene transfer for Leber's congenital amaurosis," *N. Engl. J. Med.*, 358(21): 2240-2248 (2008).

Mah, C et al., "Adeno-associated virus type 2-mediated gene transfer: role of epidermal growth factor receptor protein tyrosine kinase in transgene expression," *J. Virol.*, 72:9835-9843 (1998).

Mahadevan, M et al., "Generation of robust cytotoxic T lymphocytes against prostate specific antigen by transduction of dendritic cells using protein and recombinant adeno-associated virus," *Cancer Immunol. Immunother.*, 56(10):1615-1624 (2007).

Maina, N et al., "Optimization of recombinant adeno-associated viral vectors for human beta-globin gene transfer and transgene expression," *Hum. Gene Ther.*, 19:365-375 (2008).

Maina, N et al., "Recombinant self-complementary adeno-associated virus serotype vector-mediated hematopoietic stem cell transduction and lineage-restricted, long-term transgene expression in a murine serial bone marrow transplantation model," *Hum. Gene Ther.*, 19:376-383 (2008).

Malecki, M et al., "Recombinant adeno-associated virus derived vectors (rAAV2) efficiently transduce ovarian and hepatocellular carcinoma cells—implications for cancer gene therapy," *Acta Poloniae Pharmaceutica*, 66:93-99 (2009).

Mali, P et al., "Butyrate greatly enhances derivation of human induced pluripotent stem cells by promoting epigenetic remodeling and the expression of pluripotency-associated genes," *Stem Cells*, 28:713-720 (2010).

Malik, P et al., "Recombinant adeno-associated virus mediates a high level of gene transfer but less efficient integration in the K562 human hematopoietic cell line," *J. Virol.* 71:1776-1783 (1997).

Manno, C S et al., "Successful transduction of liver in hemophilia by AAV-Factor IX and limitations imposed by the host immune response," *Nat. Med.*, 12(3):342-347 (2006).

Markusic, D M et al., "High-efficiency transduction and correction of murine hemophilia B using AAV2 vectors devoid of multiple surface-exposed tyrosines," *Mol. Ther.*, 18(12):2048-2056 (2010).

Martin, E et al., "Antigen-specific suppression of a primed immune response by dendritic cells mediated by regulatory T cells secreting interleukin-10," *Immunity*, 18(1): 155-167 (2003).

Mattis, A E et al., "Analyzing cytotoxic T lymphocyte activity: a simple and reliable flow cytometry-based assay," *J. Immunol. Methods*, 204(2):135-142 (1997).

May, C et al., "Therapeutic haemoglobin synthesis in β-thalassaemic mice expressing lentivirus-encoded human β-globin," *Nature*, 406:82-86 (2000).

Mays, L E et al., "Adeno-associated virus capsid structure drives CD4-dependent CD8+ T cell response to vector encoded proteins," *J. Immunol.*, 182(10):6051-6060 (2009).

McCarty, D M et al., "Integration of adeno-associated virus (AAV) and recombinant AAV vectors," *Annu. Rev. Genet.*, 38:819-845 (2004).

McCarty, D M et al., "Adeno-associated virus terminal repeat (TR) mutant generates self-complementary vectors to overcome the rate-limiting step to transduction in vivo," *Gene Ther.*, 10:2112-2118 (2003).

McDermott, S P et al., "Comparison of human cord blood engraftment between immunocompromised mouse strains," *Blood*, 116:193-200 (2010).

Meilinger, D et al., "Np95 interacts with de novo DNA methyltransferases, Dnmt3α and Dnmt3β, and mediates epigenetic silencing of the viral CMV promoter in embryonic stem cells," *EMBO Rep.*, 10:1259-1264 (2009).

Mendell, J R et al., "Dystrophin immunity in Duchenne's muscular dystrophy," *N. Engl. J. Med.*, 363:1429-1437 (2010).

Mendell, J R et al., "Gene therapy for muscular dystrophy: lessons learned and path forward," *Neurosci. Lett.*, 12:341-355 (2012).

Miller, J L et al., "Single-copy transduction and expression of human gamma-globin in K562 erythroleukemia cells using recombinant adeno-associated virus vectors: the effect of mutations in NF-E2 and GATA-1 binding motifs within the hypersensitivity site 2 enhancer," *Blood*, 82:1900-1906 (1993).

Mineva, N D et al., "CD40 ligand-mediated activation of the de novo RelB NF-κB synthesis pathway in transformed B cells promotes rescue from apoptosis," *J. Biol. Chem.*, 282(24):17475-17485 (2007).

Mingozzi, F et al., "CD8(+) T-cell responses to adeno-associated virus capsid in humans," *Nat. Med.*, 13(4):419-422 (2007).

Mingozzi, F, and High, K A, "Immune responses to AAV in clinical trials," *Curr. Gene Ther.*, 7(5):316-324 (2007).

Mingozzi, F, and High, K A, "Therapeutic in vivo gene transfer for genetic disease using AAV: progress and challenges," *Nat. Rev. Genet.*, 12:341-355 (2011).

Miyachi, T et al., "Butyrate augments interferon alpha-induced S phase accumulation and persistent tyrosine phosphorylation of cdc2 in K562 cells," *Br. J. Cancer*, 79:1018-1024 (1999).

Mueller, C, and Flotte, T R, "Clinical gene therapy using recombinant adeno-associated virus vectors," *Gene Ther.*, 15(11):858-863 (2008).

Muramatsu, S et al., "Nucleotide sequencing and generation of an infectious clone of adeno-associated virus 3," *Virology*, 221:208-217 (1996).

Muruve, D A et al., "The inflammasome recognizes cytosolic microbial and host DNA and triggers an innate immune response," *Nature*, 452(7183):103-107 (2008).

Muzyczka, N, "Use of adeno-associated virus as a general transduction vector for mammalian cells," *Curr. Top. Microbiol. Immunol.*, 158:97-129 (1992).

Muzyczka, N, and Warrington, K H, "Custom adeno-associated virus capsids: the next generation of recombinant vectors with novel tropism," *Hum. Gene Ther.*, 16:408-416 (2005).

Myklebust, J H et al., "Protein kinase C-α isoform is involved in erythropoietin-induced erythroid differentiation of CD34(+) progenitor cells from human bone marrow," *Blood*, 95:510-518 (2000).

Nakabayashi, H et al., "Growth of human hepatoma cells lines with differentiated functions in chemically-defined medium," *Cancer Res.*, 42:3858-3863 (1982).

Nakagawa, M et al., "Generation of induced pluripotent stem cells without Myc from mouse and human fibroblasts," *Nat. Biotechnol.*, 26:101-106 (2008).

Nakahara, T et al., "Differential role of MAPK signaling in human dendritic cell maturation and Th1/Th2 engagement," *J. Dermatol. Sci.*, 42(1):1-11 (2006).

Nakahara, T et al., "Role of c-Jun N-terminal kinase on lipopolysaccharide induced maturation of human monocyte-derived dendritic cells," *Int. Immunol.*, 16(12):1701-1709 (2004).

Nakai, H et al., "Extra-chromosomal recombinant adeno-associated virus vector genomes are primarily responsible for stable liver transduction in vivo," *J. Virol.* 75:6969-6976 (2001).

Nakai, H et al., "Isolation of recombinant adeno-associated virus vector-cellular DNA junctions from mouse liver," *J. Virol.*, 73:5438-5447 (1999).

Nam, H J et al., "Structural studies of adeno-associated virus serotype 8 capsid transitions associated with endosomal trafficking," *J. Virol.*, 85:11791-11799 (2011).

Nathwani, A C et al., "Adenovirus-associated virus vector-mediated gene transfer in hemophilia B," *N. Engl. J. Med.*, 365:2357-2365 (2011).

Nathwani, A C et al., "Self-complementary adeno-associated virus vectors containing a novel liver-specific human factor IX expression cassette enable highly efficient transduction of murine and nonhuman primate liver," *Blood*, 107(7):2653-2661 (2006).

Naumer, M et al., "Properties of the adeno-associated virus assembly-activating protein," *J. Virol.*, 86:13038-13048 (2012).

Nguyen, L et al., "Association of the multisubstrate docking protein Gab1 with the hepatocyte growth factor receptor requires a aunctional Grb2 binding site involving tyrosine 1356," *J. Biol. Chem.*, 272:20811-20819 (1997).

Ni, J et al., "Targeting anti-tumor DNA vaccines to dendritic cells via a short CD11c promoter sequence," *Vaccine*, 27:5480-5487 (2009).

Niemeyer, G P et al., "Long-term correction of inhibitor-prone hemophilia B dogs treated with liver-directed AAV2-mediated factor IX gene therapy," *Blood*, 113(4): 797-806 (2009).

Nonnenmacher, M, and Weber, T, "Intracellular transport of recombinant adeno-associated virus vectors," *Gene Ther.*, 19:649-658 (2012).

Notta, F et al., "Engraftment of human hematopoietic stem cells is more efficient in female NOD/SCID/IL-2Rgc-null recipients," *Blood*, 115:3704-3707 (2010).

Oh, I H et al., "Expression of an anti-sickling beta-globin in human erythroblasts derived from retrovirally transduced primitive normal and sickle cell disease hematopoietic cells," *Exp. Hematol.*, 32:461-469 (2004).

Okada, M, and Yoneda, Y, "The timing of retroviral silencing correlates with the quality of induced pluripotent stem cell lines," *Biochim. Biophys. Acta*, 1810:226-235 (2011).

Okita, K et al., "Generation of mouse induced pluripotent stem cells without viral vectors," *Science*, 322:949-953 (2008).

Okita, K et al., "Generation of germline-competent induced pluripotent stem cells," *Nature*, 448:313-317 (2007).

Okumura, A et al., "Interaction between Ebola virus glycoprotein and host toll-like receptor 4 leads to induction of proinflammatory cytokines and SOCS1," *J. Virol.*, 84(1): 27-33 (2010).

O'Neill, D W, and Bhardwaj, N, "Exploiting dendritic cells for active immunotherapy of cancer and chronic infections," *Mol. Biotechnol.*, 36(2):131-141 (2007).

Opie, S R et al., "Identification of amino acid residues in the capsid proteins of adeno-associated virus type 2 that contribute to heparan sulfate proteoglycan binding," *J. Virol.*, 77:6995-7006 (2003).

Owen, R T et al., "Gene therapy for pyruvate dehydrogenase Ela deficiency using recombinant adeno-associated virus 2 (rAAV2) vectors," *Mol. Ther.*, 6(3):394-399 (2002).

Palucka, K et al., "Recent developments in cancer vaccines," *J. Immunol.*, 186(3):1325-1331 (2011).

Papadakis, E D et al., "Promoters and control elements: designing expression cassettes for gene therapy," *Curr. Gene Ther.*, 4:89-113 (2004).

Pawliuk, R et al., "Retroviral vectors aimed at the gene therapy of human beta-globin gene disorders," *Ann. NY Acad. Sci.*, 850:151-162 (1998).

Pawliuk, R et al., "Correction of sickle cell disease in transgenic mouse models by gene therapy," *Science*, 294:2368-2371 (2001).

Paz, H et al., "Quiescent subpopulations of human CD34-positive hematopoietic stem cells are preferred targets for stable recombinant adeno-associated virus type 2 transduction," *Hum. Gene Ther.*, 18:614-26 (2007).

Pearson and Lipman, "Improved tools for biological sequence comparison," *Proc. Nat'l. Acad. Sci. USA*, 85(8):2444-8 (1988).

Peng, D et al., "Transduction of hepatocellular carcinoma (HCC) using recombinant adeno-associated virus (rAAV): in vitro and in vivo effects of genotoxic agents," *J. Hepatol.*, 32:975-985 (2000).

Petrs-Silva, H et al., "High-efficiency transduction of the mouse retina by tyrosine-mutant AAV serotype vectors," *Mol. Ther.*, 17:463-471 (2009).

Pierce, J W et al., "Novel inhibitors of cytokine-induced IκBα phosphorylation and endothelial cell adhesion molecule expression show anti-inflammatory effects in vivo," *J. Biol. Chem.*, 272(34):21096-21103 (1997).

Ponnazhagan, S et al., "Transcriptional transactivation of parvovirus B19 promoters in in non-permissive cells by adenovirus type 2," *J. Virol.*, 69:8096-8101 (1995).

Ponnazhagan, S et al., "Adeno-associated virus type 2-mediated transduction of murine hematopoietic cells with long-term repopulating ability and sustained expression of a human globin gene in vivo," *J. Virol.*, 71:3098-3104 (1997).

Ponnazhagan, S et al., "Adeno-associated virus type 2-mediated transduction in primary human bone marrow-derived CD34$^+$ hematopoietic progenitor cells: donor variation and correlation of transgene expression with cellular differentiation," *J. Virol.*, 71:8262-8267 (1997).

Ponnazhagan, S et al., "Adeno-associated virus type 2-mediated transduction of human monocyte-derived dendritic cells: implications for ex vivo immunotherapy," *J. Virol.*, 75(19):9493-9501 (2001).

Puthenveetil, G et al., "Successful correction of the human beta-thalassemia major phenotype using a lentiviral vector," *Blood*, 104:3445-3453 (2004).

Qiao, C et al., "AAV6 Capsid tyrosine to phenylalanine mutations improve gene transfer to skeletal muscle," *Hum. Gene Ther.*, 21:1343-1348 (2010).

Qing, G et al., "Stabilization of basally translated NF-κB-inducing kinase (NIK) protein functions as a molecular switch of processing of NF-κB2 p100," *J. Biol. Chem.*, 280(49):40578-40582 (2005).

Qing, K et al., "Adeno-associated virus type 2-mediated gene transfer: role of cellular FKBP52 protein in transgene expression," *J. Virol.*, 75:8968-8976 (2001).

Qing, K et al., "Human fibroblast growth factor receptor 1 is a co-receptor for infection by adeno-associated virus 2," *Nature Med.*, 5:71-77 (1999).

Qing, K et al., "Role of tyrosine phosphorylation of a cellular protein in adeno-associated virus 2-mediated transgene expression," *Proc. Nat'l. Acad. Sci. USA*, 94(20):10879-10884 (1997).

Robert-Guroff, M, "Replicating and non-replicating viral vectors for vaccine development," *Curr. Opin. Biotechnol.*, 18(6):546-556 (2007).

Ross, C J et al., "Correction of feline lipoprotein lipase deficiency with adeno-associated virus serotype 1-mediated gene transfer of the lipoprotein lipase S447X beneficial mutation," *Hum. Gene Ther.*, 17(5):487-499 (2006).

Rutledge, E A et al., "Infectious Clones and Vectors Derived from Adeno-Associated Virus (AAV) Serotypes Other Than AAV Type 2," *J. Virol.*, 72:309-319 (1998).

Sanlioglu, S et al., "Endocytosis and Nuclear Trafficking of Adeno-Associated Virus Type 2 are Controlled by Rac1 and Phosphatidylinositol-3 Kinase Activation," *J. Virol.*, 74:9184-9196 (2000).

Santat, L et al., "Recombinant AAV2 transduction of primitive human hematopoietic stem cells capable of serial engraftment in immune-deficient mice," *Proc. Nat'l. Acad. Sci. USA*, 102:11053-11058 (2005).

Scallan, C D et al., "Sustained phenotypic correction of canine hemophilia A using an adeno-associated viral vector," *Blood*, 102(6):2031-2037 (2003).

Schimmentim, S et al., "Long-term genetic modification of Rhesus monkey hematopoietic cells following transplantation of adeno-associated virus vector-transduced CD34+ cells," *Hum. Gene Ther.*, 9:2727-2734 (1998).

Schlom, J et al., "Role of vaccine therapy in cancer: biology and practice," *Curr. Oncol.*, 14:238-245 (2007).

Schnepp, B C et al., "Genetic fate of recombinant adeno-associated virus vector genomes in muscle," *J. Virol.*, 77:3495-3504 (2003).

Schroeder, G M et al., "Discovery of N-(4-(2-amino-3-chloropyridin-4-yloxy)-3-fluorophenyl)-4-ethoxy-1-(4-fluorophenyl)-2-oxo-1,2-dihydropyridine-3-carboxamide (BMS-777607), a selective and orally efficacious inhibitor of the Met kinase superfamily," *J. Med. Chem.*, 52:1251-1254 (2009).

Schuhmann, N K et al., "Gene transfer into human cord blood-derived CD34(+) cells by adeno-associated viral vectors," *Exp. Hematol.*, 38:707-717 (2010).

Shade, R O et al., "Nucleotide sequence and genome organization of human parvovirus B19 isolated from the serum of a child during aplastic crisis," *J. Virol.*, 58:921-936 (1986).

Shin, O et al., "Effective transduction by self-complementary adeno-associated viruses of human dendritic cells with no alteration of their natural characteristics," *J. Gene Med.*, 10(7):762-769 (2008).

Simonelli, F et al., "Gene therapy for Leber's congenital amaurosis is safe and effective through 1.5 years after vector administration," *Mol. Ther.*, 18:643-650 (2010).

Snyder, R O et al., "Correction of hemophilia B in canine and murine models using recombinant adeno-associated viral vectors," *Nature Med.*, 5(1):64-70 (1999).

Sommer, C A et al., "Induced pluripotent stem cell generation using a single lentiviral stem cell cassette," *Stem Cells*, 27:543-549 (2009).

Song, L et al., "Optimizing the transduction efficiency of human hematopoietic stem cells using capsid-modified AAV6 vectors in vitro and in a xenograft mouse model in vivo," *Cytotherapy*, 15(8):986-998 (2013).

Song, L et al., "High-efficiency transduction of primary human hematopoietic stem cells and erythroid lineage-restricted expression by optimized AAV6 serotype vectors in vitro and in a murine xenograft model in vivo," *PloS One*, 8:e58757 (2013).

Song, S et al., "Sustained secretion of human α-1-antitrypsin from murine muscle transduced with adeno-associated virus vectors," *Proc. Nat'l. Acad. Sci. USA*, 95:14384-14388 (1998).

Song, S et al., "Stable therapeutic serum levels of human −1 antitrypsin (AAT) after portal vein injection of recombinant adeno-associated virus (rAAV) vectors," *Gene Ther.*, 8:1299-1306 (2001a).

Song, S et al., "Effect of DNA-dependent protein kinase on the molecular fate of the rAAV2 genome in skeletal muscle," *Proc. Nat'l. Acad. Sci. USA*, 98:4084-4088 (2001b).

Song, S et al., "DNA-dependent PK inhibits adeno-associated virus DNA integration," *Proc. Nat'l. Acad. Sci. USA*, 101:2112-2116 (2004).

Song, S et al., "Recombinant adeno-associated virus-mediated alpha-1 antitrypsin gene therapy prevents type I diabetes in NOD mice," *Gene Ther.*, 11(2):181-186 (2004).

Srivastava, A, "Adeno-associated virus-mediated gene transfer," *J. Cell. Biochem.*, 105(1):17-24 (2008).

Srivastava, A, "Hematopoietic stem cell transduction by recombinant adeno-associated virus vectors: problems and solutions," *Hum. Gene Ther.*, 16:792-798 (2005).

Srivastava, A, "Obstacles to human hematopoietic stem cell transduction by recombinant adeno-associated virus 2 vectors," *J. Cell Biochem.*, 38:39-45 (2002).

Stadtfeld, M, and Hochedlinger, K, "Induced pluripotency: History, mechanisms, and applications," *Genes Dev.*, 24:2239-2263 (2010).

Su, H et al., "Adeno-associated viral-mediated gene transfer to hepatoma: thymidine kinase/interleukin 2 is more effective in tumor killing in non-ganciclovir (GCV)-treated than in GCV-treated animals," *Mol. Ther.*, 1:509-515 (2000).

Su, H et al., "Selective killing of AFP-positive hepatocellular carcinoma cells by adeno-associated virus transfer of the Herpes simplex virus thymidine kinase gene," *Hum. Gene Ther.*, 7:463-470 (1996).

Summerford, C et al., "AlphaVbeta5 Integrin: A co-receptor for adeno-associated virus type 2 infection," *Nature Med.*, 5:78-82 (1999).

Summerford, C, and Samulski, R J, "Membrane-associated heparan sulfate proteoglycan is a receptor for adeno-associated virus type 2 virions," *J. Virol.*, 72:1438-1445 (1998).

Sun, N et al., "Feeder-free derivation of induced pluripotent stem cells from adult human adipose stem cells," *Proc. Nat'l. Acad. Sci. USA*, 106:15720-15725 (2009).

Tacken, P J et al., "Dendritic-cell immunotherapy: from ex vivo loading to in vivo targeting," *Nat. Rev. Immunol.*, 7(10):790-802 (2007).

Takahashi, K et al., "Induction of pluripotent stem cells from adult human fibroblasts by defined factors," *Cell*, 131:861-872 (2007).

Takahashi, K, and Yamanaka, S, "Induction of pluripotent stem cells from mouse embryonic and adult fibroblast cultures by defined factors," *Cell*, 126:663-676 (2006).

Takenaka, C et al., "Effective generation of iPS cells from $CD34^+$ cord blood cells by inhibition of p53," *Exp. Hematol.*, 38:154-162 (2010).

Tan, M et al., "Adeno-associated virus 2-mediated transduction and erythroid lineage-restricted long-term expression of the human beta-globin gene in hematopoietic cells from homozygous beta-thalassemic mice," *Mol. Ther.*, 3:940-946 (2001).

Tang, Z Y, "Hepatocellular carcinoma surgery—review of the past and prospects for the 21st century," *J. Surg. Oncol.*, 91:95-96 (2005).

Tannous, B A "*Gaussia* luciferase reporter assay for monitoring biological processes in culture and in vivo," *Nat. Protoc.*, 4:582-591 (2009).

Taylor, J, and Ussher, J E, "Optimized Transduction of Human Monocyte-Derived Dendritic Cells by Recombinant Adeno-Associated Virus Serotype 6 (rAAV6)," *Hum. Gene Ther.*, 21:1675-1686 (2010).

Thomas, C E et al., "Rapid uncoating of vector genomes is the key to efficient liver transduction with pseudotyped adeno-associated virus vectors," *J. Virol.*, 78:3110-3122 (2004).

Tian, J et al., "Recombinant AAV2-mediated β-globin expression in human fetal hematopoietic cells from the aborted fetuses with β-thalassemia major," *Int. J. Hematol.*, 93:691-699 (2011).

Tse, L Y et al., "Adeno-associated virus-mediated expression of kallistatin suppresses local and remote hepatocellular carcinomas," *J. Gene Med.*, 10:508-517 (2008).

Tuan, D et al., "Transcription of the hypersensitive site HS2 enhancer in erythroid cells," *Proc. Nat'l. Acad. Sci. USA*, 89:11219-11223 (1992).

Ueno, H et al., "Harnessing human dendritic cell subsets for medicine," *Immunol. Rev.*, 234:199-212 (2010).

Ueno, H et al., "Targeting human dendritic cell subsets for improved vaccines," *Semin. Immunol.*, 23:21-27 (2011).

Ussher, J E, and Taylor, J A, "Optimized transduction of human monocyte-derived dendritic cells by recombinant adeno-associated virus serotype 6," *Hum. Gene Ther.*, 21:1675-1686 (2010).

Vandenberghe, L H et al., "Tailoring the AAV vector capsid for gene therapy," *Gene Ther.*, 16(3):311-319 (2009).

Vandenberghe, L H, and Wilson, J M, "AAV as an immunogen," *Curr. Gene Ther.*, 7(5):325-333 (2007).

Veldwijk, M R et al., "Pseudotyped recombinant adenoassociated viral vectors mediate efficient gene transfer into primary human CD34(+) peripheral blood progenitor cells. Cytotherapy," 12:107-112 (2010).

Veron, P et al., "Major subsets of human dendritic cells are efficiently transduced by self-complementary adeno-associated virus vectors 1 and 2," J. Virol., 81(10):5385-5394 (2007).

Walsh, C E et al., "Regulated high level expression of a human gamma-globin gene introduced into erythroid cells by an adeno-associated virus vector," Proc. Nat'l. Acad. Sci. USA, 89:7257-7261 (1992).

Wang, C et al., "Melittin, a major component of bee venom, sensitizes human hepatocellular carcinoma cells to tumor necrosis factor-related apoptosis-inducing ligand (TRAIL)-induced apoptosis by activating CaMKII-TAK1-JNK/p38 and inhibiting IκBα kinase-NFκB," J. Biol. Chem., 284:3804-3813 (2009).

Wang, L et al., "The pleiotropic effects of natural AAV infections on liver-directed gene transfer in macaques," Mol. Ther., 18(1):126-134 (2010).

Wang, W, and Malcolm, B A, "Two-stage PCR protocol allowing introduction of multiple Mutations, deletions and insertions using QuikChange site-directed mutagenesis," Biotechniques; 26(4):680-682 (1999).

Wang, X S et al., "Parvovirus B19 promoter at map unit 6 confers autonomous replication competence and erythroid specificity to adeno-associated virus 2 in primary human hematopoietic progenitor cells," Proc. Nat'l. Acad. Sci. USA, 92:12416-12420 (1995).

Wang, Y et al., "Potent antitumor effect of TRAIL mediated by a novel adeno-associated viral vector targeting to telomerase activity for human hepatocellular carcinoma," J. Gene Med., 10:518-526 (2008).

Wang, Y et al., "The efficacy of combination therapy using adeno-associated virus-TRAIL targeting to telomerase activity and cisplatin in a mice model of hepatocellular carcinoma," J. Cancer Res. Clin. Oncol., 136:1827-1837 (2010).

Wang, Z et al., "Rapid and Highly Efficient Transduction by Double-Stranded Adeno-Associated Virus Vectors in vitro and in vivo," Gene Ther., 10(26):2105-2111 (2003).

Warren, L et al., "Highly efficient reprogramming to pluripotency and directed differentiation of human cells with synthetic modified mRNA. Cell Stem Cell 7:618-630 (2010).

Weller, M L et al., "Epidermal growth factor receptor is a co-receptor for adeno-associated virus serotype 6. Nat Med 16:662-664 (2010).

Weltner, J et al., "Induced pluripotent stem cell clones reprogrammed via recombinant adeno-associated virus-mediated transduction contain integrated vector sequences," J. Virol., 86:4463-4467 (2012a).

Wilber, A et al., "Therapeutic levels of fetal hemoglobin in erythroid progeny of beta-thalassemic CD34+ cells after lentiviral vector-mediated gene transfer," Blood, 117: 2817-2826 (2011).

Witt, O et al., "Butyrate-induced erythroid differentiation of human K562 leukemia cells involves inhibition of ERK and activation of p38 MAP kinase pathways," Blood, 95:2391-2396 (2000).

Wu, J et al., "Self-complementary recombinant adeno-associated viral vectors: packaging capacity and the role of Rep proteins in vector purity," Hum. Gene Ther., 18:171-182 (2007).

Wu, P et al., "Mutational analysis of the adeno-associated virus type 2 (AAV2) capsid gene and construction of AAV2 vectors with altered tropism," J. Virol., 74:8635-8647 (2000).

Wu, Z et al., "Adeno-associated virus serotypes: vector toolkit for human gene therapy," Mol. Ther., 14(3):316-327 (2006).

Wu, Z et al., "Single amino acid changes can influence titer, heparin binding, and tissue tropism in different adeno-associated virus serotypes," J. Virol., 80(22):11393-11397 (2006).

Wu, Z H, and Miyamoto, S, "Induction of a pro-apoptotic ATM-NF-kappaB pathway and its repression by ATR in response to replication stress," EMBO J., 27:1963-1973 (2008).

Wurdinger, T et al., "A secreted luciferase for ex vivo monitoring of in vivo processes," Nat. Methods, 5:171-173 (2008).

Xia, X et al., "Trans-genes delivered by lentiviral vector are suppressed in human embryonic stem cells in a promoter-dependent manner," Stem Cells Dev., 16:167-176 (2007).

Xiao, C, and Rossmann, M G, "Interpretation of electron density with stereographic roadmap projections," J. Struct. Biol., 158:182-187 (2007).

Xiao, P J, and Samulski, R J, "Cytoplasmic trafficking, endosomal escape, and perinuclear accumulation of AAV2 particles are facilitated by microtubule network," J. Virol., 86:10462-10473 (2012).

Xiao, W et al., "Adenovirus-facilitated nuclear translocation of adeno-associated virus type 2," J. Virol., 76:11505-11517 (2002).

Xiao, W et al., "Adenovirus-facilitated nuclear translocation of adeno-associated virus type 2," J. Virol., 76:11505-11517 (2002).

Xiao, X et al., "Production of high-titer recombinant adeno-associated virus vectors in the absence of helper adenovirus," J. Virol., 72:2224-2232 (1998).

Xie, Q et al., "The atomic structure of adeno-associated virus (AAV-2), A Vector for Human Gene Therapy," Proc. Nat'l. Acad. Sci. USA, 99(16):10405-10410 (2002).

Yakobson, B et al., "Replication of adeno-associated virus in synchronized cells without the addition of a helper virus," J. Virol., 61:972-981 (1987).

Yan, Z et al., "Ubiquitination of both adeno-associated virus type 2 and 5 capsid Proteins affects the transduction efficiency of recombinant vectors," J. Virol., 76:2043-2053 (2002).

Yanagawa, Y, and Onoe, K, "Distinct regulation of CD40-mediated interleukin-6 and interleukin-12 productions via mitogen-activated protein kinase and nuclear factor kappaB-inducing kinase in mature dendritic cells," Immunology, 117(4):526-535 (2006).

Yang, C S et al., "Discovery of NSAID and anticancer drugs enhancing reprogramming and IPS cell generation," Stem Cells, 29:1528-1536 (2011).

Yoshida, Y et al., "Hypoxia enhances the generation of induced pluripotent stem cells," Cell Stem Cell, 5:237-241 (2009).

Yu, Y et al., "rAAV/Her-2/neu loading of dendritic cells for a potent cellular-mediated MHC class I restricted immune response against ovarian cancer," Viral Immunol., 21(4): 435-442 (2008).

Zaiss, A K et al., "Complement is an essential component of the immune response to adeno-associated virus vectors," J. Virol., 82(6):2727-2740 (2008).

Zaiss, A K et al., "Differential activation of innate immune responses by adenovirus and adeno-associated virus vectors," J. Virol., 76(9):4580-4590 (2002).

Zaiss, A K, and Muruve, D A, "Immune responses to adeno-associated virus vectors," Curr. Gene Ther., 5(3): 323-331 (2005).

Zaiss, A K, and Muruve, D A, "Immunity to adeno-associated virus vectors in animals and humans: a continued challenge," *Gene Ther.*, 15(11):808-816 (2008).

Zhang, C et al., "Characterization of a bipartite recombinant adeno-associated viral vector for site-specific integration," *Hum. Gene Ther.*, 18:787-797 (2007).

Zhang, C et al., "Effects of melittin on expressions of mitochondria membrane protein 7A6, cell apoptosis-related gene products fas and fas ligand in hepatocarcinoma cells," *J. Chinese Integrat. Med.*, 5:559-563 (2007).

Zhang, Y et al., "AAV-mediated TRAIL gene expression driven by hTERT promoter suppressed human hepatocellular carcinoma growth in mice," *Life Sci.*, 82:1154-1161 (2008).

Zhao, W et al., "Role of cellular FKBP52 protein in intracellular trafficking of recombinant adeno-associated virus 2 vectors," *Virology*, 353:283-293 (2006).

Zhong, L et al., "Evaluation of primitive murine hematopoietic stem and progenitor cell transduction in vitro and in vivo by recombinant adeno-associated virus vector serotypes 1 through 5," *Hum. Gene Ther.*, 17:321-333 (2006).

Zhong, L et al., "Heat-shock treatment-mediated increase in transduction by recombinant adeno-associated virus 2 vectors is independent of the cellular heat-shock protein 90," *J. Biol. Chem.*, 279:12714-12723 (2004).

Zhong, L et al., "Tyrosine-phosphorylation of AAV2 vectors and its consequences on viral intracellular trafficking and transgene expression," *Virology*, 381:194-202 (2008).

Zhong, L et al., "A dual role of EGFR protein tyrosine kinase signaling in ubiquitination of AAV2 capsids and viral second-strand DNA synthesis," *Mol. Ther.*, 15(7):1323-30 (2007).

Zhong, L et al., "Impaired nuclear transport and uncoating limit recombinant adeno-associated virus 2 vector-mediated transduction of primary murine hematopoietic cells," *Hum. Gene Ther.*, 15:1207-1218 (2004).

Zhong, L et al., "Improved transduction of primary murine hepatocytes by recombinant adeno-associated virus 2 vectors in vivo," *Gene Ther.*, 11:1165-1169 (2004).

Zhong, L et al., "Next-generation of adeno-associated virus 2 vectors: point mutations in tyrosines lead to high-efficiency transduction at lower doses," *Proc. Nat'l. Acad. Sci. USA*, 105(22):7827-7832 (2008).

Zhong, L et al., "Single-polarity recombinant adeno-associated virus 2 vector-mediated transgene expression in vitro and in vivo: mechanism of transduction," *Mol. Ther.*, 16:290-295 (2008).

Zhong, L et al., "Tyrosine-phosphorylation of AAV2 vectors and its consequences on viral intracellular trafficking and transgene expression," *Virology*, 381:194-202 (2008).

Zhou, H et al., "Generation of induced pluripotent stem cells using recombinant proteins," *Cell Stem Cell*, 4:381-384 (2009).

Zhou, S Z et al., "Adeno-associated virus 2-mediated transduction and erythroid cell-specific expression of a human beta-globin gene," *Gene Ther.*, 3:223-229 (1996).

Zhou, S Z et al., "Adeno-associated virus 2-mediated high efficiency gene transfer into immature and mature subsets of hematopoietic progenitor cells in human umbilical cord blood," *J. Exp. Med.*, 179:1867-75 (1994).

Zhou, W, and Freed, C R, "Adenoviral gene delivery can reprogram human fibroblasts to induced pluripotent stem cells," *Stem Cells*, 27:2667-2674 (2009).

Zhu, J et al., "The TLR9-MyD88 pathway is critical for adaptive immune responses to adeno-associated virus gene therapy vectors in mice," *J. Clin. Invest.*, 119(8):2388-2398 (2009).

Zhu, Y et al., "Adipose-derived stem cell: A better stem cell than BMSC," *Cell Biochem. Funct.*, 26:664-675 (2008).

Zincarelli, C et al., "Analysis of AAV serotypes 1-9 mediated gene expression and tropism in mice after systemic injection," *Mol. Ther.*, 16:1073-1080 (2008).

Zincarelli, C et al., "Comparative cardiac gene delivery of adeno-associated virus serotypes 1-9 reveals that AAV6 mediates the most efficient transduction in mouse heart," *Clin. Translat. Sci.*, 3:81-89 (2008).

Zolotukhin, S et al., "Production and purification of serotype 1, 2, and 5 recombinant adeno-associated viral vectors," *Methods*, 28(2):158-167 (2002).

It should be understood that the examples and embodiments described herein are for illustrative purposes only and that various modifications or changes in light thereof will be suggested to persons skilled in the art and are to be included within the spirit and purview of this application and the scope of the appended claims. All references (including publications, patent applications and patents, cited herein) are incorporated herein by reference to the same extent as if each reference was individually and specifically indicated to be incorporated by reference and was set forth in its entirety herein. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order, unless otherwise indicated herein, or otherwise clearly contradicted by context. The use of any and all examples, or exemplary language (e.g., "such as") provided herein, is intended merely to better illustrate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are chemically and/or physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A modified adeno-associated virus (AAV) viral protein 3 (VP3) capsid protein comprising a valine substitution at a position corresponding to T492 of SEQ ID NO: 6, and further comprising:
   a) phenylalanine substitutions at positions corresponding to each of Y705 and Y731 of SEQ ID NO: 6;
   b) phenylalanine substitutions at positions corresponding to each of Y445, Y705, and Y731 of SEQ ID NO: 6; or
   c) a valine substitution at a position corresponding to S663 of SEQ ID NO: 6, or a position corresponding to an equivalent threonine, tyrosine, or serine residue in a wild-type AAV1, AAV2, AAV3, AAV4, AAV5, AAV7, AAV8, AAV9, or AAV10 capsid protein, as set forth in SEQ ID NO: 1, SEQ ID NO: 2, SEQ ID NO: 3, SEQ ID NO: 4, SEQ ID NO: 5, SEQ ID NO: 7, SEQ ID NO: 8, SEQ ID NO: 9, and SEQ ID NO: 10, respectively.

2. A modified adeno-associated virus (AAV) viral protein 3 (VP3) capsid protein comprising a valine substitution at a position corresponding to T492 of SEQ ID NO: 6 and phenylalanine substitutions at positions corresponding to each of Y705 and Y731 of SEQ ID NO: 6, or a position corresponding to an equivalent threonine or tyrosine residue in a wild-type AAV1, AAV2, AAV3, AAV4, AAV5, AAV7, AAV8, AAV9, or AAV10 capsid protein, as set forth in SEQ ID NO: 1, SEQ ID NO: 2, SEQ ID NO: 3, SEQ ID NO: 4, SEQ ID NO: 5, SEQ ID NO: 7, SEQ ID NO: 8, SEQ ID NO: 9, and SEQ ID NO: 10, respectively.

3. A modified adeno-associated virus (AAV) viral protein 3 (VP3) capsid protein comprising a valine substitution at a position corresponding to T492 of SEQ ID NO: 6 and a valine substitution at a position corresponding to S663 of SEQ ID NO: 6, or a position corresponding to an equivalent threonine or serine residue in a wild-type AAV1, AAV2, AAV3, AAV4, AAV5, AAV7, AAV8, AAV9, or AAV10 capsid protein, as set forth in SEQ ID NO: 1, SEQ ID NO: 2, SEQ ID NO: 3, SEQ ID NO: 4, SEQ ID NO: 5, SEQ ID NO: 7, SEQ ID NO: 8, SEQ ID NO: 9, and SEQ ID NO: 10, respectively.

4. An isolated polynucleotide that encodes the modified AAV VP3 capsid protein of claim 1.

5. An isolated mammalian host cell comprising a polynucleotide that encodes the modified AAV VP3 capsid protein of claim 1.

6. A recombinant adeno-associated viral (rAAV) particle comprising:
   a) the modified AAV VP3 capsid protein of claim 1; and
   b) a polynucleotide having a gene of interest.

7. The rAAV particle of claim 6, wherein the gene of interest encodes a diagnostic or a therapeutic protein.

8. The rAAV particle of claim 7, wherein the diagnostic or therapeutic protein is or comprises one or more of a molecular marker, an adrenergic agonist, an anti-apoptosis factor, an apoptosis inhibitor, a cytokine receptor, a cytokine, a cytotoxin, an erythropoietic agent, a glutamic acid decarboxylase, a glycoprotein, a growth factor, a growth factor receptor, a hormone, a hormone receptor, an interferon, an interleukin, an interleukin receptor, a kinase, a kinase inhibitor, a nerve growth factor, a netrin, a neuroactive peptide, a neuroactive peptide receptor, a neurogenic factor, a neurogenic factor receptor, a neuropilin, a neurotrophic factor, a neurotrophin, a neurotrophin receptor, an N-methyl-D-aspartate antagonist, a plexin, a protease, a protease inhibitor, a protein decarboxylase, a protein kinase, a protein kinsase inhibitor, a proteolytic protein, a proteolytic protein inhibitor, a semaphorin, a semaphorin receptor, a serotonin transport protein, a serotonin uptake inhibitor, a serotonin receptor, a serpin, a serpin receptor, a tumor suppressor, and any combination thereof.

9. The rAAV particle of claim 6, wherein the modified AAV VP3 capsid protein is of a serotype selected from the group consisting of AAV1, AAV2, AAV3, AAV4, AAV5, AAV6, AAV7, AAV8, AAV9, and AAV10.

10. The rAAV particle of claim 6, wherein the polynucleotide further comprises a promoter, an enhancer, a post-transcriptional regulatory sequence, a polyadenylation signal, or any combination thereof, each operably linked to the polynucleotide.

11. The rAAV particle of claim 10, wherein the promoter is or comprises a CMV promoter, a β-globin promoter, a β-actin promoter, an insulin promoter, an enolase promoter, a BDNF promoter, an NGF promoter, an EGF promoter, a growth factor promoter, an axon-specific promoter, a dendrite-specific promoter, a brain-specific promoter, a hippocampal-specific promoter, a kidney-specific promoter, an elafin promoter, a cytokine promoter, an interferon promoter, a growth factor promoter, an alpha-1 antitrypsin promoter, a brain-specific promoter, a neural cell-specific promoter, a central nervous system cell-specific promoter, a peripheral nervous system cell-specific promoter, an interleukin promoter, a serpin promoter, a hybrid CMV promoter, a hybrid β-actin promoter, an EF1 promoter, a U1a promoter, a U1b promoter, a Tet-inducible promoter, a human parvovirus promoter, or a VP16-LexA promoter.

12. The rAAV particle of claim 10, wherein the enhancer is or comprises a CMV enhancer, a synthetic enhancer, a liver-specific enhancer, a vascular-specific enhancer, a brain-specific enhancer, a neural cell-specific enhancer, a lung-specific enhancer, a muscle-specific enhancer, a kidney-specific enhancer, a pancreas-specific enhancer, or an islet cell-specific enhancer.

13. A plurality of rAAV particles comprising the modified AAV VP3 capsid protein of claim 1.

14. A composition comprising:
a) a viral particle comprising:
(i) the modified AAV VP3 capsid protein of claim 1; and
(ii) a polynucleotide having a gene of interest; and
b) a pharmaceutically-acceptable buffer, diluent, or excipient.

15. The composition of claim 14, wherein the gene of interest encodes a diagnostic or a therapeutic protein.

16. The composition of claim 15, wherein the diagnostic or therapeutic protein is or comprises one or more of a molecular marker, an adrenergic agonist, an anti-apoptosis factor, an apoptosis inhibitor, a cytokine receptor, a cytokine, a cytotoxin, an erythropoietic agent, a glutamic acid decarboxylase, a glycoprotein, a growth factor, a growth factor receptor, a hormone, a hormone receptor, an interferon, an interleukin, an interleukin receptor, a kinase, a kinase inhibitor, a nerve growth factor, a netrin, a neuroactive peptide, a neuroactive peptide receptor, a neurogenic factor, a neurogenic factor receptor, a neuropilin, a neurotrophic factor, a neurotrophin, a neurotrophin receptor, an N-methyl-D-aspartate antagonist, a plexin, a protease, a protease inhibitor, a protein decarboxylase, a protein kinase, a protein kinase inhibitor, a proteolytic protein, a proteolytic protein inhibitor, a semaphorin, a semaphorin receptor, a serotonin transport protein, a serotonin uptake inhibitor, a serotonin receptor, a serpin, a serpin receptor, a tumor suppressor, and any combination thereof.

17. A method of transducing a population of mammalian cells, comprising contacting one or more cells of the population with an effective amount of a composition comprising the modified AAV VP3 capsid protein of claim 1.

18. A method of preventing, treating, or ameliorating the symptoms of one or more diseases, disorders, or dysfunctions in a subject in need thereof, comprising administering to the subject an effective amount of a composition comprising the modified AAV VP3 capsid protein of claim 1.

19. The method of claim 18, wherein administering comprises intramuscular, intravenous, subcutaneous, intrathecal, intraperitoneal, or direct injection into an organ or a tissue.

20. The method of claim 19, wherein the organ is or comprises the heart, liver, lung, pancreas, intestine, or brain.

* * * * *

SEQUENCE LISTING

```
Sequence total quantity: 44
SEQ ID NO: 1                moltype = AA   length = 736
FEATURE                     Location/Qualifiers
source                      1..736
                            mol_type = protein
                            note = Adeno-associated virus serotype 1
                            organism = unidentified
SEQUENCE: 1
MAADGYLPDW LEDNLSEGIR EWWDLKPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ  120
AKKRVLEPLG LVEEGAKTAP GKKRPVEQSP QEPDSSSGIG KTGQQPAKKR LNFGQTGDSE  180
SVPDPQPLGE PPATPAAVGP TTMASGGGAP MADNNEGADG VGNASGNWHC DSTWLGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTTNDGV TTIANNLTST VQVFSDSEYQ LPYVLGSAHQ  360
GCLPPFPADV FMIPQYGYLT LNNGSQAVGR SSFYCLEYFP SQMLRTGNNF TFSYTFEEVP  420
FHSSYAHSQS LDRLMNPLID QYLYYLNRTQ NQSGSAQNKD LLFSRGSPAG MSVQPKNWLP  480
GPCYRQQRVS KTKTDNNNSN FTWTGASKYN LNGRESIINP GTAMASHKDD EDKFFPMSGV  540
MIFGKESAGA SNTALDNVMI TDEEEIKATN PVATERFGTV AVNFQSSSTD PATGDVHAMG  600
ALPGMVWQDR DVYLQGPIWA KIPHTDGHFH PSPLMGGFGL KNPPPQILIK NTPVPANPPA  660
EFSATKFASF ITQYSTGQVS VEIEWELQKE NSKRWNPEVQ YTSNYAKSAN VDFTVDNNGL  720
YTEPRPIGTR YLTRPL                                                 736

SEQ ID NO: 2                moltype = AA   length = 735
FEATURE                     Location/Qualifiers
source                      1..735
                            mol_type = protein
                            note = Adeno-associated virus serotype 2
                            organism = unidentified
SEQUENCE: 2
MAADGYLPDW LEDTLSEGIR QWWKLKPGPP PPKPAERHKD DSRGLVLPGY KYLGPFNGLD  60
KGEPVNEADA AALEHDKAYD RQLDSGDNPY LKYNHADAEF QERLKEDTSF GGNLGRAVFQ  120
AKKRVLEPLG LVEEPVKTAP GKKRPVEHSP VEPDSSSGTG KAGQQPARKR LNFGQTGDAD  180
SVPDPQPLGQ PPAAPSGLGT NTMATGSGAP MADNNEGADG VGNSSGNWHC DSTWMGDRVI  240
TTSTRTWALP TYNNHLYKQI SSQSGASNDN HYFGYSTPWG YFDFNRFHCH FSPRDWQRLI  300
NNNWGFRPKR LNFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFT HSSYAHSQSL  420
HSSYAHSQSL DRLMNPLIDQ YLYYLSRTNT PSGTTTQSRL QFSQAGASDI RDQSRNWLPG  480
PCYRQQRVSK TSADNNNSEY SWTGATKYHL NGRDSLVNPG PAMASHKDDE EKFFPQSGVL  540
IFGKQGSEKT NVDIEKVMIT DEEEIRTTNP VATEQYGSVS TNLQRGNRQA ATADVNTQGV  600
LPGMVWQDRD VYLQGPIWAK IPHTDGHFHP SPLMGGFGLK HPPPQILIKN TPVPANPSTT  660
FSAAKFASFI TQYSTGQVSV EIEWELQKEN SKRWNPEIQY TSNYNKSVNV DFTVDTNGVY  720
SEPRPIGTRY LTRNL                                                  735

SEQ ID NO: 3                moltype = AA   length = 736
FEATURE                     Location/Qualifiers
source                      1..736
                            mol_type = protein
                            note = Adeno-associated virus serotype 3
                            organism = unidentified
SEQUENCE: 3
MAADGYLPDW LEDNLSEGIR EWWALKPGVP QPKANQQHQD NRRGLVLPGY KYLGPGNGLD  60
KGEPVNEADA AALEHDKAYD QQLKAGDNPY LKYNHADAEF QERLQEDTSF GGNLGRAVFQ  120
AKKRILEPLG LVEEAAKTAP GKKGAVDQSP QEPDSSSGVG KSGKQPARKR LNFGQTGDSE  180
SVPDPQPLGE PPAAPTSLGS NTMASGGGAP MADNNEGADG VGNSSGNWHC DSQWLGDRVI  240
TTSTRTWALP TYNNHLYKQI SSQSGASNDN HYFGYSTPWG YFDFNRFHCH FSPRDWQRLI  300
NNNWGFRPKK LSFKLFNIQV RGVTQNDGTT TIANNLTSTV QVFTDSEYQL PYVLGSAHQG  360
CLPPFPADVF MVPQYGYLTL NNGSQAVGRS SFYCLEYFPS QMLRTGNNFQ FSYTFEDVPF  420
HSSYAHSQSL DRLMNPLIDQ YLYYLNRTQG TTSGTTNQSR LLFSQAGPQS MSLQARNWLP  480
GPCYRQQRLS KTANDNNSN FPWTAASKYH LNGRDSLVNP GPAMASHKDD EEKFFPMHGN  540
LIFGKEGTTA SNAELDNVMI TDEEEIRTTN PVATEQYGTV ANNLQSSNTA PTTGTVNHQG  600
ALPGMVWQDR DVYLQGPIWA KIPHTDGHFH PSPLMGGFGL KHPPPQIMIK NTPVPANPPT  660
TFSPAKFASF ITQYSTGQVS VEIEWELQKE NSKRWNPEIQ YTSNYNKSVN VDFTVDTNGV  720
YSEPRPIGTR YLTRNL                                                 736

SEQ ID NO: 4                moltype = AA   length = 734
FEATURE                     Location/Qualifiers
source                      1..734
                            mol_type = protein
                            note = Adeno-associated virus serotype 4
                            organism = unidentified
SEQUENCE: 4
MTDGYLPDWL EDNLSEGVRE WWALQPGAPK PKANQQHQDN ARGLVLPGYK YLGPGNGLDK  60
GEPVNAADAA ALEHDKAYDQ QLKAGDNPYL KYNHADAEFQ QRLQGDTSFG GNLGRAVFQA  120
KKRVLEPLGL VEQAGETAPG KKRPLIESPQ QPDSSTGIGK KGKQPAKKKL VFEDETGAGD  180
GPPEGSTSGA MSDDSEMRAA AGGAAVEGGQ GADGVGNASG DWHCDSTWSE GHVTTTSTRT  240
WVLPTYNNHL YKRLGESLQS NTYNGFSTPW GYFDFNRFHC HFSPRDWQRL INNNWGMRPK  300
AMRVKIFNIQ VKEVTTSNGE TTVANNLTST VQIFADSSYE LPYVMDAGQE GSLPPFPNDV  360
FMVPQYGYCG LVTGNTSQQQ TDRNAFYCLE YFPSQMLRTG NNFEITYSFE KVPFHSMYAH  420
```

```
SQSLDRLMNP LIDQYLWGLQ STTTGTTLNA GTATTNFTKL RPTNFSNFKK NWLPGPSIKQ    480
QGFSKTANQN YKIPATGSDS LIKYETHSTL DGRWSALTPG PPMATAGPAD SKFSNSQLIF    540
AGPKQNGNTA TVPGTLIFTS EEELAATNAT DTDMWGNLPG GDQSNSNLPT VDRLTALGAV    600
PGMVWQNRDI YYQGPIWAKI PHTDGHFHPS PLIGGFGLKH PPPQIFIKNT PVPANPATTF    660
SSTPVNSFIT QYSTGQVSVQ IDWEIQKERS KRWNPEVQFT SNYGQQNSLL WAPDAAGKYT    720
EPRAIGTRYL THHL                                                     734

SEQ ID NO: 5            moltype = AA  length = 724
FEATURE                 Location/Qualifiers
source                  1..724
                        mol_type = protein
                        note = Adeno-associated virus serotype 5
                        organism = unidentified
SEQUENCE: 5
MSFVDHPPDW LEEVGEGLRE FLGLEAGPPK PKPNQQHQDQ ARGLVLPGYN YLGPGNGLDR    60
GEPVNRADEV AREHDISYNE QLEAGDNPYL KYNHADAEFQ EKLADDTSFG GNLGKAVFQA    120
KKRVLEPFGL VEEGAKTAPT GKRIDDHFPK RKKARTEEDS KPSTSSDAEA GPSGSQQLQI    180
PAQPASSLGA DTMSAGGGGP LGDNNQGADG VGNASGDWHC DSTWMGDRVV TKSTRTWVLP    240
SYNNHQYREI KSGSVDGSNA NAYFGYSTPW GYFDFNRFHS HWSPRDWQRL INNYWGFRPR    300
SLRVKIFNIQ VKEVTVQDST TTIANNLTST VQVFTDDDYQ LPYVVGNGTE GCLPAFPPQV    360
FTLPQYGYAT LNRDNTENPT ERSSFFCLEY FPSKMLRTGN NFEFTYNFEE VPFHSSFAPS    420
QNLFKLANPL VDQYLYRFVS TNNTGGVQFN KNLAGRYANT VKVFPGPMG RTQGWNLGSG    480
VNRASVSAFA TTNRMELEGA SYQVPPQPNG MTNNLQGSNT YALENTMIFN SQPANPGTTA    540
TYLEGNMLIT SESETQPVNR VAYNVGGQMA TNNQSSTTAP ATGTYNLQEI VPGSVWMERD    600
VYLQGPIWAK IPETGAHFHP SPAMGGFGLK HPPPMMLIKN TPVPGNITSF SDVPVSSFIT    660
QYSTGQVTVE MEWELKKENS KRWNPEIQYT NNYNDPQFVD FAPDSTGEYR TTRPIGTRYL    720
TRPL                                                                724

SEQ ID NO: 6            moltype = AA  length = 736
FEATURE                 Location/Qualifiers
source                  1..736
                        mol_type = protein
                        note = Adeno-associated virus serotype 6
                        organism = unidentified
SEQUENCE: 6
MAADGYLPDW LEDNLSEGIR EWWDLKPGAP KPKANQQKQD DGRGLVLPGY KYLGPFNGLD    60
KGEPVNAADA AALEHDKAYD QQLKAGDNPY LRYNHADAEF QERLQEDTSF GGNLGRAVFQ    120
AKKRVLEPFG LVEEGAKTAP GKKRPVEQSP QEPDSSSGIG KTGQQPAKKR LNFGQTGDSE    180
SVPDPQPLGE PPATPAAVGP TTMASGGGAP MADNNEGADG VGNASGNWHC DSTWLGDRVI    240
TTSTRTWALP TYNNHLYKQI SSASTGASND NHYFGYSTPW GYFDFNRFHC HFSPRDWQRL    300
INNNWGFRPK RLNFKLFNIQ VKEVTTNDGV TTIANNLTST VQVFSDSEYQ LPYVLGSAHQ    360
GCLPPFPADV FMIPQYGYLT LNNGSQAVGR SSFYCLEYFP SQMLRTGNNF TFSYTFEDVP    420
FHSSYAHSQS LDRLMNPLID QYLYYLNRTQ NQSGSAQNKD LLFSRGSPAG MSVQPKNWLP    480
GPCYRQQRVS KTKTDNNNSN FTWTGASKYN LNGRESIINP GTAMASHKDD KDKFFPMSGV    540
MIFGKESAGA SNTALDNVMI TDEEEIKATN PVATERFGTV AVNLQSSSTD PATGDVHVMG    600
ALPGMVWQDR DVYLQGPIWA KIPHTDGHFH PSPLMGGFGL KHPPPQILIK NTPVPANPPA    660
EFSATKFASF ITQYSTGQVS VEIEWELQKE NSKRWNPEVQ YTSNYAKSAN VDFTVDNNGL    720
YTEPRPIGTR YLTRPL                                                   736

SEQ ID NO: 7            moltype = AA  length = 737
FEATURE                 Location/Qualifiers
source                  1..737
                        mol_type = protein
                        note = Adeno-associated virus serotype 7
                        organism = unidentified
SEQUENCE: 7
MAADGYLPDW LEDNLSEGIR EWWDLKPGAP KPKANQQKQD NGRGLVLPGY KYLGPFNGLD    60
KGEPVNAADA AALEHDKAYD QQLKAGDNPY LRYNHADAEF QERLQEDTSF GGNLGRAVFQ    120
AKKRVLEPLG LVEEGAKTAP AKKRPVEPSP QRSPDSSTGI GKKGQQPARK RLNFGQTGDS    180
ESVPDPQPLG EPPAAPSSVG SGTVAAGGGA PMADNNEGAD GVGNASGNWH CDSTWLGDRV    240
ITTSTRTWAL PTYNNHLYKQ ISSETAGSTN DNTYFGYSTP WGYFDFNRFH CHFSPRDWQR    300
LINNNWGFRP KKLRFKLFNI QVKEVTTNDG VTTIANNLTS TIQVFSDSEY QLPYVLGSAH    360
QGCLPPFPAD VFMIPQYGYL TLNNGSQSVG RSSFYCLEYF PSQMLRTGNN FEFSYSFEDV    420
PFHSSYAHSQ SLDRLMNPLI DQYLYYLART QSNPGGTAGN RELQFYQGGP STMAEQAKNW    480
LPGPCFRQQR VSKTLDQNNN SNFAWTGATK YHLNGRNSLV NPGVAMATHK DDEDRFFPSS    540
GVLIFGKTGA TNKTTLENVL MTNEEEIRPT NPVATEEYGI VSSNLQAANT AAQTQVVNNQ    600
GALPGMVWQN RDVYLQGPIW AKIPHTDGNF HPSPLMGGFG LKHPPPQILI KNTPVPANPP    660
EVFTPAKFAS FITQYSTGQV SVEIEWELQK ENSKRWNPEI QYTSNFEKQT GVDFAVDSQG    720
VYSEPRPIGT RYLTRNL                                                  737

SEQ ID NO: 8            moltype = AA  length = 738
FEATURE                 Location/Qualifiers
source                  1..738
                        mol_type = protein
                        note = Adeno-associated virus serotype 8
                        organism = unidentified
SEQUENCE: 8
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ    120
```

```
AKKRVLEPLG LVEEGAKTAP GKKRPVEPSP QRSPDSSTGI GKKGQQPARK RLNFGQTGDS  180
ESVPDPQPLG EPPAAPSGVG PNTMAAGGGA PMADNNEGAD GVGSSSGNWH CDSTWLGDRV  240
ITTSTRTWAL PTYNNHLYKQ ISNGTSGGAT NDNTYFGYST PWGYFDFNRF HCHFSPRDWQ  300
RLINNNWGFR PKRLSFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFQFTYTFED  420
VPFHSSYAHS QSLDRLMNPL IDQYLYYLSR TQTTGGTANT QTLGFSQGGP NTMANQAKNW  480
LPGPCYRQQR VSTTTGQNNN SNFAWTAGTK YHLNGRNSLA NPGIAMATHK DDEERFFPSN  540
GILIFGKQNA ARDNADYSDV MLTSEEEIKT TNPVATEEYG IVADNLQQQN TAPQIGTVNS  600
QGALPGMVWQ NRDVYLQGPI WAKIPHTDGN FHPSPLMGGF GLKHPPPQIL IKNTPVPADP  660
PTTFNQSKLN SFITQYSTGQ VSVEIEWELQ KENSKRWNPE IQYTSNYYKS TSVDFAVNTE  720
GVYSEPRPIG TRYLTRNL                                               738

SEQ ID NO: 9              moltype = AA  length = 736
FEATURE                   Location/Qualifiers
source                    1..736
                          mol_type = protein
                          note = Adeno-associated virus serotype 9
                          organism = unidentified
SEQUENCE: 9
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEY FPSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 10             moltype = AA  length = 738
FEATURE                   Location/Qualifiers
source                    1..738
                          mol_type = protein
                          note = Adeno-associated virus serotype 10
                          organism = unidentified
SEQUENCE: 10
MAADGYLPDW LEDNLSEGIR EWWDLKPGAP KPKANQQKQD DGRGLVLPGY KYLGPFNGLD   60
KGEPVNAADA AALEHDKAYD QQLKAGDNPY LRYNHADAEF QERLQEDTSF GGNLGRAVFQ  120
AKKRVLEPLG LVEEGAKTAP GKKRPVEPSP QRSPDSSTGI GKKGQQPAKK RLNFGQTGDS  180
ESVPDPQPIG EPPAGPSGLG SGTMAAGGGA PMADNNEGAD GVGSSSGNWH CDSTWLGDRV  240
ITTSTRTWAL PTYNNHLYKQ ISNGTSGGST NDNTYFGYST PWGYFDFNRF HCHFSPRDWQ  300
RLINNNWGFR PKRLNFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFEFSYQFED  420
VPFHSSYAHS QSLDRLMNPL IDQYLYYLSR TQSTGGTAGT QQLLFSQAGP NNMSAQAKNW  480
LPGPCYRQQR VSTTLSQNNN SNFAWTGATK YHLNGRDSLV NPGVAMATHK DDEERFFPSS  540
GVLMFGKQGA GKDNVDYSSV MLTSEEEIKT TNPVATEQYG VVADNLQQQN AAPIVGAVNS  600
QGALPGMVWQ NRDVYLQGPI WAKIPHTDGN FHPSPLMGGF GLKHPPPQIL IKNTPVPADP  660
PTTFSQAKLA SFITQYSTGQ VSVEIEWELQ KENSKRWNPE IQYTSNYYKS TNVDFAVNTD  720
GTYSEPRPIG TRYLTRNL                                               738

SEQ ID NO: 11             moltype = DNA  length = 45
FEATURE                   Location/Qualifiers
misc_feature              1..45
                          note = Forward Oligonucleotide Primer
source                    1..45
                          mol_type = other DNA
                          organism = synthetic construct
SEQUENCE: 11
accagaacct gggctctgcc cactttcaac aaccatctct acaag          45

SEQ ID NO: 12             moltype = DNA  length = 45
FEATURE                   Location/Qualifiers
misc_feature              1..45
                          note = Reverse Oligonucleotide Primer
source                    1..45
                          mol_type = other DNA
                          organism = synthetic construct
SEQUENCE: 12
caatcaggag cttcgaacga caaccacttc tttggctaca gcacc          45

SEQ ID NO: 13             moltype = DNA  length = 45
FEATURE                   Location/Qualifiers
misc_feature              1..45
                          note = Oligonucleotide Primer
source                    1..45
```

-continued

```
                              mol_type = other DNA
                              organism = synthetic construct
SEQUENCE: 13
cttatcgatc agtatctgta cttcctgaac agaacgcaag gaaca              45

SEQ ID NO: 14           moltype = DNA   length = 48
FEATURE                 Location/Qualifiers
misc_feature            1..48
                        note = Oligonucleotide Primer
source                  1..48
                        mol_type = other DNA
                        organism = synthetic construct
SEQUENCE: 14
gctaacgaca acaacaacag taactatcca tggacagcgg ccagcaaa            48

SEQ ID NO: 15           moltype = DNA   length = 45
FEATURE                 Location/Qualifiers
misc_feature            1..45
                        note = Oligonucleotide Primer
source                  1..45
                        mol_type = other DNA
                        organism = synthetic construct
SEQUENCE: 15
tggaatccag agattcagtt cacgtccaac tacaacaagt ctgtt              45

SEQ ID NO: 16           moltype = DNA   length = 45
FEATURE                 Location/Qualifiers
misc_feature            1..45
                        note = Oligonucleotide Primer
source                  1..45
                        mol_type = other DNA
                        organism = synthetic construct
SEQUENCE: 16
gagattcagt acacgtccaa cttcaacaag tctgttaatg tggac              45

SEQ ID NO: 17           moltype = DNA   length = 44
FEATURE                 Location/Qualifiers
misc_feature            1..44
                        note = Oligonucleotide Primer
source                  1..44
                        mol_type = other DNA
                        organism = synthetic construct
SEQUENCE: 17
gtgaacctcg ccctattgga acccggtttc tcacacgaaa cttg               44

SEQ ID NO: 18           moltype = DNA   length = 21
FEATURE                 Location/Qualifiers
misc_feature            1..21
                        note = Oligonucleotide Primer
source                  1..21
                        mol_type = other DNA
                        organism = synthetic construct
SEQUENCE: 18
tcccatagta acgccaatag g                                        21

SEQ ID NO: 19           moltype = DNA   length = 23
FEATURE                 Location/Qualifiers
misc_feature            1..23
                        note = Oligonucleotide Primer
source                  1..23
                        mol_type = other DNA
                        organism = synthetic construct
SEQUENCE: 19
cttggcatat gatacacttg atg                                      23

SEQ ID NO: 20           moltype = DNA   length = 21
FEATURE                 Location/Qualifiers
misc_feature            1..21
                        note = Oligonucleotide Primer
source                  1..21
                        mol_type = other DNA
                        organism = synthetic construct
SEQUENCE: 20
tcccatagta acgccaatag g                                        21

SEQ ID NO: 21           moltype = DNA   length = 23
FEATURE                 Location/Qualifiers
misc_feature            1..23
                        note = Oligonucleotide Primer
```

```
                    source          1..23
                                    mol_type = other DNA
                                    organism = synthetic construct
SEQUENCE: 21
cttggcatat gatacacttg atg                                                  23

SEQ ID NO: 22           moltype = DNA   length = 145
FEATURE                 Location/Qualifiers
misc_feature            1..145
                        note = Synthetic Sequence
source                  1..145
                        mol_type = other DNA
                        organism = synthetic construct
SEQUENCE: 22
aggaacccct agtgatggag ttggccactc cctctctgcg cgctcgctcg ctcactgagg           60
ccgggcgacc aaaggtcgcc cgacgcccgg gctttgcccg ggcggcctca gtgagcgagc          120
gagcgcgcag agagggagtg gccaa                                                145

SEQ ID NO: 23           moltype = DNA   length = 20
FEATURE                 Location/Qualifiers
misc_feature            1..20
                        note = Oligonucleotide Primer
source                  1..20
                        mol_type = other DNA
                        organism = synthetic construct
SEQUENCE: 23
ctccatcact aggggttcct                                                      20

SEQ ID NO: 24           moltype = DNA   length = 20
FEATURE                 Location/Qualifiers
misc_feature            1..20
                        note = Oligonucleotide Primer
source                  1..20
                        mol_type = other DNA
                        organism = synthetic construct
SEQUENCE: 24
ctccatcact aggggttcct                                                      20

SEQ ID NO: 25           moltype = DNA   length = 20
FEATURE                 Location/Qualifiers
misc_feature            1..20
                        note = Oligonucleotide Primer
source                  1..20
                        mol_type = other DNA
                        organism = synthetic construct
SEQUENCE: 25
gaggtagtga tccccaagga                                                      20

SEQ ID NO: 26           moltype = DNA   length = 25
FEATURE                 Location/Qualifiers
misc_feature            1..25
                        note = Oligonucleotide Primer
source                  1..25
                        mol_type = other DNA
                        organism = synthetic construct
SEQUENCE: 26
cgtgtacggt gggaggtcta tataa                                                25

SEQ ID NO: 27           moltype = DNA   length = 18
FEATURE                 Location/Qualifiers
misc_feature            1..18
                        note = Oligonucleotide Primer
source                  1..18
                        mol_type = other DNA
                        organism = synthetic construct
SEQUENCE: 27
ggatcggtcc cggtgtct                                                        18

SEQ ID NO: 28           moltype = DNA   length = 24
FEATURE                 Location/Qualifiers
misc_feature            1..24
                        note = Oligonucleotide Primer
source                  1..24
                        mol_type = other DNA
                        organism = synthetic construct
SEQUENCE: 28
acgccatcca cgctgttttg acct                                                 24

SEQ ID NO: 29           moltype = DNA   length = 21
```

```
FEATURE                 Location/Qualifiers
misc_feature            1..21
                        note = Oligonucleotide Primer
source                  1..21
                        mol_type = other DNA
                        organism = synthetic construct
SEQUENCE: 29
ccaacgagaa gagtatgagg c                                              21

SEQ ID NO: 30           moltype = DNA  length = 21
FEATURE                 Location/Qualifiers
misc_feature            1..21
                        note = Oligonucleotide Primer
source                  1..21
                        mol_type = other DNA
                        organism = synthetic construct
SEQUENCE: 30
gtgcttttaa tccctcctca g                                              21

SEQ ID NO: 31           moltype = DNA  length = 20
FEATURE                 Location/Qualifiers
misc_feature            1..20
                        note = Oligonucleotide Primer
source                  1..20
                        mol_type = other DNA
                        organism = synthetic construct
SEQUENCE: 31
tctgtggtca agtccgaggc                                                20

SEQ ID NO: 32           moltype = DNA  length = 20
FEATURE                 Location/Qualifiers
misc_feature            1..20
                        note = Oligonucleotide Primer
source                  1..20
                        mol_type = other DNA
                        organism = synthetic construct
SEQUENCE: 32
ttctccagtt cgcagtccag                                                20

SEQ ID NO: 33           moltype = DNA  length = 21
FEATURE                 Location/Qualifiers
misc_feature            1..21
                        note = Oligonucleotide Primer
source                  1..21
                        mol_type = other DNA
                        organism = synthetic construct
SEQUENCE: 33
ggcgagaaac cttaccactg t                                              21

SEQ ID NO: 34           moltype = DNA  length = 22
FEATURE                 Location/Qualifiers
misc_feature            1..22
                        note = Oligonucleotide Primer
source                  1..22
                        mol_type = other DNA
                        organism = synthetic construct
SEQUENCE: 34
tactgaactc tctctcctgg ca                                             22

SEQ ID NO: 35           moltype = DNA  length = 20
FEATURE                 Location/Qualifiers
misc_feature            1..20
                        note = Oligonucleotide Primer
source                  1..20
                        mol_type = other DNA
                        organism = synthetic construct
SEQUENCE: 35
tcaagcagac gagcacaagc                                                20

SEQ ID NO: 36           moltype = DNA  length = 20
FEATURE                 Location/Qualifiers
misc_feature            1..20
                        note = Oligonucleotide Primer
source                  1..20
                        mol_type = other DNA
                        organism = synthetic construct
SEQUENCE: 36
tacagtccca aagccccagc                                                20
```

```
SEQ ID NO: 37              moltype = DNA   length = 21
FEATURE                    Location/Qualifiers
misc_feature               1..21
                           note = Oligonucleotide Primer
source                     1..21
                           mol_type = other DNA
                           organism = synthetic construct
SEQUENCE: 37
aggtcggtgt gaacggattt g                                                 21

SEQ ID NO: 38              moltype = DNA   length = 23
FEATURE                    Location/Qualifiers
misc_feature               1..23
                           note = Oligonucleotide Primer
source                     1..23
                           mol_type = other DNA
                           organism = synthetic construct
SEQUENCE: 38
tgtagaccat gtagttgagg tca                                               23

SEQ ID NO: 39              moltype = DNA   length = 20
FEATURE                    Location/Qualifiers
misc_feature               1..20
                           note = Oligonucleotide Primer
source                     1..20
                           mol_type = other DNA
                           organism = synthetic construct
SEQUENCE: 39
acacctgcga actcacacag                                                   20

SEQ ID NO: 40              moltype = DNA   length = 20
FEATURE                    Location/Qualifiers
misc_feature               1..20
                           note = Oligonucleotide Primer
source                     1..20
                           mol_type = other DNA
                           organism = synthetic construct
SEQUENCE: 40
agttgctttc cactcgtgct                                                   20

SEQ ID NO: 41              moltype = DNA   length = 20
FEATURE                    Location/Qualifiers
misc_feature               1..20
                           note = Oligonucleotide Primer
source                     1..20
                           mol_type = other DNA
                           organism = synthetic construct
SEQUENCE: 41
acccagaaga ctgtggatgg                                                   20

SEQ ID NO: 42              moltype = DNA   length = 20
FEATURE                    Location/Qualifiers
misc_feature               1..20
                           note = Oligonucleotide Primer
source                     1..20
                           mol_type = other DNA
                           organism = synthetic construct
SEQUENCE: 42
ccctgttgct gtagccgtat                                                   20

SEQ ID NO: 43              moltype = DNA   length = 20
FEATURE                    Location/Qualifiers
misc_feature               1..20
                           note = Oligonucleotide Primer
source                     1..20
                           mol_type = other DNA
                           organism = synthetic construct
```

```
SEQUENCE: 43
tagttgccag ccatctgttg                                                  20

SEQ ID NO: 44          moltype = DNA  length = 20
FEATURE                Location/Qualifiers
misc_feature           1..20
                       note = Oligonucleotide Primer
source                 1..20
                       mol_type = other DNA
                       organism = synthetic construct
SEQUENCE: 44
gcgatgcaat ttcctcattt                                                  20
```